(12) United States Patent
Ibrahim et al.

(10) Patent No.: US 8,067,434 B2
(45) Date of Patent: Nov. 29, 2011

(54) COMPOUNDS AND METHODS FOR DEVELOPMENT OF RET MODULATORS

(75) Inventors: Prabha Ibrahim, Mountain View, CA (US); Dean Richard Artis, Kensington, CA (US); Ryan Bremer, Oakland, CA (US); Gaston Habets, Pleasant Hill, CA (US); Clarence R. Hurt, San Ramon, CA (US); Shumeye Mamo, Oakland, CA (US); Marika Nespi, Berkeley, CA (US); Chao Zhang, Moraga, CA (US); Jiazhong Zhang, Foster City, CA (US); Yong-Liang Zhu, Fremont, CA (US); Rebecca Zuckerman, Alameda, CA (US); Heike Krupka, Hayward, CA (US); Abhinav Kumar, Pleasant Hill, CA (US); Brian West, San Francisco, CA (US)

(73) Assignee: Plexxikon Inc., Berkeley, CA (US)

( * ) Notice: Subject to any disclaimer, the term of this patent is extended or adjusted under 35 U.S.C. 154(b) by 589 days.

(21) Appl. No.: 12/082,665

(22) Filed: Apr. 11, 2008

(65) Prior Publication Data

US 2010/0324065 A1    Dec. 23, 2010

Related U.S. Application Data

(63) Continuation of application No. 11/016,350, filed on Dec. 17, 2004, now Pat. No. 7,504,509.

(60) Provisional application No. 60/531,281, filed on Dec. 19, 2003, provisional application No. 60/558,581, filed on Mar. 31, 2004.

(51) Int. Cl.
*A01N 43/42* (2006.01)
*A61K 31/44* (2006.01)

(52) U.S. Cl. ...................................... 514/300
(58) Field of Classification Search .................... 514/300
See application file for complete search history.

(56) References Cited

U.S. PATENT DOCUMENTS

| | | |
|---|---|---|
| 2,234,705 A | 3/1941 | Normington et al. |
| 2,413,258 A | 12/1946 | Soday et al. |
| 4,150,949 A | 4/1979 | Smith |
| 4,568,649 A | 2/1986 | Bertoglio-Matte |
| 4,626,513 A | 12/1986 | Burton et al. |
| 4,727,395 A | 2/1988 | Oda et al. |
| 5,120,782 A | 6/1992 | Hubsch et al. |
| 5,143,854 A | 9/1992 | Pirrung et al. |
| 5,338,849 A | 8/1994 | Festal et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,877,007 A | 3/1999 | Housey |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |

(Continued)

FOREIGN PATENT DOCUMENTS

DE                24 13 258 A1    10/1975

(Continued)

OTHER PUBLICATIONS

Coelho et al., Pediatric surgery international, (Sep. 2008) vol. 24, No. 9, pp. 1017-1021.*
Amiel et al., J Med Genet (2008), vol. 45, pp. 1-14.*
Machens et al., Endocrine-Related cancer (2009), vol. 16, pp. 171-177.*
Wells et al., Clin Cancer res 2009, 15(23), pp. 7119-7123.*
Castellone et al., Clinical Endocrinology (2010), 73, pp. 529-534.*
Galofre et al., Mount sinai Journal of medicine 75:299-311, 2008.*
Gassman, Specific ortho substitution of aromatic heterocyclic amines. Conversions of 2-aminopyridines. Journal of the American Chemical Society, 95(13): 4453-4455, 1973.

(Continued)

*Primary Examiner* — D M Seaman
*Assistant Examiner* — Niloofar Rahmani
(74) *Attorney, Agent, or Firm* — Foley & Lardner LLP; Stephen E. Reiter

(57) ABSTRACT

Compounds active on Ret are described, as well as methods of using such compounds. Also described are crystal structures of Ret surrogates that were determined using X-ray crystallography. The use of such Ret surrogate crystals and structural information can, for example, be used for identifying molecular scaffolds and for developing ligands that bind to and modulate Ret and for identifying improved ligands based on known ligands.

10 Claims, 5 Drawing Sheets

U.S. PATENT DOCUMENTS

| | | | |
|---|---|---|---|
| 6,110,456 A | 8/2000 | During | |
| 6,110,458 A | 8/2000 | Freeman et al. | |
| 6,113,913 A | 9/2000 | Brough et al. | |
| 6,117,681 A | 9/2000 | Salmons et al. | |
| 6,161,776 A | 12/2000 | Byles | |
| 6,178,384 B1 | 1/2001 | Kolossváry | |
| 6,235,769 B1 | 5/2001 | Clary | |
| 6,243,980 B1 | 6/2001 | Bronstein et al. | |
| 6,258,606 B1 | 7/2001 | Kovacs | |
| 6,261,776 B1 | 7/2001 | Pirrung et al. | |
| 6,277,489 B1 | 8/2001 | Abbott et al. | |
| 6,277,628 B1 | 8/2001 | Johann et al. | |
| 6,288,234 B1 | 9/2001 | Griffin | |
| 6,294,330 B1 | 9/2001 | Michnick et al. | |
| 6,310,074 B1 | 10/2001 | Depreux et al. | |
| 6,545,014 B2 | 4/2003 | Verner | |
| 6,858,860 B2 | 2/2005 | Hosono et al. | |
| 7,259,165 B2 | 8/2007 | Bernotas et al. | |
| 7,361,763 B2 | 4/2008 | Arnold et al. | |
| 7,361,764 B2 | 4/2008 | Arnold et al. | |
| 7,452,993 B2 | 11/2008 | Arnold et al. | |
| 7,498,342 B2 | 3/2009 | Ibrahim et al. | |
| 7,504,509 B2 | 3/2009 | Ibrahim et al. | |
| 7,582,637 B2 | 9/2009 | Arnold et al. | |
| 7,601,839 B2 | 10/2009 | Arnold et al. | |
| 7,626,021 B2 | 12/2009 | Arnold et al. | |
| 2001/0008765 A1 | 7/2001 | Shinoke et al. | |
| 2001/0012537 A1 | 8/2001 | Anderson et al. | |
| 2001/0014448 A1 | 8/2001 | Chappa et al. | |
| 2001/0014449 A1 | 8/2001 | Nerenberg et al. | |
| 2001/0016322 A1 | 8/2001 | Caren et al. | |
| 2001/0018642 A1 | 8/2001 | Balaban et al. | |
| 2001/0019827 A1 | 9/2001 | Dawson et al. | |
| 2003/0003004 A1 | 1/2003 | Stones et al. | |
| 2004/0002534 A1 | 1/2004 | Lipson et al. | |
| 2004/0022534 A1 | 2/2004 | Amano et al. | |
| 2004/0077595 A1 | 4/2004 | Cheng et al. | |
| 2004/0142864 A1 | 7/2004 | Bremer et al. | |
| 2004/0167030 A1 | 8/2004 | Bernotas et al. | |
| 2005/0085463 A1 | 4/2005 | Weiner et al. | |
| 2005/0154014 A1 | 7/2005 | Bloxham et al. | |
| 2005/0164300 A1 | 7/2005 | Artis et al. | |
| 2005/0170431 A1 | 8/2005 | Ibrahim et al. | |
| 2005/0256151 A1 | 11/2005 | Salom et al. | |
| 2006/0035898 A1 | 2/2006 | Arnold et al. | |
| 2006/0058339 A1 | 3/2006 | Ibrahim et al. | |
| 2006/0058340 A1 | 3/2006 | Ibrahim et al. | |
| 2007/0032519 A1 | 2/2007 | Zhang et al. | |
| 2007/0049615 A1 | 3/2007 | Ibrahim et al. | |
| 2007/0287711 A1 | 12/2007 | Arnold et al. | |
| 2008/0167338 A1 | 7/2008 | Spevak et al. | |
| 2008/188514 A1 | 8/2008 | Wu et al. | |
| 2009/0005356 A1 | 1/2009 | Blaney et al. | |
| 2009/0076046 A1 | 3/2009 | Zhang et al. | |
| 2009/0143352 A1 | 6/2009 | Arnold et al. | |
| 2009/0306056 A1 | 12/2009 | Arnold et al. | |

FOREIGN PATENT DOCUMENTS

| | | |
|---|---|---|
| EP | 0154734 | 9/1985 |
| EP | 0465970 | 6/1991 |
| EP | 1 057 826 | 12/2000 |
| EP | 870768 | 5/2002 |
| EP | 1 267 111 A1 | 12/2002 |
| EP | 1 749 829 | 2/2007 |
| GB | 02292143 | 2/1996 |
| GB | 02292145 | 2/1996 |
| GB | 02298198 | 8/1996 |
| GB | 2299581 | 10/1996 |
| JP | 6135946 | 5/1994 |
| JP | 10-130269 | 5/1998 |
| JP | 15073357 | 3/2003 |
| WO | WO93/13099 | 7/1993 |
| WO | WO 94/14808 | 7/1994 |
| WO | WO94/20459 | 9/1994 |
| WO | WO 94/20497 | 9/1994 |
| WO | WO95/04742 | 2/1995 |
| WO | WO 95/07910 | 3/1995 |
| WO | WO 95/28387 | 10/1995 |
| WO | WO 96/00226 | 1/1996 |
| WO | WO96/11929 | 2/1996 |
| WO | WO96/05200 | 4/1996 |
| WO | WO 96/17958 | 6/1996 |
| WO | WO 96/18738 | 6/1996 |
| WO | WO 97/46313 | 12/1997 |
| WO | WO 97/46558 | 12/1997 |
| WO | WO97/49703 | 12/1997 |
| WO | WO 98/06433 | 2/1998 |
| WO | WO98/22457 | 5/1998 |
| WO | WO98/47899 | 10/1998 |
| WO | WO 99/00386 | 1/1999 |
| WO | WO 99/09217 | 2/1999 |
| WO | WO99/51231 | 10/1999 |
| WO | WO 99/51232 | 10/1999 |
| WO | WO 99/51233 | 10/1999 |
| WO | WO 99/51234 | 10/1999 |
| WO | WO 99/51595 | 10/1999 |
| WO | WO 99/51596 | 10/1999 |
| WO | WO 99/51773 | 10/1999 |
| WO | WO 00/09162 | 2/2000 |
| WO | WO00/12074 | 3/2000 |
| WO | WO00/12514 | 3/2000 |
| WO | WO 00/29411 | 5/2000 |
| WO | WO00/53582 | 9/2000 |
| WO | WO 00/64898 | 11/2000 |
| WO | WO00/71537 | 11/2000 |
| WO | WO00/75139 | 12/2000 |
| WO | WO/2004/009600 | 1/2001 |
| WO | WO01/09121 | 2/2001 |
| WO | WO 01/24236 | 4/2001 |
| WO | WO 01/29036 | 4/2001 |
| WO | WO-01/46196 | 6/2001 |
| WO | WO 01/60822 | 8/2001 |
| WO | WO01/62255 | 8/2001 |
| WO | WO 01/62255 | 8/2001 |
| WO | WO01/98299 | 12/2001 |
| WO | WO02/00657 | 1/2002 |
| WO | WO02/18346 | 3/2002 |
| WO | WO02/083175 | 10/2002 |
| WO | WO02/085896 | 10/2002 |
| WO | WO02/102783 | 12/2002 |
| WO | WO03/000258 | 1/2003 |
| WO | WO-03/003004 A2 | 1/2003 |
| WO | WO03/006459 | 1/2003 |
| WO | WO03/008422 | 1/2003 |
| WO | WO03/011868 | 2/2003 |
| WO | WO 03/020698 | 3/2003 |
| WO | WO03/028724 | 4/2003 |
| WO | WO03/037862 | 5/2003 |
| WO | WO03/051838 | 6/2003 |
| WO | WO-03/064413 | 8/2003 |
| WO | WO03/068221 | 8/2003 |
| WO | WO03/082289 | 10/2003 |
| WO | WO03/082868 | 10/2003 |
| WO | WO03/082869 | 10/2003 |
| WO | WO03/087087 | 10/2003 |
| WO | WO03/101990 | 12/2003 |
| WO | WO2004/009600 | 1/2004 |
| WO | WO-2004/016609 | 2/2004 |
| WO | WO-2004/016610 | 2/2004 |
| WO | WO-2004/024895 | 3/2004 |
| WO | WO2004/065393 | 8/2004 |
| WO | WO2004/065394 | 8/2004 |
| WO | WO2004/074286 | 9/2004 |
| WO | WO2004/078756 | 9/2004 |
| WO | WO-2004/078923 | 9/2004 |
| WO | WO2004/101565 | 11/2004 |
| WO | WO2005/028475 | 3/2005 |
| WO | WO-2005/028624 | 3/2005 |
| WO | WO2005/044181 | 5/2005 |
| WO | WO2005/058891 | 6/2005 |
| WO | WO2005/062795 | 7/2005 |
| WO | WO2005/063746 | 7/2005 |
| WO | WO2005/063747 | 7/2005 |
| WO | WO2005/082367 | 9/2005 |
| WO | WO2005/085244 | 9/2005 |
| WO | WO2005/095400 | 10/2005 |

| WO | WO2005/103050 | 11/2005 |
| WO | WO2005/115363 | 12/2005 |
| WO | WO2006/004984 | 1/2006 |
| WO | WO-2006/009755 | 1/2006 |
| WO | WO-2006/009797 | 1/2006 |
| WO | WO2006/015123 | 2/2006 |
| WO | WO-2006/015124 | 2/2006 |
| WO | WO-2006/114180 | 11/2006 |
| WO | WO2006/127587 | 11/2006 |
| WO | WO-2007/002325 | 1/2007 |
| WO | WO-2007/002433 | 1/2007 |
| WO | WO-2007/013896 | 2/2007 |
| WO | WO-2007/106236 | 9/2007 |

OTHER PUBLICATIONS

Uriskaya et al., Azaindole derivatives. XLIII. Synthesis of 1-acetyl-4-methyl-7-azatryptamine. Document No. 80:27133 (Abstract); Khimiya Geterotsiklicheskikh Soedinenii, 10, 1370-3, 1973.

Minakata et al., "Functionalization of 1H-Pyrrolo[2,3-b]pyridine." Bulletin of the Chemical Society of Japan (1992), 65(11): 2992-2997.

Sawada et al., "4-(Benzoylindolizinyl)butyric acids; Novel nonsteroidal inhibitors of steroid 5α-reductase. III." Chemical and Pharmaceutical Bulletin (2001), 49(7): 799-813.

Song et al., "Isomerism of Bis(7-azaindolyl)methane." Organic Letters (2002), 4:23, 4049-4052, "Table of content" p. 1-16 and "Supporting information" p. 1-15.

Yakhontov et al., Derivatives of 7-azaindole. XV. Electrophilic substitution of 4-methyl-7-azaindole and its derivatives. Zhurnal Obshchei Khimii (1965), 1(11): 2032-2040. (English abstract only).

Yeung et al., "Friedel-Crafts acylation of indoles in acidic imidazolium chloroaluminate ionic liquid at room temperature." Tetrahedron Letters (2002), 43(33), 5793-5795.

Zhang et al., "An effective procedure for the acylation of azaindoles at C-3." Journal of Organic Chemistry (2002), 67(17): 6226-6227 and p. S1-S30.

Alfthan, K., "Surface Plasmon Resonance Biosensors as a Tool in Antibody Engineering" Biosensors & Bioelectronics 13:653-663 (1998).

Allegretti, et al., "Palladium-Catalysed Functionalisation at 4- and 6- Position of the 7-Azaindole System" Synlett 5:609-612 (2001).

Al-Obeidi, et al., "Peptide and Peptidomimetic Libraries" Mol Biotechnol 9(3):205-223 (1998).

Alvarez, et al., "Synthesis of 3-Aryl- and 3-Heteroaryl-7-Azaindoles" Synthesis 4:615-620 (1999).

Amersdorfer P. and Marks J., "Phage Libraries for Generation of Anti-Botulinum scFv Antibodies," Methods in Molecular Biology 145:219-240 (2001).

Anderson, et al., "Cooperative Catalyst Effects in Palladium-Mediated Cyanation Reactions of Aryl Halides and Triflates" J. Org. Chem. 63:8224-8228 (1998).

Antonini, et al., "Synthesis of 4-Amino-1-β-D-Ribofuranosy1-1H-pyrrolo[2,3-b]pyridine (1-Deazatubercidin) as a Potential Antitumor Agent" J. Med. Chem. 25:1258-1261 (1982).

Bartlett, et al., "CAVEAT: A Program to Facilitate the Structure-derived Design of Biologically Active Molecules" Dept. of Chemistry (Univ. of Exeter) 78:I82-I96 (1989).

Bagshaw and Harris, "Measurement of Ligand Binding to Proteins" Spectrophotometry and Spectrofluorometry: A Practical Approach 4:91-114 (1987).

Bell, J.E., "Fluorescence: Solution Studies" Spectroscopy In Biochemistry I(4):155-194 (1981).

Blundell, et al., "Knowledge-Based Protein Modelling and Design" Eur. J. Biochem. 172:513-520 (1988).

Bolger, et al., "Computer Modeling of Combining Site Structure of Anti-hapten Monoclonal Antibodies" Methods Enz. 203:21-45 (1991).

Bohm, H., "On the Use of LUDI to Search the Fine Chemicals Directory for Ligands of Proteins of Known Three-Dimensional Structure" Journ. Comp. Aided Molec. Des. 8:623-632 (1994).

Bongarzone, et al., "High Frequency of Activation of Tyrosine Kinase Oncogenes in Human Papillary Thyroid Carcinoma" Oncogene 4(12):1457-1462 (1989).

Bowtell, D.L., "Options Available—From Start to Finish—For Obtaining Expression Data by Microarray" Nature Genetics Supp. 21:25-32 (1999).

Brenner and Lerner, "Encoded Combinatorial Chemistry" Proc. Natl. Acad. Sci. USA, 89:5381-5383 (1992).

Brünger, A.T., "Free R Value: a Novel Statistical Quantity for Assessing the Accuracy of Crystal Structures" Nature 355:472-475 (1992).

Buchschacher and Panganiban, "Human Immunodeficiency Virus Vectors for Inducible Expression of Foreign Genes" J. Virol. 66:2731-2739 (1992).

Capon, et al., "Designing CD4 Immunoadhesins for AIDS Therapy" Nature 337:525-531 (1989).

Carell, et al., "New Promise in Combinatorial Chemistry: Synthesis, Characterization, and Screening of Small-Molecule Libraries in Solution" Chem. Biol. 3:171-183 (1995).

Chabala, J.C., "Solid-Phase Combinatorial Chemistry and Novel Tagging Methods for Identifying Leads" Curr Opin Biotechnol 6:632-639 (1995).

Chayer, et al., "Synthesis of Carboranylpyrroles" Tetrahedron Lett. 42(44):7759-7761 (2001).

Checovich, et al., "Fluorescence Polarization—a New Tool for Cell and Molecular Biology" Nature 375:254-256 (1995).

Clark, et al., "PRO_LIGAND: An Approach to De Novo Molecular Design. 1. Application to the Design of Organic Molecules" J. Comp. Aided Molec. Design 9:13-32 (1995).

Coe and Storer, "Solution-Phase Combinatorial Chemistry" Mol Divers 4(1):31-38 (1999).

Colliuod, et al., "Oriented and Covalent Immobilization of Target Molecules to Solid Supports: Synthesis and Application of a Light-Activatable and Thiol-Reactive Cross-Linking Reagent" Bioconjugate Chem. 4:528-536 (1993).

Colman, P.M., "Structure-Based Drug Design" Current Opinion in Struc. Biol. 4: 868-874 (1994).

Coste, et al., "Coupling N-Methylated Amino Acids Using PyBroP[1] and PyCloP Halogenophosphonium Salts: Mechanism and Fields of Application" Journal of Organic Chemistry 59:2437-2446 (1994).

Creighton, T.E., "An Empirical Approach to Protein Conformation Stability and Flexibility" Biopolymers 22(1):49-58 (1983).

Cwirla, et al., "Peptides on Phage: A Vast Library of Peptides for Identifying Ligands" Biochemistry 87:6378-6382 (1990).

Dandliker, et al., "Equilibrium and Kinetic Inhibition Assays Based Upon Fluorescence Polarization" Methods in Enzymology 74:3-28 (1981).

Dobeli, et al., "Recombinant Fusion Proteins for the Industrial Production of Disulfide Bridge Containing Peptides: Purification, Oxidation Without Concatamer Formation, and Selective Cleavage" Protein Expr. Purif. 12:404-414 (1998).

Dolle and Nelson, "Comprehensive Survey of Combinatorial Library Synthesis: 1998" J Comb Chem. 1(4):235-282 (1999).

Donis-Keller, et al., "Mutations in the RET Proto-Oncogene are Associated with MEN 2A and FMTC" Hum Mol Genet. 2(7):851-856 (1993).

Dube and Scholte "Reductive N-Alkylation of Amides, Carbamates and Ureas" Tetrahedron Lett. 40:2295-2298 (1999).

Durbec, et al., "GDNF Signalling Through the Ret Receptor Tyrosine Kinase" Nature 381:789-793 (1996).

Eliseev and Lehn, "Dynamic Combinatorial Chemistry: Evolutionary Formation and Screening of Molecular Libraries" Current Topics in Microbiology & Immunology 243:159-172 (1999).

Enjalbal, et al., "Mass Spectrometry in Combinatorial Chemistry" Mass Spectrometry Reviews 19:139-161 (2000).

Feng, et al., "Stable in Vivo Gene Transduction Via a Novel Adenoviral / Retroviral Chimeric Vector" Nature Biotechnology 15:866-870 (1997).

Fivash et al., "BIAcore for Macromolecular Interaction" Current Opinion in Biotechnology 9:97-101 (1998).

Franz and Martin "Sulfuranes. X. A Reagent for the Facile Cleavage of Secondary Amides," JACS, 95(6):2017-2019 (1973).

Gallop et al., "Applications of Combinatorial Technologies to Drug Discovery. 1. Background and Peptide Combinatorial Libraries" J. Med. Chem. 37:1233-1251 (1994).

Girgis et al., "The Synthesis of 5-Azaindoles by Substitution-Rearrangement of 7-Azaindoles Upon Treatment with Certain Primary Amines" *J. Heterocyclic Chemistry* 26:317-325 (1989).

Goodford, P.J., "A Computational Procedure for Determining Energetically Favorable Binding Sites on Biologically Important Macromolecules" *J. Med. Chem.* 28:849-857 (1985).

Goodsell and Olson, "Automated Docking of Substrates to Proteins by Simulated Annealing" *Proteins: Structure, Function, and Genetics* 8:195-202 (1990).

Gordon et al., "Applications of Combinatorial Technologies to Drug Discovery. 2. Combinatorial Organic Synthesis, Library Screening Strategies, and Future Directions" *J. Med. Chem.* 37:1385-1401 (1994).

Gordon, and Ford, "Detection of Peroxides and Their Removal" *The Chemist's Companion: A Handbook Of Practical Data, Techniques, And References* p. 437 (1972).

Gram H., "Phage Display in Proteolysis and Signal Transduction" *Combinatorial Chemistry & High Throughput Screening.* 2:19-28 (1999).

Gravert and Janda, "Synthesis on Soluble Polymers: New Reactions and the Construction of Small Molecules" *Curr Opin Chem Biol* 1:107-113 (1997).

Greer, J., "Model Structure for the Inflammatory Protein C5a" *Science* 228:1055-1060 (1985).

Grieco, et al., "PTC is a Novel Rearranged Form of the *ret* Proto-Oncogene and is Frequently Detected in Vivo in Human Thyroid Papillary Carcinomas" *Cell* 60(4):557-563 (1990).

Guide, W., "Software for Structure-Based Drug Design" *Current Opinion in Struc. Biol.* 4:777-781 (1994).

Hafner, et al., "Isothermal Amplification and Multimerization of DNA by *Bst* DNA Polymerase" *Biotechniques* 30:852-867 (2001).

Hanselman, et al., "A cDNA-Dependant Scintillation Proximity Assay for Quantifying Apolipoprotein A-1" *J. Lipid Res.* 38:2365-2373 (1997).

Hayashi, et al., "Dichloro[1,1'-bis(diphenylophosphino)ferrocene]palladium-(II) An Effective Catalyst for Cross-Coupling of Secondary and Primary Alkyl Grignard and Alkylzinc Reagents with Organic Halides" *J. Am. Chem. Soc.* 106:158-163 (1984).

Heim and Tsien, "Engineering Green Fluorescent Protein for Improved Brightness, Longer Wavelengths and Fluorescence Resonance Energy Transfer" *Curr. Biol.* 6:178-182 (1996).

Houghten, et al., "Generation and Use of Synthetic Peptide Combinatorial Libraries for Basic Research and Drug Discovery" *Nature* 354:84-86 (1991).

Houghten, R., "Parallel Array and Mixture-Based Synthetic Combinatorial Chemistry: Tools for the Next Millennium" *Annu Rev Pharmacol Toxicol* 40:273-282 (2000).

Hughes-Jones, et al., "Synthesis of Rh Fv Phage-Antibodies Using VH and VL Germline Genes" *British Journal of Haematology* 105:811-816 (1999).

Ishizaka, et al., "Human *ret* Proto-Oncogene Mapped to Chromsome 10q11.2" *Oncogene* 4(12):1519-1521 (1989).

Iwane, et al., "Myosin Subfragment-1 is Fully Equipped with Factors Essential for Motor Function" *Biophys. Biochem. Res. Comm.* 230:76-80 (1997).

Jing, et al. "GDNF-Induced Activation of the Ret Protein Tyrosine Kinase is Mediated by GDNFR-a, a Novel Receptor for GDNF" *Cell* 85:1113-1124 (1996).

Johann, et al., "GLVR1, a Receptor for Gibbon Ape Leukemia Virus, Is Homologous to a Phosphate Permease of *Neurospora crassa* and is Expressed at High Levels in the Brain and Thymus" *J. Virol.* 66:1635-1640 (1992).

Johnston, M., "Gene Chips: Array of Hope for Understanding Gene Regulation" *Curr. Biol.* 8:R171-R174 (1998).

Jones, T., "Interactive Computer Graphics: FRODO" *Methods in Enzymology* 115:157-171 (1985).

Joseph-McCarthy D., "Computational Approaches to Structure-Based Ligand Design" *Pharmacology & Therapeutics* 84:179-191 (1999).

Kahl, et al., "A Multiple-Approach Scintillation Proximity Assay to Measure the Association Between Ras and Raf" *Anal. Biochem.* 243:282-283 (1996).

Katritzky, et al., "Regiospecific C-Acylation of Pyrroles and Indoles Using *N*-Acylbenzotriazoles" *J. Org. Chem.* 68:5720-5723 (2003).

Kern and Hampton, "Direct Hybridization of Large-Insert Genomic Clones on High-Density Gridded cDNA Filter Arrays" *Biotechniques* 23:120-124 (1997).

Kim and Kahn, "A Merger of Rational Drug Design and Combinatorial Chemistry: Development and Application of Peptide Secondary Structure Mimetics" *Combinatorial Chemistry & High Throughput Screening* 3:167-183 (2000).

Kirkpatrick, et al. "Structure-Based Drug Design: Combinatorial Chemistry and Molecular Modeling" *Combinatorial Chemistry & High Throughput Screening* 2:211-221 (1999).

Kline, et al., "Studies by $^1$H Nuclear Magnetic Resonance and Distance Geometry of the Solution Conformation of the x-Amylase Inhibitor Tendamistat" *J. Mol. Biol.* 189:377-382 (1986).

Knighton, et al., "Structural Basis of the Intrasteric Regulation of Myosin Light Chain Kinases" *Science* 258:130-I35 (1992).

Kolaskar and Tongaonkar "A Semi-Empirical Method for Prediction of Antigenic Determinants on Protein Antigens" *FEBS Lett.* 276(1-2):172-174 (1990).

Kroll, et al., "A Multifunctional Prokaryotic Protein Expression System: Overproduction, Affinity Purification, and Selective Detection" *DNA Cell. Biol.* 12:441-453 (1993).

Kundu, et al., "Combinatorial Chemistry: Polymer Supported Synthesis of Peptide and Non-Peptide Libraries" *Progress in Drug Research* 53:89-156 (1999).

Kuntz, et al., "Structure-Based Molecular Design" *Acc. Chem. Res.* 27:117-123 1994).

Kuntz, et al., "A Geometric Approach to Macromolecule-Ligand Interactions" *J. Mol. Biol.* 161:269-288 (1982).

Lam, et al., "A New Type of Synthetic Peptide Library for Identifying Ligand-Binding Activity" *Nature* 354:82-84 (1991).

Lebl, et al., "One-Bead-One-Structure Combinatorial Libraries" *Biopolymers* 37:177-198 (1995).

Liparoto and Ciardelli, "Biosensor Analysis of the Interleukin-2 Receptor Complex" *Journal of Molecular Recognition* 12:316-321 (1999).

Lipinski et al., "Experimental and Computational Approaches to Estimate Solubility and Permeability in Drug Discovery and Development Settings" *Advanced Drug Delivery Reviews* 23:3-25 (1997).

Lipschultz, et al., "Experimental Design for Analysis of Complex Kinetics Using Surface Plasmon Resonance" *Methods* 20:310-318 (2000).

Lu, et al., "Oriented Immobilization of Fab' Fragments on Silica Surfaces" *Anal. Chem.* 67:83-87 (1995).

Luo, et al., "Close Linkage with the RET Proto-Oncogene and Boundaries of Deletion Mutations in Autosomal Dominant Hirschsprung Disease" *Hum Mol Genet.* 2(11):1803-1808 (1993).

Madden, et al., "Synthetic Combinatorial Libraries: Views on Techniques and Their Application" *Perspectives in Drug Discovery and Design* 2:269-285 (1994).

Malmborg and Borrebaeck, "BIAcore As a Tool in Antibody Engineering" *Journal of Immunological Methods* 183:7-13 (1995).

Malmqvist and Karlsson, "Biomolecular Interaction Analysis: Affinity Biosensor Technologies for Functional Analysis of Proteins" *Current Opinion in Chemical Biology* 1:378-383 (1997).

Malmqvist, M., "BIACORE: an Affinity Biosensor System for Characterization of Biomolecular Interactions" *Biochemical Society Transactions* 27:335-340 (1999).

Markiewicz, et al., "Synthetic Oligonucleotide Combinatorial Libraries and Their Applications" *II Farmaco* 55:174-177 (2000).

Martin, Y., "Computer-Assisted Rational Drug Design" *Methods Enz.* 203:587-613 (1991).

Mazeas, et. al., "Synthesis of New Melatoninergic Ligands Including Azaindole Moiety" *Heterocycles* 50(2):1065-1080 (1999).

McCall, A.M., "Characterization of Anti-Mouse Fcγ RII Single-Chain Fv Fragments Derived from Human Phage Display Libraries" *Immunotechnology* 4:71-87 (1998).

McPherson, A., "Current Approaches to Macromolecular Crystallization" *Eur. J. Biochem.* 189:1-23 (1990).

Meng, et al., "Automated Docking with Grid-Based Energy Evaluation" *J. Compt. Chem.* 13(4):505-524 (1992).

Mérour and Joseph, "Synthesis and Reactivity of 7-Azaindoles (1*H*-Pyrrolo[2,3-*b*]pyridine)" *Current Organic Chemistry* 5:471-506 (2001).

Merritt, A.T., "Solution Phase Combinatorial Chemistry" *Comb Chem High Throughput Screen* 1(2):57-72 (1998).

Miller, et al., "FLOG: A System to Select 'Quasi-Flexible' Ligands Complementary to a Receptor of Known Three-Dimensional Structure" *J. Comp.-Aided Molec. Design* 8:153-174 (1994).

Minakata, et al., "Regioselective Funtionalization of 1*H*-Pyrrolo[2,3-*b*]pyridine Via its *N*-Oxide" *Synthesis* pp. 661-663 (1992).

Miranker and Karplus, "Functionality Maps of Binding Sites: A Multiple Copy Simultaneous Search Method" *Proteins: Structure, Function, and Genetics* 11:29-34 (1991).

Mitra, et al., "Fluorescence Resonance Energy Transfer Between Blue-Emitting and Red-Shifted Excitation Derivatives of the Green Fluorescent Protein" *Gene* 173:13-17 (1996).

Nagafuji and Cushman, "A General Synthesis of Pyrroles and Fused Pyrrole Systems from Ketones and Amino Acids" *J. Org. Chem.* 61:4999-5003 (1996).

Nahm and Weinreb, "N-Methoxy-N-Methylamides as Effective Acylating Agents" *Tetrahedron Lett.* 22(39):3815-3818 (1981).

Navaza, J., "*AMoRe*: an Automated Package for Molecular Replacement" *Acta Cryst.* A50:157-163 (1994).

Neidle and Jenkins, "Molecular Modeling to Study DNA Intercalation by Anti-Tumor Drugs" *Methods Enz.* 203:433-458 (1991).

Ng, et al., "Engineering Protein-Lipid Interactions: Targeting of Histidine-Tagged Proteins to Metal-Chelating Lipid Monolayers" *Langmuir* 11:4048-4055 (1995).

Nicholis, et al., "Protein Folding and Association: Insights From the Interfacial and Thermodynamic Properties of Hydrocarbons" *PROTEINS: Struct., Funct. and Gen.* 11:281-296 (1991).

Nichols, et al., "Development of a Scintillation Proximity Assay for Peroxisome Proliferator-Activated Receptor γ Ligand Binding Domain" *Anal. Biochem.* 257:112-119 (1998).

O'Shannessy, et al., "Interpretation of Deviations from Pseudo-First-Order Kinetic Behavior in the Characterization of Ligand Binding by Biosensor Technology" *Analytical Biochemistry* 236:275-283 (1996).

O'Shannessy, J., "Determination of Kinetic Rate and Equilibrium Binding Constants for Macromolecular Interactions: a Critique of the Surface Plasmon Resonance Literature" *Current Opinions in Biotechnology* 5:65-71 (1994).

Okada, et al., "Gene Therapy Against an Experimental Glioma Using Adeno-Associated Virus Vectors" *Gene Ther.* 3:957-964 (1996).

Olah, et.al., "Synthetic Methods and Reactions: Part 209. Improved Preparation of Aldehydes and Ketones from *N,N*-Dimethylamides and Grignard Reagents" *Synthesis* pp. 228-230 (1984).

Ottoni, et al., "Efficient and Simple Methods for the Introduction of the Sulfonyl, Acyl and Alkyl Protecting Groups on the Nitrogen of Indole and its Derivatives" *Tetrahedron* 54:13915-13928 (1998).

Parker, et al., "Development of High Throughput Screening Assays Using Fluorescence Polarization: Nuclear Receptor-Ligand-Binding and Kinase/Phosphatase Assays" *J Biomol Screen* 5:77-88 (2000).

Perrin, D.M., "Nucleic Acids for Recognition and Catalysis: Landmarks, Limitations, and Looking to the Future" *Combinatorial Chemistry & High Throughput Screening* 3:243-269 (2000).

Pflugrath, et al., "Crystal Structure Determination, Refinement and the Molecular Model of the α-Amylase Inhibitor Hoe-467A" *J. Mol. Biol.* 189:383-386 (1986).

Plunkett and Ellman, "A Silicon-Based Linker for Traceless Solid-Phase Synthesis" *J. Org. Chem.* 60:6006-6007 (1995).

Poul, et al., "Selection of Tumor-Specific Internalizing Human Antibodies from Phage Libraries" *Journal of Molecular Biology* 301:1149-1161 (2000).

Price, et al., "Summary Report on the ISOBM TD-4 Workshop: Analysis of 56 Monoclonal Antibodies against the MUC1 Mucin" *Tumor Biology* 19(Suppl 1):1-20 (1998).

Roberts, et al., "Generation of an Antibody with Enhanced Affinity and Specificity for its Antigen by Protein Engineering" *Nature* 328:731-734 (1987).

Robison & Robison, "7-Azaindole. I. Synthesis and Conversion to 7-Azatryptophan and Other Derivatives" *J. Am. Chem. Soc.* 77:457-460 (1955).

Rosenfeld, M., "Human Artificial Chromosomes Get Real" *Nat. Genet.* 15:333-335 (1997).

Saiki, R., "Amplification of Genomic DNA" *PCR Protocols: A Guide to Meth. and Applic.* 2:13-20 (1990).

Sambrook, et al., "Introduction of Recombinant Vectors into Mammalian Cells" *Molecular Cloning: a Laboratory Manual* 2:6.30-16.37 (1989).

Santoro, et al., "The *ret* Proto-Oncogene is Consistently Expressed in Human Pheochromocytomas and Thyroid Medullary Carcinomas" *Oncogene* 5(10):1595-1598 (1990).

Schneider, et al., "Functional Purification of a Bacterial ATP-Binding Cassette Transporter Protein (MalK) from the Cytoplasmic Fraction of an Overproducing Strain" *Protein Expr. Purif.* 6:10-14 (1995).

Schneller and Luo, "Synthesis of 4-Amino-1*H*-Pyrrolo[2,3-*b*]Pyridine (1,7-Dideazaadenine) and 1*H*-Pyrrolo[2,3-*b*]Pyridin-4-ol (1,7-Dideazahypoxanthine)" *J. Org. Chem.* 45:4045-4048 (1980).

Schuhmann, et al., "Immobilization of Enzymes on Langmuir-Blodgett Films via a Membrane-Bound Receptor. Possible Applications for Amperometric Biosensors" *Adv. Mater.* 3:388-391 (1991).

Schummer, et al., "Inexpensive Handheld Device for the Construction of High-Density Nucleic Acid Arrays" *Biotechniques* 23:1087-1092 (1997).

Schweizer and Hindsgaul, "Combinatorial Synthesis of Carbohydrates" *Curr Opin Chem Biol.* 3(3):291-298 (1999).

Selvin, P., "Fluorescence Resonance Energy Transfer" *Meth. Enzymol.* 246:300-345 (1995).

Sheets, et al., "Efficient Construction of a Large Nonimmune Phage Antibody Library: The Production of High-Affinity Human Single-Chain Antibodies to Protein Antigens" *Proc Natl Acad Sci USA* 95:6157-6162 (1998).

Siegel, et al., "Mass Spectral Analysis of a Protein Complex Using Single-Chain Antibodies Selected on a Peptide Target: Applications to Functional Genomics" *J. Mol. Biol.* 302:285-293 (2000).

Sigal, et al., "A Self-Assembled Monolayer for the Binding and Study of Histidine-Tagged Proteins by Surface Plasmon Resonance" *Anal. Chem.* 68:490-497 (1996).

Solinas-Toldo, et al., "Matrix-Based Comparative Genomic Hybridization: Biochips to Screen for Genomic Imbalances" *Genes, Chromosomes & Cancer* 20:399-407 (1997).

Sun, C., "Recent Advances in Liquid-Phase Combinatorial Chemistry" *Comb. Chem. & High Throughput Screening* 2:299-318 (1999).

Takahashi, et al., "Activation of a Novel Human Transforming Gene, *ret*, by DNA Rearrangement" *Cell* 42(2):581-588 (1985).

Takahashi, et al., "Cloning and Expression of the *ret* Proto-Oncogene Encoding a Tyrosine Kinase with Two Potential Transmembrane Domains" *Oncogene* 3(5):571-578 (1988).

Thibault, et al., "Concise and Efficient Synthesis of 4-Fluoro-1*H*-pyrrolo[2,3-*b*]pyridine" *Organic Letters* 5:5023-5025 (2003).

Thomas, et. al., "Light-Emitting Carbazole Derivatives: Potential Electroluminescent Materials" *J. Am. Chem. Soc.* 123:9404-9411 (2001).

Toste, et al., "A Versatile Procedure for the Preparation of Aryl Thiocyanates Using N-Thiocyanatosuccinimide (NTS)" *Synth. Comm.* 25(8):1277-1286 (1995).

Trupp, et al., "Functional Receptor for GDNF Encoded by the c-*ret* Proto-Oncogene" *Nature* 381:785-789 (1996).

Udenfriend, et al., "Scintillation Proximity Assay: A Sensitive and Continuous Isotopic Method for Monitoring Ligand/Receptor and Antigen/Antibody Interactions" *Anal. Biochem.* 161:494-500 (1987).

Van Heyningen, V., "One Gene—Four Syndromes" *Nature* 367:319-320 (1994).

Van Regenmortel, M.H.V., "Use of Biosensors to Characterize Recombinant Proteins" *Dev. Biol. Stand.* 83:143-151 (1994).

Vély, et al., "BIAcore® Analysis to Test Phosphopeptide-SH2 Domain Interactions" *Methods in Molecular Biology* 121:313-321 (2000).

Wessjohann, L., "Synthesis of Natural-Product-Based Compound Libraries" *Curr Opin Chem Biol* 4:303-309 (2000).

Wharam, et al., "Specific Detection of DNA and RNA Targets Using a Novel Isothermal Nucleic Acid Amplification Assay Based on the Formation of a Three-Way Junction Structure" *Nucleic Acids Res.* 29(11):1-8 (2001).

Williams, et al., "Dissection of the Extracellular Human Interferon γ Receptor a-Chain into Two Immunoglobulin-Like Domains. Production in an *Escherichia coli* Thioredoxin Gene Fusion Expression System and Recognition by Neutralizing Antibodies" *Biochemistry* 34:1787-1797 (1995).

Woon, et al., "Construction and Characterization of a 10-Fold Genome Equivalent Rat P1-Derived Artificial Chromosome Library" *Genomics* 50:306-316 (1998).

Yang, et al., "Synthesis of Some 5-Substituted Indoles" *Heterocycles* 34:1169-1175 (1992).

Zanon, et. al., "Copper-Catalyzed Domino Halide Exchange-Cyanation of Aryl Bromides" *J. Am. Chem. Soc.* 125:2890-2891 (2003).

Ashman et al., The biology of stem cell factor and its receptor C-kit, The International Journal of Biochemistry & Cell Biology, 31:1037-1051, 1999.

Baghestanian, et al., A Case of Malignant Mastocytosis with Circulating Mast Cell Precursors: Biologic and Phenotypic Characterization of the Malignant Clone, Leuk. 10:159-166 (1996).

Bagshawe, Antibody-Directed Enzyme Prodrug Therapy: A Review; 1995, Drug Dev. Res., 34:220-230.

Balak, et. al., Novel D761Y and common secondary T790M mutations in epidermal growth factor receptor-mutant lung adenocarcinomas with acquired resistance to kinase inhibitors. Clin. Cancer Res. 12:6494-501 (2006).

Bancalari, et al., Blood Markers of Early and Late Airway Responses to Allergen in Asthmatic Subjects. Relationship with Functional Findings Allergy 52:32-40, 1997.

Barton et al, The chemistry of pentavalent organobismuth reagants. Part X. Studies on the phenylation and oxidation of phenols, Tetrahedron, vol. 43, No. 2, 1987, pp. 323-332.

Bashford and Harris, Measurement of Ligand Binding to Proteins, Spectrophotometry and Spectrofluorimetry: A Practical Approach 4:91-113 (1987).

Basta et al, High-dose Intravenous Immunoglobulin Exerts Its Beneficial Effect in Patients with Dermatomyositis by Blocking Endomysial Deposition of Activated Complement Fragments; J Clin Invest 1994, 94:1729-1735.

Bedi, et al., BCR-ABL-Mediated Inhibition of Apoptosis With Delay of G2/M Transition After DNA Damage: A Mechanism of Resistance to Multiple Anticancer Agents; Blood 1995, 86:1148-1158.

Bellone, et al., Growth Stimulation of Colorectal Carcinoma Cells Via the c-Kit Receptor is Inhibited by TGF-β1, J. Cell Physiol. 172:1-11 (1997).

Berdel, et al., Recombinant Human Stem Cell Factor Stimulates Growth of a Human Glioblastoma Cell Line Expressing c-kit Protooncogene, Canc. Res. 52:3498-3502 (1992).

Bertolini et al., A new Rational Hypothesis for the Pharmacophore of the Active Metabolite of Leflunomide, a Potent Immunosuppressive Drug; 1997, J. Med. Chem., 40:2011-2016.

Bjorntorp, Neuroendocrine Pertuirbations as a Cause of Insulin Resistance; Diabetes Metab. Res. Rev., 1999, 15: 427-441.

Bloom, A. and Day. A.R., The Preparation of 2-Alkylaminobenzimidazoles, J. Org. Chem. 14, 17 (1939).

Bode, et al, Mutations in the tyrosine kinase domain of the EGFR gene are rare in synovial sarcoma, Modern Pathology, (2006), 19:541-547.

Bokenmeyer, et al., Expression of Stem-Cell Factor and Its Receptor c-kit Protein in Normal Testicular Tissue and Malignant Germ-Cell Tumours, J. Cancer Res. Clin. Oncol. 122:301-306 (1996).

Bothwell, M., Keeping Track of Neurotrophin Receptors, Cell, 65:915-918, 1991.

Bouzakri, K. and Zierath, J.R., MAP4K4 Gene silencing in Human Skeletal Muscle Prevents Tumor Necrosis Factor-α-induced Insulin Resistance, J. Biol. Chem. 282:7783-7789 (2007).

Broudy, V., Stem Cell Factor and Hematopoiesis, Blood 90:1345-1364 (1997).

Carpino, et al., p62dok: A Constitutively Tyrosine-Phosphorylated, GAP-Associated Protein in Chronic Myelogenous Leukemia Progenitor Cells; Cell 1997, 88:197-204.

Castells, et al., The Presence of Membrane-Bound Stem Cell Factor on Highly Immature Nonmetachromatic Mast Cells in the Peripheral Blood of a Patient with Aggressive Systemic Mastocytosis, J. Aller. Clin. Immunol. 98:831-840 (1996).

Chou et al., Computerized Quantitation of Synergism and Antagonism of Taxol, Topotecan, and Cisplatin Against Human Teratocarcinoma Cell Growth: a Rational Approach to Clinical Protocol Design, J. Natl. Cancer Inst. 86:1517-24 (1994).

Chou, T. and Talalay, P., Quantitative analysis of Dose-Effect Relationships: The Combined Effects of Multiple Drugs or Enzyme Inhibitors, Adv. Enzyme Regul. 22:27-55 (1984).

Chou, T. et al., Chemotherapeutic Synergism, Potentiation and Antagonism, Encyclopedia of Human Biology, Academic Press, 2:371-9 (1991).

Chou, T.C. and Rideout, D.C., editors: Synergism and Antagonism in Chemotherapy, San Diego, CA: Academic Press, Chapter 2, 61-102 (1991).

Clohisy et al, Review of Cellular Mechanisms of Tumor Osteolysis; Clin. Orthop. 2000, 373: 104-14.

Cohen, et al., Expression of Stem Cell Factor and C-Kit in Human Neuroblastoma; 1994, Blood 84:3465-3472.

Collins et al., A small interfereing RNA screen for modulators of tumor cell motility identifies MAP4K4 as a promigratory kinase, Proc. Natl. Acad. Sci. USA, 103:3775-3780 (2006).

Columbo, et al., The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils, J. Immunol 149:599-608 (1992).

Communication Pursuant to Article 94(3) EPC dated Feb. 15, 2010 for EP Application No. 05789913.0.

Communication Pursuant to Article 94(3)EPC dated Apr. 17, 2009 for European Application No. 06813186.1.

Communication Pursuant to Article 94(3)EPC dated Jul. 9, 2009 for European Application No. 06773861.7.

Communication Pursuant to Article 94(3)EPC dated Sep. 15, 2009 for European Application No. 06813186.1.

Communication Pursuant to Article 94(3)EPC dated Dec. 2, 2009 for EP Application No. 07864681.7.

Communication Pursuant to Article 94(3)EPC dated Dec. 21, 2009 for European Application No. 06773861.7.

Costa, et al., The Cells of the Allergic Response, JAMA 278:1815-1822 (1997).

Coulie et al, Recombinant Human Neurotropic Factors Accelerate Colonic Transit and Relieve Constipation in Humans, Gastroenterology 119:41-50 (2000).

Crouch et al., The use of ATP bioluminescence as a measure of cell proliferation and cytotoxicity. Journal of Immunological Methods, 160:81-8 (1993).

Crump, M., Inhibition of Raf Kinase in the Treatment of Acute Myeloid Leukemia, Curr. Pharm. Design 8(25):2243-8 (2002).

Curtin et al., Discovery and Evaluation of a Series of 3-Acylindole Imidazopyridine Platelet-Activating Factor Antagonists, J. Med. Chem., vol. 41, 1998, pp. 74-95.

Dai et al., Targeted disruption of the mouse colony-stimulating factor 1 receptor gene results in osteopetrosis, mononuclear phagocyte deficiency, increased primitive progenitor cell frequencies, and reproductive defects; Blood, 2002, 99: 111-120.

Dastych, et al., Stem Cell Factor Induces Mast Cell Adhesion to Fibronectin; 1994, J. Immunol. 152:213-219.

Demetri, Targeting c-kit mutations in solid tumors: Scientific rationale and novel therapeutic options, Seminars in Oncology, 28(5), Supp. 17, 19-26, 2001.

Dewar et al., Inhibition of c-fms by Imatinib Expanding the Spectrum of Treatment; Cell Cycle 2005, 4(7):851-3.

Douma, S. et al, Suppression of anoikis and induction of metastasis by the neurotropic receptor TrkB, Nature 430:1034-9 (2004).

Doyle and Bryker, Alkyl Nitrite-Metal Halide Deamination Reactions. 6. Direct Synthesis of Arenediazonium Tetrafluoroborate Salts from Aromatic Amines, tert-Butyl Nitrite, and Boron Trifluoride Etherate in Anhydrous Media; J. Org. Chem. 1979, 44:1572.

Dyson, et al., The Human Papilloma Virus 16 E7 Oncoprotein is Able to Bind to the Retinoblastoma Gene Product, Science 243:934-937 (1989).

Eklund and Joensuu, Treatment of rheumatoid arthritis with imatinib mesylate: clinical improvement in three refractory cases, Annals of Medicine, 35:362-367, 2003.

Escribano, et al., Expression of the c-kit (CD117) Molecule in Normal and Malignant Hematopoiesis, Leuk. Lymph. 30:459-466 (1998).
Felder, E.R., The Challenge of Preparing and Testing Combinatorial Compound Libraries in the Fast Lane, at the Front End of Drug Development, Chimia 48:531-541 (1994).
Feng et al, Tyrosines 559 and 807 in the Cytoplasmic Tail of the Macrophage Colony-Stimulating Factor Receptor Play Distinct Roles in Osteoclast Differentiation and Function; Endocrinology 2002, 143: 4868-74.
Finotto, et al., Glucocorticoids Disease Tissue Mast Cell Number by Reducing the Production of the c-kit Ligand, Stem Cell Factor, by Resident Cells, J. Clin. Invest. 99:1721-1728 (1997).
Flanagan & Lader, Macrophages and the various isoforms of macrophage colony-stimulating factor; Curr Opin Hematol. 1998, 5:181-5.
Furitsu, et al., Identification of Mutations in the Coding Sequence of the Proto-oncogene c-kit in a Human Mast Cell Leukemia Cell Line Causing Ligand-independent Activation of the c-kit Product; 1993, J. Clin. Invest. 92:1736-1744.
Furuta, et al., Stem Cell Factor Influences Mast Cell Mediator Release in Response to Eosinophil-Derived Granule Major Basic Protein, Blood 92:1055-1061 (1998).
Golkar, et al., Mastocytosis, Lancet 349:1379-1385 (1997).
Hallek, et al., Interaction of the Receptor Tyrosine Kinase p145c-kit with the p210bcr/abl Kinase in Myeloid Cells, Brit. J Haem. 94:5-16 (1996).
Halvorson, K.G. et al., A Blocking Antibody to Nerve Growth Factor Attenuates Skeletal Pain Induced by Prostate Tumor Cells Growing in Bone, Cancer Res. 65:9426-35 (2005).
Hamel, et al., The Road Less Travelled: c-kit and Stem Cell Factor, J. Neuro-Onc. 35:327-333 (1997).
Hands et. al., A Convenient Method for the Preparation of 5-, 6- and 7-Azaindoles and Their Derivatives; Synthesis 1996, 877-882.
Hassan and Zander, Stem Cell Factor as a Survival and Growth Factor in Human Normal and Malignant Hematopoiesis, Acta. Hem. 95:257-262 (1996).
Hassan, et al., Expression of Protooncogene c-kit and Its Ligand Stem Cell Factor (SCF) in Gastric Carcinoma Cell Lines; 1998, Digest. Dis. Science 43:8-14.
Heacock et al., Orientation and Relative Reaction Rate Factors in Aromatic Substitution by the Benzensulfonimido Radical, J. Am. Chem. Soc., vol. 82, 1960, pp. 3460-3463.
Heinrich, et al., PDGFRA Activating Mutations in Gastrointestinal Stromal Tumors; (Science 2003, 299:708-10).
Heinrich, M. C. et al., "Inhibition of KIT Tyrosine Kinase Activity: A Novel Molecular Approach to the Treatment of KIT-Positive Malignancies," J. Clin. Oncol., vol. 20, No. 6, pp. 1692-1703, Mar. 15, 2002.
Herbst, et al., Differential Effects of W Mutations on p145c-kit Tyrosine Kinase Activity and Substrate Interaction, J. Biol. Chem. 267:13210-13216 (1992).
Hibi, et al., Coexpression of the stem cell factor and the c-kit genes in small-cell lung cancer; 1991, Oncogene 6:2291-2296.
Hirota, et al., Gain-of-function Mutations of c-kit in Human Gastrointestinal Stromal Tumors; 1998, Science 279:577-580.
Hoffmann, m-Trifluoromethylbenzenesulfonyl Chloride, Organic Syntheses, Coll. vol. 60, p. 121-126, 1981.
Hogaboam, et al., Novel Role of Transmembrane SCF for Mast Cell Activation and Eotaxin Production in Mast Cell-Fibroblast Interactions, J. Immunol. 160:6166-6171 (1998).
Hood, J.D. et al., Tumor Regression by Targeted Gene Delivery to the Neovasculature, Science 296, 2404 (2002).
Houghten, R., Peptide Libraries: Criteria and Trends, Trends Genet. 9:235-239 (1993).
Hudson, P. B. et al., A Simple Method for the Determination of Serum Acid Phosphatase, Journal of Urology 58:89-92 (1947).
Iemura, et al., The c-kit Ligand, Stem Cell Factor, Promotes Mast Cell Survival by Suppressing Apoptosis, Amer. J. Pathol 144:321-328 (1994).
Inoue, et al., Coexpression of the c-kit Receptor and the Stem Cell Factor in Gynecological Tumors, Cancer Res. 54:3049-3053 (1994).
International Search Report and Written Opinion of the ISA dated Oct. 24, 2006 for PCT Application No. PCT/US2006/024524.
International Search Report and Written Opinion of the ISA dated Apr. 4, 2007 for PCT Application No. PCT/US2006/018726.
International Search Report and Written Opinion of the ISA dated Apr. 20, 2006 for PCT Application No. PCT/US2005/021231.
International Search Report and Written Opinion of the ISA dated Jun. 4, 2008 for PCT Application No. PCT/US2007/088231.
International Search Report and Written Opinion of the ISA dated Jun. 4, 2008 for PCT Application No. PCT/U52007/088237.
International Search Report and Written Opinion of the ISA dated Jun. 5, 2008 for PCT Application No. PCT/US2007/083910.
International Search Report and Written Opinion of the ISA dated Jun. 5, 2008 for PCT Application No. PCT/US2007/085289.
International Search Report and Written Opinion of the ISA dated Jun. 5, 2008 for PCT Application No. PCT/US2007/088243.
International Search Report and Written Opinion of the ISA dated Jul. 25, 2008 for PCT Application No. PCT/US2007/088443.
International Search Report and Written Opinion of the ISA dated Jul. 28, 2008 for PCT Application No. PCT/US2007/085299.
International Search Report and Written Opinion of the ISA dated Oct. 24, 2006 for PCT Application No. PCT/US2006/024361.
International Search Report and Written Opinion of the ISA dated Nov. 17, 2008 for PCT Application No. PCT/US07/088412.
International Search Report and Written Opinion of the ISA dated Nov. 25, 2005 for PCT Application No. PCT/US04/42470.
Isbel et al., Local macrophage proliferation correlates with increased renal M-CSF expression in human glomerulonephritis; Nephrol Dial Transplant 2001, 16: 1638-1647.
Isozaki, et al., Deficiency of c-kit cells in patients with a myopathic form of chronic idiopathic intestinal pseudo-obstruction; 1997, Amer. J. of Gast. 9 332-334.
Izquierdo, et al., Differential Expression of the c-kit Proto-Oncogene in Germ Cel Tumours, J. Pathol. 177:253-258 (1995).
Jarugula et al., Nonlinear pharmacokinetics of 5-fluorouracil in rats. 1997, J Pharm Sci 86(7):756-757.
Jensen et al, Brit J Pharmacology, (2008), 154:1572-1582.
Jones, R., Biology and Treatment of Chronic Myeloid Leukemia, Curr. Opin. Onc. 9:3-7 (1997).
Jose et al., Blockade or Macrophage colony-Stimulating Factor Reduces Macrophage Proliferation and Accumulation in Renal Allograft Rejection; Am J Transplant 2003, 3(3):294-300.
Kassel, O. et al., Local increase in the number of mast cells and expression of nerve growth factor in the bronchus of asthmatic patients after repeated inhalation of allergen at low-dose, Clin. Exp. Allergy 31:1432-40 (2001).
Kay, et al., Eosinophils and Eosinophil-Associated Cytokines in Allergic Inflammation, Int. Arch. Aller. Immunol. 113:196-199 (1997).
Kim et al, Database CAS on STN (Columbus, OH, USA) No. 138:55974, Preparation of 2-anilino-4-indolyl pyrimidines as tyrosine kinase inhibitors, abstract, 2002) see whole article.
Kinashi and Springer, Steel Factor and c-kit Cell-Matrix Adhesion; Blood 83:1033-1038 (1994).
Kitamura, et al., Synthesis of Quinolines and 2H-Dihydropyrroles by Nucleophilic Substitution at the Nitrogen Atom of Oxime Derivatives, Synthesis 15:2415-2426 (2003).
Kodama et al, Congenital Osteoclast Deficiency in Osteopetrotic (op/op) Mice Is Cured by Injections of Macrophage colony-stimulating Factor; J. Exp,. Med. 1991, 173: 269-72.
Komoyira, S. et. al., Design, synthesis and biological activity of amidinobicyclic compounds (derivatives of DX-9065a) as a factor Xa inhibitors: SAR study of S1 and aryl binding sites, Bioorg. Med. Chem. 12, 2099 (2004).
Kondoh, et al., An in vivo model for receptor tyrosine kinase autocrine/paracrine activation: auto-stimulated Kit receptor acts as a tumor promoting factor in papillomavirus-induced tumorigenesis; 1995, Oncogene 10:341-347.
Kondoh, et al., Establishment and Further Characterization of a Line of Transgenic Mice Showing Testicular Tumorigenesis at 100% Incidence, J. Urol. 152:2151-2154 (1994).

Kondoh, et al., Very High Incidence of Germ Cell tumorigenesis (Seminomagenesis) in Human Papillomavirus Type 16 Transgenic Mice; 1991, J. Virol. 65:3335-3339.

Konishi, et al, Brit J Cancer, (2003), 88:1223-1228.

Kunisada, et al., Murine Cutaneous Mastocytosis and Epidermal Melanocytosis Induced by Keratinocyte Expression of Transgenic Stem Cell Factor; 1998, J. Exp. Med. 187:1565-1573.

Kunkel, T., Rapid and Efficient Site-Specific Mutagenesis Without Phenotypic Selection, Proc. Natl. Acad. Sci. USA 82:488-492 (1985).

Kunnimalaiyaan, M. and Chen, H. et al., The Raf-1 pathway: a molecular target for treatment of select neuroendocrine tumors? Anticancer Drugs 17(2):139-42 (2006).

Lahm, et al., Interleukin 4 Down-Regulates Expression of c-kit and Autocrine Stem Cell Factor in Human Colorectal Carcinoma Cells, Cell Growth & Differ 6:1111-1118 (1995).

Langham et al., Metalation of Halogen-Metal Interconversion Reactions of Some Halogenated Phenyl Ethers, J. Am. Chem. Soc., vol. 63, 1941, pp. 545-549.

Lawicki et al., The pretreatment plasma level and disgnostic utility of M-CSF in benign breast tumor and breast cancer patients, Clinica Chimica Acta, 371: 112-116, 2006.

Le Meur et.al., Macrophage accumulation at a site of renal inflammation is dependent on the M-CSF/c-fms pathway; J Leukocyte Biology, 2002, 72: 530-537.

Lee, et al., HLA-DR-Triggered Inhibition of Hemopoiesis Involves Fas/Fas Ligand Interactions and is Prevented by c-kit Ligand, J. Immunol. 159:3211-3219 (1997).

Lee, et al., Mast Cells: A Cellular Link Between Autoantibodies and Inflammatory Arthritis, Science 297:1689-1692 (2002).

Levin, et al., Neoplasms of the Central Nervous System, Cancer Principles & Practice of Oncology 2:2022-2082 (1997).

Li, et al., Abrogation of c-kit/Steel Factor-Dependent Tumorigenesis by Kinase Defective Mutants of the c-kit Receptor: c-kit Kinase Defective Mutants as Candidate Tools for Cancer Gene Therapy, Canc. Res. 56:4343-4346 (1996).

Libby, Inflammation in atherosclerosis, Nature, 2002;420:868-874.

London, et al., Expression of Stem Cell Factor Receptor (c-kit) by the Malignant Mast Cells from Spontaneous Canine Mast Cell Tumors, 1996, J. Compar. Pathol. 115:399-414.

Longley, et al., Altered Metabolism of Mast-cell Growth Factor (c-kit Ligand) in Cutaneous Mastocytosis, 1993, New Engl. J. Med. 328:1302-1307.

Longley, et al., Chymase Cleavage of Stem Cell Factor Yields a Bioactive Soluble Product, Proc. Natl. Acad. Sci. 94:9017-9021 (1997).

Longley, et al., Somatic c-Kit Activating Mutation in *Urticaria pigmentosa* and Aggressive Mastocytosis: Establishment of Clonality in a Human Mast Cell Neoplasm, Nat. Gen. 12:312-314 (1996).

Loveland, et al., Stem Cell Factor and c-kit in the Mammalian Testis: Lessons Originating from Mother Nature's Gene Knockouts, J. Endocrinol 153:337-344 (1997).

Lukacs, et al., Stem Cell Factor (c-kit Ligand) Influences Eosinophil Recruitment and Histamine Levels in Allergic Airway Inflammation, J. Immunol. 156:3945-3951 (1996).

Lyman, et al., c-kit Ligand and Flt3 Ligand: Stem/Progenitor Cell Factors With Overlapping Yet Distinct Activities, Blood 91:1101-1134 (1998).

Ma et al., Indolinone Derivatives Inhibit Constitutively Activated KIT Mutants and Kill Neoplastic Mast Cells, 2000, J Invest Dermatol. 114:392-394.

Ma, et al., The c-KIT Mutation Causing Human Mastocytosis is Resistant to ST1571 and Other KiT Kinase Inhibitors; Kinases with Enzymatic Site Mutations Show Different Inhibitor Sensitivity Profiles Than Wild-type Kinases and Those With Regulatory-Type Mutations, Blood 99:1741-1744 (2002).

Machida, N. et al., Mitogen-activated Protein Kinase Kinase Kinase Kinase 4 as a Putative Effector of Rap2 to Activate the c-Jun N-terminal Kinase, J. Biol. Chem. 279: 15711-15714 (2004).

Mack, K.D. et al., Functional identification of kinases essential for T-cell activation through a genetic suppression screen, Immunol. Lett. 96, 129-145 (2005).

Matayoshi, S. et al, Actions of brain-derived neurotrophic factor on spinal nociceptive transmission during inflammation in the rat, J Physiol. 569:685-95 (2005).

Mekori, et al., Transforming Growth Factor-β Prevents Stem Cell Factor-Mediated Rescue of Mast Cells from Apoptosis After IL-3 Deprivation, 1994, J. Immunol 153:2194-2203.

Mekori, et al., The Role of c-Kit and Its Ligand, Stem Cell Factor, in Mast Cell Apoptosis, 1995, Int. Arch. Allergy Immunol. 107:136-138.

Meltzer, The pharmacological basis for the treatment of perennial allergic rhinitis and non-allergic rhinitis with topical corticosteroids, 1997, Aller. 52:33-40.

Metcalf, D., Lineage Commitment in the Progeny of Murine Hematopoietic Preprogenitor Cells: Influence of Thrombopoietin and Interleukin 5, Proc. Natl. Acad. Sci. USA 95:6408-6412 (1998).

Metcalfe, Classification and Diagnosis of Mastocytosis: Current Status, 1991, J. Invest. Derm 93:2S-4S.

Metcalfe, et al., Mast Cells, Physiol. Rev. 77:1033-1079 (1997).

Miyaura and Suzuki, Palladium-Catalyzed Cross-Coupling Reactions of Organoboron Compounds, Chem. Rev. 1995, 95:2457.

Mokhtari, et al, Potential utility of small tyrosine kinase inhibitors in the treatment of diabetes, Clinical Science, (2010), 118(4):241-247.

Mol, et al. Structural Basis for the Autoinhibition and STI-571 Inhibition of c-Kit Tyrosine Kinase, J. Biol. Chem. 279:31655-31663 (2004).

Mol, et al., Structure of a c-Kit Product Complex Reveals the Basis for Kinase Transactivation, J. Biol. Chem. 278:31461-31464 (2003).

Morgan, C., Pollard, J.W., and Stanley, E.R., Isolation and Characterization of a Cloned Growth Factor Dependent Macrophage Cell Line, BAC1.2F5, Journal of Cellular Physiology, 130:420-427 (1987).

Motoyoshi, Biological activities and clinical application of M-CSF, Int J Hematol. 1998, 67:109-22.

Murty, et al., A Genetic Perspective of Male Germ Cell tumors, 1998, Sem. Oncol. 25:133-144.

Naclerio, et al., Rhinitis and Inhalant Allergens, JAMA 278:1842-1848 (1997).

Nagata, et al., Elevated Expression of the Proto-Oncogene c-kit in Patients with Mastocytosis, Leukemia 12:175-181 (1998).

Nakagawara, A. et al., Expression and Function of TRK-B an BDNF in Human Neuroblastomas, Mol. Cell Biol. 14:759-767 (1994).

Nassentein, C. et al, The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma, J. Exp. Med. 198:455-467 (2003).

Niihori, T. et al., Germline KRAS and BRAF mutations in cardio-facio-cutaneous syndrome, Nature Genet. 38(3):294-6 (2006).

Notice of Allowance dated Dec. 26, 2007 for U.S. Appl. No. 11/016,350.

Notice of Allowance dated Jun. 18, 2010 in U.S. Appl. No. 11/473,347.

Notice of Allowance dated Jun. 6, 2008 for U.S. Appl. No. 11/154,988.

Ochs, G. et al, A phase I/II trial of recombinant methionyl human brain derived neurotrophic factor administered by intrathecal infusion to patients with amyotrophic lateral sclerosis, Amyotroph Lateral Scler Other Motor Neuron Disord. 1:201-6 (2000).

Office Communication dated Apr. 22, 2010 from related application EP 06773861.

Okayama, et al., Human Lung Mast Cells are Enriched in the Capacity to Produce Granulocyte-Macrophage Colony-Stimulating Factor in Response to IgE-Dependent Stimulation, Eur. J. Immunol. 28:708-715 (1998).

Okayama, et al., Activation of Eosinophils with Cytokines Produced by Lung Mast Cells, Int. Arch. Aller. Immunol. 114(suppl. 1):75-77 (1997).

Otwinowski, Z., Maximum Likelihood Refinement of Heavy Atom Parameters, Dept. of Molecular Biophysics and Biochemistry pp. 80-86 (1991).

Owicki et al., Application of Fluorescence Polarization Assays in High-Throughput Screening, (1997), Genetic Engineering News, 17:27.

Petty et al, The effect of systemically administered recombinant human nerve growth factor in healthy human subjects. Ann Neurol. 36:244-6 (1994).

Pierce et al., Local anaesthetics. I. beta-Monoaklylaminoethyl Esters of Alkoxybenzoic Acids, J. Am. Chem. Soc., vol. 64, 1942, pp. 1691-1694.

Pignon, J.M., C-kit mutations and mast cell disorders a model of activating mutations of growth factor receptors, Hermatol Cell Ther 39:114-116 (1997).

Qiao, et. al., Role of Macrophage Colony-Stimulating Factor in Atherosclerosis, Am. J. Path. 1997;150:1687-1699.

Rajavashisth, et. al., Heterozygous Osteopetrotic (op) Mutation Reduces Atherosclerosis in LDL Receptor-deficient Mice, J. Clin. Invest. 1998;101:2702-2710.

Rajpert-de Meyts, et al., Expression of the c-kit Protein Product in Carcinoma-in-situ and Invasive Testicular Germ Cell Tumours, Int. J. Androl. 17:85-92 (1994).

Ricotti, et al., c-kit Is Expressed in Soft Tissue Sarcoma of Neuroectodermic Origin and Its Ligand Prevents Apoptosis of Neoplastic Cells, Blood 91:2397-2405 (1998).

Ridge et al, FMS mutations in myelodysplastic, leukemic, and normal subjects, Proc. Nat. Acad. Sci., 1990, 87:1377-1380.

Robinson et al., Stimulation of Bone Marrow Colony Growth In Vitro by Human Urine; Blood, 1969, 33:396-9.

Rodan, G., et al., Therapeutic Approaches to Bone Diseases, Science. 2000;289:1508.

Ryan, et al., Role for the Stem Cell Factor/KIT Complex in Schwann Cell Neoplasia and Mast Cell Proliferation Associated with Neurofibromatosis, 1994, J. Neuro. Res. 37:415-432.

Saify et al, Database CAS on STN (Columbus, OH, USA) No. 124:170379, Synthesis of some 2-azaindole derivatives: their cyctotoxicity and antibacterial activity, abstract, (1996), See RN 271-63-6.

Sandlow, et al., Expression of c-Kit and its Ligand, Stem Cell Factor, in Normal and Subfertile Human Testicular Tissue, 1996, J. Androl. 17:403-408.

Sawada, et al., Role of Cytokines in Leukemic type Growth of Myelodysplastic CD34+ Cells, 1996, Blood 88:319-327.

Sawai, et al., Aberrant growth of granulocyte-macrophage progenitors in juvenile chronic myelogenous leukemia in serum-free culture, 1996, Exp. Hem. 2:116-122.

Scheffner, et al., The E6 Oncoprotein Encoded by Human Papillomavirus Types 16 and 18 Promotes the Degredation of p53, Cell 63:1129-1136 (1990).

Schiemann and Winkelmüller, p-Fluorobenzoic Acid, Org. Syn. Coll. vol. 2:299, 1943.

Sclabas, G.M. et al, Overexpression of Tropomyosin-Related Kinase B in Metastatic Human Pancreatic Cancer Cells, Clin. Cancer. Res. V11:440-449 (2005).

Secor, et al., Mast cells are essential for early onset and severe disease in a murine model of multiple sclerosis. J. Exp. Med. 5:813-821 (2000).

Shibata et al, Alveolar macrophage deficiency in osteopetrotic mice deficient in macrophage colony-stimulating factor is spontaneously corrected with age and associated with matrix metalloproteinase expression and emphysema, Blood 2001, 98: pp. 2845-2852.

Smalley et al., c-KIT signaling as the driving oncogenic event in sub-groups of melanomas, Histol Histopathol, 24:643-650, 2009.

Sperling, et al., Expression of the Stem Cell Factor Receptor C-Kit (CD117) in Acute Leukemias, Haemat 82:617-621 (1997).

Stanulla, et al., Coexpression of Stem Cell Factor and Its Receptor c-Kit in Human Malignant Glioma Cell Lines, Act Neuropath 89:158-165 (1995).

Steinman, Multiple sclerosis: A coordinated immunological attack against myelin in the central nervous system. Cell 85:299-302 (1996).

Strohmeyer, et al., Expression of the C-kit Proto-Oncogene and its Ligand Stem Cell Factor (SCF) in Normal and Malignant Human Testicular Tissue, 1995, J. Urol. 153:511-515.

Strohmeyer, et al., Expression of the hst-1 and c-kit Protooncogenes in Human Testicular Germ Cell Tumors, Canc. Res. 51:1811-1816 (1991).

Su & Tsou, Synthesis of bromo-substituted Idoxyl Esters for Cytochemical Demonstration of Enzyme Activity, J. Am. Chem. Soc.,82, 1960, 1187.

Sun, et al., Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases, J. Med. Chem. 42:5120-5130 (1999).

Supplemental Notice of Allowance dated Jul. 23, 2008 for U.S. Appl. No. 11/154,988.

Supplemental Notice of Allowance dated Sep. 8, 2008 for U.S. Appl. No. 11/154,988.

Supplemental Notice of Allowance dated Sep. 8, 2010 in U.S. Appl. No. 11/473,347.

Tada, et al., Analysis of Cytokine Receptor Messenger RNA Expression in Human Glioblastoma Cells and Normal Astrocytes by Reverse-Transcription Polymerase Chain Reaction, J. Neuro 80:1063-1073 (1994).

Takahashi et al, ret Transforming Gene Encodes a Fusion Protein Homologous to Tyrosine Kinases, Mol Cell Biol. 7:1378-1385 (1987).

Tang, X. et al., An RNA interference-based screen identifies MAP4K4/NIK as a negative regulator of PPARγ, adipogenesis, and insulin-responsive hexose transport, Proc. Natl. Acad. Sci. U. S. A. 103:2087-2092 (2006).

Taylor et al. The Rapid Generation of Oligonucleotide-directed Mutations at High Frequency Using Phosphorothloate-Modified DNA; (1985) Nucl. Acids Res. 13:8764-8785.

Teitelbaum, Bone Resorption by Osteoclasts, Science. 2000;289:1504.

Thomas et al, The Eosinophil and its Role in Asthma, Gen. Pharmac 27:593-597 (1996).

Toyota, et al., Expression of c-kit and kit Ligand in Human Colon Carcinoma Cells, 1993, Turn Biol 14:295-302.

Tsujimura, et al., Substitution of an Aspartic Acid Results in Constitutive Activation of c-kit Receptor Tyrosine Kinase in a Rat Tumor Mast Cell Line RBL-2H3, 1995, Int. Arch. Aller. Immunol 106:377-385.

Tsujimura, et al.,Ligand-Independent Activation of c-kit Receptor Tyrosine Kinase in a Murine Mastocytoma Cell Line P-815 Generated by a Point Mutation, Blood 9:2619-2626 (1994).

Tsujimura, T., Role of c-kit Receptor Tyrosine Kinase in the Development, Survival and Neoplastic Transformation of Mast Cells, Pathol Int 46:933-938 (1996).

Turner, et al., Nonhematopoeietic Tumor Cell Lines Express Stem Cell Factor and Display c-kit Receptors, 1992, Blood 80:374-381.

US Notice of Allowance dated Jul. 27, 2010 in related U.S. Appl. No. 11/435,381.

US Notice of Allowance dated Aug. 11, 2010 in U.S. Appl. No. 11/960,590.

US Notice of Allowance dated Aug. 13, 2010 in related U.S. Appl. No. 11/962,044.

US Notice of Allowance dated Aug. 6, 2010 in U.S. Appl. No. 11/986,667.

US Notice of Allowance dated May 27, 2010 in related U.S. Appl. No. 11/435,381.

US Office Action dated Jan. 4, 2008 for U.S. Appl. No. 11/154,988.
US Office Action dated Jun. 6, 2007 for U.S. Appl. No. 11/016,350.
US Office Action dated Aug. 22, 2007 for U.S. Appl. No. 11/487,134.
US Office Action dated Sep. 22, 2009 for U.S. Appl. No. 11/986,667.
US Office Action dated Sep. 23, 2009 for U.S. Appl. No. 11/962,044.
US Office Action dated Oct. 19, 2007 for U.S. Appl. No. 11/154,988.
US Office Action dated Oct. 26, 2007 for U.S. Appl. No. 11/016,350.
US Office Action dated Feb. 17, 2010 for U.S. Appl. No. 11/962,044.
US Office Action dated Jul. 22, 2010 in related U.S. Appl. No. 12/244,730.
US Office Action dated Aug. 2, 2007 in related U.S. Appl. No. 11/016,350.
US Office Action dated Feb. 19, 2010 for U.S. Appl. No. 11/435,381.
US Office Action dated Feb. 26, 2010 for U.S. Appl. No. 11/986,667.
US Office Action dated Jun. 1, 2009 for U.S. Appl. No. 11/435,381.
US Office Action dated Mar. 4, 2009 for U.S. Appl. No. 11/435,381.
US Office Action dated May 15, 2008 in related U.S. Appl. No. 11/487,134.

US Office Action Dec. 18, 2009 for U.S. Appl. No. 11/473,347.
Valent, P., Biology, Classification and Treatment of Human Mastocytosis, Wein/Klin Wochenschr 108:385-397 (1996).
Verfaillie, Chronic myelogenous leukemia: too much or too little growth, or both?; Leukemia, 1998, 12:136-138.
Viskochil, D., It Takes Two to Tango: Mast Cell and Schwann Cell Interactions in Neurofibromas, J Clin Invest., 112:1791-1793 (2003).
Vliagoftis, et al., The protooncogene c-kit and c-kit ligand in human disease, Journ. Clin. Immunol, 100:435-440 (1997).
Weber, P., Physical Principles of Protein Crystallization, Adv. Protein Chem., 41:1-36 (1991).
Wendt, et al, Identification of novel binding interactions in the development of potent, selective 2-naphthamidine inhibitors of urokinase, synthesis, structural analysis, and SAR of y-Phenyl amide 6-substitution. J. Med. Chem., 47(2):303 (2004).
Werness, et al., Association of Human Papillomavirus Types 16 and 18 E6 Proteins with p53, Science 248:76-79 (1990).
Wild, K.D. et al, Antibodies to Nerve Growth Factor Reverse Established Tactile Allodynia in Rodent Models of Neuropathic Pain without Tolerance, J. Pharmacol. Exp. Ther. 322:282-287 (2007).
Wright, J.H. et al., The STE20 Kinase KGK Is Broadly Expressed in Human tumor Cells and Can Modulate Cellular Transformation, Invasion, and Adhesion, Mol. Cell. Biol. 23:2068-2082 (2003).
Wuthrich, K., Chapter 10: Three-Dimensional Protein Structures by NMR, NMR of Proteins and Nucleic Acids, 10:176-199 (1986).
Wyckoff et al., Direct visualization of macrophage-assisted tumor cell intravasation in mammary tumors. Cancer Research, 67(6): 2649-2656, 2007.
Xu et al, Modulation of Endothelial Cell function by Normal Polyspecific Human Intraveneous immunoglobulins, Am. J. Path. 1998;153:1257-1266.

Yang et al., Nf1-Dependent tumors require a microenvironment containing Nf1+/_-and c-kit-Dependent bone marrow, Cell, 135:437-448, 2008.
Yang, et al., Neurofibromin-Deficient Schwann Cells Secrete a Potent Migratory Stimulus for NF1+/-Mast Cells, J Clin Invest., 112:1851-1861 (2003).
Yang, Z.F. et al, Identification of Brain-Derived Neurotrophic Factor as a Novel Functional Protein in Hepatocellular Carcinoma, Cancer Res. 65:219-225 (2005).
Yao, Z. et al., A Novel Human STE20-related Protein Kinase, HGK, That Specifically Activates the c-Jun N-terminal Kinase Signaling Pathway, J. Biol. Chem. 274:2118-2125 (1999).
Yee, et al., Role of kit-Ligand in Proliferation and Suppression of Apoptosis in Mast Cells: Basis for Radiosensitivity of White Spotting and Steel Mutant Mice, J. Exp. Med., 179:1777-1787 (1994).
Yuan, et al., Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1), J. Exp. Med. 186:313-323 (1997).
US Notice of Allowance dated Jan. 6, 2011 in U.S. Appl. No. 12/244,730.
Communication pursuant to Article 94(3) EPC for EPO Patent Application No. 04814626.0-2101, (Dec. 15, 2009).
Saify et al., Synthesis of some 7-azaindole derivatives: Their cytotoxicity and antibacterial activity. Pakistan Journal of Scientific and Industrial Research, 37(10): 439-441, 1994.
Supplementary Partial European Search Report for EP Application No. 04814626.0-2101, (Aug. 4, 2009).

* cited by examiner

Full Length RetD3

Staurosporine

Exemplary compound of Formula I

Compound 68  Compound 14  Compound 28

```
                              SEQUENCE LISTING

<160> NUMBER OF SEQ ID NOS: 89

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cactgttatc acaaattcgc acataaaccg ccgatttctt ctgc                     44

<210> SEQ ID NO 2
```

```
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccggacgacg aaaggtcatt tccgcagaag aaatcggcgg ttta                           44

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaatgacctt tcgtcgtccg gctcaggcat tcccagtgtc ttac                           44

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcgacgtgca ccagaggaag agtaagacac tgggaatgcc tg                             42

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttcctctggt gcacgtcgcc cgtctctgga ctccatggaa aacc                           44

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tttgaacgca tcaacagata cctggttttc catggagtcc agag                           44

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtatctgtt gatgcgttca aaatcctgga agatccgaag tggg                           44

<210> SEQ ID NO 8
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 8
gtaccaggtt cttacgcgga aattcccact tcggatcttc cagg                    44

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttccgcgtaa gaacctggta ctgggcaaaa ccctgggtga agg                     43

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tagctttcac aactttacca aactcgcctt cacccagggt tttgcc                  46

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtttggtaaa gttgtgaaag ctactgcatt tcacctgaaa ggcc                    44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgctacagtg gtgtaacctg cgcggccttt caggtgaaat gcag                    44

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcaggttaca ccactgtagc agttaagatg ctgaaagaaa acgcg                   45

<210> SEQ ID NO 14
<211> LENGTH: 43
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 14
atcacgcagt tcggatggag acgcgttttc tttcagcatc tta                    43

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctccatccga actgcgtgat ctgctgtccg aatttaatgt tctg                   44

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acgtgcggat ggtttacctg tttcagaaca ttaaattcgg acagc                  45

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acaggtaaac catccgcacg tgatcaaact gtacggcgca tgtt                   44

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagcagcggg ccatcctggg aacatgcgcc gtacagtttg a                      41

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caggatggcc cgctgctgct gattgtagaa tatgcgaaat acggc                  45

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 20
gcaggaagcc acgcagggag ccgtatttcg catattctac a                41

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccctgcgtgg cttcctgcgt gagtcccgca aagttggccc gg               42

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agagccacca gagcccaggt aacccgggcc aactttgcgg ga               42

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cctgggctct ggtggctctc gtaactcttc ctctctggat cacc             44

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atggtcagcg cacgctcatc cgggtgatcc agagaggaag agt              43

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gatgagcgtg cgctgaccat gggcgatctg atctccttcg cgt              43

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
ctgcatgccc tgggagatct gccacgcgaa ggagatcaga tcg              43
```

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
agatctccca gggcatgcag tacctggcag aaatgaaact ggtg             44
```

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
cgagccgcca gatcgcggtg caccagtttc atttctgcca g                41
```

<210> SEQ ID NO 29
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
ccgcgatctg gcggctcgta acattctggt agcggaaggc cgt              43
```

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
gccaaagtcg gagatcttca tcttacggcc ttccgctacc agaa             44
```

<210> SEQ ID NO 31
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
atgaagatct ccgactttgg cctgtctcgt gatgtgtatg aaga             44
```

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
gggaacgttt tacataggag tcctcttcat acacatcacg agaca            45
```

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gactcctatg taaaacgttc ccagggccgt atcccggtta aatgg            45

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atcaaacaga gattcgattg ccatccattt aaccgggata cggcc            45

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggcaatcgaa tctctgtttg atcatatcta caccactcag tccg             44

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agaacgccga aggaccatac atcggactga gtggtgtaga tat              43

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtatggtcct tcggcgttct gctgtgggaa atcgtgactc tgg              43

<210> SEQ ID NO 38
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaatacctgg gtacgggtta ccgcccagag tcacgatttc ccac             44

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gtaacccgta cccaggtatt ccgccagaac gcctgttcaa cctg        44

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ttccatacgg tgaccagttt tcagcaggtt gaacaggcgt tctgg        45

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gaaaactggt caccgtatgg aacgcccgga taactgctcc gaa        43

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
ctgcagcatc aggcggtaca tctcttcgga gcagttatcc gggc        44

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
atgtaccgcc tgatgctgca gtgctggaaa caggaaccgg acaa        44

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
gatgtccgca aacaccggac gtttgtccgg ttcctgtttc cag        43

<210> SEQ ID NO 45
<211> LENGTH: 44

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtccggtgtt tgcggacatc tctaaagacc tggagaagat gatg            44

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tccaggtaat cgcgacgttt caccatcatc ttctccaggt cttta           45

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gaaacgtcgc gattacctgg acctggcagc gtctaccccg tc              42

<210> SEQ ID NO 48
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gccgtcatcg taaatcagag aatcggacgg ggtagacgct gcca            44

<210> SEQ ID NO 49
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tctctgattt acgatgacgg cctgtctgaa gaggaaaccc cact            44

<210> SEQ ID NO 50
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcggagcatt gttgcagtca accagtgggg tttcctcttc agac            44

<210> SEQ ID NO 51
<211> LENGTH: 43
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 51
ttgactgcaa caatgctccg ctgccgcgtg ctctgccgtc tac                    43

<210> SEQ ID NO 52
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
accatacagt ttgttttcaa tccaggtaga cggcagagca cgcg                   44

<210> SEQ ID NO 53
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggattgaaaa caaactgtat ggtatgtctg acccgaactg gccg                   44

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtcagcggaa ccggagattc gcccggccag ttcgggtcag ac                     42

<210> SEQ ID NO 55
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gaatctccgg ttccgctgac tcgtgcagac ggcaccaaca ccg                    43

<210> SEQ ID NO 56
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aatcgttcgg gtaacgcgga aaaccggtgt tggtgccgtc tgc                    43

<210> SEQ ID NO 57
<211> LENGTH: 44
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 57
ttccgcgtta cccgaacgat tccgtttacg cgaactggat gctg                44

<210> SEQ ID NO 58
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcagtttcgc agcggacgga gacagcatcc agttcgcgta aac                 43

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gttggatccc actgttatca caaattcgca c                              31

<210> SEQ ID NO 60
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gttgaattcg gagtcaaagg tatccatcag tttcgcagcg gacgga              46

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gggaatttcc gcgtgacaac ctggtactgg                                30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ccagtaccag gttgtcacgc ggaaattccc                                30

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 63
gaaagaaaac gcgtctcagt ccgaactgtc tgatctgctg tccg                                44

<210> SEQ ID NO 64
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cggacagcag atcagacagt tcggactgag acgcgttttc tttc                                44

<210> SEQ ID NO 65
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ctgcagtgct ggcaccagga accggacgaa cgtccggtgt ttg                                 43

<210> SEQ ID NO 66
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
caaacaccgg acgttcgtcc ggttcctggt gccagcactg cag                                 43

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cttcctgcgt gagtccggcg atctgatctc c                                              31

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggagatcaga tcgccggact cacgcaggaa g                                              31

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gttcttcata tgtctctgga ctccatggaa aac                                    33

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gttcttcata tgtctgttga tgcgttcaaa atcct                                  35

<210> SEQ ID NO 71
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gttcttgtcg acacgtttca ccatcatctt ctcc                                   34

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 72

Val Asp His His His His His His
 1               5

<210> SEQ ID NO 73
<211> LENGTH: 297
<212> TYPE: PRT
<213> ORGANISM: Homo sapiens

<400> SEQUENCE: 73

Met Ser Leu Asp Ser Met Glu Asn Gln Val Ser Val Asp Ala Phe Lys
 1               5                  10                  15

Ile Leu Glu Asp Pro Lys Trp Glu Phe Pro Arg Asp Asn Leu Val Leu
            20                  25                  30

Gly Lys Thr Leu Gly Glu Gly Glu Phe Gly Lys Val Val Lys Ala Thr
        35                  40                  45

Ala Phe His Leu Lys Gly Arg Ala Gly Tyr Thr Thr Val Ala Val Lys
    50                  55                  60

Met Leu Lys Glu Asn Ala Ser Gln Ser Glu Leu Ser Asp Leu Leu Ser
65                  70                  75                  80

Glu Phe Asn Val Leu Lys Gln Val Asn His Pro His Val Ile Lys Leu
                85                  90                  95

Tyr Gly Ala Cys Ser Gln Asp Gly Pro Leu Leu Leu Ile Val Glu Tyr
            100                 105                 110

Ala Lys Tyr Gly Ser Leu Arg Gly Phe Leu Arg Glu Ser Gly Asp Leu
        115                 120                 125

Ile Ser Phe Ala Trp Gln Ile Ser Gln Gly Met Gln Tyr Leu Ala Glu
    130                 135                 140

Met Lys Leu Val His Arg Asp Leu Ala Ala Arg Asn Ile Leu Val Ala
145                 150                 155                 160

```
Glu Gly Arg Lys Met Lys Ile Ser Asp Phe Gly Leu Ser Arg Asp Val
                165                 170                 175

Tyr Glu Glu Asp Ser Tyr Val Lys Arg Ser Gln Gly Arg Ile Pro Val
            180                 185                 190

Lys Trp Met Ala Ile Glu Ser Leu Phe Asp His Ile Tyr Thr Thr Gln
        195                 200                 205

Ser Asp Val Trp Ser Phe Gly Val Leu Leu Trp Glu Ile Val Thr Leu
    210                 215                 220

Gly Gly Asn Pro Tyr Pro Gly Ile Pro Pro Glu Arg Leu Phe Asn Leu
225                 230                 235                 240

Leu Lys Thr Gly His Arg Met Glu Arg Pro Asp Asn Cys Ser Glu Glu
                245                 250                 255

Met Tyr Arg Leu Met Leu Gln Cys Trp His Gln Glu Pro Asp Glu Arg
            260                 265                 270

Pro Val Phe Ala Asp Ile Ser Lys Asp Leu Glu Lys Met Met Val Lys
        275                 280                 285

Arg Val Asp His His His His His His
    290                 295

<210> SEQ ID NO 74
<211> LENGTH: 288
<212> TYPE: PRT
<213> ORGANISM: Homo sapiens

<400> SEQUENCE: 74

Met Ser Val Asp Ala Phe Lys Ile Leu Glu Asp Pro Lys Trp Glu Phe
1               5                   10                  15

Pro Arg Asp Asn Leu Val Leu Gly Lys Thr Leu Gly Glu Gly Glu Phe
            20                  25                  30

Gly Lys Val Val Lys Ala Thr Ala Phe His Leu Lys Gly Arg Ala Gly
        35                  40                  45

Tyr Thr Thr Val Ala Val Lys Met Leu Lys Glu Asn Ala Ser Gln Ser
    50                  55                  60

Glu Leu Ser Asp Leu Leu Ser Glu Phe Asn Val Leu Lys Gln Val Asn
65                  70                  75                  80

His Pro His Val Ile Lys Leu Tyr Gly Ala Cys Ser Gln Asp Gly Pro
                85                  90                  95

Leu Leu Leu Ile Val Glu Tyr Ala Lys Tyr Gly Ser Leu Arg Gly Phe
            100                 105                 110

Leu Arg Glu Ser Gly Asp Leu Ile Ser Phe Ala Trp Gln Ile Ser Gln
        115                 120                 125

Gly Met Gln Tyr Leu Ala Glu Met Lys Leu Val His Arg Asp Leu Ala
    130                 135                 140

Ala Arg Asn Ile Leu Val Ala Glu Gly Arg Lys Met Lys Ile Ser Asp
145                 150                 155                 160

Phe Gly Leu Ser Arg Asp Val Tyr Glu Glu Asp Ser Tyr Val Lys Arg
                165                 170                 175

Ser Gln Gly Arg Ile Pro Val Lys Trp Met Ala Ile Glu Ser Leu Phe
            180                 185                 190

Asp His Ile Tyr Thr Thr Gln Ser Asp Val Trp Ser Phe Gly Val Leu
        195                 200                 205

Leu Trp Glu Ile Val Thr Leu Gly Gly Asn Pro Tyr Pro Gly Ile Pro
    210                 215                 220

Pro Glu Arg Leu Phe Asn Leu Leu Lys Thr Gly His Arg Met Glu Arg
225                 230                 235                 240
```

```
Pro Asp Asn Cys Ser Glu Glu Met Tyr Arg Leu Met Leu Gln Cys Trp
                245                 250                 255

His Gln Glu Pro Asp Glu Arg Pro Val Phe Ala Asp Ile Ser Lys Asp
            260                 265                 270

Leu Glu Lys Met Met Val Lys Arg Val Asp His His His His His His
        275                 280                 285

<210> SEQ ID NO 75
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ctggtcttag gcaaaaccct gggagagggc gaatttgggc aggtgg            46

<210> SEQ ID NO 76
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccacctgccc aaattcgccc tctcccaggg ttttgcctaa gaccag            46

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctcagaaatg gagatgctga agatgatcgg g                            31

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cccgatcatc ttcagcatct ccatttctga g                            31

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cagggctgga atacagctac aaccccagc                               29

<210> SEQ ID NO 80
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 80
gctggggttg tagctgtatt ccagccctg                                        29

<210> SEQ ID NO 81
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gtatgcctcc aagggctctc tgcggggtta cctgcaggcc c                          41

<210> SEQ ID NO 82
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gggcctgcag gtaaccccgc agagagccct tggaggcata c                          41

<210> SEQ ID NO 83
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
caatgtgatg aagatatctg actttggcct cg                                    32

<210> SEQ ID NO 84
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cgaggccaaa gtcagatatc ttcatcacat tg                                    32

<210> SEQ ID NO 85
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gactcctcat atggcagggg tctctgagta tga                                   33

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 86
caggtcgtcg actactcctg gttggaggtc aagg                                          34

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 87

Met Gly His His His His His His Met
  1               5

<210> SEQ ID NO 88
<211> LENGTH: 317
<212> TYPE: PRT
<213> ORGANISM: Homo sapiens

<400> SEQUENCE: 88

Met Gly His His His His His Met Ala Gly Val Ser Glu Tyr Glu
  1               5                  10                  15

Leu Pro Glu Asp Pro Arg Trp Glu Leu Pro Arg Asp Arg Leu Val Leu
                 20                  25                  30

Gly Lys Thr Leu Gly Glu Gly Glu Phe Gly Gln Val Val Leu Ala Glu
             35                  40                  45

Ala Ile Gly Leu Asp Lys Asp Lys Pro Asn Arg Val Thr Lys Val Ala
         50                  55                  60

Val Lys Met Leu Lys Ser Asp Ala Thr Glu Lys Asp Leu Ser Asp Leu
 65                  70                  75                  80

Ile Ser Glu Met Glu Met Met Lys Met Ile Gly Lys His Lys Asn Ile
                 85                  90                  95

Ile Asn Leu Leu Gly Ala Cys Thr Gln Asp Gly Pro Leu Tyr Val Ile
            100                 105                 110

Val Glu Tyr Ala Ser Lys Gly Ser Leu Arg Gly Tyr Leu Gln Ala Arg
            115                 120                 125

Arg Pro Pro Gly Leu Glu Tyr Ser Tyr Asn Pro Ser His Asn Pro Glu
        130                 135                 140

Glu Gln Leu Ser Ser Lys Asp Leu Val Ser Cys Ala Tyr Gln Val Ala
145                 150                 155                 160

Arg Gly Met Glu Tyr Leu Ala Ser Lys Lys Cys Ile His Arg Asp Leu
                165                 170                 175

Ala Ala Arg Asn Val Leu Val Thr Glu Asp Asn Val Met Lys Ile Ser
            180                 185                 190

Asp Phe Gly Leu Ala Arg Asp Ile His His Ile Asp Tyr Tyr Lys Lys
        195                 200                 205

Thr Thr Asn Gly Arg Leu Pro Val Lys Trp Met Ala Pro Glu Ala Leu
    210                 215                 220

Phe Asp Arg Ile Tyr Thr His Gln Ser Asp Val Trp Ser Phe Gly Val
225                 230                 235                 240

Leu Leu Trp Glu Ile Phe Thr Leu Gly Gly Ser Pro Tyr Pro Gly Val
                245                 250                 255

Pro Val Glu Glu Leu Phe Lys Leu Leu Lys Glu Gly His Arg Met Asp
            260                 265                 270

Lys Pro Ser Asn Cys Thr Asn Glu Leu Tyr Met Met Arg Asp Cys
        275                 280                 285

```
Trp His Ala Val Pro Ser Gln Arg Pro Thr Phe Lys Gln Leu Val Glu
        290                 295                 300

Asp Leu Asp Arg Ile Val Ala Leu Thr Ser Asn Gln Glu
305                 310                 315

<210> SEQ ID NO 89
<211> LENGTH: 317
<212> TYPE: PRT
<213> ORGANISM: Homo sapiens

<400> SEQUENCE: 89

Met Gly His His His His His His Met Ala Gly Val Ser Glu Tyr Glu
  1               5                  10                  15

Leu Pro Glu Asp Pro Arg Trp Glu Leu Pro Arg Asp Arg Leu Val Leu
             20                  25                  30

Gly Lys Thr Leu Gly Glu Gly Glu Phe Gly Gln Val Val Leu Ala Glu
         35                  40                  45

Ala Ile Gly Leu Asp Lys Asp Lys Pro Asn Arg Val Thr Lys Val Ala
     50                  55                  60

Val Lys Met Leu Lys Ser Asp Ala Thr Glu Lys Asp Leu Ser Asp Leu
 65                  70                  75                  80

Ile Ser Glu Met Glu Met Leu Lys Met Ile Gly Lys His Lys Asn Ile
                 85                  90                  95

Ile Asn Leu Leu Gly Ala Cys Thr Gln Asp Gly Pro Leu Tyr Val Ile
            100                 105                 110

Val Glu Tyr Ala Ser Lys Gly Ser Leu Arg Gly Tyr Leu Gln Ala Arg
        115                 120                 125

Arg Pro Pro Gly Leu Glu Tyr Ser Tyr Asn Pro Ser His Asn Pro Glu
    130                 135                 140

Glu Gln Leu Ser Ser Lys Asp Leu Val Ser Cys Ala Tyr Gln Val Ala
145                 150                 155                 160

Arg Gly Met Glu Tyr Leu Ala Ser Lys Lys Cys Ile His Arg Asp Leu
                165                 170                 175

Ala Ala Arg Asn Val Leu Val Thr Glu Asp Asn Val Met Lys Ile Ser
            180                 185                 190

Asp Phe Gly Leu Ala Arg Asp Ile His His Ile Asp Tyr Tyr Lys Lys
        195                 200                 205

Thr Thr Asn Gly Arg Leu Pro Val Lys Trp Met Ala Pro Glu Ala Leu
    210                 215                 220

Phe Asp Arg Ile Tyr Thr His Gln Ser Asp Val Trp Ser Phe Gly Val
225                 230                 235                 240

Leu Leu Trp Glu Ile Phe Thr Leu Gly Gly Ser Pro Tyr Pro Gly Val
                245                 250                 255

Pro Val Glu Glu Leu Phe Lys Leu Leu Lys Glu Gly His Arg Met Asp
            260                 265                 270

Lys Pro Ser Asn Cys Thr Asn Glu Leu Tyr Met Met Met Arg Asp Cys
        275                 280                 285

Trp His Ala Val Pro Ser Gln Arg Pro Thr Phe Lys Gln Leu Val Glu
    290                 295                 300

Asp Leu Asp Arg Ile Val Ala Leu Thr Ser Asn Gln Glu
305                 310                 315
```

COMPOUNDS AND METHODS FOR DEVELOPMENT OF RET MODULATORS

CROSS-REFERENCE TO RELATED PATENT APPLICATIONS

This application claims the benefit of U.S. Provisional Application 60/531,281, filed Dec. 19, 2003, and U.S. Provisional Application 60/558,581, filed Mar. 31, 2004, which are incorporated herein by reference in their entirety, including drawings.

BACKGROUND OF THE INVENTION

This invention relates to the field of development of ligands for Ret and to the use of models of Ret binding site derived from crystal structures. The information provided is intended solely to assist the understanding of the reader. None of the information provided nor references cited is admitted to be prior art to the present invention. Each of the references cited herein is incorporated in its entirety.

The present invention relates to Ret protein and the development of modulators of Ret activity.

Ret (Rearranged during Transformation) was identified as a rearranged human oncogene in the classic NIH3T3 transformation assay (Takahashi et al., 1985, *Cell* 42(2):581-8) and subsequently characterized as a Receptor Tyrosine kinase (Takahashi et al., 1988, *Oncogene* 3(5):571-8).

Ret and NTRK1 are receptor tyrosine kinase (RTK) proteins which play a role in the development and maturation of specific components of the nervous system. Their alterations have been associated to several human diseases, including some forms of cancer and developmental abnormalities. These features have contributed to the concept that one gene can be responsible for more than one disease. Moreover, both genes encoding for the two RTKs show genetic alterations that belong to either "gain of function" or "loss of function" class of mutations. In fact, receptor rearrangements or point mutations convert Ret and NTRK1 into dominantly acting transforming genes leading to thyroid tumors, whereas inactivating mutations, associated with Hirschsprung's disease (HSCR) and congenital insensitivity to pain with anhidrosis (CIPA), impair Ret and NTRK1 functions, respectively.

Implication of Ret in human tumorigenesis was indicated by the frequent identification of rearranged Ret sequences that transformed NIH3T3 cells in the DNA isolated from Papillary Thyroid Carcinoma DNAs. Bongarzone et al., 1989, *Oncogene* 4(12):1457-62). In these cases, the Ret gene was fused to as yet unknown PTC DNA sequences in the tumor DNA but not the normal patient DNA (Grieco et al., 1990, *Cell* 60(4):557-63). In addition, the chromosomal mapping of Ret to chromosome 10q11.2 co-localized with genetic mapping data that implicated a gene involved in patients with MEN2A (Multiple Endocrine Neoplasia 2A) (Ishizaka et al. 1989 *Oncogene* 4(12):1519-21). Expression analysis of the RET oncogene in a number of human tumors consistently detected expression of normal-sized transcripts of the RET proto-oncogene in human pheochromocytomas and in human medullary thyroid carcinomas (MTC), both of familial and sporadic type (Santoro et al., 1990, *Oncogene* 5(10):1595-8).

Further analysis of the tumor DNA of patients with Multiple endocrine neoplasia type 2A (MEN 2A) and familial medullary thyroid carcinoma (FMTC) identified mutations in the RET sequence resulting in amino acid changes in the encoded Ret protein (Donis-Keller 1993, *Hum Mol. Genet.* 2(7):851-6). Likewise, mutations in the RET gene were correlated with Hirschprung disease, a developmental disorder with genetic deletions and mutations in the chromosomal location of the RET gene (Luo et al., 1993, *Hum Mol. Genet.* 2(11):1803-8).

By early 1994, multiple papers describe the inactivation of the RET gene in patients with Hirschsprung disease and similar phenotype in knock out mice. In addition, activating mutations in Ret are now identified in patients with MEN2A, MEN2B, and FMTC (reviewed by van Heyningen V., 1994, *Nature* 367(6461):319-20).

It was determined that c-Ret regulates cell survival. Signal transduction molecules that form a complex with c-Ret as a result of these phosphoryl moieties, such as GRB2, SOS, ras, and raf, propagate a signal in the cell that promotes neural survival. Thus, compounds that promote the interactions of the se stimulatory molecules of c-Ret would enhance the activity of c-Ret. Alternatively, protein phosphatases can remove the phosphoryl moieties placed on the intracellular region of c-Ret in response to GDNF, and thus inhibit the signaling capability c-Ret. Thus, compounds that inhibit phosphatases of c-Ret will probably enhance the signaling capacity of c-Ret.

C-Ret is implicated in the development and survival of enteric, synaptic, and sensory neurons and neurons of the renal system upon stimulation by GDNF (Jing, et al., 1996, Cell 85:1113-1124; Trupp, et al., 1996, Nature 381:785-789; Durbec, et al., 1996, Nature 381:789-793). Lack of function mutations in c-Ret can lead to Hirschsprung's disease, for example, which manifests itself as a decrease in intestinal tract innervation in mammals. Thus, compounds that activate c-Ret are potential therapeutic agents for the treatment of neurodegenerative disorders, including, but not limited to, Hirschsprung's disease, Parkinson's disease, Alzheimer's disease, and amyotrophic lateral sclerosis. Compounds that inhibit c-Ret function can also be anti-cancer agents as overexpression of c-Ret in cells is implicated in cancers, such as cancer of the thyroid.

Modulation of c-Ret activity may also be useful in treating cancers of the nerve tissue, such as neuroblastoma, even if an abnormality is not found the signaling pathway.

As stated above, RET gene is responsible for MEN2 syndromes, which are inherited in an autosomal dominant fashion with high penetrance and diverse clinical manifestations. The predominant RET mutation is missense mutation which is restricted to 9 codons (codons 609, 611, 618, 620, 630, 634, 768, 804 and 918). The MEN2 syndromes have 3 subtypes: multiple endocrine neoplasia type 2A (MEN2A), MEN2B, and familial medullary thyroid carcinoma (FMTC). Missense mutations at exon 10 (codons 609, 611, 618, and 620) and exon 11 (codons 630 and 634) have been identified in 98% of MEN2A families and in 85% of FMTC families. Missense mutations at codons 768 and 804 have been known to be responsible for 5.about.10% of FMTC cases. In addition, missense mutations at exon 16 (codon 918) have been found in 95% of MEN2B cases.

SUMMARY OF THE INVENTION

The present invention concerns compounds active on Ret, and the use of structural information about Ret to derive additional Ret modulators. In particular, the invention concerns compounds of Formula I as described below. Thus, the invention provides novel compounds that can be used for therapeutic methods involving modulation of Ret, as well as providing molecular scaffolds for developing additional modulators of Ret.

The compounds of Formula I have the following structure:

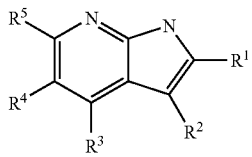

Formula I where, with reference to Formula I:

$R^1$ and $R^5$ are independently hydrogen, halo, hydroxy, optionally substituted alkoxyl, optionally substituted thioalkoxy, optionally substituted lower alkyl (e.g., trifluoromethyl), optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, —C(X)NR$^{16}$R$^{17}$, —C(X)R$^{20}$, —NR$^{22}$R$^{23}$ $R^2$, $R^3$, and $R^4$ are independently hydrogen, halo, hydroxy, optionally substituted alkoxyl, optionally substituted thioalkoxy, optionally substituted lower alkyl (e.g., trifluoromethyl), optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, or optionally substituted heteroaralkyl, —C(X)R$^{20}$, C(X)NR$^{16}$R$^{17}$, S(O)$_2$NR$^{16}$R$^{17}$, —NR$^{22}$R$^{23}$, or —S(O)$_n$R$^{21}$;

$R^{16}$ and $R^{17}$ are independently hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, or $R^{16}$ and $R^{17}$ together form a 5-7 membered carbocyclic or heterocyclic ring;

$R^{20}$ is hydroxyl, optionally substituted lower alkoxy, optionally substituted amine, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, or optionally substituted heteroaralkyl;

$R^{21}$ is hydrogen, optionally substituted lower alkyl, optionally substituted amine, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl;

$R^{22}$ and $R^{23}$ are independently hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, —C(X)R$^{20}$, C(X)NR$^{16}$R$^{17}$, or —S(O)$_2$R$^{21}$;

$R^{24}$ is optionally substituted lower alkyl, optionally substituted aryl, optionally substituted aralkyl, optionally substituted heteroaryl, or optionally substituted heteroaralkyl;

w, y, and z are independently O, S, N, or CR$^2$;

q is N or C;

X=O or S; and

N=0, 1, or 2.

In connection with the compounds of Formula I the following definitions apply.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1-15, more preferably 1 to 8, even more preferably 1-6, yet more preferably 1-4 and most preferably 1-2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3-8, more preferably 3-6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2-20, preferably 2-17, more preferably 2-10, even more preferably 2-8, most preferably 2-4, carbon atoms and at least one, preferably 1-3, more preferably 1-2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2-20, preferably 2-17, more preferably 2-10, even more preferably 2-8, most preferably 2-4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-disubstituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'''R'''', where R is lower alkyl, or substituted lower alkyl, R', R''', R'''' may independently be hydrogen, halogen, lower alkyl, substituted lower alkyl, acyl, aryl, substituted aryl, hetaryl, or substituted hetaryl as defined below.

"Alkyl alkynyl" refers to a groups —RCCR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" or "thioalkoxy" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" or substituted amine denotes the group NRR', where R and R' may independently by hydrogen, lower alkyl, substituted lower alkyl, aryl, substituted aryl, hetaryl, or substituted heteroaryl as defined herein, acyl or sulfonyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5-7, more preferably 5-6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, heteroaryl, substituted heteroaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5-6 ring members and/or are optionally substituted as in the case of cycloalkyl. Heterocyyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted heterocyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like:

"Cycloheteroalkyl" refers to a cycloalkyl group wherein one or more of the ring carbon atoms is replaced with a heteroatom (e.g., N, O, S or P).

Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, heteroaryl, substituted heteroaryl, nitro, cyano, thiol, sulfamido and the like.

The description above of substituents in Formula I, includes description of each combination of the specified substituents, R', $R^2$, $R^3$, $R^4$, and $R^5$.

In particular embodiments involving compounds of Formula I, $R^1$ and $R^5$ are hydrogen. In particular embodiments, compounds of Formula I have non-hydrogen substitution at $R^2$; non-hydrogen substitution at $R^3$, non-hydrogen substitution at $R^4$, non-hydrogen substitution at $R^2$ and $R^3$; non-hydrogen substitution at $R^2$ and $R^4$. In certain embodiments, the substitutions as listed are the only substitutions; the substitutions as listed are combined with $R^1$ and $R^5$ as H; the substitutions as listed are combined with substitution at one other of the substitution positions shown in Formula I.

In particular embodiments the compound of Formula I has a structure according to one of the following sub-generic structures.

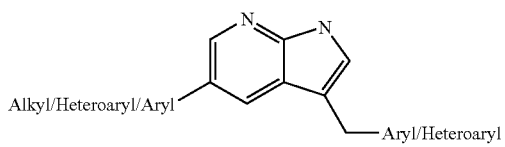

-continued

In the above compounds, the alkyl, heteroaryl, and aryl groups of $R^2$ and $R^4$ may be independently unsubstituted or substituted. In further embodiments of the above compounds with substitutions at $R^2$ and $R^4$, the alkyl, aryl, or heteroaryl group at $R^4$ is linked through a nitrogen, e.g., —NH-aryl, —NH-heteroaryl, or —NH-alkyl, or through oxygen, e.g., —O-aryl, —O-heteroaryl, or —O-alkyl.

Further, in certain embodiments of compounds with $R^2$ and $R^4$ substituents, the aryl or heteroaryl group at $R^2$ is optionally substituted aryl or heteroaryl and the aryl or heteroaryl group at $R^4$ is optionally substituted aryl or heteroaryl, which is directly linked to the bicyclic structure or is linked to the bi-cyclic structure through a nitrogen or an oxygen; in further embodiments, the aryl or heteroaryl group at $R^2$ is an optionally substituted six-membered carbocyclic or heterocyclic group and the aryl or heteroaryl group at $R^4$ is an optionally substituted six-membered carbocyclic or heterocyclic group; the aryl or heteroaryl group at $R^2$ is an optionally substituted six-membered carbocyclic or heterocyclic group and the aryl or heteroaryl group at $R^4$ is an optionally substituted five-membered carbocyclic or heterocyclic group; the aryl or heteroaryl group at $R^2$ is an optionally substituted five-membered carbocyclic or heterocyclic group and the aryl or heteroaryl group at $R^4$ is an optionally substituted six-membered carbocyclic or heterocyclic group; the aryl or heteroaryl group at $R^2$ is an optionally substituted five-membered carbocyclic or heterocyclic group and the aryl or heteroaryl group at $R^4$ is an optionally substituted five-membered carbocyclic or heterocyclic group; the aryl or heteroaryl group at $R^2$ is an optionally substituted phenyl group and the aryl or heteroaryl group at $R^4$ is an optionally substituted six-membered carbocyclic or heterocyclic group; the aryl or heteroaryl group at $R^2$ is an optionally substituted phenyl group and the aryl or heteroaryl group at $R^4$ is an optionally substituted five-membered carbocyclic or heterocyclic group; the aryl or heteroaryl group at $R^2$ is an optionally substituted five-membered carbocyclic or heterocyclic group and the aryl or heteroaryl group at $R^4$ is an optionally substituted phenyl group; the aryl or heteroaryl group at $R^2$ is an optionally substituted six-membered carbocyclic or heterocyclic group and the aryl or heteroaryl group at $R^4$ is an optionally substituted phenyl group; the aryl or heteroaryl group at $R^2$ is an optionally substituted phenyl group and the aryl or heteroaryl group at R[4] is an optionally substituted phenyl group. In further embodiments, the aryl or heteroaryl group at R[2] is a six-membered carbocyclic or heterocyclic group substituted at the ortho and/or meta positions (preferably when bi-substituted, the substitutions are para to each other) and the aryl or heteroaryl group at R[4] is a six-membered carbocyclic or heterocyclic group substituted at the meta position; the aryl or heteroaryl group at R[2] is a mono or bi-substituted five-membered carbocyclic or heterocyclic group and the aryl or heteroaryl group at R[4] is a six-membered carbocyclic or heterocyclic group substituted at the meta position; the aryl or heteroaryl group at R[2] is a six-membered carbocyclic or heterocyclic group substituted at the meta position with hydroxyl or —NH—SO$_2$-alkyl (e.g., —NH—SO$_2$-methyl) and the aryl or heteroaryl group at R[4] is a six-membered carbocyclic or heterocyclic group substituted at the meta position; the aryl or heteroaryl group at R[2] is a six-membered carbocyclic or heterocyclic group substituted at the ortho position with halo (i.e., F, Cl, Br, I) and at the meta position with hydroxyl or —NH—SO$_2$-alkyl (e.g., —NH—SO$_2$-methyl) with the substitutions being para to each other and the aryl or heteroaryl group at R[4] is a six-membered carbocyclic or heterocyclic group substituted at the meta position; the aryl or heteroaryl group at R[2] is a mono- or bi-substituted six-membered carbocyclic or heterocyclic group substituted at the ortho and meta positions (when bi-substituted the substitutions are preferably para to each other) and the aryl or heteroaryl group at R[4] is a six-membered carbocyclic or heterocyclic group substituted at the meta position with —N—C(O)-alkyl; the aryl or heteroaryl group at R[2] is a mono- or bi-substituted six-membered carbocyclic or heterocyclic group substituted at the ortho and meta positions (when bi-substituted the substitutions are preferably para to each other) and the aryl or heteroaryl group at R[4] is a six-membered carbocyclic or heterocyclic group substituted at the meta position with —N—C(O)-alkyl, —C═C-carboxyl, or —C—C-carboxyl. In further embodiments, for each of the selections of R[4] described in this paragraph, R[2] is —C(O)-(6-membered carbocyclic or heterocyclic group), where the carbocyclic or heterocyclic group is substituted at the ortho and meta positions with those substitutions being para to each other; R[2] is —C(O)-phenyl, where the phenyl is substituted at the ortho and meta positions with those substitutions being para to each other; R[2] is —C(O)-phenyl, where the phenyl is substituted at the ortho position with halo (preferably F) and at the meta position with hydroxyl or —NH—SO$_2$-alkyl (e.g., —NH—SO$_2$-methyl) with those substitutions being para to each other; R[2] is —C(O)-phenyl, where the phenyl is substituted at the meta position; R[2] is —C(O)-phenyl, where the phenyl is substituted at the meta position with hydroxyl or —NH—SO$_2$-alkyl (e.g., —NH—SO$_2$-methyl). In further particular embodiments, each of the selections for the aryl or heteroaryl group at R[4] described in this paragraph is linked to the bi-cyclic structure through a nitrogen for each of the selections for R[2] described in this paragraph; each of the selections for the aryl or heteroaryl group at R[4] described in this paragraph is linked to the bi-cyclic structure through an oxygen for each of the selections for R[2] described in this paragraph; R[4] is —NH-phenyl; R[4] is —NH-(meta substituted phenyl).

In additional embodiments, R[4] is —C(O)—NR[16]R[17] and R[2] is each of the selections described in the preceding paragraph; R[4] is —SO$_2$—NR[16]R[17] and R[2] is each of the selections described in the preceding paragraph.

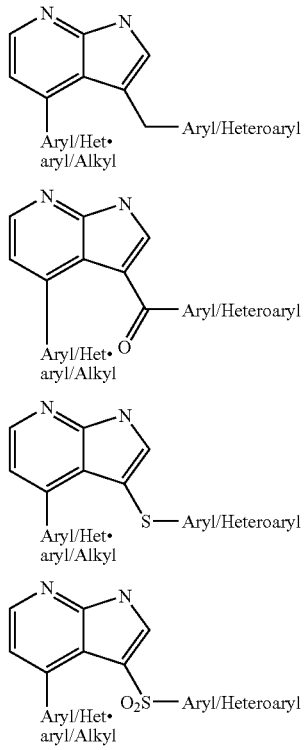

In the above compounds, the alkyl, heteroaryl, and aryl groups of R[2] and R[3] may be independently unsubstituted or substituted. In further embodiments of the above compounds with substitutions at R[2] and R[3], the alkyl, aryl, or heteroaryl group at R[3] is linked through a nitrogen, e.g., —NH-aryl, —NH-heteroaryl, or —NH-alkyl.

For each of the selection for R[2] in compounds as shown above with as described with R[2] and R[3] substitutents, R[2] is each of the selections of R[2] described above for the compounds with R[2] and R[4] substituents, and R[3] is optionally substituted aryl, heteroaryl, —NH-aryl, or —NH-heteraryl; the aryl or heteroaryl is monosubstituted; the aryl or heteroaryl is bi-substituted; the aryl or heteroaryl is substituted with halo; the aryl is optionally substituted phenyl; the phenyl is substituted with halo; the phenyl is bi-substituted at both meta positions; the halo is fluoro.

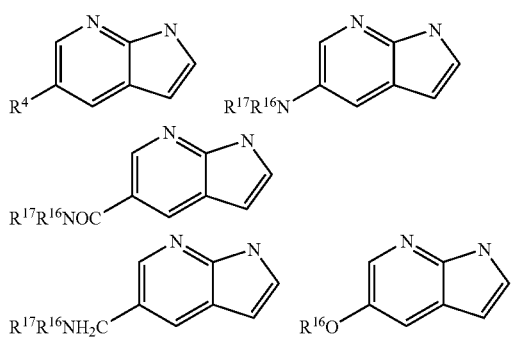

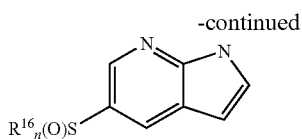

In addition to these are compounds where $R^4$ is CN, $CO_2R$, aryl, and heteroaryl.

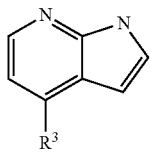

$R^3$ = Aryl, heteroaryl, NHR, ether, carboxamide, ester

$R^2$ = benzyl, benzoyl, thioether, sulfone, sulfoxide, amine, carboxamide, ester, ether An additional aspect of this invention relates to pharmaceutical formulations, that include a therapeutically effective amount of a compound of Formula I (or a compound within a sub-group of compounds within any of the generic formula) and at least one pharmaceutically acceptable carrier or excipient. The composition can include a plurality of different pharmacalogically active compounds.

An additional aspect of this invention concerns pharmaceutical formulations, that include a therapeutically effective amount of a compound of Formula I (or a compound within a sub-group of compounds within any of those generic formulas) and at least one pharmaceutically acceptable carrier or excipient.

In particular embodiments, the composition includes a plurality of different pharmacalogically active compounds, which can be a plurality of compounds of Formula I, and can also include other compounds in combination with one or more compounds of Formula I.

Thus, in a first aspect, the invention concerns a novel compound of Formula I as described herein.

In particular embodiments involving compounds of Formula I, the compound is different from compounds described in one more more (including all of the reference and each combination of two or more of the references) WO 03028724, WO 9822457, EP 00465970, WO 00162255, WO 095047421, WO 00124236, WO 00029411, WO 09504742, WO 09414808, WO 09507910, WO 00160822, WO 00200657, WO 00129036, WO 09951231, WO 09951232, WO 09951233, WO 09951595, WO 09951596, WO 09951234, GB 02299581, U.S. Pat. No. 5,712,285, GB 02292145, WO 09420497, GB 02292143, GB 02298198, WO 09420459, U.S. Pat. No. 5,576,319, WO 09605200, WO 09528387, WO 09806433, JP 15073357, JP 10130269, WO 09847899, EP 00870768, WO 00798399, WO 09600226, WO 09900386, WO 09746558, WO 00009162, WO 02083175, WO 03028724, WO 09611929, WO 02085896, and WO 00064898.

A related aspect of this invention concerns pharmaceutical compositions that include a compound of Formula I and at least one pharmaceutically acceptable carrier, excipient, or diluent. The composition can include a plurality of different pharmacalogically active compounds.

In another related aspect, compounds of Formula I can be used in the preparation of a medicament for the treatment of a Ret-mediated disease or condition, such as a cancer.

In another aspect, the invention concerns a method of treating or prophylaxis of a disease or condition in a mammal, by administering to the mammal a therapeutically effective amount of a compound of Formula I, a prodrug of such compound, or a pharmaceutically acceptable salt of such compound or prodrug. The compound can be alone or can be part of a pharmaceutical composition.

In aspects and embodiments involving treatment or prophylaxis of a disease or conditions, the disease or condition is multiple endocrine neoplasia, type IIA (MEN2A), multiple endocrine neoplasia, type IIB (MEN2B), Hirschsprung disease (HSCR; aganglionic megacolon), or medullary thyroid carcinoma (MTC), familial medullary thyroid carcinomas (FMTC), and papillary thyroid carcinomas (PTC).

The identification of compounds of Formula I active on Ret also provides a method for identifying or developing additional compounds active on Ret, e.g., improved modulators, by determining whether any of a plurality of test compounds of Formula I active on Ret provides an improvement in one or more desired pharmacologic properties relative to a reference compound active on Ret, and selecting a compound 1f any, that has an improvement in the desired pharmacologic property, thereby providing an improved modulator.

In particular embodiments of aspects of modulator development, the desired pharmacologic property is serum half-life longer than 2 hr or longer than 4 hr or longer than 8 hr, aqueous solubility, oral bioavailability more than 10%, oral bioavailability more than 20%.

Also in particular embodiments of aspects of modulator development, the reference compound is a compound of Formula I. The process can be repeated multiple times, i.e., multiple rounds of preparation of derivatives and/or selection of additional related compounds and evaluation of such further derivatives of related compounds, e.g., 1, 2, 3, 4, 5, 6, 7, 8, 9, 10 or more additional rounds.

In additional aspects, structural information about Ret is utilized, e.g., in conjunction with compounds of Formula I or a molecular scaffold or scaffold core of Formula I. In addition, structural information about one or or more Ret surrogates can be used, e.g., surrogates as described herein.

The invention also provides a method for developing ligands binding to Ret, where the method includes identifying as molecular scaffolds one or more compounds that bind to a binding site of the kinase; determining the orientation of at least one molecular scaffold in co-crystals with the kinase or a surrogate; identifying chemical structures of one or more of the molecular scaffolds, that, when modified, alter the binding affinity or binding specificity or both between the molecular scaffold and the kinase; and synthesizing a ligand in which one or more of the chemical structures of the molecular scaffold is modified to provide a ligand that binds to the kinase with altered binding affinity or binding specificity or both. Such a scaffold can, for example, be a compound of Formula I, or include the core of Formula I.

The terms "Ret" and "c-Ret" mean an enzymatically active kinase that contains a portion with greater than 90% amino acid sequence identity to amino acid residues including the ATP binding site, for a maximal alignment over an equal length segment; or that contains a portion with greater than 90% amino acid sequence identity to at least 200 contiguous amino acids of native Ret that retains binding to natural Ret ligand. Preferably the sequence identity is at least 95, 97, 98, 99, or even 100%. Preferably the specified level of sequence identity is over a sequence at least 300 contiguous amino acid residues in length.

The term "Ret kinase domain" refers to a reduced length Ret (i.e., shorter than a full-length Ret by at least 100 amino acids that includes the kinase catalytic region in Ret. Highly preferably for use in this invention, the kinase domain retains kinase activity, preferably at least 50% the level of kinase activity as compared to the native Ret, more preferably at least 60, 70, 80, 90, or 100% of the native activity.

As used herein, the terms "ligand" and "modulator" are used equivalently to refer to a compound that modulates the activity of a target biomolecule, e.g., an enzyme such as a kinase or kinase. Generally a ligand or modulator will be a small molecule, where "small molecule refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined by a person for a particular biological system or therapeutic use. In terms of the development of ligands from scaffolds, a ligand is a derivative of a scaffold.

In the context of binding compounds, molecular scaffolds, and ligands, the term "derivative" or "derivative compound" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

Thus, the term "parent compound" refers to a reference compound for another compound, having structural features continued in the derivative compound. Often but not always, a parent compound has a simpler chemical structure than the derivative.

By "chemical structure" or "chemical substructure" is meant any definable atom or group of atoms that constitute a part of a molecule. Normally, chemical substructures of a scaffold or ligand can have a role in binding of the scaffold or ligand to a target molecule, or can influence the three-dimensional shape, electrostatic charge, and/or conformational properties of the scaffold or ligand.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($k_d$) of 1 mM or less. A binding compound can bind with "low affinity", "very low affinity", "extremely low affinity", "moderate affinity", "moderately high affinity", or "high affinity" as described herein.

In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of Ret, other tyrosine kinases or even other type of enzymes. In particular embodiments, the greater specificity is at least 2, 3, 4, 5, 8, 10, 50, 100, 200, 400, 500, or 1000-fold greater specificity.

As used in connection with binding of a compound with a target, the term "interact" indicates that the distance from a bound compound to a particular amino acid residue will be 5.0 angstroms or less. In particular embodiments, the distance from the compound to the particular amino acid residue is 4.5 angstroms or less, 4.0 angstroms or less, or 3.5 angstroms or less. Such distances can be determined, for example, using co-crystallography, or estimated using computer fitting of a compound in an active site.

Reference to particular amino acid residues in Ret polypeptide residue number is defined by the numbering provided in NCBI NP_065681.1 (cDNA sequence as NM_0020630.2).

Reference to particular amino acid residues in FGFR1 is by reference to NCBI NP_000595.1 (cDNA sequence as NM_000604.2).

"Ret surrogate 1" refers to the FGFR fragment A458 to E765 with six substitutions that mutate two surface exposed cystein residues (C488 and C584) and modify active site residues to the Ret counterparts based on sequence alignment. The substitutions are P483T, C488E, N568S, E571G, C584S, and A640S. "Ret surrogate 2 is the same as Ret surrogate 1 except having the additional substitution M535L.

In a related aspect, the invention provides a method for developing ligands specific for Ret, where the method involves determining whether a derivative of a compound that binds to a plurality of kinases has greater specificity for that particular kinase than the parent compound with respect to other kinases.

As used herein in connection with binding compounds or ligands, the term "specific for Ret kinase", "specific for Ret" and terms of like import mean that a particular compound binds to Ret to a statistically greater extent than to other kinases that may be present in a particular organism. Also, where biological activity other than binding is indicated, the term "specific for Ret" indicates that a particular compound has greater biological activity associated with binding Ret than to other tyrosine kinases. Preferably, the specificity is also with respect to other biomolecules (not limited to tyrosine kinases) that may be present from an organism.

In another aspect, the invention provides a method for obtaining improved ligands binding to Ret, where the method involves identifying a compound that binds to that particular kinase, determining whether that compound interacts with one or more conserved active site residues, and determining whether a derivative of that compound binds to that kinase with greater affinity or greater specificity or both than the parent binding compound. Binding with greater affinity or greater specificity or both than the parent compound indicates that the derivative is an improved ligand. This process can also be carried out in successive rounds of selection and derivatization and/or with multiple parent compounds to provide a compound or compounds with improved ligand characteristics. Likewise, the derivative compounds can be tested and selected to give high selectivity for that kinase, or to give cross-reactivity to a particular set of targets, for example to a subset of kinases that includes Ret. In particular embodiments, known Ret inhibitors can be used, and derivatives with greater affinity and/or greater specificity can be developed, preferably using Ret or Ret surrogate structure information; greater specificity for Ret relative to other tyrosine kinases is developed.

By "molecular scaffold" or "scaffold" is meant a simple target binding molecule to which one or more additional chemical moieties can be covalently attached, modified, or eliminated to form a plurality of molecules with common structural elements. The moieties can include, but are not limited to, a halogen atom, a hydroxyl group, a methyl group, a nitro group, a carboxyl group, or any other type of molecular group including, but not limited to, those recited in this application. Molecular scaffolds bind to at least one target molecule, preferably to a plurality of molecules in a protein family, and the target molecule can preferably be a enzyme, receptor, or other protein. Preferred characteristics of a scaffold can include binding at a target molecule binding site such that one or more substituents on the scaffold are situated in binding pockets in the target molecule binding site; having chemically tractable structures that can be chemically modified, particularly by synthetic reactions, so that a combinatorial library can be easily constructed; having chemical positions where moieties can be attached that do not interfere with binding of the scaffold to a protein binding site, such that the scaffold or library members can be modified to form ligands, to achieve additional desirable characteristics, e.g., enabling the ligand to be actively transported into cells and/or to specific organs, or enabling the ligand to be attached to a chromatography column for additional analysis. Thus, a molecular scaffold is an identified target binding molecule prior to modification to improve binding affinity and/or specificity, or other pharmacalogic properties.

The term "scaffold core" refers to the core structure of a molecular scaffold onto which various substituents can be attached. Thus, for a number of scaffold molecules of a particular chemical class, the scaffold core is common to all the scaffold molecules. In many cases, the scaffold core will consist of or include one or more ring structures.

By "binding site" is meant an area of a target molecule to which a ligand can bind non-covalently. Binding sites embody particular shapes and often contain multiple binding pockets present within the binding site. The particular shapes are often conserved within a class of molecules, such as a molecular family. Binding sites within a class also can contain conserved structures such as, for example, chemical moieties, the presence of a binding pocket, and/or an electrostatic charge at the binding site or some portion of the binding site, all of which can influence the shape of the binding site.

By "binding pocket" is meant a specific volume within a binding site. A binding pocket can often be a particular shape, indentation, or cavity in the binding site. Binding pockets can contain particular chemical groups or structures that are important in the non-covalent binding of another molecule such as, for example, groups that contribute to ionic, hydrogen bonding, or van der Waals interactions between the molecules.

By "orientation", in reference to a binding compound bound to a target molecule is meant the spatial relationship of the binding compound (which can be defined by reference to at least some of its constituent atoms) to the binding pocket and/or atoms of the target molecule at least partially defining the binding pocket.

In the context of target molecules in this invention, the term "crystal" refers to a regular assemblage of a target molecule of a type suitable for X-ray crystallography. That is, the assemblage produces an X-ray diffraction pattern when illuminated with a beam of X-rays. Thus, a crystal is distinguished from an agglomeration or other complex of target molecule that does not give a diffraction pattern.

By "co-crystal" is meant a complex of the compound, molecular scaffold, or ligand bound non-covalently to the target molecule and present in a crystal form appropriate for analysis by X-ray or protein crystallography. In preferred embodiments the target molecule-ligand complex can be a protein-ligand complex.

The phrase "alter the binding affinity or binding specificity" refers to changing the binding constant of a first compound for another, or changing the level of binding of a first compound for a second compound as compared to the level of binding of the first compound for third compounds, respectively. For example, the binding specificity of a compound for a particular protein is increased if the relative level of binding to that particular protein is increased as compared to binding of the compound to unrelated proteins.

As used herein in connection with test compounds, binding compounds, and modulators (ligands), the term "synthesizing" and like terms means chemical synthesis from one or more precursor materials.

The phrase "chemical structure of the molecular scaffold is modified" means that a derivative molecule has a chemical structure that differs from that of the molecular scaffold but still contains common core chemical structural features. The phrase does not necessarily mean that the molecular scaffold is used as a precursor in the synthesis of the derivative.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

By a "set" of compounds is meant a collection of compounds. The compounds may or may not be structurally related.

As used herein, the term "azaindole scaffold" or "azaindole scaffold structure" refers to a compound of Formula I or the structure of such compound having no more than two substitutents. Similarly, the term "azaindole core" refers to the structure shown above as Formula I excluding the R groups.

In another aspect, structural information about Ret or Ret surrogate can also be used to assist in determining a structure for another tyrosine kinase by creating a homology model from an electronic representation of a Ret or Ret surrogate structure.

Typically creating such a homology model involves identifying conserved amino acid residues between the known tyrosine kinase having known structures, e.g., Ret, and the other tyrosine kinase of interest; transferring the atomic coordinates of a plurality of conserved amino acids in the known structure to the corresponding amino acids of the other tyrosine kinase to provide a rough structure of that tyrosine kinase; and constructing structures representing the remainder of the other tyrosine kinase using electronic representations of the structures of the remaining amino acid residues in the other kinase. In particular, for Ret coordinates from Table 2 can be used, and for Ret surrogate, coordinates from Table 3, 4, or 5 can be used. Conserved residues in a binding site can be used.

To assist in developing other portions of the kinase structure, the homology model can also utilize, or be fitted with, low resolution x-ray diffraction data from one or more crystals of the kinase, e.g., to assist in linking conserved residues and/or to better specify coordinates for terminal portions of a polypeptide.

The Ret or Ret surrogate structural information used can be for a variety of different variants, including full-length wild type, naturally-occurring variants (e.g., allelic variants and splice variants), truncated variants of wild type or naturally-occurring variants, and mutants of full-length or truncated wild-type or naturally-occurring variants (that can be mutated at one or more sites). For example, in order to provide a surrogate structure closer to a Ret structure, a mutated FGFR1 that includes a plurality of mutations to change residues in FGFR1 to the residues in Ret for corresponding sites, e.g., binding site residues, can be used.

In another aspect, the invention provides a crystalline form of Ret (e.g., Ret kinase domain) or Ret surrogate, which may be a reduced length surrogate, e.g., created from FGFR1, such as a kinase domain, e.g., having atomic coordinates as described in Table 3, 4, or 5. The crystalline form can contain one or more heavy metal atoms, for example, atoms useful for X-ray crystallography. The crystalline form can also include a binding compound in a co-crystal, e.g., a binding compound that interacts with one more more conserved active site residues in the kinase, or any two, any three, any four, any five, any six of those residues, and can, for example, be a known Ret or other kinase inhibitor. Such Ret or Ret surrogate crystals can be in various environments, e.g., in a crystallography plate, mounted for X-ray crystallography, and/or in an X-ray beam. The Ret surrogate may be of various forms, e.g., a wild-type, variant, truncated, and/or mutated form as described herein.

The invention further concerns co-crystals of Ret as well as Ret surrogate, which may be a reduced length protein, e.g., a kinase domain, and a Ret binding compound. Advantageously, such co-crystals are of sufficient size and quality to allow structural determination to at least 3 Angstroms, 2.5 Angstroms, 2.0 Angstroms, 1.8 Angstroms, 1.7 Angstroms, 1.5 Angstroms, 1.4 Angstroms, 1.3 Angstroms, or 1.2 Angstroms. The co-crystals can, for example, be in a crystallography plate, be mounted for X-ray crystallography and/or in an X-ray beam. Such co-crystals are beneficial, for example, for obtaining structural information concerning interaction between the Ret or Ret surrogate and binding compounds.

In particular embodiments, the binding compound includes the core structure of Formula I.

Ret binding compounds can include compounds that interact with at least one of conserved active site residues, or any 2, 3, 4, 5, or 6 of those residues. Exemplary compounds that bind to Ret include compounds described in references cited herein.

Likewise, in additional aspects, methods for obtaining Ret and Ret surrogate crystals and co-crystals are provided. In one aspect, Ret crystals are obtained by subjecting Ret polypeptide Protein at 5-20 mg/ml, e.g., 8-15, 10-14, or 12 mg/ml, to crystallization conditions substantially equivalent to 30% PEG 2000 MME, 0.15M KBr and 1 mM DTT, which can be in the presence of binding compound, e.g., binding compound at 0.5-5 mg/ml, 1-3 mg/ml, 1-2 mg/ml, or 1 mg/ml, typically carried out at 4° C.

In another aspect is provided a method for obtaining a crystal of FGFR1-based Ret surrogate, by subjecting Ret surrogate protein at 5-20 mg/ml, e.g., 8-12 mg/ml, to crystallization conditions substantially equivalent to 10-20% PEG 3350 (e.g., 10-12, 12-14, 14-16, 16-18, 18-20), 0.1M Hepes pH 6.5, 0.2M $(NH_4)_2SO_4$, 10% ethylene glycol at 4° C.

Crystallization conditions can be initially identified using a screening kit, such as a Hampton Research (Riverside, Calif.) screening kit 1. Conditions resulting in crystals can be selected and crystallization conditions optimized based on the demonstrated crystallization conditions. To assist in subsequent crystallography, the protein can be seleno-methionine labeled. Also, as indicated above, the protein may be any of various forms, e.g., truncated to provide a catalytic domain, which can be selected to be of various lengths.

In another aspect, provision of compounds active on Ret (such as compounds described herein and/or developed using methods described herein) also provides a method for modulating the Ret activity by contacting Ret with a compound that binds to Ret and interacts with one more conserved active site residues. The compound is preferably provided at a level sufficient to modulate the activity of the Ret by at least 10%, more preferably at least 20%, 30%, 40%, or 50%. In many embodiments, the compound will be at a concentration of about 1 μM, 100 μM, or 1 mM, or in a range of 1-100 nM, 100-500 nM, 500-1000 nM, 1-100 μM, 100-500 μM, or 500-1000 μM.

As used herein, the term "modulating" or "modulate" refers to an effect of altering a biological activity, especially a biological activity associated with a particular biomolecule such as Ret. For example, an agonist or antagonist of a particular biomolecule modulates the activity of that biomolecule, e.g., an enzyme.

The term "Ret activity" refers to a biological activity of Ret, particularly including kinase activity.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

In a related aspect, the invention provides a method for treating a patient suffering from a disease or condition characterized by abnormal Ret activity (e.g., kinase activity), where the method involves administering to the patient a compound as described herein or identified by a method as described herein.

Specific diseases or disorders which might be treated or prevented include those described in the Detailed Description herein, and in the references cited therein.

As crystals of Ret and Ret surrogate have been developed and analyzed, and binding modes determined, another aspect concerns an electronic representation of such Ret polypeptides and Ret surrogates (which may be a reduced length FGFR1-based Ret surrogate), for example, an electronic representation containing atomic coordinate representations for Ret or Ret surrogate corresponding to the coordinates listed for Ret in Table 2 or for Ret surrogate in Table 3, 4, or 5, or a schematic representation such as one showing secondary structure and/or chain folding, and may also show conserved active site residues.

The electronic representation can also be modified by replacing electronic representations of particular residues with electronic representations of other residues. Thus, for example, an electronic representation containing atomic coordinate representations corresponding to the coordinates for Ret or Ret surrogate listed in Table 2, 3, 4, or 5 can be modified by the replacement of coordinates for a particular conserved residue in a binding site by a different amino acid. Following a modification or modifications, the representation of the overall structure can be adjusted to allow for the known interactions that would be affected by the modification or modifications. In most cases, a modification involving more than one residue will be performed in an iterative manner.

In addition, an electronic representation of a Ret binding compound or a test compound in the binding site can be included, e.g., a compound of Formula I.

Likewise, in a related aspect, the invention concerns an electronic representation of a portion of Ret or Ret surrogate, which can be a binding site (which can be an active site) or catalytic domain, for example, a domain as described herein. A binding site or catalytic domain can be represented in various ways, e.g., as representations of atomic coordinates of residues around the binding site and/or as a binding site surface contour, and can include representations of the binding character of particular residues at the binding site, e.g., conserved residues. The binding site preferably includes no more than 1 heavy metal atom; a binding compound or test compound such as a compound including the core structure of Formula I may be present in the binding site; the binding site may be of a wild type, variant, mutant form, or surrogate; the electronic representation includes representations coordinates of conserved residues as in Table 2, 3, 4, or 5.

In yet another aspect, the structural and sequence information of Ret or Ret surrogate can be used in a homology model for another tyrosine kinase. It is helpful if high resolution structural information for Ret or Ret surrogate is used for such a model, e.g., at least 1.7, 1.5, 1.4, 1.3, or 1.2 Angstrom resolution.

In still another aspect, the invention provides an electronic representation of a modified Ret or Ret surrogate crystal structure, that includes an electronic representation of the atomic coordinates of a modified Ret based on the atomic coordinates of Table 2, 3, 4, or 5. In an exemplary embodiment, atomic coordinates of one of the listed tables can be modified by the replacement of atomic coordinates for a conserved residue with atomic coordinates for a different amino acid. Modifications can include substitutions, deletions (e.g., C-terminal and/or N-terminal deletions), insertions (internal, C-terminal, and/or N-terminal) and/or side chain modifications.

In another aspect, the Ret or Ret surrogate structural information provides a method for developing useful biological agents based on Ret, by analyzing a Ret or Ret surrogate structure to identify at least one sub-structure for forming the biological agent. Such sub-structures can include epitopes for antibody formation, and the method includes developing antibodies against the epitopes, e.g., by injecting an epitope presenting composition in a mammal such as a rabbit, guinea pig, pig, goat, or horse. The sub-structure can also include a mutation site at which mutation is expected to or is known to alter the activity of Ret, and the method includes creating a mutation at that site. Still further, the sub-structure can include an attachment point for attaching a separate moiety, for example, a peptide, a polypeptide, a solid phase material (e.g., beads, gels, chromatographic media, slides, chips, plates, and well surfaces), a linker, and a label (e.g., a direct label such as a fluorophore or an indirect label, such as biotin or other member of a specific binding pair). The method can include attaching the separate moiety.

In another aspect, the invention provides a method for identifying potential Ret binding compounds by fitting at least one electronic representation of a compound in an electronic representation of the Ret or Ret surrogate binding site. The representation of the binding site may be part of an electronic representation of a larger portion(s) or all of a Ret or Ret surrogate molecule or may be a representation of only the catalytic domain or of the binding site or active site. The electronic representation may be as described above or otherwise described herein. For Ret and Ret surrogates the electronic representation includes representations of coordinates according to Table 2, 3, 4, or 5.

In particular embodiments, the method involves fitting a computer representation of a compound from a computer database with a computer representation of the active site of the kinase, and involves removing a computer representation of a compound complexed with the kinase molecule and identifying compounds that best fit the active site based on favorable geometric fit and energetically favorable complementary interactions as potential binding compounds. In particular embodiments, the compound is a known Ret inhibitor, e.g., as described in a reference cited herein, or a derivative thereof.

In other embodiments, the method involves modifying a computer representation of a compound complexed with the kinase molecule, by the deletion or addition or both of one or more chemical groups; fitting a computer representation of a compound from a computer database with a computer representation of the active site of the kinase molecule; and identifying compounds that best fit the active site based on favorable geometric fit and energetically favorable complementary interactions as potential binding compounds.

In still other embodiments, the method involves removing a computer representation of a compound complexed with the kinase, and searching a database for compounds having structural similarity to the complexed compound using a compound searching computer program or replacing portions of the complexed compound with similar chemical structures using a compound construction computer program.

Fitting a compound can include determining whether a compound will interact with one or more conserved active site residues for the kinase. Compounds selected for fitting or that are complexed with the kinase can, for example, be a known Ret inhibitor compound, or a compound including the core structure of such compound.

In another aspect, the invention concerns a method for attaching a Ret binding compound to an attachment component, as well as a method for identifying attachment sites on a Ret binding compound. The method involves identifying energetically allowed sites for attachment of an attachment component for the binding compound bound to a binding site of Ret; and attaching the compound or a derivative thereof to the attachment component at the energetically allowed site.

Attachment components can include, for example, linkers (including traceless linkers) for attachment to a solid phase or to another molecule or other moiety. Such attachment can be formed by synthesizing the compound or derivative on the linker attached to a solid phase medium e.g., in a combinatorial synthesis in a plurality of compound. Likewise, the attachment to a solid phase medium can provide an affinity medium (e.g., for affinity chromatography).

The attachment component can also include a label, which can be a directly detectable label such as a fluorophore, or an indirectly detectable such as a member of a specific binding pair, e.g., biotin.

The ability to identify energetically allowed sites on a Ret binding compound, also, in a related aspect, provides modified binding compounds that have linkers attached, preferably at an energetically allowed site for binding of the modified compound to Ret. The linker can be attached to an attachment component as described above.

Another aspect concerns a modified Ret polypeptide that includes a modification that makes the modified Ret more similar than native Ret to another tyrosine kinase, and can also include other mutations or other modifications. In various embodiments, the polypeptide includes a full-length Ret polypeptide, includes a modified Ret binding site, includes at least 20, 30, 40, 50, 60, 70, or 80 contiguous amino acid residues derived from Ret including a conserved site.

Still another aspect of the invention concerns a method for developing a ligand for Ret that includes conserved residues matching any one, 2, 3, 4, 5, or 6 of conserved Ret active site residues respectively, by determining whether a compound binds to Ret and interacts with such active site residues in a Ret or Ret surrogate crystal or a Ret binding model having coordinates as in Table 2, 3, 4, or 5. The method can also include determining whether the compound modulates the activity of the kinase. Preferably the kinase has at least 50, 55, 60, or 70% identity over an equal length kinase domain segment.

In particular embodiments, the determining includes computer fitting the compound in a binding site of the kinase and/or the method includes forming a co-crystal of the kinase and the compound. Such co-crystals can be used for determining the binding orientation of the compound with the kinase and/or provide structural information on the kinase, e.g., on the binding site and interacting amino acid residues. Such binding orientation and/or other structural information can be accomplished using X-ray crystallography.

The invention also provides compounds that bind to and/or modulate (e.g., inhibit) Ret activity e.g., compounds identified by the methods described herein. Accordingly, in aspects and embodiments involving Ret binding compounds, molecular scaffolds, and ligands or modulators, the compound is a weak binding compound; a moderate binding compound; a strong binding compound; the compound interacts with one or more conserved active site residues in the kinase; the compound is a small molecule; the compound binds to a plurality of different kinases (e.g., at least 2, 3, 4, 5, 7, 10, or more different kinases). In particular, the invention concerns compounds identified or selected using the methods described herein, or compounds of Formula I.

In the various aspects described above that involve atomic coordinates for Ret binding site or Ret surrogate in connection with binding compounds, the coordinates provided in Tables 2, 3, 4, or 5 can be used. Those coordinates can then be adjusted using conventional modeling methods to fit compounds having structures different from the compounds identified herein, and can thus be used for development of Ret modulators different from currently described Ret modulators.

Another aspect concerns a FGFR-based homology model for Ret, that includes an atomic coordinate set derived by replacing FGFR amino acids with corresponding Ret residues. Examples include Ret surrogates 1 and 2 described herein. Additional embodiments can be constructed by replacing other and/or additional residues, e.g., substituting a Ret binding site sequence.

Still another aspect concerns a method for modeling binding of a compound in Ret kinase binding site, by modeling binding of such compound in binding site of Ret or a Ret surrogate, e.g., as described herein. Such compounds can be compounds of Formula I.

Another aspect concerns a Ret surrogate protein that includes a FGFR kinase domain sequence modified by the substitution of at least 4 binding site amino acid residues to amino acids present at the corresponding sites in Ret. In particular embodiments, the Ret surrogate protein is Ret surrogate 1 or 2, or includes a Ret binding site sequence. A related aspect concerns an isolated or purified nucleic acid sequence that includes a sequence encoding a Ret surrogate protein.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the particular molecule constitutes a significantly greater proportion of the biomolecules in a composition than in a prior composition, e.g., in a cell culture. The greater proportion can be 2-fold, 5-fold, 10-fold or more greater.

Additional aspects and embodiments will be apparent from the following Detailed Description and from the claims.

DETAILED DESCRIPTION OF THE PREFERRED EMBODIMENTS

Figure 1:
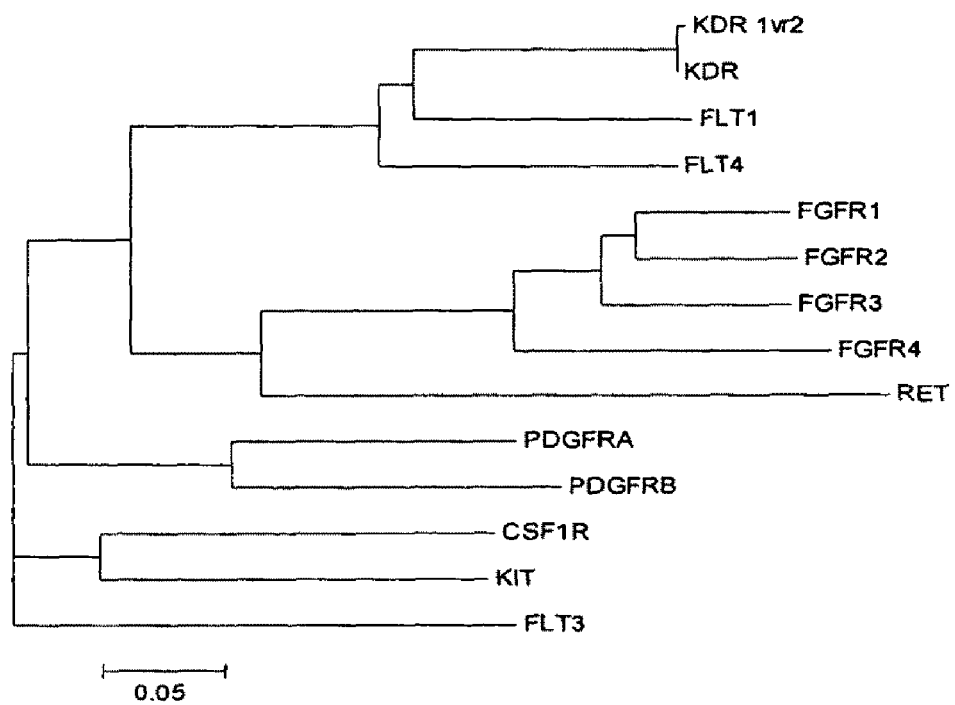
FIG. 1 shows a partial kinase family tree showing the relationship of the FGFR group and Ret.

The Tables will first be briefly described.

Table 1 provides the structures, molecular weights, and names of a set of exemplary compounds of Formula I active on Ret, and having an $IC_{50}$ of equal to or less than 10.

Table 2 provides atomic coordinates for Ret kinase domain co-crystallized with an exemplary compound of Formula I. The exemplary binding compound has the following structure:

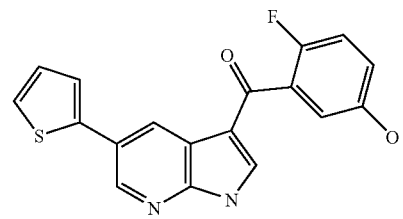

In this table, the various columns have the following content, beginning with the left-most column:

ATOM: Refers to the relevant moiety for the table row.

Atom number: Refers to the arbitrary atom number designation within the coordinate table.

Atom Name Identifier for the atom present at the particular coordinates.

Chain ID: Chain ID refers to one monomer of the protein in the crystal, e.g., chain "A", or to other compound present in the crystal, e.g., HOH for water, and L for a ligand or binding compound. Multiple copies of the protein monomers will have different chain Ids.

Residue Number The amino acid residue number in the chain.

X, Y, Z: Respectively are the X, Y, and Z coordinate values.

Occupancy: Describes the fraction of time the atom is observed in the crystal. For example, occupancy=1 means that the atom is present all the time; occupancy=0.5 indicates that the atom is present in the location 50% of the time.

B-factor: A measure of the thermal motion of the atom.

Element: Identifier for the element.

Table 3 provides atomic coordinates for Ret surrogate 2 co-crystallized with an exemplary compound of Formula I (Compound 68: 5-Thiophen-3-yl-1H-pyrrolo[2,3-b]pyridine).

Table 4 provides atomic coordinate data for Ret surrogate 2 phosphodiesterase domain together with an exemplary compound of Formula I (Compound 14: 3-(3-Methoxy-benzyl)-5-thiophen-3-yl-1H-pyrrolo[2,3-b]pyridine). Entries are as for Table 2.

Table 5 provides atomic coordinate data for Ret surrogate 2 phosphodiesterase domain together with an exemplary compound of Formula I (Compound 28: (3-Methoxy-phenyl)-(1H-pyrrolo[2,3-b]pyridin-3-yl)-methanone). Entries are as for Table 2.

I. General

The present invention concerns compounds of Formula I that are inhibitors of Ret, and the use of models of the binding site of Ret, structural information, and related compositions for developing improved compounds with those structures that modulate Ret activity.

A number of articles have indicated that different Ret inhibitors have been identified. For example, inhibition of Ret was studied to revert the transformed phenotype of transfected NIH3T3 and TPC-1 papillary thyroid carcinoma cells. Treatment of the Ret transformed NIH3T3 with the tyrosine kinase inhibitor herbimycin A reverted the cellular phenotype to a more untransformed flat morphology. Also the intracellular Ret kinase activity was decreased by incubation with the inhibitor (Taniguchi M, et al. 1993).

Likewise, the tyrosine kinase inhibitor K-252b inhibited the normal functioning of Ret in GDNF-induced differentiation in DAergic neuron cultures (Pong K, et al., 1997).

A hammerhead ribozyme-mediated specific for a prevalent mutation in MEN2A reverted the transformant phenotype of Ret transformed NIH3T3 in which the ribozyme was expressed (Parthasarathy R, et al. 1999).

Inhibition of transforming activity of the ret/ptc1 oncoprotein by a 2-indolinone derivative has been described. Lanzi C, et al., 2000.

An MTC cell line (TT cells, with RetC634 mutant) cultured in RPMI medium was exposed to varying concentrations of STI571, genistein, or allyl-geldanamycin inhibiting cell growth. Cohen M S, Hussain H B. Moley J F.

A group of indolinone compounds was described as c-Ret inhibitors in Clary, U.S. Pat. No. 6,235,769, entitled METHODS OF PREVENTING AND TREATING NEUROLOGICAL DISORDERS WITH COMPOUNDS THAT MODULATE THE FUNCTION OF THE C-RET RECEPTOR PROTEIN TYROSINE KINASE, which is incorporated herein by reference in its entirety.

ZD6474, VEGF inhibitor from Astra Zeneca was stated to inhibit Ret in cells and in vitro. Carlomagno, F. et al. 2002

In addition, the Ret kinase is closely related to the family of FGFR TK receptors with over 50% identity in the catalytic domain (see FIG. 1 for partial kinase family tree showing relationship of FGFR group and Ret).

Thus, the availability of inhibitors for kinases related to Ret like FGFR, PDGF, FLT and KDR can be useful as reference compounds and in the design of specific inhibitors. Moreover, the FGFR1 kinase domain has been co-crystallized with oxoindole VEGF inhibitor compounds. This information and the Ret homology model based on the FGFR-derived Ret surrogate structure can be used in the design of potent Ret inhibitors, e.g., in methods described herein.

Exemplary Diseases Associated with Ret.

Normal Ret function: The c-Ret receptor functions in the signaling pathways that control the differentiation and morphogenesis of cells derived from the neural crest tissue. The ligands controlling these processes are members of the GDNF (Glial cell derived neurotrophic factor) family that act through the Ret receptor via a GPI-anchored co-receptor subunit termed GFR☐1. Ret initiates many of the same signal transduction pathways activated by other receptor tyrosine kinases including the Ras/Raf and PI3K pathways.

Mutations in the RET gene are associated with the disorders multiple endocrine neoplasia, type IIA (MEN2A), multiple endocrine neoplasia, type BB (MEN2B), Hirschsprung disease (HSCR; aganglionic megacolon), and medullary thyroid carcinoma (MTC). A variety of point mutations and chromosomal rearrangements are identified in the c-Ret kinase and result in largely two phenotypes (OMIM database with genetic mutations)

Loss of function mutations in c-Ret lead in humans to developmental failure of enteric neurons (Hirschsprung's disease HSCR). This syndrome is an autosomal dominant complex developmental disorder; individuals with functional null mutations present with mental retardation, delayed motor development, epilepsy, and a wide spectrum of clinically heterogeneous features suggestive of neurocristopathies at the cephalic, cardiac, and vagal levels (Hirschprung's OMIM record). Hirschsprung disease or aganglionic megacolon is a congenital disorder characterized by absence of enteric ganglia along a variable length of the intestine.

Hereditary and spontaneous mutations that activate the Ret kinase lead to several types of cancers, including multiple endocrine neoplasias type 2A and 2B (MEN2A and MEN2B), familial medullary thyroid carcinomas (FMTC), and papillary thyroid carcinomas (PTC). Subsets of mutations associate with each of these cancer types. Missense mutations in one of five cysteines of the Ret extracellular domain are present in nearly all cases of MEN2A and FMTC, and presumably constitutively activate Ret's tyrosine kinase activity by mimicking the effects of ligand binding to the extracellular domain. Most patients with MEN2B harbor mutations in codon 918 (Met->Thr) in the ATP binding pocket of intracellular tyrosine kinase domain. This mutation presumably activates the kinase and alters its substrate specificity.

PTC is the most prevalent endocrine malignancy, often associated with exposure to ionizing radiation. In PTC, chromosomal inversions or translocations cause the recombination of the intracellular tyrosine-kinase-encoding domain of Ret with the 5'-end of heterologous genes. The resulting chimeric sequences are called "RET/PTC" and exert oncogenic activity. RET/PTC1 (the H4-RET fusion) and RET/PTC3 (the RFG-RET fusion) are the most prevalent variants. RET/PTC3 has been particularly frequent in PTCs that have occurred after the Chernobyl accident and is associated with aggressive PTC variants.

Modulators of Ret function thus can be used against diseases such as those indicated above.

II. Ret Polypeptide and Ret Surrogate Structures

It was discovered that a soluble, crystallizable Ret kinase domain could be constructed. Nucleic acid sequences encoding such polypeptides were constructed and expressed as described in the examples.

In addition, to assist in developing Ret modulators, it may be useful to create and use protein surrogates, where such surrogates are related proteins (surrogate parents) that have been mutated to make them structurally more similar to Ret than the wild type protein. By doing this, a surrogate protein can be made that has advantageous handling characteristics, e.g., crystallization characteristics, of the surrogate parent, but has close structural similarity to Ret at the binding site. A surrogate parent is selected for which a structure is available and/or that can be readily crystallized. Mutation sites can be selected based on sequence alignment of Ret with the surrogate parent, and the selection can beneficially utilize the surrogate parent structure as a further guide on significant residues to make the surrogate structurally more similar to Ret. Useful mutations can include substitution of particular amino acid residues (e.g., replacing surrogate parent residues with corresponding Ret residues), as well as substitution of Ret sequences into the surrogate parent sequence.

In the present case, Ret kinase is closely related to the family of FGFR TK receptors with over 50% identity in the catalytic domain (see FIG. 1 for partial kinase family tree showing relationship of FGFR group and Ret). Therefore, FGFR1 was selected for use in creating Ret surrogates.

Two Ret surrogates (Ret surrogates 1 and 2) have been constructed, with 5 and 6 residue substitutions respectively. These Ret surrogates crystallize readily (both as apo proteins and as cocrystals with binding compounds) and give high quality atomic coordinate data.

Amino Acid Substitutions in Ret Surrogates 1 and 2

Five amino acids in FGFR1 were substituted to make Ret surrogate 1. PRO483 was substituted by THR, ALA488 by GLU, ASN568 by SER, GLU571 by GLY and ALA640 by SER. These five residues were substituted because they are in the ATP binding site as shown in the FGFR1 X-ray crystal structure. PRO483 and ALA488 are located in the P-loop that sits on the top of the binding site in FGFR1 structures. ASN568 and GLU571 are just after the hinge region in linear sequence and are located in the opening of the binding site. ALA640 is located just before the conserved DFG motif in linear sequence and sits at the bottom of the binding site.

An additional amino acid, MET535 in FGFR1 was substituted by LEU to make Ret surrogate 2. MET535 is in the conserved C a-helix in the small lobe. In three-dimensional structures of FGFR1, the side chain of this residue points to the cavity of the binding site.

Ret Surrogate Structure

The structure of Ret surrogate 1 is very similar to that of FGFR1. Its root mean square distance (RMSD) of C-alpha atoms to 1FGI (PDB code of one of the FGFR1 structures in Protein Data Bank, PDB) is 0.98 A°. In the structures of Ret surrogate 1, the P-loop was in good order and tended to be on the top of the binding site. This is in contrast to the FGFR1 structures in which the P-loop can be disordered, or bent down to the cavity of the binding site or stretch straight.

Crystalline Ret Surrogate

Crystalline Ret surrogates includes apoprotein crystals, derivative crystals and co-crystals. The native crystals generally comprise substantially pure polypeptides corresponding to Ret surrogate in crystalline form. Ret surrogate kinase domain crystals generally comprise substantially pure kinase domain in crystalline form. In connection with the development of inhibitors of Ret kinase function, it is advantageous to use Ret or Ret surrogate kinase domain respectively for structural determination, because use of the reduced sequence simplifies structure determination. To be useful for this purpose, the kinase domain should be active and/or retain native-type binding, thus indicating that the kinase domain takes on substantially normal 3D structure.

It is to be understood that the crystalline kinases and kinase domains of the invention are not limited to naturally occurring or native kinase. Indeed; the crystals of the invention include crystals of mutants of native kinases. Mutants of native kinases are obtained by replacing at least one amino acid residue in a native kinase with a different amino acid residue, or by adding or deleting amino acid residues within the native polypeptide or at the N- or C-terminus of the native polypeptide, and have substantially the same three-dimensional structure as the native kinase from which the mutant is derived.

By having substantially the same three-dimensional structure is meant having a set of atomic structure coordinates that have a root-mean-square deviation of less than or equal to about 2A when superimposed with the atomic structure coordinates of the native kinase from which the mutant is derived when at least about 50% to 100% of the Cα atoms of the native kinase domain are included in the superposition.

Amino acid substitutions, deletions and additions which do not significantly interfere with the three-dimensional structure of the kinase will depend, in part, on the region of the kinase where the substitution, addition or deletion occurs. In highly variable regions of the molecule, non-conservative substitutions as well as conservative substitutions may be tolerated without significantly disrupting the three-dimensional, structure of the molecule. In highly conserved regions, or regions containing significant secondary structure, conservative amino acid substitutions are preferred. Such conserved and variable regions can be identified by sequence alignment of Ret with other kinases, e.g., kinases in the FGFR kinase group.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

For Ret or Ret surrogate obtained in whole or in part by chemical synthesis, the selection of amino acids available for substitution or addition is not limited to the genetically encoded amino acids. Indeed, the mutants described herein may contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues to a native kinase in order to provide convenient cloning sites in cDNA encoding the polypeptide, to aid in purification of the polypeptide, and for crystallization of the polypeptide. Such substitutions, deletions and/or additions which do not substantially alter the three dimensional structure of the native kinase domain will be apparent to those of ordinary skill in the art.

It should be noted that the mutants contemplated herein need not all exhibit kinase activity. Indeed, amino acid substitutions, additions or deletions that interfere with the kinase activity but which do not significantly alter the three-dimensional structure of the domain are specifically contemplated by the invention. Such crystalline polypeptides, or the atomic structure coordinates obtained therefrom, can be used to identify compounds that bind to the native domain. These compounds can affect the activity of the native domain.

The derivative crystals of the invention can comprise a crystalline kinase polypeptide in covalent association with one or more heavy metal atoms. The polypeptide may correspond to a native or a mutated kinase. Heavy metal atoms useful for providing derivative crystals include, by way of example and not limitation, gold, mercury, selenium, etc.

The co-crystals of the invention generally comprise a crystalline kinase domain polypeptide in association with one or more compounds. The association may be covalent or non-covalent. Such compounds include, but are not limited to, cofactors, substrates, substrate analogues, inhibitors, allosteric effectors, etc.

III. Three Dimensional Structure Determination Using X-Ray Crystallography

X-ray crystallography is a method of solving the three dimensional structures of molecules. The structure of a molecule is calculated from X-ray diffraction patterns using a crystal as a diffraction grating. Three dimensional structures of protein molecules arise from crystals grown from a concentrated aqueous solution of that protein. The process of X-ray crystallography can include the following steps:

(a) synthesizing and isolating (or otherwise obtaining) a polypeptide;
(b) growing a crystal from an aqueous solution comprising the polypeptide with or without a modulator; and
(c) collecting X-ray diffraction patterns from the crystals, determining unit cell dimensions and symmetry, determining electron density, fitting the amino acid sequence of the polypeptide to the electron density, and refining the structure.

Production of Polypeptides

The native and mutated kinase polypeptides described herein may be chemically synthesized in whole or part using techniques that are well-known in the art (see, e.g., Creighton (1983) *Biopolymers* 22(1):49-58).

Alternatively, methods which are well known to those skilled in the art can be used to construct expression vectors containing the native or mutated kinase polypeptide coding sequence and appropriate transcriptional/translational control signals. These methods include in vitro recombinant DNA techniques, synthetic techniques and in vivo recombination/genetic recombination. See, for example, the techniques described in Maniatis, T (1989). *Molecular cloning: A laboratory Manual*. Cold Spring Harbor Laboratory, New York. Cold Spring Harbor Laboratory Press; and Ausubel, F. M. et al. (1994) *Current Protocols in Molecular Biology*. John Wiley & Sons, Secaucus, N.J.

A variety of host-expression vector systems may be utilized to express the kinase coding sequence. These include but are not limited to microorganisms such as bacteria transformed with recombinant bacteriophage DNA, plasmid DNA or cosmid DNA expression vectors containing the kinase domain coding sequence; yeast transformed with recombinant yeast expression vectors containing the kinase domain coding sequence; insect cell systems infected with recombinant virus expression vectors (e.g., baculovirus) containing the kinase domain coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the kinase domain coding sequence; or animal cell systems. The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the kinase domain DNA, SV40-, BPV- and EBV-based vectors may be used with an appropriate selectable marker.

Exemplary methods describing methods of DNA manipulation, vectors, various types of cells used, methods of incorporating the vectors into the cells, expression techniques, protein purification and isolation methods, and protein concentration methods are disclosed in detail in PCT publication WO 96/18738. This publication is incorporated herein by reference in its entirety, including any drawings. Those skilled in the art will appreciate that such descriptions are applicable to the present invention and can be easily adapted to it.

Crystal Growth

Crystals are grown from an aqueous solution containing the purified and concentrated polypeptide by a variety of techniques. These techniques include batch, liquid, bridge, dialysis, vapor diffusion, and hanging drop methods. McPherson (1982) John Wiley, New York; McPherson (1990) *Eur. J. Biochem.* 189:1-23; Webber (1991) *Adv. Protein Chem.* 41:1-36, incorporated by reference herein in their entireties, including all figures, tables, and drawings.

The native crystals of the invention are, in general, grown by adding precipitants to the concentrated solution of the polypeptide. The precipitants are added at a concentration just below that necessary to precipitate the protein. Water is removed by controlled evaporation to produce precipitating conditions, which are maintained until crystal growth ceases.

For crystals of the invention, exemplary crystallization conditions are described in the Examples. Those of ordinary skill in the art will recognize that the exemplary crystallization conditions can be varied. Such variations may be used alone or in combination. In addition, other crystallization conditions may be found, e.g., by using crystallization screening plates to identify such other conditions. Those alternate conditions can then be optimized if needed to provide larger or better quality crystals.

Derivative crystals of the invention can be obtained by soaking native crystals in mother liquor containing salts of heavy metal atoms. It has been found that soaking a native crystal in a solution containing about 0.1 mM to about 5 mM thimerosal, 4-chloromeruribenzoic acid or KAu(CN)$_2$ for about 2 hr to about 72 hr provides derivative crystals suitable for use as isomorphous replacements in determining the X-ray crystal structure.

Co-crystals of the invention can be obtained by soaking a native crystal in mother liquor containing compound that binds the kinase, or can be obtained by co-crystallizing the kinase polypeptide in the presence of a binding compound.

Generally, co-crystallization of kinase and binding compound can be accomplished using conditions identified for crystallizing the corresponding kinase without binding compound. It is advantageous if a plurality of different crystallization conditions have been identified for the kinase, and these can be tested to determine which condition gives the best co-crystals. It may also be benficial to optimize the conditions for co-crystallization. Alternatively, new crystallization conditions can be determined for obtaining co-crystals, e.g., by screening for crystallization and then optimizing those conditions. Exemplary co-crystallization conditions are provided in the Examples.

Determining Unit Cell Dimensions and the Three Dimensional Structure of a Polypeptide or Polypeptide Complex Once the crystal is grown, it can be placed in a glass capillary tube or other mounting device and mounted onto a holding device connected to an X-ray generator and an X-ray detection device. Collection of X-ray diffraction patterns are well documented by those in the art. See, e.g., Ducruix and Geige, (1992), IRL Press, Oxford, England, and references cited therein. A beam of X-rays enters the crystal and then diffracts from the crystal. An X-ray detection device can be utilized to record the diffraction patterns emanating from the crystal. Although the X-ray detection device on older models of these instruments is a piece of film, modern instruments digitally record X-ray diffraction scattering. X-ray sources can be of various types, but advantageously, a high intensity source is used, e.g., a synchrotron beam source.

Methods for obtaining the three dimensional structure of the crystalline form of a peptide molecule or molecule complex are well known in the art. See, e.g., Ducruix and Geige, (1992), IRL Press, Oxford, England, and references cited therein. The following are steps in the process of determining the three dimensional structure of a molecule or complex from X-ray diffraction data.

After the X-ray diffraction patterns are collected from the crystal, the unit cell dimensions and orientation in the crystal can be determined. They can be determined from the spacing between the diffraction emissions as well as the patterns made from these emissions. The unit cell dimensions are characterized in three dimensions in units of Angstroms (one Å=$10^{-10}$ meters) and by angles at each vertices. The symmetry of the unit cell in the crystals is also characterized at this stage. The symmetry of the unit cell in the crystal simplifies the complexity of the collected data by identifying repeating patterns. Application of the symmetry and dimensions of the unit cell is described below.

Each diffraction pattern emission is characterized as a vector and the data collected at this stage of the method determines the amplitude of each vector. The phases of the vectors can be determined using multiple techniques. In one method, heavy atoms can be soaked into a crystal, a method called isomorphous replacement, and the phases of the vectors can be determined by using these heavy atoms as reference points in the X-ray analysis. (Otwinowski, (1991), Daresbury, United Kingdom, 80-86). The isomorphous replacement method usually utilizes more than one heavy atom derivative.

In another method, the amplitudes and phases of vectors from a crystalline polypeptide with an already determined structure can be applied to the amplitudes of the vectors from a crystalline polypeptide of unknown structure and consequently determine the phases of these vectors. This second method is known as molecular replacement and the protein structure which is used as a reference must have a closely related structure to the protein of interest. (Naraza (1994) *Proteins* 11:281-296). Thus, the vector information from a kinase of known structure, such as those reported herein, are useful for the molecular replacement analysis of another kinase with unknown structure.

Once the phases of the vectors describing the unit cell of a crystal are determined, the vector amplitudes and phases, unit cell dimensions, and unit cell symmetry can be used as terms in a Fourier transform function. The Fourier transform function calculates the electron density in the unit cell from these measurements. The electron density that describes one of the molecules or one of the molecule complexes in the unit cell can be referred to as an electron density map. The amino acid structures of the sequence or the molecular structures of compounds complexed with the crystalline polypeptide may then be fitted to the electron density using a variety of computer programs. This step of the process is sometimes referred to as model building and can be accomplished by using computer programs such as Turbo/FRODO or "O". (Jones (1985) *Methods in Enzymology* 115:157-171).

A theoretical electron density map can then be calculated from the amino acid structures fit to the experimentally determined electron density. The theoretical and experimental electron density maps can be compared to one another and the agreement between these two maps can be described by a parameter called an R-factor. A low value for an R-factor describes a high degree of overlapping electron density between a theoretical and experimental electron density map.

The R-factor is then minimized by using computer programs that refine the theoretical electron density map. A computer program such as X-PLOR can be used for model refinement by those skilled in the art. (Brunger (1992) *Nature* 355:472-475.) Refinement may be achieved in an iterative process. A first step can entail altering the conformation of atoms defined in an electron density map. The conformations of the atoms can be altered by simulating a rise in temperature, which will increase the vibrational frequency of the bonds and modify positions of atoms in the structure. At a particular point in the atomic perturbation process, a force field, which typically defines interactions between atoms in terms of allowed bond angles and bond lengths, Van der Waals interactions, hydrogen bonds, ionic interactions, and hydrophobic interactions, can be applied to the system of atoms. Favorable interactions may be described in terms of free energy and the atoms can be moved over many iterations until a free energy minimum is achieved. The refinement process can be iterated until the R-factor reaches a minimum value.

The three dimensional structure of the molecule or molecule complex is described by atoms that fit the theoretical electron density characterized by a minimum R-value. A file can then be created for the three dimensional structure that defines each atom by coordinates in three dimensions. An example of such a structural coordinate file is shown in Table 2.

IV. Structures of Ret binding site and Ret surrogates

High-resolution three-dimensional structures and atomic structure coordinates of crystalline Ret kinase domain and Ret surrogate kinase domain co-complexed with exemplary binding compounds are described. The methods used to obtain the structure coordinates are provided in the examples. The atomic structure coordinates of crystalline Ret surrogate kinase domain co-crystallized with binding compounds are listed in Tables 2-5. Co-crystal coordinates can be used in the same way, e.g., in the various aspects described herein, as coordinates for the protein by itself, but can be advantageous because such co-crystals demonstrate or confirm the binding mode of binding compound, and can also include shifts of protein atoms in response to the presence of the binding compound.

Those having skill in the art will recognize that atomic structure coordinates as determined by X-ray crystallography are not without error. Thus, it is to be understood that generally any set of structure coordinates obtained for crystals of a kinase, whether native crystals, kinase domain crystals, derivative crystals or co-crystals, that have a root mean square deviation ("r.m.s.d.") of less than or equal to about 1.5 Å when superimposed, using backbone atoms (N, $C_\alpha$, C and 0), on the structure coordinates listed in a coordinate table herein are considered to be identical with the structure coordinates listed in that table when at least about 50% to 100% of the backbone atoms of the crystallized protein are included in the superposition.

V. Uses of the Crystals and Atomic Structure Coordinates

The crystals of the invention, and particularly the atomic structure coordinates obtained therefrom, have a wide variety of uses. For example, the crystals described herein can be used as a starting point in any of the methods of use for kinases known in the art or later developed. Such methods of use include, for example, identifying molecules that bind to the native or mutated catalytic domain of kinases. The crystals and structure coordinates are particularly useful for identifying ligands that modulate kinase activity as an approach towards developing new therapeutic agents. In particular, the crystals and structural information are useful in methods for ligand development utilizing molecular scaffolds.

The structure coordinates described herein can be used as phasing models for determining the crystal structures of additional kinases, as well as the structures of co-crystals of such kinases with ligands such as inhibitors, agonists, antagonists, and other molecules. The structure coordinates, as well as models of the three-dimensional structures obtained therefrom, can also be used to aid the elucidation of solution-based structures of native or mutated kinases, such as those obtained via NMR.

VI. Electronic Representations of Ret and Ret Surrogate Structures

Structural information of kinases or portions of kinases (e.g., kinase active sites) can be represented in many different ways. Particularly useful are electronic representations, as such representations allow rapid and convenient data manipulations and structural modifications. Electronic representations can be embedded in many different storage or memory media, frequently computer readable media. Examples include without limitations, computer random access memory (RAM), floppy disk, magnetic hard drive, magnetic tape (analog or digital), compact disk (CD), optical disk, CD-ROM, memory card, digital video disk (DVD), and others. The storage medium can be separate or part of a computer system. Such a computer system may be a dedicated, special purpose, or embedded system, such as a computer system that forms part of an X-ray crystallography system, or may be a general purpose computer (which may have data connection with other equipment such as a sensor device in an X-ray crystallographic system. In many cases, the information provided by such electronic representations can also be represented physically or visually in two or three dimensions, e.g., on paper, as a visual display (e.g., on a computer monitor as a two dimensional or pseudo-three dimensional image) or as a three dimensional physical model. Such physical representations can also be used, alone or in connection with electronic representations. Exemplary useful representations include, but are not limited to, the following:

Atomic Coordinate Representation

One type of representation is a list or table of atomic coordinates representing positions of particular atoms in a molecular structure, portions of a structure, or complex (e.g., a co-crystal). Such a representation may also include additional information, for example, information about occupancy of particular coordinates. One such atomic coordinate representation contains the coordinate information of Table 5 in electronic form.

Energy Surfac or Surface of Interaction Representation

Another representation is an energy surface representation, e.g., of an active site or other binding site, representing an energy surface for electronic and steric interactions. Such a representation may also include other features. An example is the inclusion of representation of a particular amino acid residue(s) or group(s) on a particular amino acid residue(s), e.g., a residue or group that can participate in H-bonding or ionic interaction. Such energy surface representations can be readily generated from atomic coordinate representations using any of a variety of available computer programs.

Structural Representation

Still another representation is a structural representation, i.e., a physical representation or an electronic representation of such a physical representation. Such a structural representation includes representations of relative positions of particular features of a molecule or complex, often with linkage between structural features. For example, a structure can be represented in which all atoms are linked; atoms other than hydrogen are linked; backbone atoms, with or without representation of sidechain atoms that could participate in significant electronic interaction, are linked; among others. However, not all features need to be linked. For example, for structural representations of portions of a molecule or complex, structural features significant for that feature may be represented (e.g., atoms of amino acid residues that can have significant binding interation with a ligand at a binding site. Those amino acid residues may not be linked with each other.

A structural representation can also be a schematic representation. For example, a schematic representation can represent secondary and/or tertiary structure in a schematic manner. Within such a schematic representation of a polypeptide, a particular amino acid residue(s) or group(s) on a residue(s) can be included, e.g., conserved residues in a binding site, and/or residue(s) or group(s) that may interact with binding compounds. Electronic structural representations can be generated, for example, from atomic coordinate information using computer programs designed for that function and/or by constructing an electronic representation with manual input based on interpretation of another form of structural information. Physical representations can be created, for example, by printing an image of a computer-generated image or by constructing a 3D model. An example of such a printed representation is the ribbon diagram presented in FIG. 2.

VII. Structure Determination for Kinases with Unknown Structure Using Structural Coordinates Structural coordinates, such as those set forth in Table 2, can be used to determine the three dimensional structures of kinases with unknown structure. The methods described below can apply structural coordinates of a polypeptide with known structure to another data set, such as an amino acid sequence, X-ray crystallographic diffraction data, or nuclear magnetic resonance (NMR) data. Preferred embodiments of the invention relate to determining the three dimensional structures of modified kinases, other native kinases, and related polypeptides.

Structures Using Amino Acid Homology

Homology modeling is a method of applying structural coordinates of a polypeptide of known structure to the amino acid sequence of a polypeptide of unknown structure. This method is accomplished using a computer representation of the three dimensional structure of a polypeptide or polypeptide complex, the computer representation of amino acid sequences of the polypeptides with known and unknown structures, and standard computer representations of the structures of amino acids. Homology modeling generally involves (a) aligning the amino acid sequences of the polypeptides with and without known structure; (b) transferring the coordinates of the conserved amino acids in the known structure to the corresponding amino acids of the polypeptide of unknown structure; refining the subsequent three dimensional structure; and (d) constructing structures of the rest of the polypeptide. One skilled in the art recognizes that conserved amino acids between two proteins can be determined from the sequence alignment step in step (a).

The above method is well known to those skilled in the art. (Greer (1985) Science 228:1055; Blundell et al. A (1988) Eur. J. Biochem. 172:513. An exemplary computer program that can be utilized for homology modeling by those skilled in the art is the Homology module in the Insight II modeling package distributed by Accelerys Inc.

Alignment of the amino acid sequence is accomplished by first placing the computer representation of the amino acid sequence of a polypeptide with known structure above the amino acid sequence of the polypeptide of unknown structure. Amino acids in the sequences are then compared and groups of amino acids that are homologous (e.g., amino acid side chains that are similar in chemical nature—aliphatic, aromatic, polar, or charged) are grouped together. This method will detect conserved regions of the polypeptides and account for amino acid insertions or deletions. Such alignment and/or can also be performed fully electronically using sequence alignment and analyses software.

Once the amino acid sequences of the polypeptides with known and unknown structures are aligned, the structures of the conserved amino acids in the computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure.

The structures of amino acids located in non-conserved regions are to be assigned manually by either using standard peptide geometries or molecular simulation techniques, such as molecular dynamics. The final step in the process is accomplished by refining the entire structure using molecular dynamics and/or energy minimization. The homology modeling method is well known to those skilled in the art and has been practiced using different protein molecules. For example, the three dimensional structure of the polypeptide corresponding to the catalytic domain of a serine/threonine protein kinase, myosin light chain protein kinase, was homology modeled from the cAMP-dependent protein kinase catalytic subunit. (Knighton et al. (1992) Science 258:130-135.)

Structures Using Molecular Replacement

Molecular replacement is a method of applying the X-ray diffraction data of a polypeptide of known structure to the X-ray diffraction data of a polypeptide of unknown sequence. This method can be utilized to define the phases describing the X-ray diffraction data of a polypeptide of unknown structure when only the amplitudes are known. X-PLOR is a commonly utilized computer software package used for molecular replacement. Brünger (1992) Nature 355:472-475. AMORE is another program used for molecular replacement. Navaza (1994) Acta Crystallogr. A50:157-163. Preferably, the resulting structure does not exhibit a root-mean-square deviation of More than 3 Å.

A goal of molecular replacement is to align the positions of atoms in the unit cell by matching electron diffraction data from two crystals. A program such as X-PLOR can involve four steps. A first step can be to determine the number of molecules in the unit cell and define the angles between them. A second step can involve rotating the diffraction data to define the orientation of the molecules in the unit cell. A third step can be to translate the electron density in three dimensions to correctly position the molecules in the unit cell. Once the amplitudes and phases of the X-ray diffraction data is determined, an R-factor can be calculated by comparing electron diffraction maps calculated experimentally from the reference data set and calculated from the new data set. An R-factor between 30-50% indicates that the orientations of the atoms in the unit cell are reasonably determined by this method. A fourth step in the process can be to decrease the R-factor to roughly 20% by refining the new electron density map using iterative refinement techniques described herein and known to those or ordinary skill in the art.

Structures Using NMR Data

Structural coordinates of a polypeptide or polypeptide complex derived from X-ray crystallographic techniques can be applied towards the elucidation of three dimensional structures of polypeptides from nuclear magnetic resonance (NMR) data. This method is used by those skilled in the art. (Wuthrich, (1986), John Wiley and Sons, New York: 176-199; Pflugrath et al. (1986) J. Mol. Biol. 189:383-386; Kline et al. (1986) J. Mol. Biol. 189:377-382.) While the secondary structure of a polypeptide is often readily determined by utilizing two-dimensional NMR data, the spatial connections between individual pieces of secondary structure are not as readily determinable. The coordinates defining a three-dimensional structure of a polypeptide derived from X-ray crystallographic techniques can guide the NMR spectroscopist to an understanding of these spatial interactions between secondary structural elements in a polypeptide of related structure.

The knowledge of spatial interactions between secondary structural elements can greatly simplify Nuclear Overhauser Effect (NOE) data from two-dimensional NMR experiments. Additionally, applying the crystallographic coordinates after the determination of secondary structure by NMR techniques only simplifies the assignment of NOEs relating to particular amino acids in the polypeptide sequence and does not greatly bias the NMR analysis of polypeptide structure. Conversely, using the crystallographic coordinates to simplify NOE data while determining secondary structure of the polypeptide would bias the NMR analysis of protein structure.

VIII. Structure-Based Design of Modulators of Ret Function Utilizing Structural Coordinates Structure-based modulator design and identification methods are powerful techniques that can involve searches of computer databases containing a wide variety of potential modulators and chemical functional groups. The computerized design and identification of modulators is useful as the computer databases contain more compounds than the chemical libraries, often by an order of magnitude. For reviews of structure-based drug design and identification (see Kuntz et al. (1994), *Acc. Chem. Res.* 27:117; Guida (1994) *Current Opinion in Struc. Biol.* 4: 777; Colman (1994) *Current Opinion in Struc. Biol.* 4: 868).

The three dimensional structure of a polypeptide defined by structural coordinates can be utilized by these design methods, for example, the structural coordinates of Table 2. In addition, the three dimensional structures of kinases determined by the homology, molecular replacement, and NMR techniques described herein can also be applied to modulator design and identification methods.

For identifying modulators, structural information for a native kinase, in particular, structural information for the active site of the kinase, can be used. However, it may be advantageous to utilize structural information from one or more co-crystals of the kinase with one or more binding compounds. It can also be advantageous if the binding compound has a structural core in common with test compounds.

Design by Searching Molecular Data Bases

One method of rational design searches for modulators by docking the computer representations of compounds from a database of molecules. Publicly available databases include, for example:
  a) ACD from Molecular Designs Limited
  b) NCI from National Cancer Institute
  c) CCDC from Cambridge Crystallographic Data Center
  d) CAST from Chemical Abstract Service
  e) Derwent from Derwent Information Limited
  f) Maybridge from Maybridge Chemical Company LTD
  g) Aldrich from Aldrich Chemical Company
  h) Directory of Natural Products from Chapman & Hall One such data base (ACD distributed by Molecular Designs Limited Information Systems) contains compounds that are synthetically derived or are natural products. Methods available to those skilled in the art can convert a data set represented in two dimensions to one represented in three dimensions. These methods are enabled by such computer programs as CONCORD from Tripos Associates or DE-Converter from Molecular Simulations Limited.

Multiple methods of structure-based modulator design are known to those in the art. (Kuntz et al., (1982), *J. Mol. Biol.* 162: 269; Kuntz et al., (1994), *Acc. Chem. Res.* 27: 117; Meng et al., (1992), *J. Compt. Chem.* 13: 505; Bohm, (1994), *J. Comp. Aided Molec. Design* 8: 623.)

A computer program widely utilized by those skilled in the art of rational modulator design is DOCK from the University of California in San Francisco. The general methods utilized by this computer program and programs like it are described in three applications below. More detailed information regarding some of these techniques can be found in the Accelerys User Guide, 1995. A typical computer program used for this purpose can perform a processes comprising the following steps or functions:
  (a) remove the existing compound from the protein;
  (b) dock the structure of another compound into the active-site using the computer program (such as DOCK) or by interactively moving the compound into the active-site;
  (c) characterize the space between the compound and the active-site atoms;
  (d) search libraries for molecular fragments which (i) can fit into the empty space between the compound and the active-site, and (ii) can be linked to the compound; and
  (e) link the fragments found above to the compound and evaluate the new modified compound.

Part (c) refers to characterizing the geometry and the complementary interactions formed between the atoms of the active site and the compounds. A favorable geometric fit is attained when a significant surface area is shared between the compound and active-site atoms without forming unfavorable steric interactions. One skilled in the art would note that the method can be performed by skipping parts (d) and (e) and screening a database of many compounds.

Structure-based design and identification of modulators of kinase function can be used in conjunction with assay screening. As large computer databases of compounds (around 10,000 compounds) can be searched in a matter of hours or even less, the computer-based method can narrow the compounds tested as potential modulators of kinase function in biochemical or cellular assays.

The above descriptions of structure-based modulator design are not all encompassing and other methods are reported in the literature and can be used, e.g.:
  (1) CAVEAT: Bartlett et al., (1989), in Chemical and Biological Problems in Molecular Recognition, Roberts, S. M.; Ley, S. V.; Campbell, M. M. eds.; *Royal Society of Chemistry: Cambridge, pp.* 182-196.
  (2) FLOG: Miller et al., (1994), *J. Comp. Aided Molec. Design* 8:153.
  (3) PRO Modulator: Clark et al., (1995), *J. Comp. Aided Molec. Design* 9:13.
  (4) MCSS: Miranker and Karplus, (1991), *Proteins: Structure, Function, and Genetics* 11:29.
  (5) AUTODOCK: Goodsell and Olson, (1990), *Proteins: Structure, Function, and Genetics* 8:195.
  (6) GRID: Goodford, (1985), *J. Med. Chem.* 28:849.

Design by Modifying Compounds in Complex with Ret or Ret Surrogate

Another way of identifying compounds as potential modulators is to modify an existing modulator in the polypeptide active site. For example, the computer representation of modulators can be modified within the computer representation of a Ret or Ret surrogate active site. Detailed instructions for this technique can be found, for example, in the Accelerys User Manual, 1995 in LUDI. The computer representation of the modulator is typically modified by the deletion of a chemical group or groups or by the addition of a chemical group or groups.

Upon each modification to the compound, the atoms of the modified compound and active site can be shifted in conformation and the distance between the modulator and the active-site atoms may be scored along with any complementary interactions formed between the two molecules. Scoring can be complete when a favorable geometric fit and favorable complementary interactions are attained. Compounds that have favorable scores are potential modulators.

Design by Modifying the Structure of Compounds that Bind Ret or Ret Surrogate

A third method of structure-based modulator design is to screen compounds designed by a modulator building or modulator searching computer program. Examples of these types of programs can be found in the Molecular Simulations Package, Catalyst. Descriptions for using this program are documented in the Molecular Simulations User Guide (1995). Other computer programs used in this application are ISIS/HOST, ISIS/BASE, ISIS/DRAW) from Molecular Designs Limited and UNITY from Tripos Associates.

These programs can be operated on the structure of a compound that has been removed from the active site of the three dimensional structure of a compound-kinase complex. Operating the program on such a compound is preferable since it is in a biologically active conformation.

A modulator construction computer program is a computer program that may be used to replace computer representations of chemical groups in a compound complexed with a kinase or other biomolecule with groups from a computer database. A modulator searching computer program is a computer program that may be used to search computer representations of compounds from a computer data base that have similar three dimensional structures and similar chemical groups as compound bound to a particular biomolecule.

A typical program can operate by using the following general steps:
 (a) map the compounds by chemical features such as by hydrogen bond donors or acceptors, hydrophobic/lipophilic sites, positively ionizable sites, or negatively ionizable sites;
 (b) add geometric constraints to the mapped features; and
 (c) search databases with the model generated in (b).

Those skilled in the art also recognize that not all of the possible chemical features of the compound need be present in the model of (b). One can use any subset of the model to generate different models for data base searches.

Modulator Design Using Molecular Scaffolds

The present invention can also advantageously utilize methods for designing compounds, designated as molecular scaffolds, that can act broadly across families of molecules and/or for using a molecular scaffold to design ligands that target individual or multiple members of those families. Such design using molecular scaffolds is described in Hirth and Milburn, U.S. patent application Ser. No. 10/377,268, which is incorporated herein by reference in its entirety. Such design and development using molecular scaffolds is described, in part, below.

In preferred embodiments, the molecules can be proteins and a set of chemical compounds can be assembled that have properties such that they are 1) chemically designed to act on certain protein families and/or 2) behave more like molecular scaffolds, meaning that they have chemical substructures that make them specific for binding to one or more proteins in a family of interest. Alternatively, molecular scaffolds can be designed that are preferentially active on an individual target molecule.

Useful chemical properties of molecular scaffolds can include one or more of the following characteristics, but are not limited thereto: an average molecular weight below about 350 daltons, or between from about 150 to about 350 daltons, or from about 150 to about 300 daltons; having a clogP below 3; a number of rotatable bonds of less than 4; a number of hydrogen bond donors and acceptors below 5 or below 4; a polar surface area of less than 50 Å$^2$; binding at protein binding sites in an orientation so that chemical substituents from a combinatorial library that are attached to the scaffold can be projected into pockets in the protein binding site; and possessing chemically tractable structures at its substituent attachment points that can be modified, thereby enabling rapid library construction.

By "clog P" is meant the calculated log P of a compound, "P" referring to the partition coefficient between octanol and water.

The term "Molecular Polar Surface Area (PSA)" refers to the sum of surface contributions of polar atoms (usually oxygens, nitrogens and attached hydrogens) in a molecule. The polar surface area has been shown to correlate well with drug transport properties, such as intestinal absorption, or blood-brain barrier penetration.

Additional useful chemical properties of distinct compounds for inclusion in a combinatorial library include the ability to attach chemical moieties to the compound that will not interfere with binding of the compound to at least one protein of interest, and that will impart desirable properties to the library members, for example, causing the library members to be actively transported to cells and/or organs of interest, or the ability to attach to a device such as a chromatography column (e.g., a streptavidin column through a molecule such as biotin) for uses such as tissue and proteomics profiling purposes.

A person of ordinary skill in the art will realize other properties that can be desirable for the scaffold or library members to have depending on the particular requirements of the use, and that compounds with these properties can also be sought and identified in like manner. Methods of selecting compounds for assay are known to those of ordinary skill in the art, for example, methods and compounds described in U.S. Pat. Nos. 6,288,234, 6,090,912, 5,840,485, each of which is hereby incorporated by reference in its entirety, including all charts and drawings.

In various embodiments, the present invention provides methods of designing ligands that bind to a plurality of members of a molecular family, where the ligands contain a common molecular scaffold. Thus, a compound set can be assayed for binding to a plurality of members of a molecular family, e.g., a protein family. One or more compounds that bind to a plurality of family members can be identified as molecular scaffolds. When the orientation of the scaffold at the binding site of the target molecules has been determined and chemically tractable structures have been identified, a set of ligands can be synthesized starting with one or a few molecular scaffolds to arrive at a plurality of ligands, wherein each ligand binds to a separate target molecule of the molecular family with altered or changed binding affinity or binding specificity relative to the scaffold. Thus, a plurality of drug lead molecules can be designed to preferentially target individual members of a molecular family based on the same molecular scaffold, and act on them in a specific manner.

IX. Binding Assays

The methods of the present invention can involve assays that are able to detect the binding of compounds to a target molecule. Such binding is at a statistically significant level, preferably with a confidence level of at least 90%, more preferably at least 95, 97, 98, 99% or greater confidence level that the assay signal represents binding to the target molecule, i.e., is distinguished from background. Preferably controls are used to distinguish target binding from non-specific binding. The assays of the present invention can also include assaying compounds for low affinity binding to the target molecule. A large variety of assays indicative of binding are known for different target types and can be used for this invention. Compounds that act broadly across protein families are not likely to have a high affinity against individual targets, due to the broad nature of their binding. Thus, assays described herein allow for the identification of compounds that bind with low affinity, very low affinity, and extremely low affinity. Therefore, potency (or binding affinity) is not the primary, nor even the most important, indicia of identification of a potentially useful binding compound. Rather, even those compounds that bind with low affinity, very low affinity, or extremely low affinity can be considered as molecular scaffolds that can continue to the next phase of the ligand design process.

By binding with "low affinity" is meant binding to the target molecule with a dissociation constant ($k_d$) of greater than 1 μM under standard conditions. By binding with "very low affinity" is meant binding with a $k_d$ of above about 100 μM under standard conditions. By binding with "extremely low affinity" is meant binding at a $k_d$ of above about 1 mM under standard conditions. By "moderate affinity" is meant binding with a $k_d$ of from about 200 nM to about 1 μM under standard conditions. By "moderately high affinity" is meant binding at a $k_d$ of from about 1 nM to about 200 nM. By binding at "high affinity" is meant binding at a $k_d$ of below about 1 nM under standard conditions. For example, low affinity binding can occur because of a poorer fit into the binding site of the target molecule or because of a smaller number of non-covalent bonds, or weaker covalent bonds present to cause binding of the scaffold or ligand to the binding site of the target molecule relative to instances where higher affinity binding occurs. The standard conditions for binding are at pH 7.2 at 37° C. for one hour. For example, 100 µl/well can be used in HEPES 50 mM buffer at pH 7.2, NaCl 15 mM, ATP 2 µM, and bovine serum albumin 1 ug/well, 37° C. for one hour.

Binding compounds can also be characterized by their effect on the activity of the target molecule. Thus, a "low activity" compound has an inhibitory concentration ($IC_{50}$) or excitation concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667$$

To design or discover scaffolds that act broadly across protein families, proteins of interest can be assayed against a compound collection or set. The assays can preferably be enzymatic or binding assays. In some embodiments it may be desirable to enhance the solubility of the compounds being screened and then analyze all compounds that show activity in the assay, including those that bind with low affinity or produce a signal with greater than about three times the standard deviation of the background signal. The assays can be any suitable assay such as, for example, binding assays that measure the binding affinity between two binding partners. Various types of screening assays that can be useful in the practice of the present invention are known in the art, such as those described in U.S. Pat. Nos. 5,763,198, 5,747,276, 5,877,007, 6,243,980, 6,294,330, and 6,294,330, each of which is hereby incorporated by reference in its entirety, including all charts and drawings.

In various embodiments of the assays at least one compound, at least about 5%, at least about 10%, at least about 15%, at least about 20%, or at least about 25% of the compounds can bind with low affinity. In general, up to about 20% of the compounds can show activity in the screening assay and these compounds can then be analyzed directly with high-throughput co-crystallography, computational analysis to group the compounds into classes with common structural properties (e.g., structural core and/or shape and polarity characteristics), and the identification of common chemical structures between compounds that show activity.

The person of ordinary skill in the art will realize that decisions can be based on criteria that are appropriate for the needs of the particular situation, and that the decisions can be made by computer software programs. Classes can be created containing almost any number of scaffolds, and the criteria selected can be based on increasingly exacting criteria until an arbitrary number of scaffolds is arrived at for each class that is deemed to be advantageous.

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, *Methods in Molecular Biology.* 121: 313-21; Liparoto et al., (1999) Biosensor analysis of the interleukin-2 receptor complex, *Journal of Molecular Recognition.* 12:316-21; Lipschultz et al., (2000) Experimental design for analysis of complex kinetics using surface plasmon resonance, *Methods.* 20(3):310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, *Biosensors & Bioelectronics.* 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. *Tumour Biology* 19 Suppl 1:1-20; Malmqvist et al, (1997) Biomolecular interaction analysis: affinity biosensor technologies for functional analysis of proteins, *Current Opinion in Chemical Biology.* 1:378-83; O'Shannessy et al., (1996) Interpretation of deviations from pseudo-first-order kinetic behavior in the characterization of ligand binding by biosensor technology, *Analytical Biochemistry.* 236:275-83; Malmborg et al., (1995) BIAcore as a tool in antibody engineering, *Journal of Immunological Methods.* 183:7-13; Van Regenmortel, (1994) Use of biosensors to characterize recombinant proteins, *Developments in Biological Standardization.* 83:143-51; and O'Shannessy, (1994) Determination of kinetic rate and equilibrium binding constants for macromolecular interactions: a critique of the surface plasmon resonance literature, *Current Opinions in Biotechnology.* 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g., by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator. Similarly, when ligands to a sphingolipid target are sought, known ligands of the target can be present in control/calibration assay wells.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) *The Chemist's Companion: A Handbook Of Practical Data, Techniques, And References*, John Wiley and Sons, N.Y., Page 437.

Fluorescence spectrometry may be used to monitor the generation of reaction products. Fluorescence methodology is generally more sensitive than the absorption methodology.

The use of fluorescent probes is well known to those skilled in the art. For reviews, see Bashford et al., (1987) *Spectrophotometry and Spectrofluorometry: A Practical Approach*, pp. 91-114, IRL Press Ltd.; and Bell, (1981) *Spectroscopy In Biochemistry*, Vol. I, pp. 155-194, CRC Press.

In spectrofluorometric methods, enzymes are exposed to substrates that change their intrinsic fluorescence when processed by the target enzyme. Typically, the substrate is non-fluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., (1997), Application of Fluorescence Polarization Assays in High-Throughput Screening, *Genetic Engineering News*, 17:27.

FP is particularly desirable since its readout is independent of the emission intensity (Checovich, W. J., et al., (1995) *Nature* 375:254-256; Dandliker, W. B., et al., (1981) *Methods in Enzymology* 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide fluorophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) *Curr. Biol.* 6:178-182; Mitra et al., (1996) *Gene* 173:13-17; and Selvin et al., (1995) *Meth. Enzymol.* 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) *J. Lipid Res.* 38:2365-2373; Kahl et al., (1996) *Anal. Biochem.* 243:282-283; Undenfriend et al., (1987) *Anal. Biochem.* 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) *Anal. Biochem.* 257:112-119).

Assay Compounds and Molecular Scaffolds

Preferred characteristics of a scaffold include being of low molecular weight (e.g., less than 350 Da, or from about 100 to about 350 daltons, or from about 150 to about 300 daltons). Preferably clog P of a scaffold is from −1 to 8, more preferably less than 6, 5, or 4, most preferably less than 3. In particular embodiments the clogP is in a range −1 to an upper limit of 2, 3, 4, 5, 6, or 8; or is in a range of 0 to an upper limit of 2, 3, 4, 5, 6, or 8. Preferably the number of rotatable bonds is less than 5, more preferably less than 4. Preferably the number of hydrogen bond donors and acceptors is below 6, more preferably below 5. An additional criterion that can be useful is a polar surface area of less than 5. Guidance that can be useful in identifying criteria for a particular application can be found in Lipinski et al., (1997) *Advanced Drug Delivery Reviews* 23 3-25, which is hereby incorporated by reference in its entirety.

A scaffold may preferably bind to a given protein binding site in a configuration that causes substituent moieties of the scaffold to be situated in pockets of the protein binding site. Also, possessing chemically tractable groups that can be chemically modified, particularly through synthetic reactions, to easily create a combinatorial library can be a preferred characteristic of the scaffold. Also preferred can be having positions on the scaffold to which other moieties can be attached, which do not interfere with binding of the scaffold to the protein(s) of interest but do cause the scaffold to achieve a desirable property, for example, active transport of the scaffold to cells and/or organs, enabling the scaffold to be attached to a chromatographic column to facilitate analysis, or another desirable property. A molecular scaffold can bind to a target molecule with any affinity, such as binding at high affinity, moderate affinity, low affinity, very low affinity, or extremely low affinity.

Thus, the above criteria can be utilized to select many compounds for testing that have the desired attributes. Many compounds having the criteria described are available in the commercial market, and may be selected for assaying depending on the specific needs to which the methods are to be applied.

A "compound library" or "library" is a collection of different compounds having different chemical structures. A compound library is screenable, that is, the compound library members therein may be subject to screening assays. In preferred embodiments, the library members can have a molecular weight of from about 100 to about 350 daltons, or from about 150 to about 350 daltons. Examples of libraries are provided above.

Libraries of the present invention can contain at least one compound than binds to the target molecule at low affinity. Libraries of candidate compounds can be assayed by many different assays, such as those described above, e.g., a fluorescence polarization assay. Libraries may consist of chemically synthesized peptides, peptidomimetics, or arrays of combinatorial chemicals that are large or small, focused or nonfocused. By "focused" it is meant that the collection of compounds is prepared using the structure of previously characterized compounds and/or pharmacophores.

Compound libraries may contain molecules isolated from natural sources, artificially synthesized molecules, or molecules synthesized, isolated, or otherwise prepared in such a manner so as to have one or more moieties variable, e.g., moieties that are independently isolated or randomly synthesized. Types of molecules in compound libraries include but are not limited to organic compounds, polypeptides and nucleic acids as those terms are used herein, and derivatives, conjugates and mixtures thereof.

Compound libraries of the invention may be purchased on the commercial market or prepared or obtained by any means including, but not limited to, combinatorial chemistry techniques, fermentation methods, plant and cellular extraction procedures and the like (see, e.g., Cwirla et al., (1990) *Biochemistry*, 87, 6378-6382; Houghten et al., (1991) *Nature*, 354, 84-86; Lam et al., (1991) *Nature*, 354, 82-84; Brenner et al., (1992) *Proc. Natl. Acad. Sci. USA*, 89, 5381-5383; R. A. Houghten, (1993) *Trends Genet.*, 9, 235-239; E. R. Felder, (1994) *Chimia*, 48, 512-541; Gallop et al., (1994) *J. Med. Chem.*, 37, 1233-1251; Gordon et al., (1994) *J. Med. Chem.*, 37, 1385-1401; Carell et al., (1995) *Chem. Biol.*, 3, 171-183; Madden et al., *Perspectives in Drug Discovery and Design* 2, 269-282; Lebl et al., (1995) *Biopolymers*, 37 177-198); small molecules assembled around a shared molecular structure; collections of chemicals that have been assembled by various commercial and noncommercial groups, natural products; extracts of marine organisms, fungi, bacteria, and plants.

Preferred libraries can be prepared in a homogenous reaction mixture, and separation of unreacted reagents from members of the library is not required prior to screening. Although many combinatorial chemistry approaches are based on solid state chemistry, liquid phase combinatorial chemistry is capable of generating libraries (Sun C M., (1999) Recent advances in liquid-phase combinatorial chemistry, *Combinatorial Chemistry & High Throughput Screening*. 2:299-318).

Libraries of a variety of types of molecules are prepared in order to obtain members therefrom having one or more preselected attributes that can be prepared by a variety of techniques, including but not limited to parallel array synthesis (Houghton, (2000) *Annu Rev Pharmacol Toxicol* 40:273-82, Parallel array and mixture-based synthetic combinatorial chemistry; solution-phase combinatorial chemistry (Merritt, (1998) *Comb Chem High Throughput Screen* 1(2):57-72, Solution phase combinatorial chemistry, Coe et al., (1998-99) *Mol Divers;* 4(1):31-8, Solution-phase combinatorial chemistry, Sun, (1999) *Comb Chem High Throughput Screen* 2(6): 299-318, Recent advances in liquid-phase combinatorial chemistry); synthesis on soluble polymer (Gravert et al., (1997) *Curr Opin Chem Biol* 1(1):107-13, Synthesis on soluble polymers: new reactions and the construction of small molecules); and the like. See, e.g., Dolle et al., (1999) *J Comb Chem* 1(4):235-82, Comprehensive survey of cominatorial library synthesis: 1998. Freidinger R M., (1999) Nonpeptidic ligands for peptide and protein receptors, Current Opinion in Chemical Biology; and Kundu et al., *Prog Drug Res;* 53:89-156, Combinatorial chemistry: polymer supported synthesis of peptide and non-peptide libraries). Compounds may be clinically tagged for ease of identification (Chabala, (1995) *Curr Opin Biotechnol* 6(6):633-9, Solid-phase combinatorial chemistry and novel tagging methods for identifying leads).

The combinatorial synthesis of carbohydrates and libraries containing oligosaccharides have been described (Schweizer et al., (1999) *Curr Opin Chem Biol* 3(3):291-8, Combinatorial synthesis of carbohydrates). The synthesis of natural-product based compound libraries has been described (Wessjohann, (2000) *Curr Opin Chem Biol* 4(3):303-9, Synthesis of natural-product Based compound libraries).

Libraries of nucleic acids are prepared by various techniques, including by way of non-limiting example the ones described herein, for the isolation of aptamers. Libraries that include oligonucleotides and polyaminooligonucleotides (Markiewicz et al., (2000) Synthetic oligonucleotide combinatorial libraries and their applications, *Farmaco*. 55:174-7) displayed on streptavidin magnetic beads are known. Nucleic acid libraries are known that can be coupled to parallel sampling and be deconvoluted without complex procedures such as automated mass spectrometry (Enjalbal C. Martinez J. Aubagnac J L, (2000) Mass spectrometry in combinatorial chemistry, *Mass Spectrometry Reviews*. 19:139-61) and parallel tagging. (Perrin D M., Nucleic acids for recognition and catalysis: landmarks, limitations, and looking to the future, *Combinatorial Chemistry & High Throughput Screening* 3:243-69).

Peptidomimetics are identified using combinatorial chemistry and solid phase synthesis (Kim H O. Kahn M., (2000) A merger of rational drug design and combinatorial chemistry: development and application of peptide secondary structure mimetics, Combinatorial Chemistry & High Throughput Screening 3:167-83; al-Obeidi, (1998) *Mol Biotechnol* 9(3): 205-23, Peptide and peptidomimetric libraries. Molecular diversity and drug design). The synthesis may be entirely random or based in part on a known polypeptide.

Polypeptide libraries can be prepared according to various techniques. In brief, phage display techniques can be used to produce polypeptide ligands (Gram H., (1999) Phage display in proteolysis and signal transduction, Combinatorial Chemistry & High Throughput Screening. 2:19-28) that may be used as the basis for synthesis of peptidomimetics. Polypeptides, constrained peptides, proteins, protein domains, antibodies, single chain antibody fragments, antibody fragments, and antibody combining regions are displayed on filamentous phage for selection.

Large libraries of individual variants of human single chain Fv antibodies have been produced. See, e.g., Siegel R W. Allen B. Pavlik P. Marks J D. Bradbury A., (2000) Mass spectral analysis of a protein complex using single-chain antibodies selected on a peptide target: applications to functional genomics, *Journal of Molecular Biology* 302:285-93; Poul M A. Becerril B. Nielsen U B. Morisson P Marks J D., (2000) Selection of tumor-specific internalizing human antibodies from phage libraries. Source *Journal of Molecular Biology.* 301:1149-61; Amersdorfer P. Marks J D., (2001) Phage libraries for generation of anti-botulinum scFv antibodies, *Methods in Molecular Biology.* 145:219-40; Hughes-Jones N C. Bye J M. Gorick B D. Marks J D. Ouwehand W H., (1999) Synthesis of Rh Fv phage-antibodies using VH and VL germline genes, *British Journal of Haematology.* 105: 811-6; McCall A M. Amoroso A R. Sautes C. Marks J D. Weiner L M., (1998) Characterization of anti-mouse Fc gamma RII single-chain Fv fragments derived from human phage display libraries, *Immunotechnology*. 4:71-87; Sheets M D. Amersdorfer P. Finnern R. Sargent P. Lindquist E. Schier R. Hemingsen G. Wong C. Gerhart J C. Marks J D. Lindquist E., (1998) Efficient construction of a large nonimmune phage antibody library: the production of high-affinity human single-chain antibodies to protein antigens (published erratum appears in *Proc Natl Acad Sci USA* 1999 96:795), *Proc Natl Acad Sci USA* 95:6157-62).

Focused or smart chemical and pharmacophore libraries can be designed with the help of sophisticated strategies involving computational chemistry (e.g., Kundu B. Khare S K. Rastogi S K., (1999) Combinatorial chemistry: polymer supported synthesis of peptide and non-peptide libraries, *Progress in Drug Research* 53:89-156) and the use of structure-based ligands using database searching and docking, de novo drug design and estimation of ligand binding affinities (Joseph-McCarthy D., (1999) Computational approaches to structure-based ligand design, *Pharmacology & Therapeutics* 84:179-91; Kirkpatrick D L. Watson S. Ulhaq S., (1999) Structure-based drug design: combinatorial chemistry and molecular modeling, *Combinatorial Chemistry & High*

Throughput Screening. 2:211-21; Eliseev A V. Lehn J M., (1999) Dynamic combinatorial chemistry: evolutionary formation and screening of molecular libraries, *Current Topics in Microbiology & Immunology* 243:159-72; Bolger et al., (1991) *Methods Enz.* 203:21-45; Martin, (1991) *Methods Enz.* 203:587-613; Neidle et al., (1991) *Methods Enz.* 203:433-458; U.S. Pat. No. 6,178,384).

X. Crystallography

After binding compounds have been determined, the orientation of compound bound to target is determined. Preferably this determination involves crystallography on co-crystals of molecular scaffold compounds with target. Most protein crystallographic platforms can preferably be designed to analyze up to about 500 co-complexes of compounds, ligands, or molecular scaffolds bound to protein targets due to the physical parameters of the instruments and convenience of operation. If the number of scaffolds that have binding activity exceeds a number convenient for the application of crystallography methods, the scaffolds can be placed into groups based on having at least one common chemical structure or other desirable characteristics, and representative compounds can be selected from one or more of the classes. Classes can be made with increasingly exacting criteria until a desired number of classes (e.g., 500) is obtained. The classes can be based on chemical structure similarities between molecular scaffolds in the class, e.g., all possess a pyrrole ring, benzene ring, or other chemical feature. Likewise, classes can be based on shape characteristics, e.g., space-filling characteristics.

The co-crystallography analysis can be performed by co-complexing each scaffold with its target at concentrations of the scaffold that showed activity in the screening assay. This co-complexing can be accomplished with the use of low percentage organic solvents with the target molecule and then concentrating the target with each of the scaffolds. In preferred embodiments these solvents are less than 5% organic solvent such as dimethyl sulfoxide (DMSO), ethanol, methanol, or ethylene glycol in water or another aqueous solvent. Each scaffold complexed to the target molecule can then be screened with a suitable number of crystallization screening conditions at both 4 and 20 degrees. In preferred embodiments, about 96 crystallization screening conditions can be performed in order to obtain sufficient information about the co-complexation and crystallization conditions, and the orientation of the scaffold at the binding site of the target molecule. Crystal structures can then be analyzed to determine how the bound scaffold is oriented physically within the binding site or within one or more binding pockets of the molecular family member.

It is desirable to determine the atomic coordinates of the compounds bound to the target proteins in order to determine which is a most suitable scaffold for the protein family. X-ray crystallographic analysis is therefore most preferable for determining the atomic coordinates. Those compounds selected can be further tested with the application of medicinal chemistry. Compounds can be selected for medicinal chemistry testing based on their binding position in the target molecule. For example, when the compound binds at a binding site, the compound's binding position in the binding site of the target molecule can be considered with respect to the chemistry that can be performed on chemically tractable structures or sub-structures of the compound, and how such modifications on the compound might interact with structures or sub-structures on the binding site of the target. Thus, one can explore the binding site of the target and the chemistry of the scaffold in order to make decisions on how to modify the scaffold to arrive at a ligand with higher potency and/or selectivity. This process allows for more direct design of ligands, by utilizing structural and chemical information obtained directly from the co-complex, thereby enabling one to more efficiently and quickly design lead compounds that are likely to lead to beneficial drug products. In various embodiments it may be desirable to perform co-crystallography on all scaffolds that bind, or only those that bind with a particular affinity, for example, only those that bind with high affinity, moderate affinity, low affinity, very low affinity, or extremely low affinity. It may also be advantageous to perform co-crystallography on a selection of scaffolds that bind with any combination of affinities.

Standard X-ray protein diffraction studies such as by using a Rigaku RU-200® (Rigaku, Tokyo, Japan) with an X-ray imaging plate detector or a synchrotron beam-line can be performed on co-crystals and the diffraction data measured on a standard X-ray detector, such as a CCD detector or an X-ray imaging plate detector.

Performing X-ray crystallography on about 200 co-crystals should generally lead to about 50 co-crystals structures, which should provide about 10 scaffolds for validation in chemistry, which should finally result in about 5 selective leads for target molecules.

Virtual Assays

Commercially available software that generates three-dimensional graphical representations of the complexed target and compound from a set of coordinates provided can be used to illustrate and study how a compound is oriented when bound to a target. (e.g., QUANTA®, Accelerys, San Diego, Calif.). Thus, the existence of binding pockets at the binding site of the targets can be particularly useful in the present invention. These binding pockets are revealed by the crystallographic structure determination and show the precise chemical interactions involved in binding the compound to the binding site of the target. The person of ordinary skill will realize that the illustrations can also be used to decide where chemical groups might be added, substituted, modified, or deleted from the scaffold to enhance binding or another desirable effect, by considering where unoccupied space is located in the complex and which chemical substructures might have suitable size and/or charge characteristics to fill it. The person of ordinary skill will also realize that regions within the binding site can be flexible and its properties can change as a result of scaffold binding, and that chemical groups can be specifically targeted to those regions to achieve a desired effect. Specific locations on the molecular scaffold can be considered with reference to where a suitable chemical substructure can be attached and in which conformation, and which site has the most advantageous chemistry available.

An understanding of the forces that bind the compounds to the target proteins reveals which compounds can most advantageously be used as scaffolds, and which properties can most effectively be manipulated in the design of ligands. The person of ordinary skill will realize that steric, ionic, hydrogen bond, and other forces can be considered for their contribution to the maintenance or enhancement of the target-compound complex. Additional data can be obtained with automated computational methods, such as docking and/or Free Energy Perturbations (FEP), to account for other energetic effects such as desolvation penalties. The compounds selected can be used to generate information about the chemical interactions with the target or for elucidating chemical modifications that can enhance selectivity of binding of the compound.

Computer models, such as homology models (i.e., based on a known, experimentally derived structure) can be constructed using data from the co-crystal structures. When the target molecule is a protein or enzyme, preferred co-crystal structures for making homology models contain high sequence identity in the binding site of the protein sequence being modeled, and the proteins will preferentially also be within the same class and/or fold family. Knowledge of conserved residues in active sites of a protein class can be used to select homology models that accurately represent the binding site. Homology models can also be used to map structural information from a surrogate protein where an apo or co-crystal structure exists to the target protein.

Virtual screening methods, such as docking, can also be used to predict the binding configuration and affinity of scaffolds, compounds, and/or combinatorial library members to homology models. Using this data, and carrying out "virtual experiments" using computer software can save substantial resources and allow the person of ordinary skill to make decisions about which compounds can be suitable scaffolds or ligands, without having to actually synthesize the ligand and perform co-crystallization. Decisions thus can be made about which compounds merit actual synthesis and co-crystallization. An understanding of such chemical interactions aids in the discovery and design of drugs that interact more advantageously with target proteins and/or are more selective for one protein family member over others. Thus, applying these principles, compounds with superior properties can be discovered.

Additives that promote co-crystallization can of course be included in the target molecule formulation in order to enhance the formation of co-crystals. In the case of proteins or enzymes, the scaffold to be tested can be added to the protein formulation, which is preferably present at a concentration of approximately 1 mg/ml. The formulation can also contain between 0%-10% (v/v) organic solvent, e.g. DMSO, methanol, ethanol, propane diol, or 1,3 dimethyl propane diol (MPD) or some combination of those organic solvents. Compounds are preferably solubilized in the organic solvent at a concentration of about 10 mM and added to the protein sample at a concentration of about 100 mM. The protein-compound complex is then concentrated to a final concentration of protein of from about 5 to about 20 mg/ml. The complexation and concentration steps can conveniently be performed using a 96-well formatted concentration apparatus (e.g., Amicon Inc., Piscataway, N.J.). Buffers and other reagents present in the formulation being crystallized can contain other components that promote crystallization or are compatible with crystallization conditions, such as DTT, propane diol, glycerol.

The crystallization experiment can be set-up by placing small aliquots of the concentrated protein-compound complex (1 μl) in a 96 well format and sampling under 96 crystallization conditions. (Other screening formats can also be used, e.g., plates with greater than 96 wells.) Crystals can typically be obtained using standard crystallization protocols that can involve the 96 well crystallization plate being placed at different temperatures. Co-crystallization varying factors other than temperature can also be considered for each protein-compound complex if desirable. For example, atmospheric pressure, the presence or absence of light or oxygen, a change in gravity, and many other variables can all be tested. The person of ordinary skill in the art will realize other variables that can advantageously be varied and considered.

Ligand Design and Preparation

The design and preparation of ligands can be performed with or without structural and/or co-crystallization data by considering the chemical structures in common between the active scaffolds of a set. In this process structure-activity hypotheses can be formed and those chemical structures found to be present in a substantial number of the scaffolds, including those that bind with low affinit, can be presumed to have some effect on the binding of the scaffold. This binding can be presumed to induce a desired biochemical effect when it occurs in a biological system (e.g., a treated mammal). New or modified scaffolds or combinatorial libraries derived from scaffolds can be tested to disprove the maximum number of binding and/or structure-activity hypotheses. The remaining hypotheses can then be used to design ligands that achieve a desired binding and biochemical effect.

But in many cases it will be preferred to have co-crystallography data for consideration of how to modify the scaffold to achieve the desired binding effect (e.g., binding at higher affinity or with higher selectivity). Using the case of proteins and enzymes, co-crystallography data shows the binding pocket of the protein with the molecular scaffold bound to the binding site, and it will be apparent that a modification can be made to a chemically tractable group on the scaffold. For example, a small volume of space at a protein binding site or pocket might be filled by modifying the scaffold to include a small chemical group that fills the volume. Filling the void volume can be expected to result in a greater binding affinity, or the loss of undesirable binding to another member of the protein family. Similarly, the co-crystallography data may show that deletion of a chemical group on the scaffold may decrease a hindrance to binding and result in greater binding affinity or specificity.

It can be desirable to take advantage of the presence of a charged chemical group located at the binding site or pocket of the protein. For example, a positively charged group can be complemented with a negatively charged group introduced on the molecular scaffold. This can be expected to increase binding affinity or binding specificity, thereby resulting in a more desirable ligand. In many cases, regions of protein binding sites or pockets are known to vary from one family member to another based on the amino acid differences in those regions. Chemical additions in such regions can result in the creation or elimination of certain interactions (e.g., hydrophobic, electrostatic, or entropic) that allow a compound to be more specific for one protein target over another or to bind with greater affinity, thereby enabling one to synthesize a compound with greater selectivity or affinity for a particular family member. Additionally, certain regions can contain amino acids that are known to be more flexible than others. This often occurs in amino acids contained in loops connecting elements of the secondary structure of the protein, such as alpha helices or beta strands. Additions of chemical moieties can also be directed to these flexible regions in order to increase the likelihood of a specific interaction occurring between the protein target of interest and the compound. Virtual screening methods can also be conducted in silico to assess the effect of chemical additions, subtractions, modifications, and/or substitutions on compounds with respect to members of a protein family or class.

The addition, subtraction, or modification of a chemical structure or sub-structure to a scaffold can be performed with any suitable chemical moiety. For example the following moieties, which are provided by way of example and are not intended to be limiting, can be utilized: hydrogen, alkyl, alkoxy, phenoxy, alkenyl, alkynyl, phenylalkyl, hydroxyalkyl, haloalkyl, aryl, arylalkyl, alkyloxy, alkylthio, alkenylthio, phenyl, phenylalkyl, phenylalkylthio, hydroxyalkyl-thio, alkylthiocarbbamylthio, cyclohexyl, pyridyl, piperidinyl, alkylamino, amino, nitro, mercapto, cyano, hydroxyl, a halogen atom, halomethyl, an oxygen atom (e.g., forming a ketone or N-oxide) or a sulphur atom (e.g., forming a thiol, thione, di-alkylsulfoxide or sulfone) are all examples of moieties that can be utilized.

Additional examples of structures or sub-structures that may be utilized are an aryl optionally substituted with one, two, or three substituents independently selected from the group consisting of alkyl, alkoxy, halogen, trihalomethyl, carboxylate, carboxamide, nitro, and ester moieties; an amine of formula —$NX_2X_3$, where $X_2$ and $X_3$ are independently selected from the group consisting of hydrogen, saturated or unsaturated alkyl, and homocyclic or heterocyclic ring moieties; halogen or trihalomethyl; a ketone of formula —$COX_4$, where $X_4$ is selected from the group consisting of alkyl and homocyclic or heterocyclic ring moieties; a carboxylic acid of formula —$(X_5)_n COOH$ or ester of formula $(X_6)_n COOX_7$, where $X_5$, $X_6$, and $X_7$ and are independently selected from the group consisting of alkyl and homocyclic or heterocyclic ring moieties and where n is 0 or 1; an alcohol of formula $(X_8)_n OH$ or an alkoxy moiety of formula —$(X_8)_n OX_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; an amide of formula $NHCOX_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; $SO_2$, $NX_{11}X_{12}$, where $X_{11}$ and $X_{12}$ are selected from the group consisting of hydrogen, alkyl, and homocyclic or heterocyclic ring moieties; a homocyclic or heterocyclic ring moiety optionally substituted with one, two, or three substituents independently selected from the group consisting of alkyl, alkoxy, halogen, trihalomethyl, carboxylate, carboxamide, nitro, and ester moieties; an aldehyde of formula —CHO; a sulfone of formula —$SO_2X_{13}$, where $X_{13}$ is selected from the group consisting of saturated or unsaturated alkyl and homocyclic or heterocyclic ring moieties; and a nitro of formula —$NO_2$.

Identification of Attachment Sites on Molecular Scaffolds and Ligands

In addition to the identification and development of ligands for kinases and other enzymes, determination of the orientation of a molecular scaffold or other binding compound in a binding site allows identification of energetically allowed sites for attachment of the binding molecule to another component. For such sites, any free energy change associated with the presence of the attached component should not destabilize the binding of the compound to the kinase to an extent that will disrupt the binding. Preferably, the binding energy with the attachment should be at least 4 kcal/mol., more preferably at least 6, 8, 10, 12, 15, or 20 kcal/mol. Preferably, the presence of the attachment at the particular site reduces binding energy by no more than 3, 4, 5, 8, 10, 12, or 15 kcal/mol.

In many cases, suitable attachment sites will be those that are exposed to solvent when the binding compound is bound in the binding site. In some cases, attachment sites can be used that will result in small displacements of a portion of the enzyme without an excessive energetic cost. Exposed sites can be identified in various ways. For example, exposed sites can be identified using a graphic display or 3-dimensional model. In a graphic display, such as a computer display, an image of a compound bound in a binding site can be visually inspected to reveal atoms or groups on the compound that are exposed to solvent and oriented such that attachment at such atom or group would not preclude binding of the enzyme and binding compound. Energetic costs of attachment can be calculated based on changes or distortions that would be caused by the attachment as well as entropic changes.

Many different types of components can be attached. Persons with skill are familiar with the chemistries used for various attachments. Examples of components that can be attached include, without limitation: solid phase components such as beads, plates, chips, and wells; a direct or indirect label; a linker, which may be a traceless linker; among others. Such linkers can themselves be attached to other components, e.g., to solid phase media, labels, and/or binding moieties.

The binding energy of a compound and the effects on binding energy for attaching the molecule to another component can be calculated approximately using any of a variety of available software or by manual calculation. An example is the following:

Calculations were performed to estimate binding energies of different organic molecules to two Kinases: PIM-1 and CDK2. The organic molecules considered included Staurosporine, identified compounds that bind to PDE5A, and several linkers.

Calculated binding energies between protein-ligand complexes were obtained using the FlexX score (an implementation of the Bohm scoring function) within the Tripos software suite. The form for that equation is shown in the equation below:

$$\Delta G\text{bind} = \Delta G\text{tr} + \Delta G\text{hb} + \Delta G\text{ion} + \Delta G\text{lipo} + \Delta G\text{arom} + \Delta G\text{rot}$$

where: $\Delta G\text{tr}$ is a constant term that accounts for the overall loss of rotational and translational entropy of the lignand, $\Delta G\text{hb}$ accounts for hydrogen bonds formed between the ligand and protein, $\Delta G\text{ion}$ accounts for the ionic interactions between the ligand and protein, $\Delta G\text{lipo}$ accounts for the lipophilic interaction that corresponds to the protein-ligand contact surface, $\Delta G\text{arom}$ accounts for interactions between aromatic rings in the protein and ligand, and $\Delta G\text{rot}$ accounts for the entropic penalty of restricting rotatable bonds in the ligand upon binding.

This method estimates the free energy that a lead compound should have to a target protein for which there is a crystal structure, and it accounts for the entropic penalty of flexible linkers. It can therefore be used to estimate the free energy penalty incurred by attaching linkers to molecules being screened and the binding energy that a lead compound should have in order to overcome the free energy penalty of the linker. The method does not account for solvation and the entropic penalty is likely overestimated for cases where the linker is bound to a solid phase through another binding complex, such as a biotin:streptavidin complex.

Co-crystals were aligned by superimposing residues of PIM-1 with corresponding residues in CDK2. The PIM-1 structure Used for these calculations was a co-crystal of PIM-1 with a binding compound. The CDK2:Staurosporine co-crystal used was from the Brookhaven database file 1aq1. Hydrogen atoms were added to the proteins and atomic charges were assigned using the AMBER95 parameters within Sybyl. Modifications to the compounds described were made within the Sybyl modeling suite from Tripos.

These calculations indicate that the calculated binding energy for compounds that bind strongly to a given target (such as Staurosporine:CDK2) can be lower than −25 kcal/mol, while the calculated binding affinity for a good scaffold or an unoptimized binding compound can be in the range of −15 to −20. The free energy penalty for attachment to a linker such as the ethylene glycol or hexatriene is estimated as typically being in the range of +5 to +15 kcal/mol.

Linkers

Linkers suitable for use in the invention can be of many different types. Linkers can be selected for particular applications based on factors such as linker chemistry compatible for attachment to a binding compound and to another component utilized in the particular application. Additional factors can include, without limitation, linker length, linker stability, and ability to remove the linker at an appropriate time. Exemplary linkers include, but are not limited to, hexyl, hexatrienyl, ethylene glycol, and peptide linkers. Traceless linkers can also be used, e.g., as described in Plunkett, M. J., and Ellman, J. A., (1995), *J. Org. Chem.,* 60:6006.

Typical functional groups, that are utilized to link binding compound(s), include, but not limited to, carboxylic acid, amine, hydroxyl, and thiol. (Examples can be found in Solid-supported combinatorial and parallel synthesis of small molecular weight compound libraries; (1998) Tetrahedron organic chemistry series Vol. 17; Pergamon; p85).

Labels

As indicated above, labels can also be attached to a binding compound or to a linker attached to a binding compound. Such attachment may be direct (attached directly to the binding compound) or indirect (attached to a component that is directly or indirectly attached to the binding compound). Such labels allow detection of the compound either directly or indirectly. Attachment of labels can be performed using conventional chemistries. Labels can include, for example, fluorescent labels, radiolabels, light scattering particles, light absorbent particles, magnetic particles, enzymes, and specific binding agents (e.g., biotin or an antibody target moiety).

Solid Phase Media

Additional examples of components that can be attached directly or indirectly to a binding compound include various solid phase media. Similar to attachment of linkers and labels, attachment to solid phase media can be performed using conventional chemistries. Such solid phase media can include, for example, small components such as beads, nanoparticles, and fibers (e.g., in suspension or in a gel or chromatographic matrix). Likewise, solid phase media can include larger objects such as plates, chips, slides, and tubes. In many cases, the binding compound will be attached in only a portion of such an objects, e.g., in a spot or other local element on a generally flat surface or in a well or portion of a well.

Identification of Biological Agents

The possession of structural information about a protein also provides for the identification of useful biological agents, such as epitpose for development of antibodies, identification of mutation sites expected to affect activity, and identification of attachment sites allowing attachment of the protein to materials such as labels, linkers, peptides, and solid phase media.

Antibodies (Abs) finds multiple applications in a variety of areas including biotechnology, medicine and diagnosis, and indeed they are one of the most powerful tools for life science research. Abs directed against protein antigens can recognize either linear or native three-dimensional (3D) epitopes. The obtention of Abs that recognize 3D epitopes require the use of whole native protein (or of a portion that assumes a native conformation) as immunogens. Unfortunately, this not always a choice due to various technical reasons: for example the native protein is just not available, the protein is toxic, or its is desirable to utilize a high density antigen presentation. In such cases, immunization with peptides is the alternative. Of course, Abs generated in this manner will recognize linear epitopes, and they might or might not recognize the source native protein, but yet they will be useful for standard laboratory applications such as western blots. The selection of peptides to use as immunogens can be accomplished by following particular selection rules and/or use of epitope prediction software.

Though methods to predict antigenic peptides are not infallible, there are several rules that can be followed to determine what peptide fragments from a protein are likely to be antigenic. These rules are also dictated to increase the likelihood that an Ab to a particular peptide will recognize the native protein.

1. Antigenic peptides should be located in solvent accessible regions and contain both hydrophobic and hydrophilic residues.

For proteins of known 3D structure, solvent accessibility can be determined using a variety of programs such as DSSP, NACESS, or WHATIF, among others.

If the 3D structure is not known, use any of the following web servers to predict accessibilities: PHD, JPRED, PredAcc (c) ACCpro 2. Preferably select peptides lying in long loops connecting Secondary Structure (SS) motifs, avoiding peptides located in helical regions. This will increase the odds that the Ab recognizes the native protein. Such peptides can, for example, be identified from a crystal structure or crystal structure-based homology model.

For protein with known 3D coordinates, SS can be obtained from the sequence link of the relevant entry at the Brookhaven data bank. The PDBsum server also offer SS analysis of pdb records.

When no structure is available secondary structure predictions can be obtained from any of the following servers: PHD, JPRED, PSI-PRED, NNSP, etc 3. When possible, choose peptides that are in the N- and C-terminal region of the protein. Because the N- and C-terminal regions of proteins are usually solvent accessible and unstructured, Abs against those regions are also likely to recognize the native protein.

4. For cell surface glycoproteins, eliminate from initial peptides those containing consensus sites for N-glycosilation.

N-glycosilation sites can be detected using Scanprosite, or NetNGlyc

In addition, several methods based on various physiochemical properties of experimental determined epitopes (flexibility, hydrophibility, accessibility) have been published for the prediction of antigenic determinants and can be used. The antigenic index and Preditop are example.

Perhaps the simplest method for the prediction of antigenic determinants is that of Kolaskar and Tongaonkar, which is based on the occurrence of amino acid residues in experimentally determined epitopes. (Kolaskar and Tongaonkar (1990) A semi-empirical method for prediction of antigenic determinants on protein antigens. *FEBBS Lett.* 276(1-2):172-174.) The prediction algorithm works as follows:

1. Calculate the average propensity for each overlapping 7-mer and assign the result to the central residue (i+3) of the 7-mer.
2. Calculate the average for the whole protein.
3. (a) If the average for the whole protein is above 1.0 then all residues having average propensity above 1.0 are potentially antigenic.
3. (b) If the average for the whole protein is below 1.0 then all residues having above the average for the whole protein are potentially antigenic.
4. Find 8-mers where all residues are selected by step 3 above (6-mers in the original paper)

The Kolaskar and Tongaonkar method is also available from the GCG package, and it runs using the command egcg.

Crystal structures also allow identification of residues at which mutation is likely to alter the activity of the protein. Such residues include, for example, residues that interact with substrate, conserved active site residues, and residues that are in a region of ordered secondary structure of involved in tertiary interactions. The mutations that are likely to affect activity will vary for different molecular contexts. Mutations in an active site that will affect activity are typically substitutions or deletions that eliminate a charge-charge or hydrogen bonding interaction, or introduce a steric interference. Mutations in secondary structure regions or molecular interaction regions that are likely to affect activity include, for example, substitutions that alter the hydrophobicity/hydrophilicity of a region, or that introduce a sufficient strain in a region near or including the active site so that critical residue(s) in the active site are displaced. Such substitutions and/or deletions and/or insertions are recognized, and the predicted structural and/or energetic effects of mutations can be calculated using conventional software.

IX. Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases described assays that can be used.

An assay for kinase activity that can be used for Ret or Ret surrogate, can be performed according to the following procedure using purified Ret or Ret surrogate using the procedure described in the Examples.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

X. Organic Synthetic Techniques

The versatility of computer-based modulator design and identification lies in the diversity of structures screened by the computer programs. The computer programs can search databases that contain very large numbers of molecules and can modify modulators already complexed with the enzyme with a wide variety of chemical functional groups. A consequence of this chemical diversity is that a potential modulator of kinase function may take a chemical form that is not predictable. A wide array of organic synthetic techniques exist in the art to meet the challenge of constructing these potential modulators. Many of these organic synthetic methods are described in detail in standard reference sources utilized by those skilled in the art. One example of suh a reference is March, 1994, *Advanced Organic Chemistry; Reactions, Mechanisms and Structure*, New York, McGraw Hill. Thus, the techniques useful to synthesize a potential modulator of kinase function identified by computer-based methods are readily available to those skilled in the art of organic chemical synthesis.

XI. Administration

The methods and compounds will typically be used in therapy for human patients. However, they may also be used to treat similar or identical diseases in other vertebrates such as other primates, sports animals, and pets such as horses, dogs and cats.

Suitable dosage forms, in part, depend upon the use or the route of administration, for example, oral, transdermal, transmucosal, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in Remington's Pharmaceutical Sciences, $18^{th}$ ed., Mack Publishing Co., Easton, Pa., 1990 (hereby incorporated by reference herein).

Compounds can be formulated as pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluene-sulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, $19^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound is dissolved in a suitable solvent, such as an aqueous or aqueous-alcohol in solution containing the appropriate acid and then isolated by evaporating the solution. In another example, a salt is prepared by reacting the free base and acid in an organic solvent.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Carriers or excipients can be used to produce pharmaceutical compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, or transdermal. Oral administration is preferred. For oral administration, for example, the compounds can be formulated into conventional oral dosage forms such as capsules, tablets, and liquid preparations such as syrups, elixirs, and concentrated drops.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The amounts of various compound to be administered can be determined by standard procedures taking into account factors such as the compound $IC_{50}$, the biological half-life of the compound, the age, size, and weight of the patient, and the disorder associated with the patient. The importance of these and other factors are well known to those of ordinary skill in the art. Generally, a dose will be between about 0.01 and 50 mg/kg, preferably 0.1 and 20 mg/kg of the patient being treated. Multiple doses may be used.

Manipulation of Ret

As the full-length coding sequence and amino acid sequence of Ret (as well as FGFR) from various mammals including human is known, cloning, construction of recombinant Ret and Ret surrogate, production and purification of recombinant protein, introduction of Ret or Ret surrogate into other organisms, and other molecular biological manipulations of Ret or Ret surrogate are readily performed.

Techniques for the manipulation of nucleic acids, such as, e.g., subcloning, labeling probes (e.g., random-primer labeling using Klenow polymerase, nick translation, amplification), sequencing, hybridization and the like are well disclosed in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., *Nucleic Acids Res.* 2001 Jun. 1; 29(11):E54-E54; Hafner et al., *Biotechniques* 2001 April; 30(4):852-6, 858, 860 passim; Zhong et al., *Biotechniques* 2001 April; 30(4):852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be performed by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACS), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) *Genomics* 50:306-316; P1-derived vectors (PACs), see, e.g., Kern (1997) *Biotechniques* 23:120-124; cosmids, recombinant viruses, phages or plasmids.

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids of the invention can also be provided in expression vectors and cloning vehicles, e.g., sequences encoding the polypeptides of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are disclosed, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) *Nature* 328:731; Schneider (1995) *Protein Expr. Purif.* 6435:10; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids of the invention are administered in vivo for in situ expression of the peptides or polypeptides' of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors may also be employed which exploit advantageous merits of each of the parent vector properties (See e.g., Feng (1997) *Nature Biotechnology* 15:866-870). Such viral genomes may be modified by recombinant DNA techniques to include the nucleic acids of the invention; and may be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) *J. Virol.* 66:2731-2739; Johann (1992) *J. Virol.* 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) *Gene Ther.* 3:957-964.

The present invention also relates to fusion proteins, and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) *Biochemistry* 34:1787-1797; Dobeli (1998) *Protein Expr. Purif.* 12:404-414). The histidine residues facilitate detection and purification while the enterokinase cleavage site provides a means for purifying the epitope from the remainder of the fusion protein. In one aspect, a nucleic acid encoding a polypeptide of the invention is assembled in appropriate phase with a leader sequence capable of directing secretion of the translated polypeptide or fragment thereof. Technology pertaining to vectors encoding fusion proteins and application of fusion proteins are well disclosed in the scientific and patent literature, see e.g., Kroll (1993) *DNA Cell. Biol.* 12:441-53.

The nucleic acids and polypeptides of the invention can be bound to a solid support, e.g., for use in screening and diagnostic methods. Solid supports can include, e.g., membranes (e.g., nitrocellulose or nylon), a microtiter dish (e.g., PVC, polypropylene, or polystyrene), a test tube (glass or plastic), a dip stick (e.g., glass, PVC, polypropylene, polystyrene, latex and the like), a microfuge tube, or a glass, silica, plastic, metallic or polymer bead or other substrate such as paper. One solid support uses a metal (e.g., cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g., utilizing single reactive thiol groups of cysteine residues (see, e.g., Colliuod (1993) *Bioconjugate Chem.* 4:528-536) or non-covalently but specifically (e.g., via immobilized antibodies (see, e.g., Schuhmann (1991) *Adv. Mater.* 3:388-391; Lu (1995) *Anal. Chem.* 67:83-87; the biotin/strepavidin system (see, e.g., Iwane (1997) *Biophys. Biochem. Res. Comm.* 230:76-80); metal chelating, e.g., Langmuir-Blodgett films (see, e.g., Ng (1995) *Langmuir* 11:4048-55); metal-chelating self-assembled monolayers (see, e.g., Sigal (1996) *Anal. Chem.* 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (STAB) and the sulfosuccinimidyl derivatives such as sulfosuccinimidyl(4-iodoacetyl)aminobenzoate (sulfo-STAB) (Pierce). Another group of coupling agents is the heterobifunctional and thiol cleavable agents such as N-succinimidyl 3-(2-pyridyldithio)propionate (SPDP) (Pierce Chemicals, Rockford, Ill.).

Antibodies can also be used for binding polypeptides and peptides of the invention to a solid support. This can be done directly by binding peptide-specific antibodies to the column or it can be done by creating fusion protein chimeras comprising motif-containing peptides linked to, e.g., a known epitope (e.g., a tag (e.g., FLAG, myc) or an appropriate immunoglobulin constant domain sequence (an "immunoadhesin," see, e.g., Capon (1989) *Nature* 377:525-531 (1989).

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a gene comprising a nucleic acid of the invention. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the invention, any known array and/or method of making and using arrays can be incorporated in whole or in part, or variations thereof, as disclosed, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) *Curr. Biol.* 8:R171-R174; Schummer (1997) *Biotechniques* 23:1087-1092; Kern (1997) *Biotechniques* 23:120-124; Solinas-Toldo (1997) *Genes, Chromosomes & Cancer* 20:399-407; Bowtell (1999) *Nature Genetics Supp.* 21:25-32. See also published U.S. patent applications Nos. 20010018642; 20010019827; 20010016322; 20010014449; 20010014448; 20010012537; 20010008765.

Host Cells and Transformed Cells

The invention also provides a transformed cell comprising a nucleic acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 μg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y., pp. 16.30-16.37. An exemplary method is as follows. Briefly, COS-1 cells are plated at a density of $5 \times 10^6$ cells/dish and then grown for 24 hours in FBS-supplemented DMEM/F12 medium. Medium is then removed and cells are washed in PBS and then in medium. A transfection solution containing DEAE dextran (0.4 mg/ml), 100 μM chloroquine, 10% NuSerum, DNA (0.4 mg/ml) in DMEM/F12 medium is then applied on the cells 10 ml volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 μg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2-3 weeks later, clonally selected and then propagated for assay purposes.

EXAMPLES

A number of examples involved in the present invention are described below. In most cases, alternative techniques could also be used. The examples are intended to be illustrative and are not limiting or restrictive to the scope of the invention.

A. Synthesis of Key Intermediates

Schemes 1 and 2 describe the synthesis of compounds 1 and 6 respectively. These compounds are used in a number of the exemplary synthetic schemes and examples described below.

Synthesis of 5-bromo-7-azaindole, Compound 1

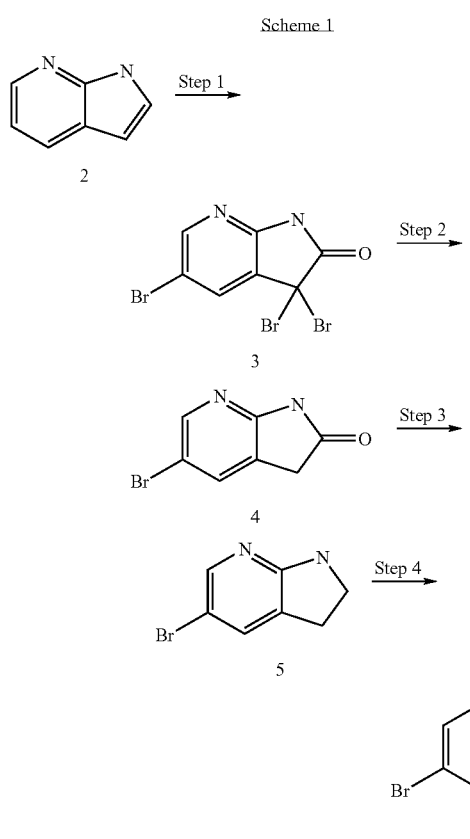

Compound 1 was synthesized as shown in scheme-1 in 4 steps following the literature procedure by Viaud et. al. *Heterocycles,* 1999, 50, 1065-1080.

Synthesis of 4-chloro-7-azaindole, compound 6

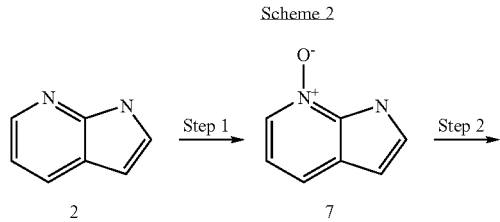

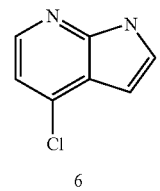

Step-1—Synthesis of Compound 7

Compound 7 was synthesized by reacting commercially available compound 2 with an oxidizing agent (e.g. m-CPBA) in an inert solvent (e.g. DME) as described by Schneller, S. W.; Luo, Jiann-Kuan. *J. Org. Chem.* 1980, 45, 4045-4048. The product was isolated by filtration of the resulting solid that forms upon standing at 5° C. for typically 1-3 h.

Step-2 —Synthesis of Compound 6

Compound of formula 6 was synthesized by reacting compound 7 with a chlorinating agent (e.g. POCl$_3$) neat as described by Schneller, S. W.; Luo, Jiann-Kuan. *J. Org. Chem.* 1980, 45, 4045-4048. The resulting solution after heating for 3-5 h at elevated temperatures (100-150° C.) was neutralized with a base (e.g. NH$_4$OH) until a solid precipitates. The solid was isolated by filtration.

B. Synthesis of Compound of Formula Ia, where $R^1$, $R^2$, $R^3$, and $R^5$ are Hydrogen Compounds of Formula Ia are Formula I compounds in which $R^4$ is the only substituent on the core structure. Exemplary synthetic schemes for groups of compounds within Formula Ia are shown in Schemes 3a, 3b, 4, 5, 6, 7, 8, and 9 for different selections of $R^4$.

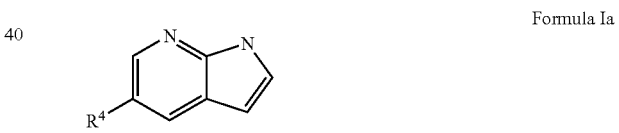

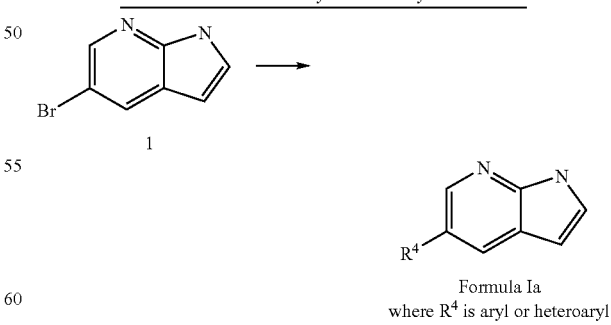

Compound of formula Ia, where $R^4$ is aryl or heteroaryl, was synthesized from compound 1 under Suzuki reaction conditions using aryl or heteroaryl boronic acids (e.g. Phenyl bornonic acid, 3-thienyl bomonic acid), in presence of a catalyst (e.g. Pd(PPh$_3$)$_4$).

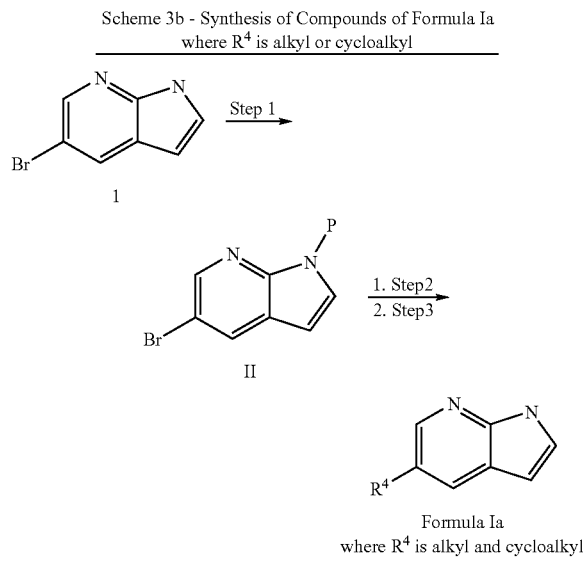

Scheme 3b - Synthesis of Compounds of Formula Ia where R⁴ is alkyl or cycloalkyl

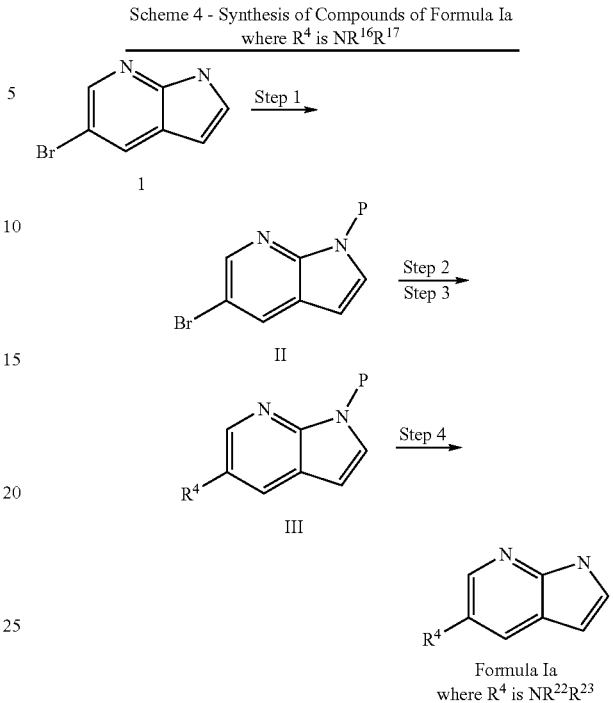

Scheme 4 - Synthesis of Compounds of Formula Ia where R⁴ is NR¹⁶R¹⁷

Step-1—Synthesis of Compound of Formula II

Compound of formula II, where P is a protecting group, was synthesized by reacting compound 1 with a base (e.g. sodium hydride) in an inert solvent (e.g. THF), followed by an appropriate reagent (P—X, e.g. triisopropylsilylchloride) for introduction of a protecting group. The reaction was allowed to proceed, typically at room temperature, for 8-12 hours and the desired product isolated by standard procedures (e.g. extraction) (Greene, T. W.; Wuts, P. G. M. *Protective Groups in Organic Synthesis I, 3$^{rd}$ ed; John Wiley & Sons*: New York, 1981).

Step-2—Synthesis of an Intermediate of Compound of Formula Ia, where R⁴ is Alkyl and Cycloalkyl An intermediate of compound of formula Ia, where R⁴ is alkyl and cycloalkyl, can be synthesized by reacting compound of formula II with alkyl or cycloalkyl Grignard (e.g. ethyl magnesium bromide) in the presence of catalyst (e.g. [1,1'-bis(diphenylphosphino)ferrocene]dichloropalladium (II)) in an inert solvent (e.g. toluene) at low temperature (e.g. −78° C.). The product was isolated by standard procedures (e.g. extraction and silica gel column chromatography) as described (T. Hayashi, M. Konishi, Y. Kobori, M. Kumada, T. Higuchi, K. Hirotsu; *J. Am. Chem. Soc.* 1984, 106, 158-163).

Step-3—Synthesis of Compound of Formula Ia, where R⁴ is Alkyl and Cycloalkyl

Compound of formula Ia, where R⁴ is alkyl or cycloalkyl, can be synthesized by reacting an intermediate of compound formula Ia from step 2 with an appropriate reagent to remove the protecting group (e.g. tetrabutylammonium fluoride) in an appropriate solvent (e.g. methanol). The product was isolated by standard procedures (e.g. extraction and silica gel column chromatography).

Step-1—Synthesis of Compound of Formula II

Compound of formula II, where P is a protecting group, was synthesized by reacting compound 1 with a base (e.g. sodium hydride) in a solvent (e.g. THF), followed by an appropriate reagent (P—X, e.g. triisopropylsilylchloride) for introduction of a protecting group. The reaction was allowed to proceed, typically at room temperature, for 8-12 hours and the desired product was isolated by standard procedures (e.g. extraction and silica gel column chromatography) (Greene, T. W.; Wuts, P. G. M. *Protective Groups in Organic Synthesis I, 3$^{rd}$ ed.; John Wiley & Sons*: New York, 1981).

Step-2—Synthesis of an Intermediate of Compound of Formula III, where R⁴ is NR¹⁶R¹⁷

An intermediate of compound of formula III, where R⁴ is NR¹⁶R¹⁷, was synthesized by reacting compound of formula II, with an amine of the formula NHR¹⁶R¹⁷ (e.g. aniline) in a solvent (e.g. toluene), in presence of a base (e.g. sodium tert-butoxide) and a catalyst composed of a metal (e.g. Tris (dibenzylideneacetone)dipalladium(0)) and a ligand (e.g. tri-tert-butylphosphine) with heating, typically to 95° C., for 8-12 hours as described (Thomas, et. al., J. Am. Chem. Soc., 2001, 123, 9404) by substituting compound of formula II for the N-substituted-3,6-dibromocarbazole. The desired compound was purified by silica gel chromatography. This intermediate was used directly in Step 4 to provide compound of formula Ia where R⁴ is NR²²R²³ and R²² and R²³ are not —C(X)R²⁰, —C(X)NR¹⁶R¹⁷, or —S(O)₂R²¹, or alternatively, it can be additionally substituted as described in Step 3.

Step-3—Synthesis of Compound of Formula III, where R⁴ is NR²²R²³

The intermediate from Step 2 can be further modified when R¹⁶ or R¹⁷ is hydrogen. In this case, the intermediate from Step 2 can be reacted with a base (e.g. sodium hydride) in a solvent (e.g. N,N-dimethylformamide), followed by reaction with an alkylating reagent (e.g. benzyl bromide) or an acylating reagent (e.g. benzoyl chloride, phenyl isocyanate, phenyl isothiocyanate, phenylsulfonyl chloride) typically at room temperature or with heating up to 80° C. for 1-12 hours. The desired product can be purified by conventional means (e.g. silica gel chromatography). Reference?

Step-4—Synthesis of Compound of Formula Ia, Where $R^4$ is $NR^{22}R^{23}$

Compound of formula Ia, where $R^4$ is $NR^{22}R^{23}$, was synthesized by reacting compound of formula III with an appropriate reagent to remove the protecting group (e.g. tetrabutylammonium fluoride) in an appropriate solvent (e.g. methanol). The final product can be isolated by standard procedures (e.g. extraction).

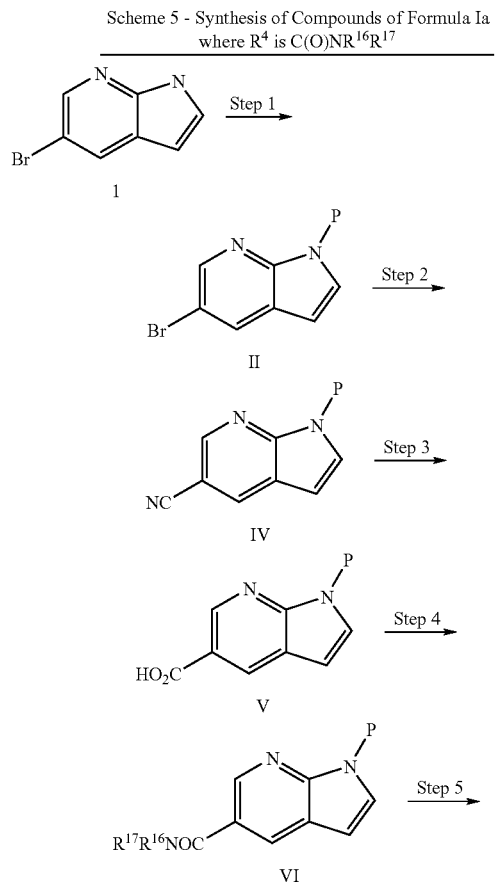

Step-1—Synthesis of Compound of Formula II

Compound of formula II, where P is a protecting group, was synthesized by reacting compound 1 with a base (e.g. sodium hydride) in a solvent (e.g. THF), followed by an appropriate reagent (P—X, e.g. triisopropylsilylchloride, benzene sulfonyl chloride) for introduction of a protecting group. The reaction was allowed to proceed, typically at room temperature, for 8-12 hours and the desired product was isolated by standard procedures (e.g. extraction and silica gel column chromatography) (Greene, T. W.; Wuts, P. G. M. *Protective Groups in Organic Synthesis I, 3rd ed.; John Wiley & Sons*: New York, 1981).

Step-2—Synthesis of Compound of Formula IV

Compound of formula IV, where $R^4$ is CN, was synthesized by reacting compound of formula II with sodium cyanide in a polar aprotic solvent (e.g. DMF) in an inert atmosphere, in presence of catalysts (e.g. Tris(dibenzylideneacetone)dipalladium(0) and cuprous iodide) following the procedure described by Buchwald et. al., J. Am. Chem. Soc., 2003, 125, 2890-2891, by substituting 5-bromo-7-azaindole for 5-bromo-indole.

Step-3—Synthesis of Compound of Formula V

Compound of formula V, where $R^4$ is COOH, was synthesized by heating compound of formula IV with aqueous base (e.g. aq. KOH) in presence of an alcohol (e.g. ethanol) at higher temperatures (e.g. 90° C.) for required time, typically 24 h, as described in Org. Syn. Collective Volume 2, 292 (1943).

Step-4—Synthesis of compound of formula VI

Compound of formula VI, where $R^4$ is $C(O)NR^{16}R^{17}$, was synthesized by reacting compound of formula V with an amine (e.g. benzylamine) in a polar aprotic solvent (e.g. DMF) in an inert atmosphere, in presence of PyBroP (Bromotri(pyrrolidino)phosphonium hexafluorophosphate following the procedure described by Coste et. al., J. Org. Chem., 1994, 59, 2437.

Step-5—Synthesis of Compound of Formula Ia

Compound of formula Ia, where $R^4$ is $C(O)NR^{16}R^{17}$, was synthesized by cleaving the protective group (e.g. TIPS) of compound of formula VI with appropriate reagents (e.g. TBAF) and isolating the product (work up and silica gel column chromatography).

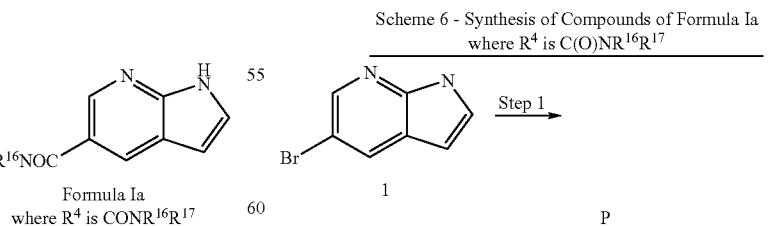
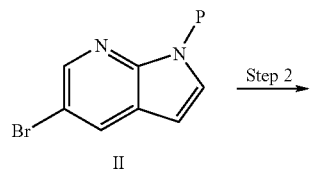

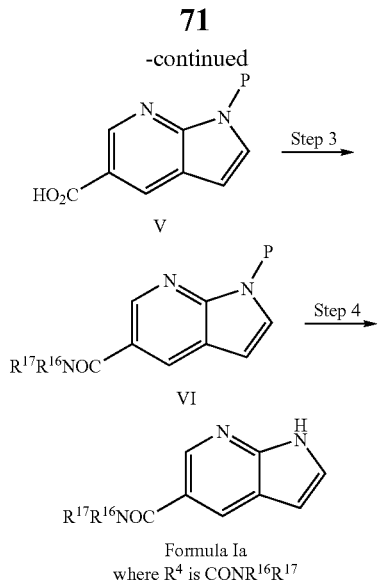

Scheme 7 - Synthesis of Compounds of Formula Ia where R$^4$ is CH$_2$NHR$^{16}$R$^{17}$

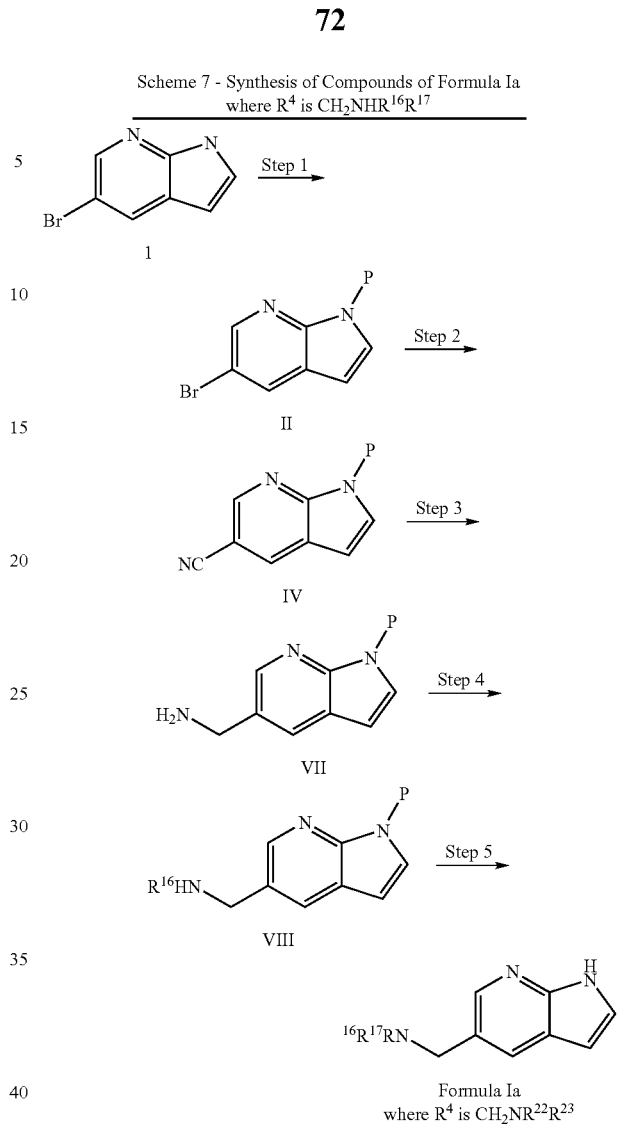

Step-1—Synthesis of Compound of Formula II

Compound of formula II, where P is a protecting group, was synthesized by reacting compound 1 with a base (e.g. sodium hydride) in a solvent (e.g. THF), followed by an appropriate reagent (P—X, e.g. triisopropylsilylchloride) for introduction of a protecting group. The reaction was allowed to proceed, typically at room temperature, for 8-12 hours and the desired product was isolated by standard procedures (e.g. extraction and silica gel column chromatography) (Greene, T. W.; Wuts, P. G. M. *Protective Groups in Organic Synthesis I*, 3$^{rd}$ ed.; *John Wiley & Sons*: New York, 1981).

Step-2—Synthesis of Compound of Formula V

Compound of formula V, where R$^4$ is COOH, was synthesized by reacting compound of formula II with a strong base (e.g. n-butyllithium) and benzyl chloroformate in an inert solvent (e.g. THF), and further debenzylation by hydrogenating the obtained benzyl ester with hydrogen, in presence of a catalyst (e.g. 20% Pd(OH)$_2$/C) at room temperature. The product was isolated by filtration and evaporation.

Step-3—Synthesis of Compound of Formula VI

Compound of formula VI, where R$^4$ is C(O)NR$^{16}$R$^{17}$, was synthesized by reacting compound of formula V with an amine (e.g. benzylamine) in a polar aprotic solvent (e.g. DMF) in an inert atmosphere, in presence of a condensing agent (PyBrop, Bromotri(pyrrolidino)phosphonium hexafluorophosphate) following the procedure described by Coste et. al., J. Org. Chem., 1994, 59, 2437.

Step-4—Synthesis of Compound of Formula Ia

Compound of formula Ia, where R$^4$ is C(O)NR$^{16}$R$^{17}$, was synthesized by cleaving the protective group (e.g. TIPS) of compound of formula VI with appropriate reagents (e.g. TBAF). The product was isolated by following standard procedure (work up and silica gel column chromatography).

Step-1—Synthesis of Compound of Formula II

Compound of formula II, where P is a protecting group, was synthesized by reacting compound 1 with a base (e.g. sodium hydride) in a solvent (e.g. THF), followed by an appropriate reagent (P—X, e.g. triisopropylsilylchloride) for introduction of a protecting group. The reaction was allowed to proceed, typically at room temperature, for 8-12 hours and the desired product was isolated by standard procedures (e.g. extraction and silica gel column chromatography) (Greene, T. W.; Wuts, P. G. M. *Protective Groups in Organic Synthesis I*, 3$^{rd}$ ed.; *John Wiley & Sons*: New York, 1981).

Step-2—Synthesis of Compound of Formula IV

Compound of formula IV, where R$^4$ is CN, was synthesized by reacting compound of formula II with sodium cyanide in a polar aprotic solvent (e.g. DMF) in an inert atmosphere, in presence of catalysts (e.g. Tris(dibenzylideneacetone)dipalladium(0) and cuprous iodide) following the procedure described by Buchwald et. al., J. Am. Chem. Soc., 2003, 125, 2890-2891, by substituting 5-bromo-7-azaindole for 5-bromo-indole.

Step-3—Synthesis of Compound of Formula VII

Compound of formula VII, where $R^4$ is $CH_2NH_2$, can be synthesized from compound of formula IV under hydrogenation condition using a catalyst (e.g. $NO_2$) in an atmosphere of $H_2$ as described by Secrist III et. al., J. Org. Chem., 1972, 37, 335-336.

Step-4—Synthesis of Compound of Formula VIII

Compound of formula VIII, where $R^4$ is $CH_2NHR^{16}$, can be synthesized from compound of formula VII with an electrophilic reagent (e.g. benzyl bromide, benzenesulfonyl chloride, benzoyl chloride, phenyl isocyanate, phenyl isothiocyanate) in a polar aprotic solvent (e.g. DMF) in an inert atmosphere, in presence of a base (e.g. $K_2CO_3$, $Et_3N$). The product was isolated by standard methods (aqueous work up and silica gel column chromatography).

Step-5—Synthesis of Compound of Formula Ia

Compound of formula VIIIa, where $R^4$ is $CH_2NHR^{16}R^{17}$, can be synthesized from compound of formula VIII with an electrophilic reagent (e.g. benzyl bromide, benzenesulfonyl chloride, benzoyl chloride, phenyl isocyanate, phenyl isothiocyanate) in a polar aprotic solvent (e.g. DMF) in an inert atmosphere, in presence of a base (e.g. $K_2CO_3$, $Et_3N$), followed by deprotection of the protective group with appropriate conditions.

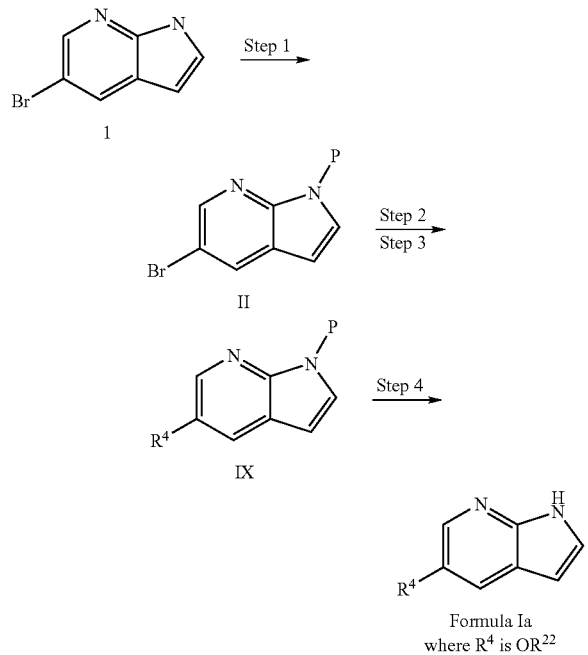

Scheme 8 - Synthesis of Compounds of Formula Ia where $R^4$ is $OR^{22}$

Step-1—Synthesis of Compound of Formula II

Compound of formula II, where P is a protecting group, was synthesized by reacting compound 1 with a base (e.g. sodium hydride) in a solvent (e.g. THF), followed by an appropriate reagent (P—X, e.g. triisopropylsilylchloride) for introduction of a protecting group. The reaction can be allowed to proceed typically at room temperature for 8-12 hours and the desired product isolated by standard procedures (e.g. extraction and silica gel column chromatography) (Greene, T. W.; Wuts, P. G. M. *Protective Groups in Organic Synthesis I, 3rd ed.*; John Wiley & Sons: New York, 1981).

Step-2—Synthesis of Intermediate of Compound of Formula IX, where $R^4$ is $OR^{16}$ An intermediate compound of formula IX, where $R^4$ is $OR^{16}$, can be synthesized by reacting compound of formula II with a reagent of formula $R^{16}OH$ (e.g. methanol or water) in the presence of base (e.g. sodium methoxide or sodium hydroxide) and copper (I) bromide in a solvent (e.g. N,N-dimethylformamide) typically with heating to reflux for 2-8 hours as described by Mazeas, et. al. in Heterocycles, 1999, 50, 1065. The desired intermediate can be purified by conventional means (e.g. silica gel chromatography). When $R^{16}$ is hydrogen, this intermediate can be additionally substituted in Step 3 or it can be used directly in Step 4 to provide compound of formula Ia where $R^4$ is $OR^{22}$ and $R^{22}$ is not $—C(X)R^{20}$, $—C(X)NR^{16}R^{17}$, or $—S(O)_2R^{21}$.

Step-3—Synthesis of Compound of Formula IX, where $R^4$ is $OR^{22}$

The intermediate from Step 2 can be further modified when $R^{16}$ is hydrogen. In this case, the intermediate from Step 2 can be reacted with a base (e.g. sodium hydride) in a solvent (e.g. N,N-dimethylformamide), followed by reaction with an alkylating reagent (e.g. benzyl bromide) or an acylating reagent (e.g. benzoyl chloride, phenyl isocyanate) typically at room temperature or with heating up to 80° C. for 1-12 hours. The desired product can be purified by conventional means (e.g. silica gel chromatography).

Step-4—Synthesis of Compound of Formula Ia, where $R^4$ is $OR^{22}$

Compound of formula Ia, where $R^4$ is $OR^{22}$, can be synthesized by reacting compound formula IX with an appropriate reagent to remove the protecting group, P, (e.g. tetrabutylammonium fluoride) in an appropriate solvent (e.g. methanol). The final product can be isolated by standard procedures (e.g. extraction).

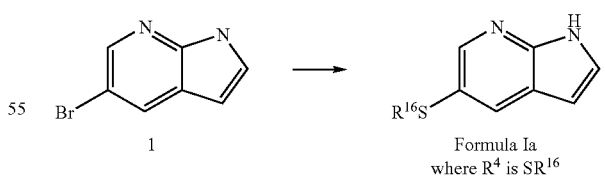

Scheme 9 - Synthesis of Compounds of Formula Ia where $R^4$ is $SR^{16}$

Compound of Formula Ia, where $R^4$ is $SR^{16}$, can be prepared by reacting compound 1 with a strong base (e.g. potassium hydride or t-butyl lithium) and dialkyldisulfides (e.g. dimethyldisulfane) or thiophenols (e.g. 4-methoxythiophenol) in a polar aprotic solvent (e.g. N,N-dimethylformamide) in an inert atmosphere following the procedure described by Yang et. al., Heterocycles, 1992, 34, 1169, by substituting 5-bromo-7-azaindole for 5-bromo-indole.

Scheme - 9a

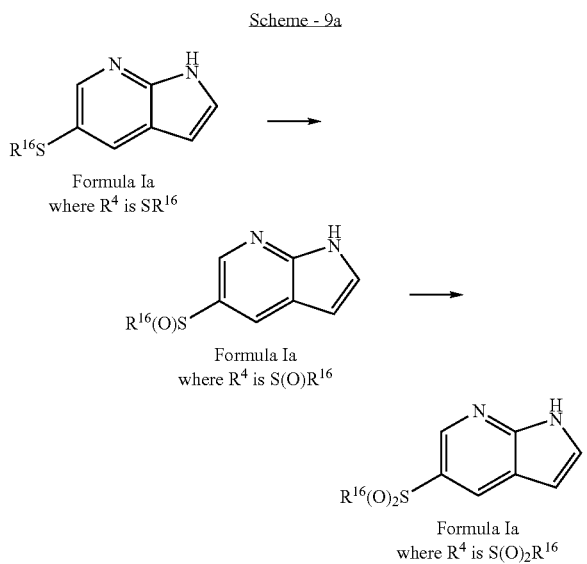

Compounds of Formula Ia, where $R^4$ is $S(O)R^{16}$, or $S(O)_2R^{16}$ can be prepared by reacting compound 1a where $R^4$ is $R^{16}$ with 1 or 2 equivaluents of Oxone, respectively in a polar solvent, using standard procedures.

C. Synthesis of Compound of Formula Ib, where $R^1$, $R^2$, $R^4$, and $R^5$ are Hydrogen

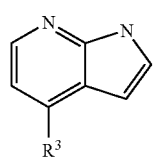

Formula Ib

Compounds of Formula Ib are Formula I compounds in which $R^3$ is the only substituent on the core structure. Exemplary synthetic schemes for groups of compounds within Formula Ib are shown in Schemes 10, 11, 12, 13, 14, and 15 for different selections of $R^3$.

Scheme 10 - Synthesis of Compounds of Formula Ib where $R^3$ is aryl or heteroaryl

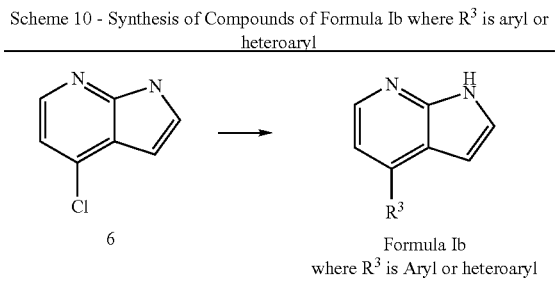

Compound of formula Ib, where $R^3$ is aryl or heteroaryl, were synthesized from compound 6 under Suzuki reaction conditions using aryl or heteroaryl bornonic acids (e.g. Phenyl bornonic acid, 3-thienyl bornonic acid) (M. Allegretti, Synlett, 2001, 5, p. 609).

Scheme 11 - Synthesis of Compounds of Formula Ib where $R^3$ is $R^3$ is $OR^{22}$

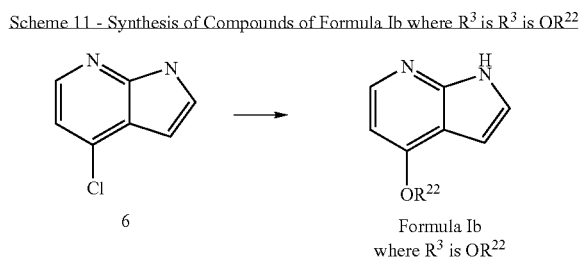

Compound of formula Ib, where $R^3$ is $OR^{22}$, can be synthesized by heating compound 6 with aqueous base (e.g. aq. NaOH) in presence of an alcohol (e.g. methanol, benzyl alcohol) at higher temperatures (e.g. 150° C.) for required time, typically 12 h, as described by Girgis et al. in J. Heterocyclic Chemistry, 1989, 26, 317. The product can be isolated by following standard work up procedure.

Scheme 12 - Synthesis of Compounds of Formula Ib where $R^3$ is $NR^{16}R^{17}$

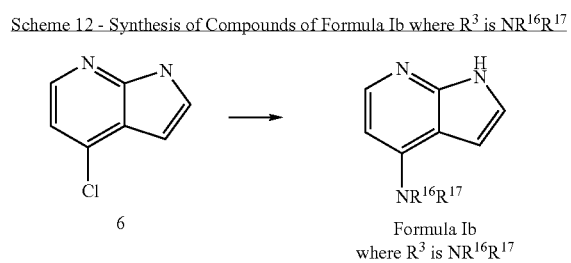

Compound of Formula Ib, where $R^3$ is $NR^{16}R^{17}$, was synthesized by heating compound 6 with an amine (e.g. dimethylamine, N-methylaniline) and heated in an oil bath, typically to 180° C., for 1-5 hours. The product can be isolated by following either standard procedures or purifying by silica gel column chromatography (Nabih, et. al. J. Heterocyclic Chemistry, 1989, 26, 317).

Scheme 13 - Synthesis of Compounds of Formula Ib where $R^3$ is $CONR^{16}R^{17}$

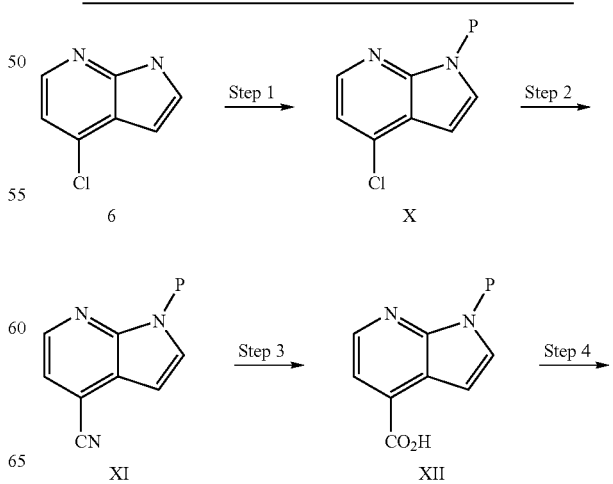

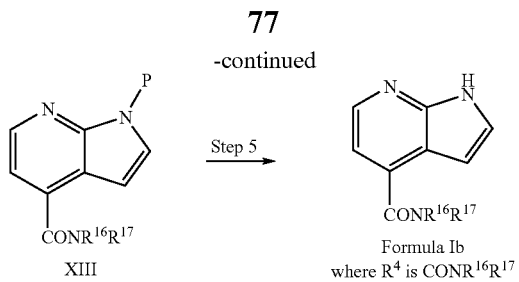

Step-1—Synthesis of Compound of Formula X

Compound of formula X can be synthesized by reacting compound 6 with a silyl chloride (e.g. triisopropylsilyl chloride) in an inert solvent (e.g. THF), in the presence of a base (e.g. NaH), as described by Greene, T. W.; Wuts, P. G. M. *Protective Groups in Organic Synthesis I*, 3$^{rd}$ ed.; John Wiley & Sons: New York, 1981. The product can be purified by standard chromatographic techniques.

Step-2—Synthesis of Compound of Formula XI

Compound of formula XI was synthesized by reacting compound X with a cyanide source (e.g. Zn(CN)$_2$) in a polar aprotic solvent (e.g. DMF), in the presence of a catalyst (e.g. Tetrakistriphenylphosphine palladium) as described in Anderson et al *J. Org. Chem.* 1998; 63, 8224 A standard workup is used and compound of formula XI can be purified by standard crystallization or chromatographic methods.

Step-3—Synthesis of Compound of Formula XII

Compound of formula XII can be prepared by reacting compound XI with a base (e.g. NaOH) in an inert solvent (e.g. EtOH) as described in Larock, R. C. *Comprehensive Organic Transformations*; VCH: NY, 1989, p. 993. Standard workup procedures and purifications are performed.

Step-4—Synthesis of Compound of Formula XIII

Compound of formula XIII can be prepared by reacting compound XII with an amine (e.g. benzyl amine) in an inert solvent (e.g. DMF), in the presence of a coupling reagent (e.g. bromotri(pyrrolidino)phosphonium hexafluorophosphate (PyBrop)), and in the presence of a base (e.g. diisopropylethyl amine) as described in Coste, J. et al *J. Org. Chem.* 1994; 158, 2437. A typical workup is utilized and purification is achieved by standard chromatographic procedures.

Step-5—Synthesis of Compound of Formula Ib, where R$^3$ is CONR$^{16}$R$^{17}$ Compound of formula Ib, where R$^3$ is CONR$^{16}$R$^{17}$ can be prepared by reacting compound XIII with a fluoride source (e.g. NH$_4$F) in an inert solvent (e.g. THF) as described in *Tetrahedron Lett.* 2001, 42(44); 7759. Purification is achieved with standard chromatographic techniques.

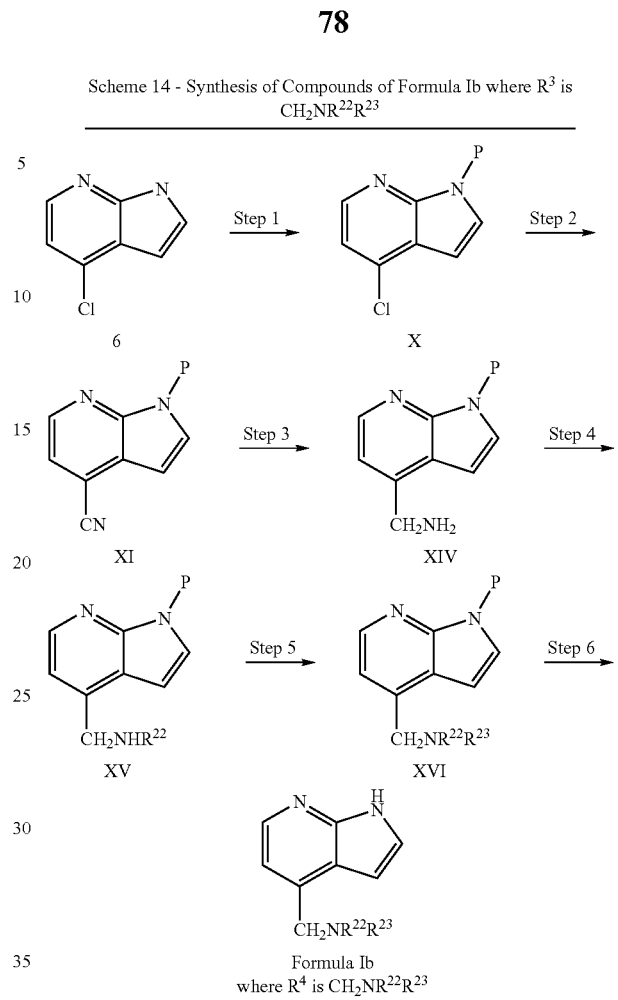

Scheme 14 - Synthesis of Compounds of Formula Ib where R$^3$ is CH$_2$NR$^{22}$R$^{23}$

Step-1—Synthesis of Compound of Formula X

Compound of formula X was synthesized by reacting compound 6 with a sulfonyl chloride (e.g. benzene sulfonyl chloride) in an inert solvent (e.g. dichloromethane), in the presence of a base (e.g. sodium hydroxide) as described in Greene, T. W.; Wuts, P. G. M. *Protective Groups in Organic Synthesis I*, 3$^{rd}$ ed; John Wiley & Sons: New York, 1981. The product can be isolated by filtration of the resulting slurry over celite.

Step-2—Synthesis of Compound of Formula XI

Compound of formula XI was synthesized by reacting compound X with a cyanide source (e.g. Zn(CN)$_2$) in a polar aprotic solvent (e.g. DMF), in the presence of a catalyst (e.g. Tetrakis triphenylphosphine palladium) as described in Anderson et al *J. Org. Chem.* 1998; 63, 8224. A standard workup is used and purified by standard crystallization or chromatographic methods.

Step-3—Synthesis of Compound of Formula XIV

Compound of formula XIV was prepared by reacting compound XI with a reducing agent (e.g. H$_2$) in an inert solvent (e.g. MeOH) with an added catalyst (e.g. palladium on carbon) as described by Stavenger, R. A. et al Pct Int Appl., WO 03/028724 A1 10 Apr. 2003. Purification can be achieved by standard chromatogreaphic procedures.

Step-4—Synthesis of Compound of Formula XV

Compound of formula XV was prepared by reacting compound XIV with an alkylating agent (e.g. benzyl bromide) in an inert solvent (e.g. DMF), in the presence of a base (e.g. Diisopropylethyl amine). A standard workup is used and purified by standard crystallization or chromatographic methods.

Step-5—Synthesis of Compound of Formula XVI

Compound of formula XVI can be prepared by reacting compound XV with an alkylating agent (e.g. benzyl bromide) in an inert solvent (e.g. DMF), in the presence of a base (e.g. Diisopropylethyl amine). A standard workup is used and purified by standard crystallization or chromatographic methods.

Step 6 —Synthesis of Compound of Formula Ib, where $R^3$ is $CH_2NR^{22}R^{23}$

Compound of formula 1b, where $R^3$ is $CH_2NR^{22}R^{23}$ was synthesized by treating compound of formula XVI with a base (e.g. KOH) in a polar aprotic solvent (e.g. EtOH) while heating from 60-80° C. for typically 1-3 h as described in in Greene, T. W.; Wuts, P. G. M. *Protective Groups in Organic Synthesis I, 3rd ed; John Wiley & Sons*: New York, 1981. A standard workup is used and purified by standard chromatographic methods.

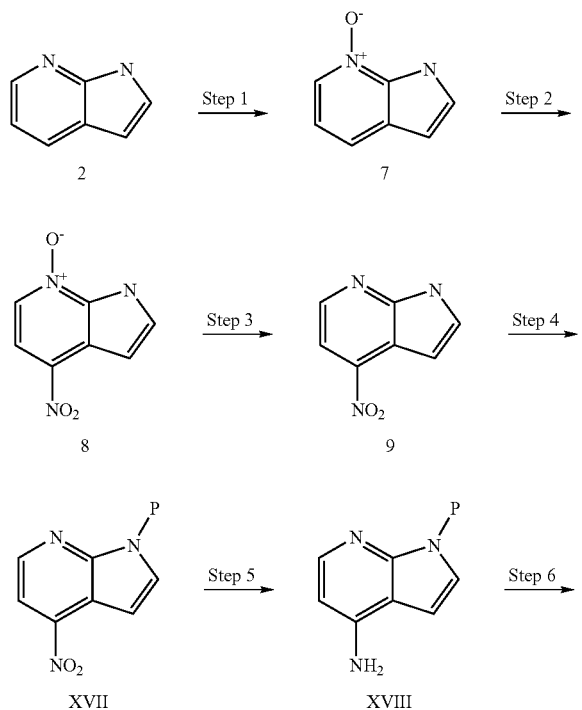

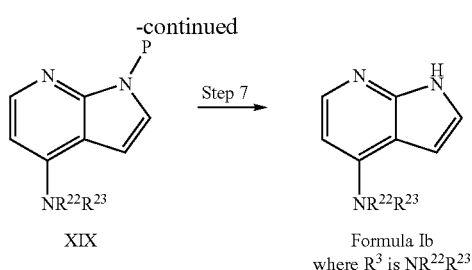

Step-1—Synthesis of Compound 7

Compound 7 was synthesized by reacting compound 2 with 85% meta-chloroperoxybenzoic acid in a solvent (e.g. 1,2-dimethoxyethane) typically at room temperature for 1-4 hours as described (Schneller and Luo, J. Org. Chem., 1980, 45, 4045). The resulting solid can be collected by filtration and washed with ethyl ether. The solid can be suspended in water and basified with an aqueous base (e.g. potassium carbonate). Upon cooling, the precipitate can be collected by filtration and purified by conventional means (e.g. recrystalliztion) to provide compound 7.

Step-2—Synthesis of Compound 8

Compound 8 was synthesized by reacting compound 7 with fuming nitric acid in a solution of trifluoroacetic acid typically at 0° C. as described (Schneller and Luo, J. Org. Chem., 1980, 45, 4045). The reaction mixture is immediately poured onto ice and basified with sodium hydroxide to provide a precipitate that can be collected by filtration. Purification by standard procedures (e.g. recrystallization) can provide compound 8.

Step-3—Synthesis of Compound 9

Compound 9 was synthesized by reacting compound 8 with phosphorous trichloride in a solvent (e.g. ethyl acetate) with heating typically at 80° C. for a few minutes as described (Schneller and Luo, J. Org. Chem., 1980, 45, 4045). The reaction mixture is cooled and neutralized with aqueous base (e.g. sodium carbonate) and extracted with an organic solvent (e.g. ethyl acetate). Compound 9 can be isolated from the organic portions and purified by conventional means (e.g. recrystallization).

Step-4—Synthesis of Compound of Formula XVII

Compound of formula XVII, where P is a protecting group, can be synthesized by reacting compound 9 with a base (e.g. sodium hydride) in a solvent (e.g. THF), followed by an appropriate reagent (P—X, e.g. triisopropylsilylchloride) for introduction of a protecting group. The reaction can be allowed to proceed typically at room temperature for 8-12 hours and the desired product isolated by standard procedures (e.g. extraction and silica gel column chromatography).

Step-5—Synthesis of Compound of Formula XVIII

Compound of formula XVIII can be synthesized by reacting compound of formula XVII with a reducing agent (e.g. hydrogen gas) in the presence of a catalyst (e.g. Raney nickel) in an appropriate solvent (e.g. methanol) typically at room temperature for 2-4 hours as described (Antonini et. al. J.

Med. Chem. 1982, 25, 1258). Compound of formula XVIII can be isolated by standard procedures (e.g. filtration and evaporation).

Step-6—Synthesis of Compound of Formula XIX

Compound of formula XIX can be synthesized by reacting compound of formula XVII with one of many possible alkylating or acylating agents (e.g. isobutyl bromide, benzoyl chloride, phenyl isocyanate, or phenylsulfonyl chloride). The compound of formula XIX can be purified by conventional means (e.g. silica gel chromatography).

Step-7—Synthesis of Compound of Formula Ib, where $R^3$ is $NR^{22}R^{23}$

Compound of Formula Ib, where $R^3$ is $NR^{22}R^{23}$, can be synthesized by reacting compound formula XIX with an appropriate reagent to remove the protecting group, P, (e.g. tetrabutylammonium fluoride) in an appropriate solvent (e.g. methanol). The final product can be isolated by standard procedures (e.g. extraction).

D. Synthesis of Compound of Formula Ic, where R', $R^3$, $R^4$, and $R^5$ are Hydrogen

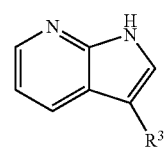

Formula Ic

Compounds of Formula Ic are Formula I compounds in which $R^2$ is the only substituent on the core structure. Exemplary synthetic schemes for groups of compounds within Formula Ic are shown in Schemes 16-32, for different selections of $R^2$.

Scheme 16 - Synthesis of Compounds of Formula Ic where $R^2$ is aralkyl or heteroearalkyl and $R^{24}$ is aryl or heteroaryl

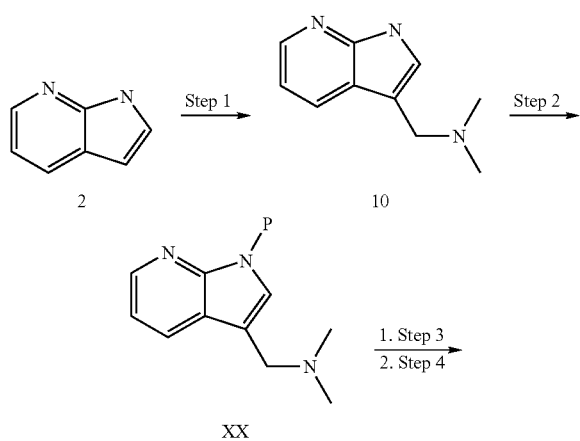

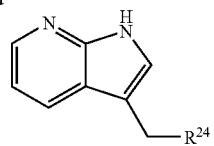

Formula Ic
where $R^2$ is aralkyl or heteroalkyl
and $R^{24}$ is aryl or heteroaryl Step-1—Synthesis of Compound 10

Compound 10 was synthesized from commercially available 7-azaindole following the literature procedure (Robinson, J. Am. Chem. Soc., 1955, 77, p. 457).

Step-2—Synthesis of Compound of Formula XX

Compound of formula XX was synthesized by deprotonation using base (e.g. BuLi, NaH) in aprotic solvent like THF or ether and reacting the anion with a silyl chloride (e.g. TIPS) or an anhydride (e.g. Boc anhydride). The product was isolated by following standard procedure (quenching with ice-cold brine, work up, and purification by flash silica gel chromatography).

Step-3—Synthesis of Compound of Formula Ic

Compounds of Formula Ic was synthesized through the reaction of compounds of formula XX with isopropyl chloroformate (or ethyl chloroformate) at room temperature in toluene to give a 3-chloromethyl intermediate. This intermediate cooled to −78° C. and was immediately reacted with an organocopper reagent, which was generated from the reaction between a Grignard reagent (or organolithium reagent) and a solution of copper cyanide and LiCl. The mixture was stirred at −78° C. for one hour then allowed to warm to room temperature. The reaction was quenched with a solution of 4:1 ammonium chloride: ammonium Hydroxide. The reaction was worked up in the usual manner and purified by flash silica gel chromatography to give the nitrogen-protected product. The final product can be realized through the deprotection of the protecting group (Boc, TIPS) using standard conditions (TFA or NH4F) at room temperature.

Scheme 17 - Alternate Synthesis of Compounds of Formula Ic where $R^2$ is aralkyl or heteroaralkyl and $R^{24}$ is aryl or heteroaryl

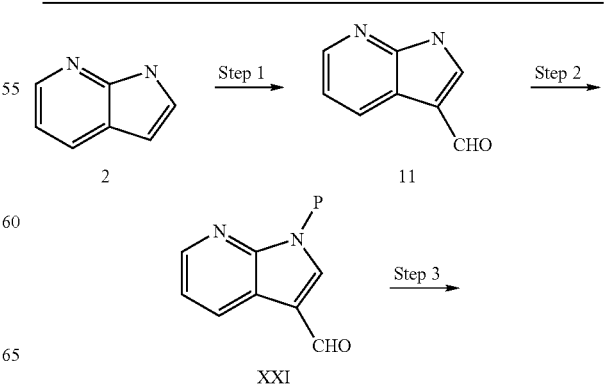

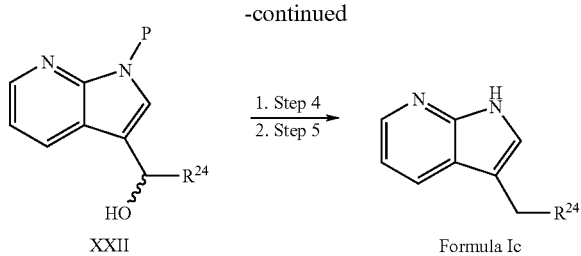

Step-1—Synthesis of Compound 11

Compound 11 was synthesized by reacting commercially available 7-azaindole, compound 2, with hexamethyltetramine and acetic acid in water with heating to reflux for two hours. After cooling, the desired product precipitated and was collected by filtration.

Step-2—Synthesis of Compound of Formula XXI

Compound of formula XXI, where P is a protecting group, was synthesized by reacting compound 11 with an appropriate reagent to introduce a protecting group (e.g. tert-butyloxycarbonyl di anhydride) and a base (e.g. sodium hydride) in a solvent (e.g. THF) typically at room temperature for 12-18 hours. The product can be isolated by conventional means (e.g. extraction).

Step-3—Synthesis of Compound of Formula XXII

Compound of formula XXII was synthesized by reacting compound of formula XXI in a solvent (e.g. 1,2-dimethoxyethane) with a Grignard reagent of the formula $R^{24}MgCl$ (e.g. phenyl magnesium bromide) or an equivalent nucleophile in a solvent (e.g. THF) under inert atmosphere cooled typically to −10° C. The reaction was typically allowed to warm to room temperature and stirred for 12-18 hours. The desired product was purified by reverse phase high pressure liquid chromatography.

Step-4—Synthesis of an Intermediate of Compound of Formula Ic where $R^2$ is Aralkyl or Heteroaralkyl and $R^{24}$ is Aryl or Heteroaryl An intermediate of compound of formula Ic was synthesized by reacting compound of formula XXII with a reducing agent (e.g. sodium borohydride) in a solvent (e.g. ethanol) typically with heating to 80° C. for 1-4 hours. The reaction was quenched with the addition of methanol and concentrated and purified by reverse phase high performance liquid chromatography.

Step-5—Synthesis of Compound of Formula Ic where $R^2$ is Aralkyl or Heteroaralkyl and $R^{24}$ is Aryl or Heteroaryl Compound of formula Ic where $R^2$ is aralkyl or heteroaralkyl and $R^{24}$ is aryl or heteroaryl was synthesized by reacting the intermediate from Step 4 with an appropriate reagent to remove the protecting group, P, (e.g. hydrochloric acid) in an appropriate solvent (e.g. dioxane). The final product was isolated by standard procedures (e.g. reverse phase preparative high pressure liquid chromatography).

Scheme 18 - Alternate of Compounds of Formula Ic where $R^2$ is aralkyl or heteroaralkyl and $R^{24}$ is aryl or heteroaryl

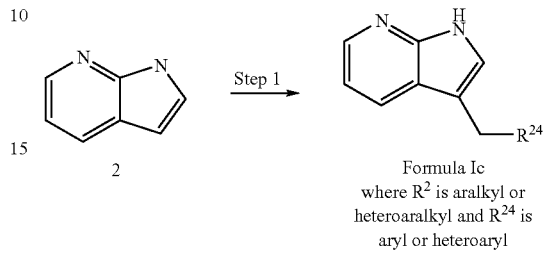

Step-1—Synthesis of Compound of Formula Ic, where $R^2$ is aralkyl or heteroaralkyl and $R^{24}$ is Aryl or Heteroaryl Compound of formula Ic, where $R^2$ is aralkyl or heteroaralkyl and $R^{24}$ is aryl or heteroaryl, was synthesized by reacting compound 2 with an activating agent (e.g. methyl magnesium bromide and zinc dichloride or anhydrous aluminum chloride) and an aralkyl bromide (e.g. benzyl bromide) or heteroaralkyl bromide (pyridine benzyl bromide) in an inert solvent (e.g. methylene chloride), under inert atmosphere (e.g. argon), at room temperature or with heating up to reflux for 18-24 hours. The product was isolated by standard procedures (e.g. extraction and silica-gel chromatography).

Scheme 19 - Synthesis of Compounds of Formula Ic where $R^2$ is $CH_2NR^{22}R^{23}$

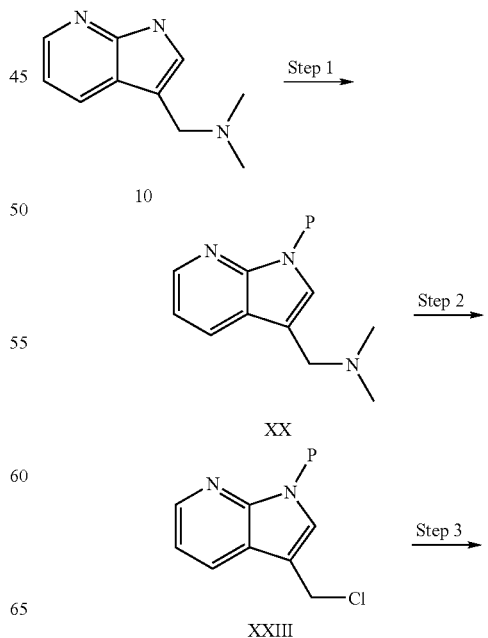

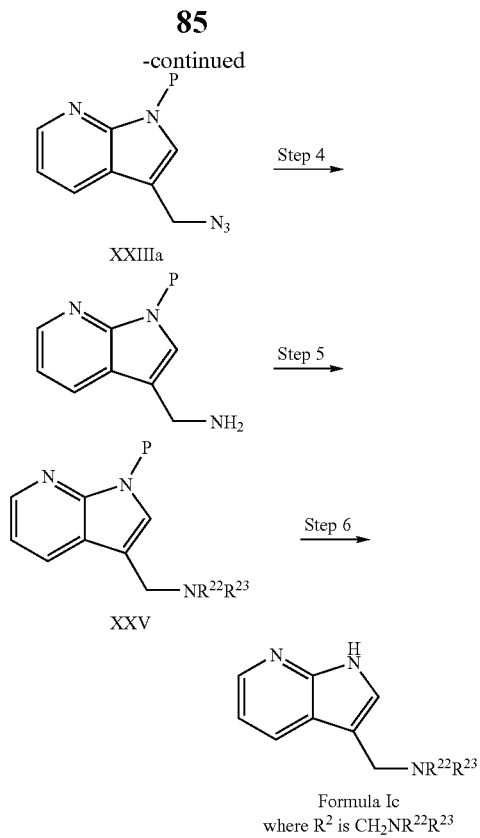

Step 1: Synthesis of Compound of Formula XX

Compound of the formula XX was prepared from the compound 10 by deprotonation with a strong base (e.g. NaH, BuLi) at 0° C. in an aprotic solvent (THF), followed by the addition of P—X (e.g. TIPS-Cl, Boc anhydride). The product was isolated by following standard workup procedure.

Step 2: Synthesis of Compound of Formula XXIII

Compound of the formula XXIII was prepared from the compound of formula XX by addition of chloroformate (e.g., ethyl formate, isopropyl formate) at 25° C. in an aprotic solvent (toluene). The product was isolated by following standard workup and silica gel flash chromatography.

Step 3: Synthesis of Intermediate Formula XXIIIa

Compound of the formula XXIIIa was prepared from the compound of formula XXIII by addition of sodium Iodide in acetone at 60° C. After several hours, typically 4 h, concentrated down to dryness and the residue was dissolved in DMF followed by addition of sodium azide. The reaction was stirred, typically at room temperature, for a a short period of time, 1 h. The product was isolated by following standard workup procedure and silica gel flash chromatography yielded azide intermediate. Reference?

Step 4: Synthesis of Compound of FORMULA XXIV

Compound of the formula XXIV was prepared from azide of formula XXIIIa by hydrogenation in an inert solvent (e.g. THF) with catalytic amount of acid (e.g., HCl, Acetic acid) and in presence of a catalyst (e.g., Pd/C). The product was isolated by following standard workup procedure. Reference?

Step 5: Synthesis of Compound of Formula XXV

Compound of the formula XXV was prepared from the compound of formula XXIV, by using various electrophilic groups (isocyanates, sulfonyl chloride) in presence of a strong base of (e.g., NaH, BuLi, TEA) in an inert solvent (e.g. THF). Products were isolated by following standard workup and silica gel flash chromatography. Reference?

Step 6: Synthesis of Compound of Formula Ic where $R^2$ is $CH_2NR^{22}R^{23}$ Compound of the formula Ic where $R^2$ is $CH_2NR^{22}R^{23}$ was prepared from the compound of formula XXV, by addition of an acid (e.g., HCl, TFA) in dichloromethane at room temperature. The product was isolated by following standard workup procedure.

Scheme 20 - Alternate Synthesis of Compounds of Formula Ic where $R^2$ is $CH_2NR^{22}R^{23}$

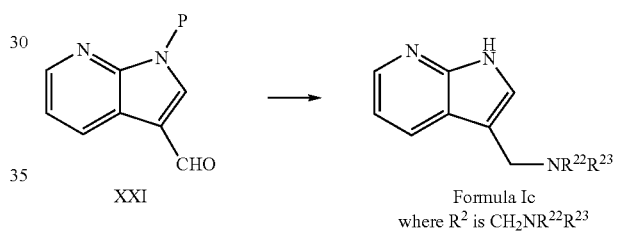

Compound of formula Ic where $R^2$ is $CH_2NR^{22}R^{23}$ was synthesized from compound of formula XXI by reductive amination with sulfonamide, amide, or urea (e.g. benzene sulfonamide, benzamide, phenyl urea) in an inert solvent (e.g. THF) and sodium triacetoxy borohydride and deprotecting the resulting product. The final product was isolated by silica gel column chromatography (Dube and Scholte; Tetrahedron Lett. 1999, 40, 2295).

Scheme 21 - Alternate Synthesis of Compounds of Formula Ic where $R^2$ is $CH_2NR^{22}R^{23}$

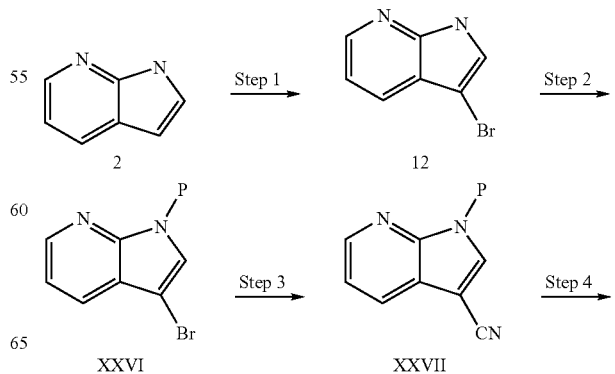

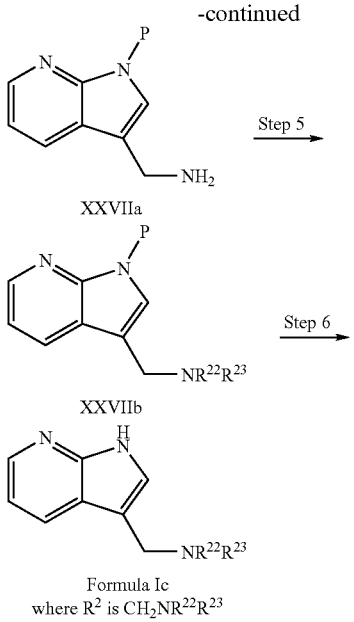

XXVIIa → Step 5 → XXVIIb → Step 6 → Formula Ic where $R^2$ is $CH_2NR^{22}R^{23}$

Step-1—Synthesis of Compound 12

Compound 12 was synthesized by reacting compound 2 with a brominating agent (e.g. Bromine) in a co-solvent (e.g. carbon tetrachloride:chloroform) as described in Synthesis 1999, 4; 615-620. A typical phase extraction is performed and the resulting aqueous layer is treated with a base (e.g. NaOH). The resulting solid is isolated by standard filtration techniques.

Step-2—Synthesis of Compound of Formula XXVI

Compound of formula XXVI was synthesized by reacting compound 12 with a sulfonyl chloride (e.g. benzene sulfonylchloride) in an inert solvent (e.g. dichloromethane), in the presence of a base (e.g. sodium hydroxide) as described in Greene, T. W.; Wuts, P. G. M. *Protective Groups in Organic Synthesis I, 3rd ed.; John Wiley & Sons*: New York, 1981. The product can be isolated by filtration of the resulting slurry over celite.

Step-3—Synthesis of Compound of Formula XXVII

Compound of formula XXVII was synthesized by reacting compound XXVI with a cyanide source (e.g. $Zn(CN)_2$) in a polar aprotic solvent (e.g. DMF), in the presence of a catalyst (e.g. Tetrakis triphenylphosphine palladium) as described in Anderson et al *J. Org. Chem.* 1998; 63, 8224. A standard workup is used and purified by standard crystallization or chromatographic methods.

Step-4—Synthesis of Compound of Formula XXVIIa

Compound of formula XXVIIa was prepared from compound of formula XXVII with a reducing agent (e.g. $H_2$) in an inert solvent (e.g. MeOH) with an added catalyst (e.g. palladium on carbon) as described by Stavenger, R. A. et al Pct Int Appl., WO 03/028724. Purification was achieved by standard chromatographic procedures.

Step-5—Synthesis of Compound of Formula XXVIIb

Compound of formula XXVIIb was prepared from compound of formula XXVIIa by treating with an alkylating agent, sulfonylating agent, acid chlorides, or isocyanates and isothiocyanates (e.g. benzyl bromide, benzene sulfonyl chloride, phenyl isocyanate) in an inert solvent (e.g. DMF), in the presence of a base (e.g. diisopropylethyl amine; DMAP). A standard workup is used and purified by standard crystallization or chromatographic methods.

Step 6—Synthesis of Compound of Formula Ic where $R^2$ is $CH_2NR^{22}R^{23}$ Compound of 1c, where $R^2$ is $CH_2NR^{22}R^{23}$ can be generated by treating compound of formula XXVIIb with a base (e.g. KOH) in a polar aprotic solvent (e.g. EtOH) while heating from 60-80° C. for typically 1-3 h as described in Greene, T. W.; Wuts, P. G. M. *Protective Groups in Organic Synthesis I, 3rd ed.; John Wiley & Sons*: New York, 1981. A standard workup is used and purified by standard chromatographic methods.

Scheme 22 - Synthesis of Compounds of Formula Ic where $R^2$ is $CONR^{16}R^{17}$

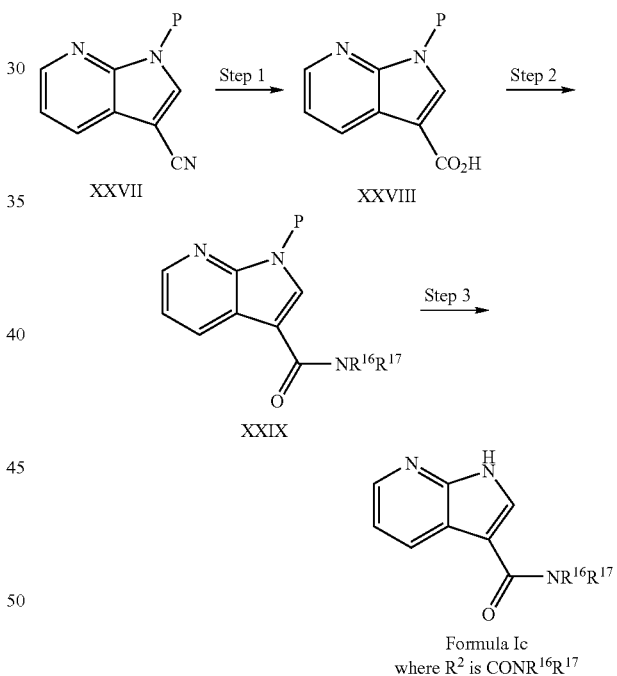

XXVII → Step 1 → XXVIII → Step 2 → XXIX → Step 3 → Formula Ic where $R^2$ is $CONR^{16}R^{17}$

Step-1—Synthesis of Compound of Formula XXVIII

Compound of formula XXVIII can be prepared by reacting compound XXVII with a base (e.g. NaOH) in an inert solvent (e.g. EtOH) as described in Larock, R. C. *Comprehensive Organic Transformations*; VCH: NY, 1989, p. 993. Standard workup procedures and purifications are performed.

Step-2—Synthesis of Compound of Formula XXIX

Compound of formula XXIX can be prepared by reacting compound XXVIII with an amine (e.g. benzyl amine) in an inert solvent (e.g. DMF) in the presence of a coupling reagent (e.g. bromotri(pyrrolidino)phosphonium hexafluorophosphate (PyBrop)), and in the presence of a base (e.g. diisopropylethyl amine) as described in Coste, J. et al *J. Org. Chem.* 1994; 158, 2437. A typical workup is utilized and purification is achieved by standard chromatographic procedures.

Step-3—Synthesis of Compound of Formula Ic where $R^2$ is $CONR^{16}R^{17}$

Compound of Formula Ic, where $R^2$ is $CONR^{16}R^{17}$ can be prepared by reacting compound XIII with a fluoride source (e.g. $NH_4F$) in an inert solvent (e.g. THF) as described in *Tetrahedron Lett.* 2001, 42(44); 7759. Purification is achieved with standard chromatographic techniques.

Scheme 23 - Alternate Synthesis of Compounds of Formula Ic where $R^2$ is $CONR^{16}R^{17}$

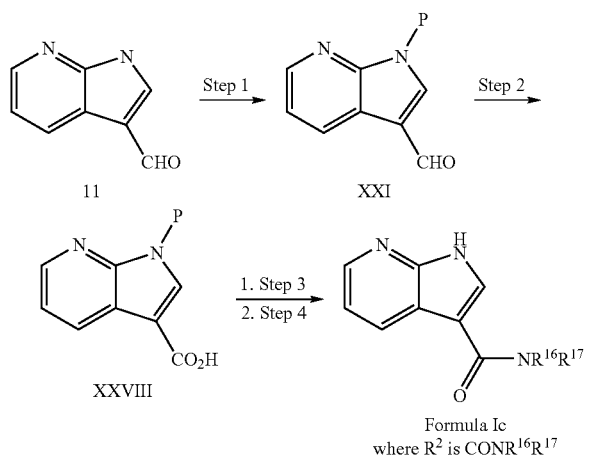

Step-1—Synthesis of Compound of Formula XXI

Compound of formula XXI, where $R^2$ is CHO, was synthesized by reacting compound 12 with appropriate protective groups (e.g. Boc, TIPS).

Step-2—Synthesis of Compound of Formula XXVIII

Compound of formula XXVIII, where $R^2$ is $CO_2H$, was synthesized by reacting compound of formula XXI with an oxidant (e.g. $NaClO_2$ and $NH_2SO_3H$) in appropriate solvents (e.g. a mixture of THF and $H_2O$) as described by Merour et. al., Synthesis, 2000, 549-556.

Step-3 & 4—Synthesis of Compound of Formula Ic where $R^2$ is $CONR^{16}R^{17}$

Compound of formula Ic, where $R^2$ is $CONR^{16}R^{17}$, was synthesized by reacting compound of formula XXVIII with an amine (e.g. aniline, dimethyl amine) in a polar aprotic solvent (e.g. DMF) in an inert atmosphere in presence of PyBrop (Bromotri(pyrrolidino)phosphonium hexafluorophosphate), followed by deprotection of the protective group with appropriate reagents.

Scheme 24 - Alternate Synthesis of Compounds of Formula Ic where $R^2$ is $CONR^{16}R^{17}$

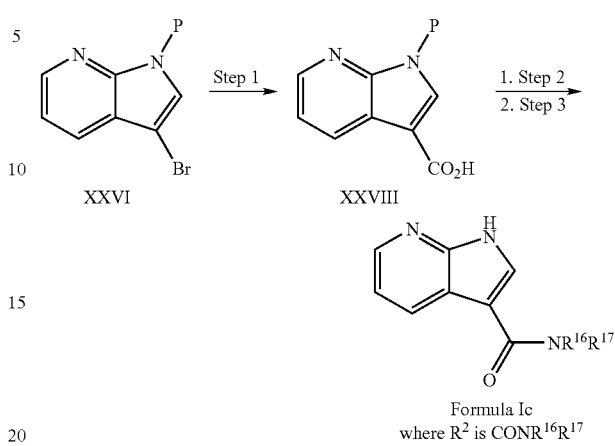

Step-1—Synthesis of Compounds of Formula XXVIII

Compound of formula XXVIII can be prepared by reacting compound of formula XXVI with a lithium reagent (e.g. t-Butyl lithium) at low temperatures, −78° C., in an inert solvent (e.g. THF) and stirring for a short period of time, 1 h, followed by the reaction with gaseous $CO_2$ and worked up in the usual manner. The product can be purified by flash silica gel chromatography.

Step-3 & 4—Synthesis of Compound of Formula Ic where $R^2$ is $CONR^{16}R^{17}$

Compound of formula Ic, where $R^2$ is $CONR^{16}R^{17}$, was synthesized by reacting compound of formula XXVIII with an amine (e.g. aniline, dimethyl amine) in a polar aprotic solvent (e.g. DMF) iq an inert atmosphere in presence of PyBrop (Bromotri(pyrrolidino)phosphonium hexafluorophosphate), followed by deprotection of the protective group with appropriate reagents.

Scheme 25 - Synthesis of Compounds of Formula Ic where $R^2$ is $CSNR^{16}R^{17}$

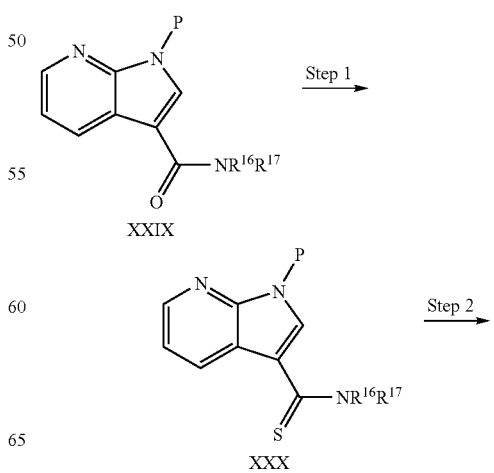

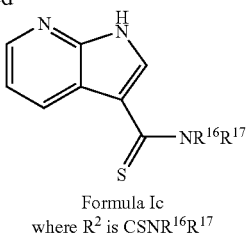

Formula Ic
where $R^2$ is $CSNR^{16}R^{17}$

Step-1—Synthesis of Compounds of Formula XXX

Compounds of formula XXX can be prepared from compounds of formula XXIX by reacting it with Lawesson's reagent (or $P_4S_{10}$) as described in the literature. (Bull. Soc. Chim. Belg., 1978, 87, 223).

Step-2—Synthesis of Compounds of Formula Ic where $R^2$ is $CSNR^{16}R^{17}$

Compounds of Formula Ic where $R^2$ is $CSNR^{16}R^{17}$ can be prepared by deprotection of compound of formula XXX with acid (e.g. HCl; TFA) and purifying the product by column chromatography.

Scheme 26 - Synthesis of Compounds of Formula Ic where $R^2$ is $NR^{22}R^{23}$

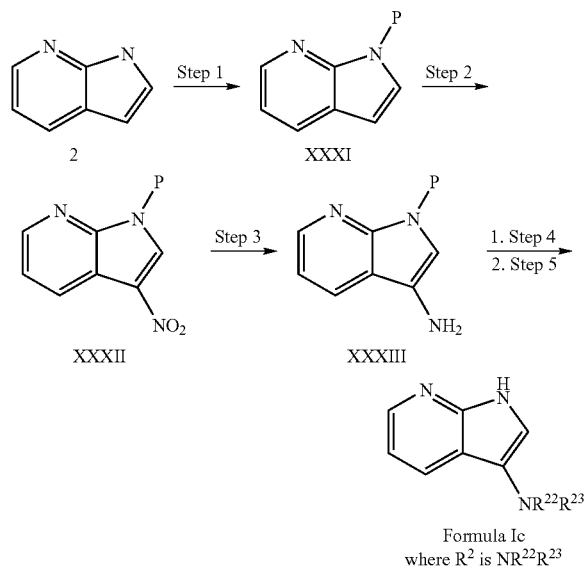

Formula Ic
where $R^2$ is $NR^{22}R^{23}$

Step-1—Synthesis of Compound of Formula XXXI

Compound of formula XXXI was synthesized by reacting compound 2 with a sulfonyl chloride (e.g. benzenesulfonyl chloride) in an inert solvent (e.g. dichloromethane), in the presence of a base (e.g. sodium hydroxide) as described in Greene, T. W.; Wuts, P. G. M. *Protective Groups in Organic Synthesis I, 3<sup>rd</sup> ed.; John Wiley & Sons*: New York, 1981. The product can be isolated by filtration of the resulting slurry over celite.

Step-2—Synthesis of Compound of Formula XXXII

Compound of formula XXXII was prepared by reacting compound XXXI with a nitrating agent (e.g. fuming $HNO_3$) neat while maintaining the temperature for 1-3 h between 0-25° C. as described in Robinson, B. L. et al J. Am. Chem. Soc. 1959, 81; 743. The mixture can be poured over ice and neutralized with a base (e.g. $NH_4OH$) and the resulting precipitate can be filtered and dried under vacuum. Purification can be achieved through standard chromatographic techniques.

Step-3—Synthesis of Compound of Formula XXXIII

Compound of formula XXXIII was prepared by reacting compound XXXII with a reducing agent (e.g. $H_2$) in a polar solvent (e.g. MeOH) with an added catalyst (e.g. palladium on carbon) as described by Stavenger, R. A. et al Pct Int Appl., WO 03/028724. Purification can be achieved by standard chromatogreaphic procedures.

Step-4 & 5—Synthesis of Compound of Formula Ic where $R^2$ is $NR^{22}R^{23}$

The precursor to compound of Formula Ic, where $R^2$ is $NR^{22}R^{23}$ can be prepared by reacting compound XXXIII with an alkylating agent, sulfonylating agent, acid chlorides, or isocyanates and isothiocyanates (e.g. benzyl bromide, benzene sulfonyl chloride, phenyl isocyanate) in an inert solvent (e.g. DMF), in the presence of a base (e.g. diisopropylethyl amine; DMAP) followed by deprotection and standard workup is used and purification by standard chromatographic methods.

Scheme 27 - Synthesis of Compounds of Formula Ic where $R^2$ is $C(X)R^{20}$ and X is 'O'

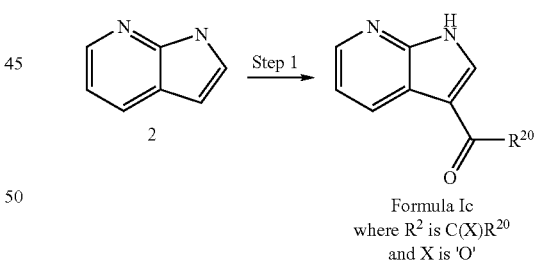

Formula Ic
where $R^2$ is $C(X)R^{20}$
and X is 'O'

Step-1—Synthesis of Compound of Formula Ic, where $R^2$ is $C(X)R^{20}$ and X is 'O'

Compound of formula Ic, where $R^2$ is $C(X)R^{20}$ and X is 'O', was synthesized by reacting compound 2 with an acid chloride (e.g. benzoyl chloride) in the presence of a Lewis acid (e.g. aluminum trichloride) in a inert solvent (e.g. methylene chloride) and under inert atmosphere (e.g. argon) at room temperature or with heating up to reflux for 1-18 hours. The product was isolated by extraction and silica gel column chromatography.

Scheme 28 - Synthesis of Compounds of Formula Ic where $R^2$ is $C(X)R^{20}$ and X is 'O'

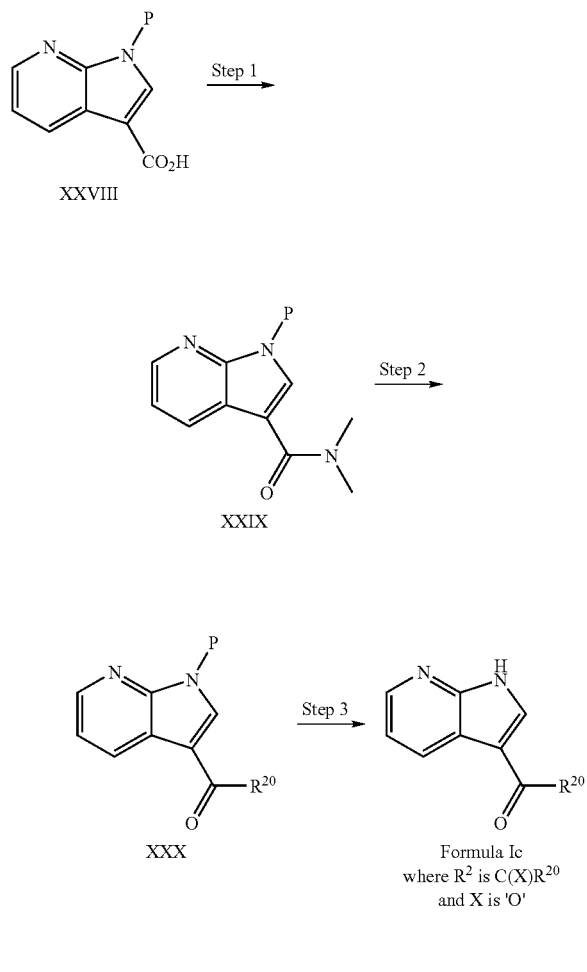

XXVIII

XXIX

XXX

Formula Ic where $R^2$ is $C(X)R^{20}$ and X is 'O'

Step-1—Synthesis of Compounds of Formula XXIX.

Compounds of formula XXIX can be prepared from compounds of formula XXVIII by reacting it with N,N-dimethylamine. HCl in the presence of a coupling reagent (BOP or 2-Chloro-1-methylpyridinium iodide) (J. Org. Chem., 1996, 61, 4999; or Synth. Commun., 1995, 25, 1277).

Step-2—Synthesis of Compounds of Formula XXX.

Compounds of formula XXX can be prepared from compounds of formula XXIX by reacting with Grignard reagents (e.g. phenyl magnesium bromide) or lithium reagents (e.g. Phenyl lithium) in inert solvent (e.g. diethyl ether or THF) at low temperature, typically 0° C., warming up to room temperature, and stirring for a short period of time, typically 1 h. The reaction can be quenched with dilute hydrochloric acid (3N HCl), subjected to standard work up conditions and purified by column chromatography (Olah, et. al. Synthesis, 1984, 3, 228).

Step-3—Synthesis of Compounds of Formula Ic where $R^2$ is $C(X)R^{20}$ and X is 'O'.

Compound of formula Ic where $R^2$ is $C(X)R^{20}$ and X is 'O' can be prepared by deprotection of compound XXX using appropriate deprotecting agent (e.g. TBAF or aqueous NaOH) and purifying the products by standard conditions.

Scheme 29 - Synthesis of Compounds of Formula Ic where $R^2$ is $C(X)R^{20}$ and X is 'O'

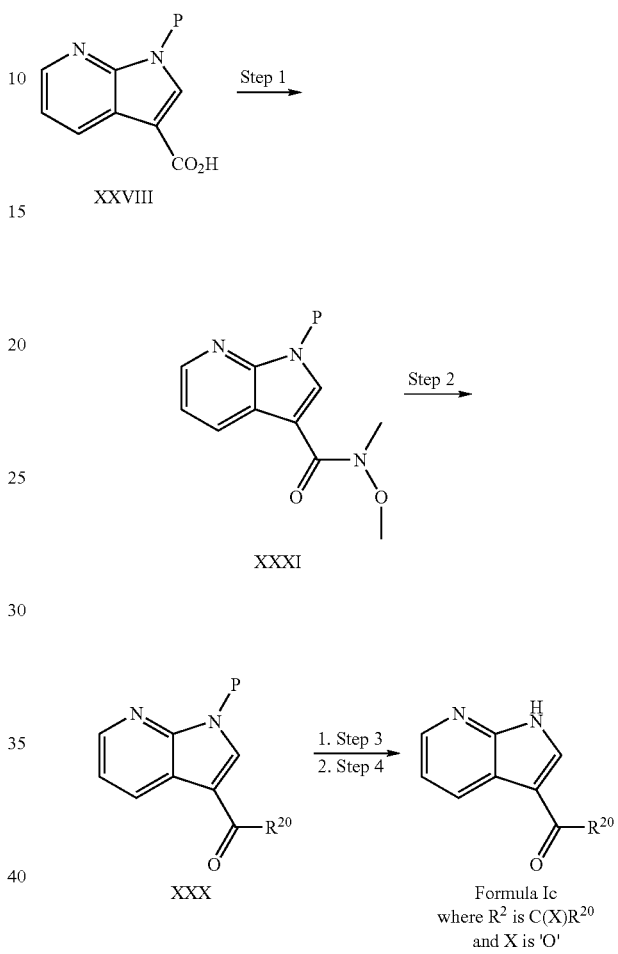

XXVIII

XXXI

XXX

Formula Ic where $R^2$ is $C(X)R^{20}$ and X is 'O'

Step-1—Synthesis of Compounds of Formula XXXI

Compounds of formula XXXI can be prepared from compounds of formula XXVIII by reacting it with N,O-dimethylhydroxylamine HCl in the presence of a coupling reagent (BOP Reagent or 2-Chloro-1-methylpyridinium iodide). (J. Org. Chem., 1996, 61, 4999; or Synth. Commun., 1995, 25, p. 1277).

Step-2—Synthesis of Compounds of Formula XXX

Compounds of formula XXX can be prepared from compounds of formula XXXI by reacting with Grignard reagents according to the reference (Tetrahedron Letters, 1981, 22, 3815).

Step-3—Synthesis of Compounds of Formula Ic

Compounds of Formula Ic can be prepared from compound of formula XXX in the same manner as shown above in scheme 24.

Scheme 30 - Synthesis of Compounds of Formula Ic where $R^2$ is $S(O)_n R^{21}$ where n = 2

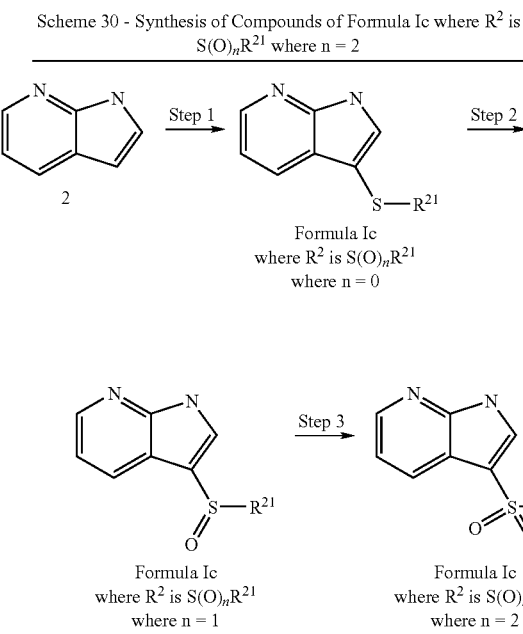

Step-1—Synthesis of Compound of Formula Ic where $R^2$ is $S(O)_n R^{21}$ and n=0

Compound of the formula Ic, where $R^2$ is $S(O)_n R^{21}$ where n=0, was prepared from commercially available compound 2 by deprotonation of a strong base (e.g. NaH) in an inert solvent (e.g. DMF), followed by addition of diaryl disulfides (e.g. PhSSPh). The reaction typically was ran overnight at room temperature and the product was isolated by following standard workup and silica gel flash chromatography (Atkins et al. 1988, 480).

Step-2—Synthesis of Compound of Formula Ic where $R^2$ is $S(O)_n R^{21}$ and n=1

Compound of the formula Ic, where $R^2$ is $S(O)_n R^{21}$ where n=1 was prepared from the compound of formula Ic where $R^2$ is $S(O)_n R^{21}$ where n=0 by addition of oxidizing reagents (m-CPBA, Oxone, 0.5 Eqiv.) in dichloromethane. The product was isolated by following standard workup and silica gel flash chromatography.

Step-3—Synthesis of Compound of Formula Ic where $R^2$ is $S(O)_n R^{21}$ and n=2

Compound of the formula Ic, where $R^2$ is $S(O)_n R^{21}$ where n=2 was prepared from the compound of formula Ic where $R^2$ is $S(O)_n R^{21}$ where n=1 by addition of oxidizing reagents (m-CPBA, Oxone, 2.0 Eqiv.) in dichloromethane. The product was isolated by following standard workup and silica gel flash chromatography.

Scheme 31 - Alternate Synthesis of Compounds of Formula Ic where $R^2$ is $S(O)_n R^{21}$ where n = 2

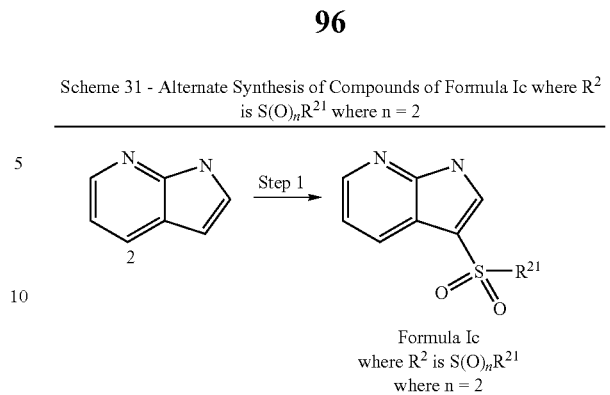

Compound of the formula Ic, where $R^2$ is $S(O)_n R^{21}$ where n=2 can be prepared from the compound 2 by reaction with a sulfonyl chloride (e.g. benzne sulfonylchloride) in a polar solvent (e.g. ethanol, acetone) at room temperature as described by Ottoni et al in Tetrahedron, 1998, 54, 13915. The product can be isolated by standard work up procedure.

Scheme 32 - Synthesis of Compounds of Formula Ic where $R^2$ is aryl or heteroaryl

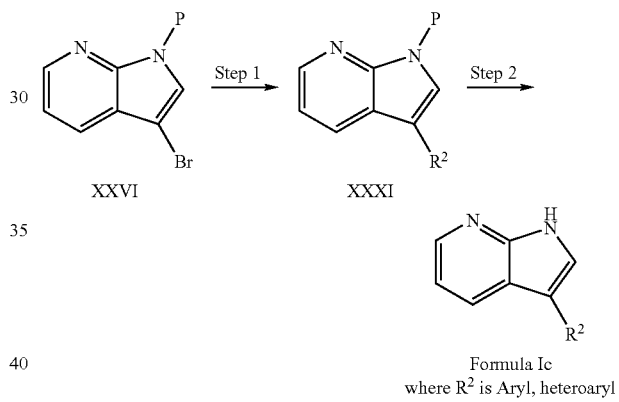

Step-1—Synthesis of Compound of Formula XXXI

Compound of formula XXXI, where P is a protecting group (e.g. phenylsulfonyl), was synthesized by reaction of compound of formula XXXVI with an aryl or heteroaryl boronic acid (e.g. phenyl boronic acid) in the presence of a base (e.g. sodium carbonate) and a catalyst composed of a metal (e.g. Tris(dibenzylideneacetone)dipalladium(0)) and a ligand (tri-tert-butylphosphine), and with heating typically to 75° C. for 8-12, hours.

Step-2—Synthesis of Compound of Formula Ic, where $R^2$ is Aryl or Heteroaryl

Compound of formula Ic, where $R^2$ is aryl or heteroaryl, was synthesized by reacting compound of formula XXXI with an appropriate reagent to remove the protecting group, P, (e.g. potassium hydroxide) in an appropriate solvent (e.g. ethanol). The final product was isolated by standard procedures (e.g. reverse phase preparative high pressure liquid chromatography).

E. Synthesis of Compound of Formula Id, where $R^1$, $R^3$, and $R^5$ are Hydrogen

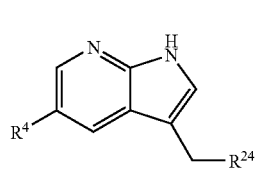

Formula Id

Compounds of Formula Id are Formula I compounds in which $R^2$ and $R^4$ are the only substituents on the core structure. Exemplary synthetic schemes for groups of compounds within Formula Id are shown in Schemes 33-38, for different selections of $R^2$ and $R^4$.

Scheme 33 - Synthesis of Compounds of Formula Id where $R^4$ is aryl or heteroaryl and $R^2$ is $(CH2)_n R^{24}$ and $R^{24}$ is aryl or heteroaryl

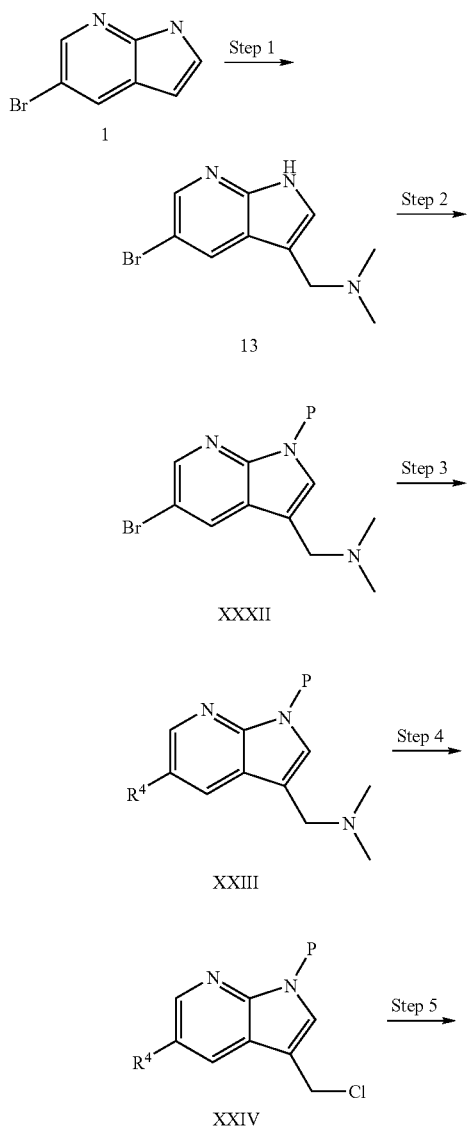

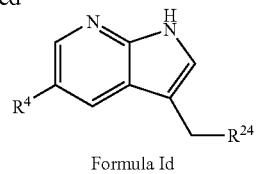

Formula Id
where $R^4$ is aryl or heteroaryl
and $R^2$ is $CH_2R^{24}$ where $R^{24}$ is aryl or heteroaryl

Step-1—Synthesis of Compound 13

Compound 13, where $R^2$ is $CH_2NMe_2$, was synthesized under Mannich reaction condition using paraformaldehyde and dimethyl amine hydrogen chloride salt in an alkanol solvent (e.g. isopropanol) as described by Robinson, in J. Am. Chem. Soc., 1955, 77, p. 457.

Step-2—Synthesis of Compound of Formula XXXII

Compound of formula XXXII, where $R^2$ is $CH_2NMe_2$, was synthesized by reacting compound 12 with appropriate protective groups (e.g. Boc, TIPS).

Step-3—Synthesis of Compound of Formula XXIII

Compound of formula XXIII, where $R^4$ is aryl or heteroaryl, was synthesized from compound XXXII under Suzuki reaction conditions using aryl or heteroaryl bornonic acids (e.g. phenyl bornonic acid, 3-thienyl bornonic acid), in presence of a catalyst (e.g. $Pd(PPh_3)_4$).

Step-4—Synthesis of Compound of Formula XXIV

Compound of formula Id, where $R^4$ is aryl or heteroaryl, can be synthesized by reacting compound of formula XXIII with ethyl chloroformate or isopropyl chloroformate in an inert solvent (e.g. toluene).

Step-5—Synthesis of Compound of Formula Id where $R^2$ is $(CH_2)_n R^{24}$ and $R^{24}$ is Aryl or Heteroaryl Compound of formula Id, where $R^2$ is $(CH_2)_n R^{24}$ and $R^{24}$ is aryl or heteroaryl, was synthesized by reacting compound of formula XXIV with a Grignard reagent (e.g. phenyl maganesium bromide, benzylmaganesium bromide) in an inert solvent (e.g. THF), in presence of a catalyst (e.g. CuCl.2LiCl). The protective group (e.g. TIPS) can either be cleaved with an appropriate reagent (e.g. TBAF), or be cleaved during the reaction (e.g. Boc).

Scheme 34 - Synthesis of Compounds of Formula Id where $R^4$ is aryl or heteroaryl and $R^2$ is $CH_2R^{24}$ and $R^{24}$ is aryl or heteroaryl

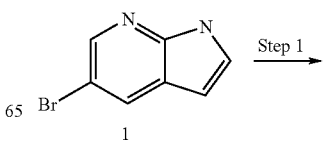

-continued

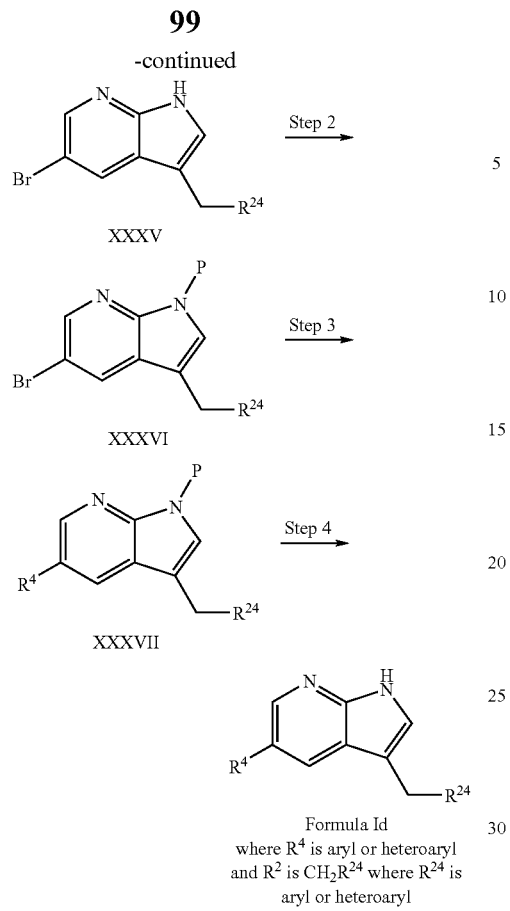

XXXV

XXXVI

XXXVII

Formula Id
where R⁴ is aryl or heteroaryl
and R² is CH₂R²⁴ where R²⁴ is
aryl or heteroaryl Step 1:

Compound of the formula XXXV was prepared from the compound of formula I, under Friedel-Craft alkylation conditions used electrophilic reagents (e.g., aryl halide, heteroaryl halide . . . ), in presence of a Lewis acid (e.g., aluminum chloride) in dichloromethane at room temperature. The product was isolated by following standard workup procedure.

Step 2:

Compound of the formula XXXVI was prepared from the compound of formula XXXV, by deprotonation with a strong base (e.g. NaH, BuLi, . . . ) at 0° C. in an aprotic solvent (THF), followed by protecting groups (Boc anhydride, . . . ). The product was isolated by following standard workup procedure.

Step 3:

Compound of the formula XXXVII was prepared from the compound of formula XXXVI, under suzuki reactions using boronic acids (e.g., aryl or heteroaryl), base (e.g., potassium carbonate, Triethylamine, Sodium hydroxide, . . . ), and catalysis (e.g. Pd(Ph₃P)₄) in aqueous/THF solvent system. After 12 hours, the product was isolated by following standard workup and silica gel flash chromatography.

Step 4:

Compound of the formula Id was prepared from the compound of formula XXXVII, deprotection of protecting groups using acids (e.g. HCl, TFA, . . . ) in dichloromethane. The product was isolated by following standard workup and silica gel flash chromatography.

Scheme 35 - Synthesis of Compounds of Formula Id where R⁴ is aryl or heteroaryl and R² is C(O)R²⁰ where R²⁰ is aryl or heteroaryl

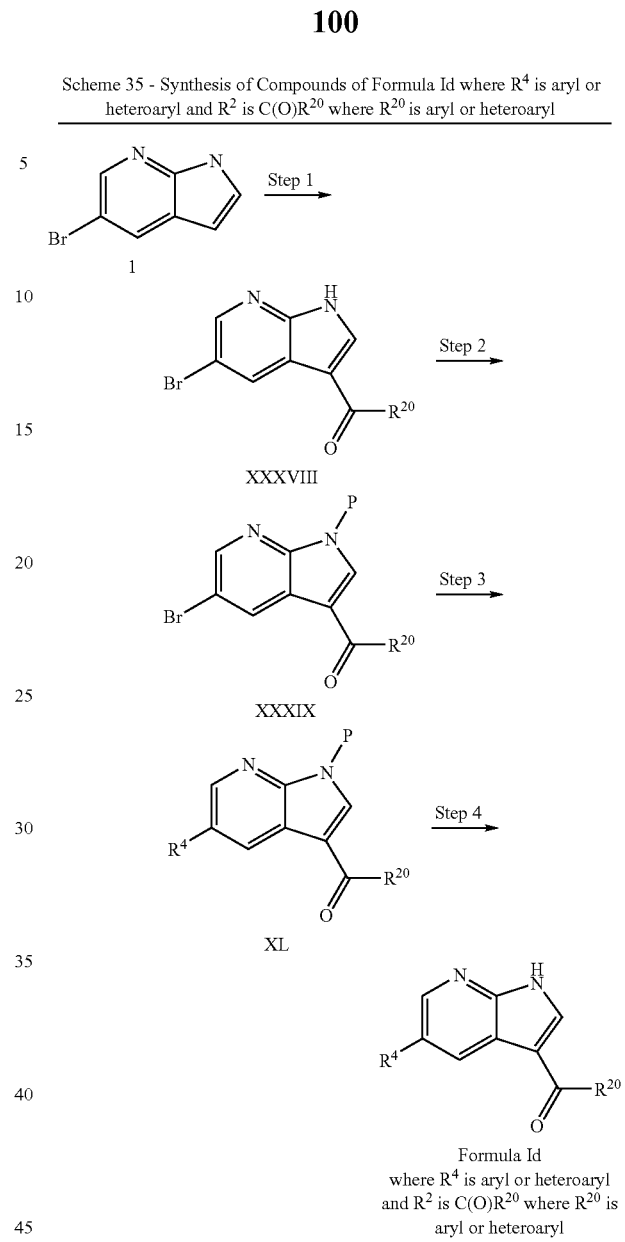

Formula Id
where R⁴ is aryl or heteroaryl
and R² is C(O)R²⁰ where R²⁰ is
aryl or heteroaryl Step 1:

Compound of the formula XXXVIII was prepared from the compound of formula I, under friedel-Craft acylation conditions acid chlorides (e.g. aryl, heteroaryl . . . ), in presence of a Lewis acid (e.g., aluminum chloride) in dichloromethane at room temperature. The product was isolated by following standard workup and silica gel flash chromatography.

Step 2:

Compound of the formula XXXIX was prepared from the compound of formula XXXVIII, by deprotonation with a strong base (e.g. NaH, BuLi, . . . ) at 0° C. in an aprotic solvent (THF), followed by addition of protecting groups (TIPS-Cl, Boc anhydride, . . . ). The product was isolated by following standard workup procedure.

Step 3:

Compound of the formula XL was prepared from the compound of formula XXXIX, under suzuki reactions using boronic acid (e.g., aryl or heteroaryl), base (e.g., potassium carbonate, Triethylamine, sodium hydroxide, . . . ), and catalysis (e.g., Pd(Ph₃P)₄) in aqueous/THF solvent system. After 12 hour, the product was isolated by following standard workup and silica gel flash chromatography.

Step 4:
Compound of the formula Id was prepared from the compound of formula XL, deprotection of protecting groups using acids (e.g., HCl, TFA) in dichloromethane. The product was isolated by following standard workup and silica gel flash chromatography.

Scheme 36 - Synthesis of Compounds of Formula Id where $R^4$ is aryl or heteroaryl and $R^2$ is $SO_2R^{21}$ where $R^{21}$ is aryl or heteroaryl

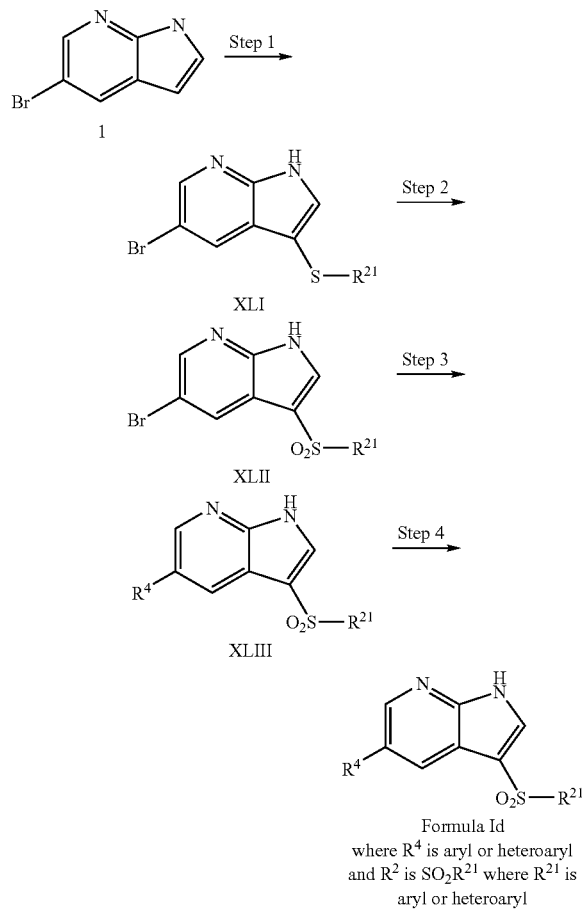

Step 1:
Compound of the formula XLI was prepared from the compound of formula I by addition of a strong base (e.g., NaH) in dichloromethane followed by addition of disulfide molecules (e.g., PhSSPh). The reaction ran overnight at room temperature. The product was isolated by following standard workup and silica gel flash chromatography.

Step 2:
Compound of the formula XLII was prepared from the compound of formula XLI by addition of oxidizing reagents (e.g., MCPBA, Oxone, 2.0 Eqiv.) in dichloromethane ran overnight. The product was isolated by following standard workup and silica gel flash chromatography.

Step 3:
The synthesis of an intermediate of compound of the formula XLIII can be prepared from the compound of formula XLII by deprotonated using a strong base (BuLi, NaH, . . . ) followed by addition of protecting groups (e.g., TIPS-Cl, Boc anhydride . . . ) in an inert solvent THF, yielded formula XLIII.

Step 4:
Compound of the formula XLIII can be prepared from the compound of formula XLII, under suzuki reactions using boronic acids (e.g., aryl or heteroaryl), base (e.g., potassium carbonate, Triethylamine, Sodium hydroxide, . . . ), and catalysis (e.g. Pd(Ph$_3$P)$_4$) in aqueous/THF solvent system. After 12 hours, the product was isolated by following standard workup and silica gel flash chromatography.

Step 5:
Compound of the formula Id can be prepared from the compound of formula deprotection of protecting groups using acids (e.g., HCl, TFA, . . . ) in dichloromethane. The product was isolated by following standard workup and silica gel flash chromatography.

Scheme 37-Synthesis of Compounds of Formula Id where $R^2$ is $C(O)R^{20}$ where $R^{20}$ is aryl or heteroaryl and $R^4$ is $NR^{22}R^{23}$

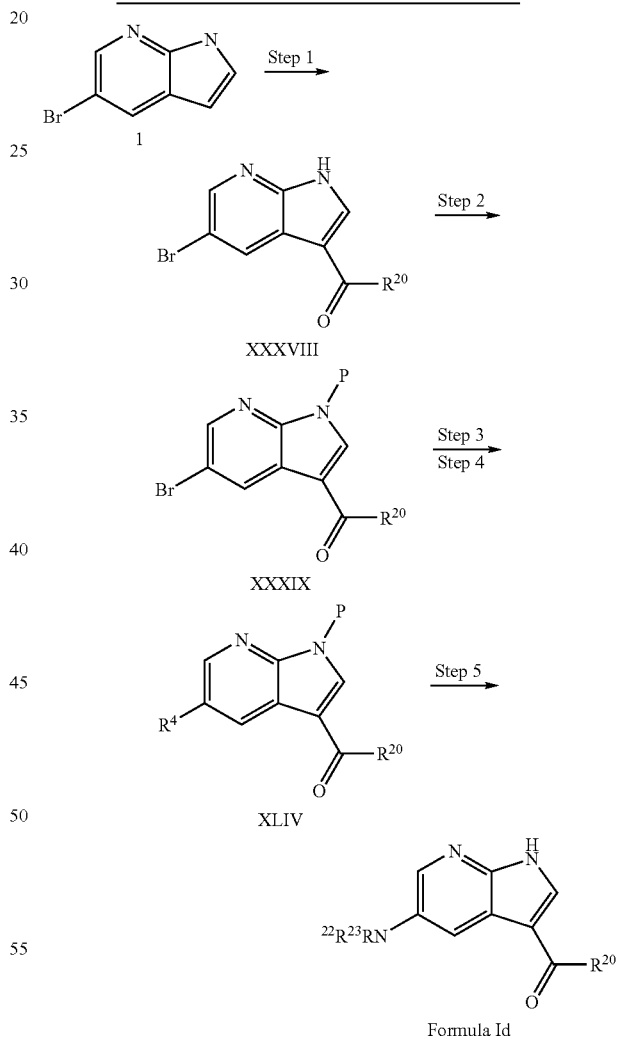

Step-1—Synthesis of Compound of Formula XXXVIII, where $R^{20}$ is Aryl or Heteroaryl Compound of formula XXXVIII was synthesized by reacting compound 1 with a Lewis acid (e.g. aluminum trichloride)

in a solvent (e.g. dichloromethane) under an inert atmosphere, typically at room temperature for 1-2 hours, followed by addition of an acid chloride (e.g. benzoyl chloride or nicotinoyl chloride) and reaction for 2-12 hours. The reaction was quenched with methanol, concentrated, and purified by silica gel chromatography.

Step-2—Synthesis of Compound of Formula XXXIX, where $R^{20}$ is aryl or heteroaryl Compound of formula XXXIX, where P is a protecting group, was synthesized by reacting compound XXXVIII with a base (e.g. sodium hydride) in a solvent (e.g. THF), followed by an appropriate reagent for introduction of a protecting group (P—X, e.g. triisopropylsilylchloride). The reaction was allowed to proceed typically at room temperature for 8-12 hours and the desired product was isolated by standard procedures (e.g. extraction and silica gel column chromatography).

Step-3—Synthesis of an Intermediate of Compound of Formula XLIV, where $R^{20}$ is Aryl or Heteroaryl and $R^4$ is $NR^{16}R^{17}$ An intermediate of compound of formula XLIV, where $R^{20}$ is aryl or heteroaryl, and $R^4$ is $NR^{16}R^{17}$ was synthesized by reacting compound of formula XXXIX, where $R^{20}$ is aryl or heteroaryl with an amine of the formula $NHR^{16}R^{17}$ (e.g. aniline) in a solvent (e.g. toluene), in presence of a base (e.g. sodium tert-butoxide) and a catalyst composed of a metal (e.g. Tris(dibenzylideneacetone)dipalladium(0)) and a ligand (e.g. tri-tert-butylphosphine) with heating typically to 95° C. for 8-12 hours as described (Thomas, et. al., J. Am. Chem. Soc., 2001, 123, 9404) by substituting compound of formula II for the N-substituted-3,6-dibromocarbazole. The desired compound was purified by silica gel chromatography. This intermediate was used directly in Step 5 to provide compound of the formula 1d where $R^{20}$ is aryl or heteroaryl, and $R^4$ is $NR^{22}R^{23}$ and $R^{22}$ and $R^{23}$ are not —C(X)$R^{20}$, —C(X)$NR^{16}R^{17}$, or —S(O)$_2R^{21}$ or alternatively, it can be additionally substituted in Step 4.

Step-4—Synthesis of Compound of Formula XLIV, where $R^{20}$ is Aryl or Heteroaryl and $R^4$ is $NR^{22}R^{23}$ The intermediate from Step 3 can be further modified when at least $R^{16}$ or $R^{17}$ is hydrogen. The intermediate from Step 3 can be reacted with a base (e.g. sodium hydride) in a solvent (e.g. N,N-dimethylformamide), followed by reaction with an alkylating reagent (e.g. benzyl bromide) or an acylating reagent (e.g. benzoyl chloride, phenyl isocyanate, or phenylsulfonyl chloride) typically at room temperature or with heating up to 80° C. for 1-12 hours. Compound of formula XLIV, where $R^{20}$ is aryl or heteroaryl and $R^4$ is $NR^{22}R^{23}$, can be purified by conventional means (e.g. silica gel chromatography).

Step-5—Synthesis of Compound of Formula Id, where $R^2$ is C(O)$R^{20}$ where $R^{20}$ is Aryl or Heteroaryl and $R^4$ is $NR^{22}R^{23}$ Compound of formula Id, where $R^2$ is C(O)$R^{20}$ where $R^{20}$ is aryl or heteroaryl and $R^4$ is $NR^{22}R^{23}$ was synthesized by reacting compound of formula XLIV with an appropriate reagent to remove the protecting group, P, (e.g. tetrabutylammonium fluoride) in an appropriate solvent (e.g. methanol). The final product can be isolated by standard procedures (e.g. extraction).

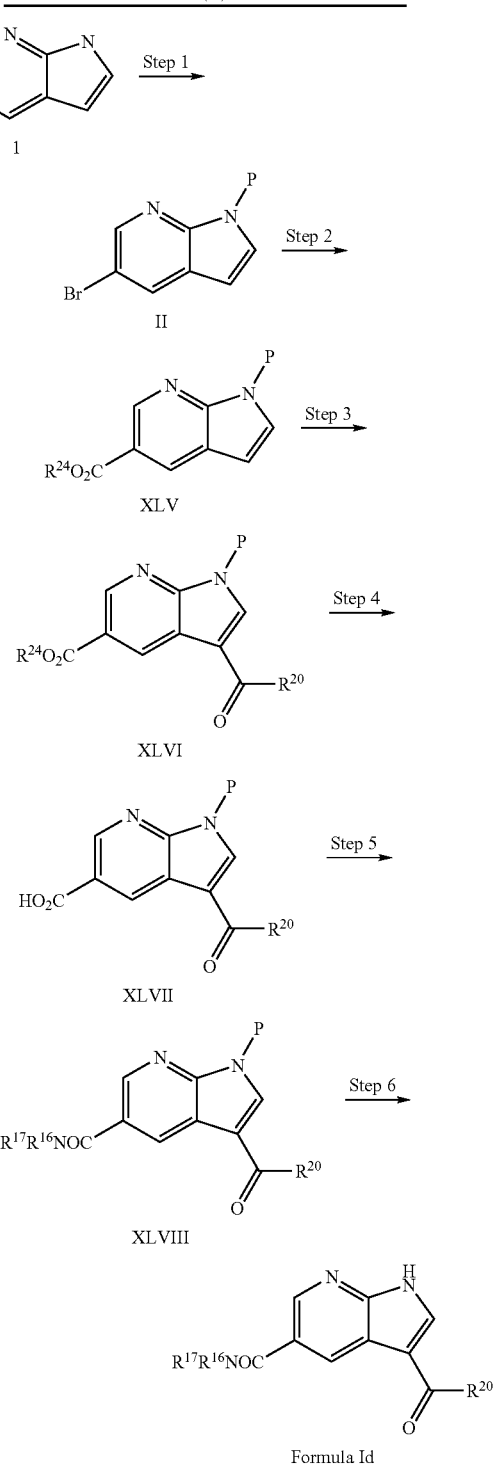

Scheme 38-Synthesis of Compounds of Formula Id where $R^2$ is C(O)$R^{20}$ where $R^{20}$ is aryl or heteroaryl and R4 is C(O)$NR^{16}R^{17}$ where $R^4$ is $CONR^{16}R^{17}$ and $R^2$ is C(O)$R^{20}$ where $R^{20}$ is aryl or heteroaryl

Step-1—Synthesis of Compound of Formula II

Compound II, where $R^4$ is Br, was synthesized by protecting compound 1 with appropriate protective groups (e.g. TIPS).

Step-2—Synthesis of Compound of Formula XLV

Compound of formula XLV, where $R^4$ is $CO_2R^{24}$, was synthesized by reacting compound of formula II with a strong base (e.g. n-butyllithium) and benzyl chloroformate or methyl chloroformate in an inert solvent (e.g. THF).

Step-3—Synthesis of Compound of Formula XLVI

Compound of formula XLVI, where $R^2$ is $C(O)R^{20}$, can be synthesized from compound XLV under Friedel-Crafts reaction conditions using acyl chloride (e.g. benzoyl chloride) in methylene dichloride, in presence of a Lewis acid (e.g. $AlCl_3$).

Step-4—Synthesis of compound of formula XLVII

Compound of formula XLVII, where $R^4$ is COOH and $R^2$ is $C(O)R^{20}$, can be synthesized by reacting compound of formula XLVI with an aqueous base (e.g. NaOH), or by hydrogenating compound of formula XLVII, where $R^4$ is COOBn, under hydrogen in alcohol solvent (e.g. MeOH), in presence of a catalyst (e.g. 5% Pd/C).

Step-3—Synthesis of Compound of Formula XLVIII

Compound of formula XLVIII, where $R^2$ is $C(O)R^{20}$ and $R^4$ is $C(O)NR^{16}R^{17}$, can be synthesized by reacting compound of formula XLVII with an amine (e.g. benzylamine, dimethyl amine) in a nonpolar aprotic solvent (e.g. DMF) in an inert atmosphere in presence of PyBrop (Bromotri(pyrrolidino)phosphonium hexafluorophosphate) following the procedure described by Coste et. al., Journal of Organic Chemistry, 1994, 59, 2437.

Step-4—Synthesis of Compound of Formula Id

Compound of formula Id, where $R^2$ is $C(O)R^{20}$ and R4 is $C(O)NR^{16}R^{17}$, can be synthesized by cleaving the protective group (e.g. TIPS) in compound of formula XLVIII appropriate condition (e.g. TBAF).

F. Synthesis of Compound of Formula Ig, where $R^1$, $R^4$, and $R^5$ are Hydrogen Compounds of Formula Ig are Formula I compounds in which $R^2$ and $R^3$ are the only substituents on the core structure. Exemplary synthetic schemes for groups of compounds within Formula Ig are shown in Schemes 39-43, for different selections of $R^2$ and $R^3$.

Scheme 39-Synthesis of Compounds of Formula Ig where $R^3$ is $NH_2$, and $R^2$ is $C(O)R^{20}$ is aryl or heteroaryl

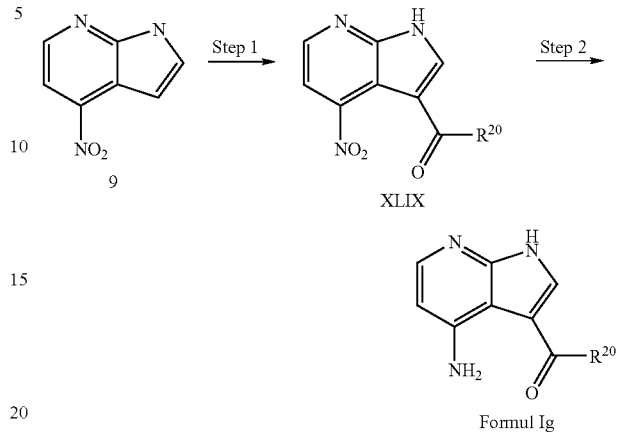

where $R^3$ is $NH_2$ and $R^2$ is $C(O)R^{20}$ where $R^{20}$ is aryl or heteroaryl

Step-1—Synthesis of Compound of Formula XLIX, where $R^{20}$ is Aryl or Heteroaryl Compound of formula XLIX, where $R^{20}$ is aryl or heteroaryl, can be synthesized by reacting compound 10 with a Lewis acid (e.g. aluminum trichloride) in a solvent (e.g. dichloromethane), typically at room temperature for 1-2 hours, followed by addition of an acid chloride (e.g. benzoyl chloride or nicotinoyl chloride) and reaction for 2-12 hours. The reaction is quenched with methanol, concentrated, and purified by silica gel chromatography.

Step-2—Synthesis of Compound of Formula Ig, where $R^3$ is $NH_2$, and $R^2$ is $C(O)R^{20}$ where $R^{20}$ is Aryl or Heteroaryl Compound of Formula Ig, where $R^3$ is $NH_2$, and $R^2$ is $C(O)R^{20}$ where $R^{20}$ is aryl or heteroaryl was synthesized by reaction of compound of formula XLIX with a reducing agent (e.g. hydrogen gas) in the presence of a catalyst (e.g. Raney nickel) in an appropriate solvent (e.g. methanol) typically at room temperature for 2-4 hours as described (Antonini et. al. J. Med. Chem. 1982, 25, 1258). The product was isolated by filtration and evaporation.

Scheme 40-Synthesis of Compounds of Formula Ig where $R^3$ is $NR^{22}R^{23}$, and $R^2$ is $C(O)R^{20}$ where $R^{20}$ is aryl or heteroaryl

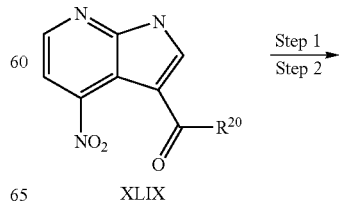

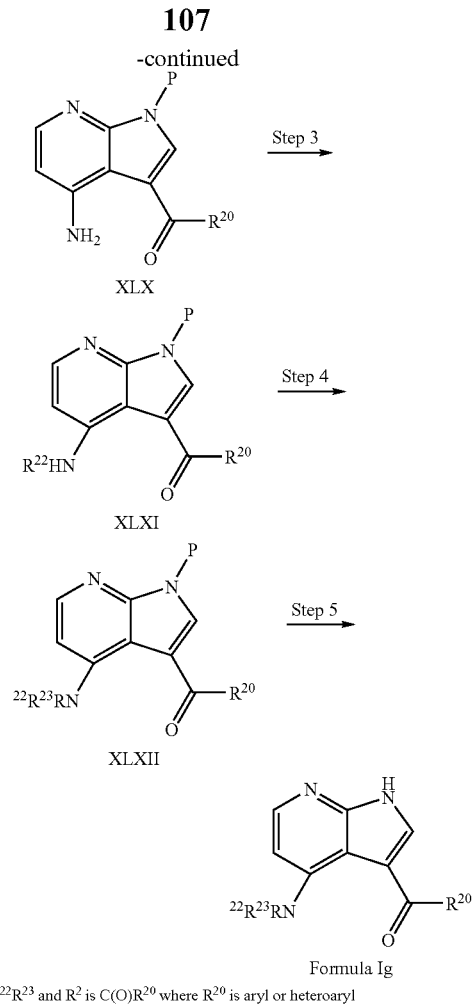

where $R^3$ is $NR^{22}R^{23}$ and $R^2$ is $C(O)R^{20}$ where $R^{20}$ is aryl or heteroaryl

Step-1—Synthesis of Intermediate of Compound of Formula XLX, where $R^{20}$ is Aryl or Heteroaryl An intermediate of compound of formula XLX, where P is a protecting group, can be synthesized by reacting compound of formula XLIX with a base (e.g. sodium hydride) in a solvent (e.g. THF), followed by an appropriate reagent for introduction of a protecting group (P—X, e.g. triisopropylsilylchloride). The reaction is allowed to proceed typically at room temperature for 2-6 hours and the product was isolated by standard procedures (e.g. extraction and silica gel column chromatography).

Step-2—Synthesis Compound of Formula XLX, where $R^{20}$ is Aryl or Heteroaryl Compound of formula formula XLX can be synthesized by reaction of the intermediate from Step 1 with a reducing agent (e.g. hydrogen gas) in the presence of a catalyst (e.g. Raney nickel) in a solvent (e.g. methanol) typically at room temperature for 2-4 hours as described (Antonini et. al. J. Med. Chem. 1982, 25, 1258). The product can be isolated by standard procedures (e.g. filtration and evaporation).

Step-3—Synthesis Compound of Formula XLXI, where $R^{20}$ is Aryl or Heteroaryl Compound of formula XLXI, where $R^{20}$ is aryl or heteroaryl, can be synthesized by reacting compound of formula XLX with a base (e.g. sodium hydride) in a solvent (e.g. dimethylformamide), followed by reaction with an alkylating reagent (e.g. benzyl bromide) or an acylating reagent (e.g. benzoyl chloride, phenyl isocyanate, phenylsulfonyl chloride) typically at room temperature or with heating up to 80° C. for 1-12 hours. The desired product can be purified by conventional means (e.g. silica gel chromatography).

Step-4—Synthesis Compound of Formula XLXII, where $R^{20}$ is Aryl or Heteroaryl Compound of formula XLXII, where $R^{20}$ is aryl or heteroaryl, can be synthesized by reacting compound of formula XLXI with a base (e.g. sodium hydride) in a solvent (e.g. dimethylformamide), followed by reaction with an alkylating reagent (e.g. benzyl bromide) or an acylating reagent (e.g. benzoyl chloride, phenyl isocyanate, phenylsulfonyl chloride) typically at room temperature or with heating up to 80° C. for 1-12 hours. The desired product can be purified by conventional means (e.g. silica gel chromatography).

Step-5—Synthesis of Compound of Formula Ig, where $R^3$ is $NR^{22}R^{23}$ and $R^2$ is $C(O)R^{20}$ where $R^{20}$ is Aryl or Heteroaryl Compound of formula Ig, where $R^3$ is $NR^{22}R^{23}$ and $R^2$ is $C(O)R^{20}$ where $R^{20}$ is aryl or heteroaryl can be synthesized by reacting compound of formula XLXII with an appropriate reagent to remove the protecting group, P, (e.g. tetrabutylammonium fluoride) in an appropriate solvent (e.g. methanol). The final product can be isolated by standard procedures (e.g. extraction).

Scheme 41-Synthesis of Compounds of Formula Ig where $R^3$ is aryl or heteroaryl and $R^2$ is $C(O)R^{20}$ where $R^{20}$ is aryl or heteroaryl

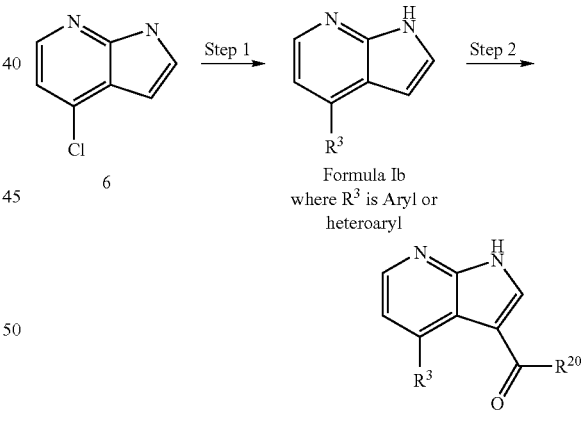

Step-1—Synthesis of Compound of Formula Ib, where $R^3$ is Aryl or Heteroaryl Compound of formula 1b, where $R^3$ is aryl or heteroaryl can be synthesized by reacting compound 6 with a boronic acid (e.g. 3-methoxyphenylboronic acid) in an inert solvent (e.g. dioxane), in the presence of a salt (e.g. KF), in the presence of a catalyst (e.g. $Pd_2(dba)_3CHCl_3$). The reaction is carried out under an inert solvent and is typically heated (100° C.) for 4-12 h as described by Allegretti, M. et. al *Synlett* 2001; 5, 609. Purification is achieved with standard chromatographic techniques.

Step-2—Synthesis of Compound of Formula Ig where $R^3$ is Aryl or Heteroaryl and $R^2$ is $C(O)R^{20}$ where $R^{20}$ is Aryl or Heteroaryl Compound of formula Ig where $R^3$ is aryl or heteroaryl and $R^2$ is $C(O)R^{20}$ where $R^{20}$ is aryl or heteroaryl can be synthesized by reacting compound of formula 1b where $R^3$ is aryl or heteroaryl with a Lewis acid (e.g. $AlCl_3$) in an inert solvent (e.g. $CH_2Cl_2$) in the presence of an acid chloride (e.g. benzoyl chloride) as described by Katritzky, A. R. et al *J. Org. Chem.* 2003, 68, 5720. Purification is achieved with standard chromatographic techniques.

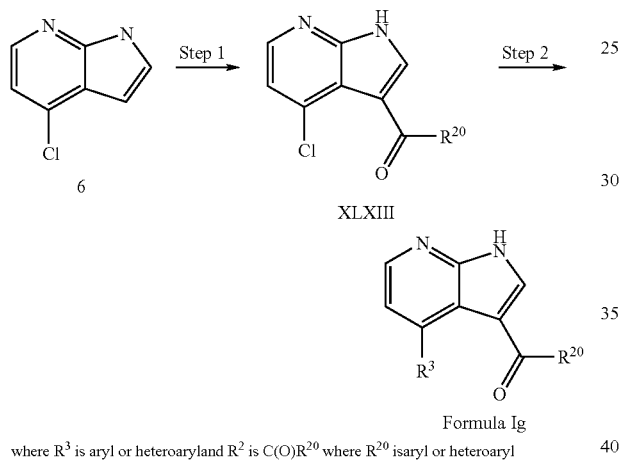

Scheme 42-Synthesis of Compounds of Formula Ig where $R^3$ is aryl or heteroaryl and $R^2$ is $C(O)R^{20}$ where $R^{20}$ is aryl or heteroaryl where $R^3$ is aryl or heteroaryl and $R^2$ is $C(O)R^{20}$ where $R^{20}$ is aryl or heteroaryl Step-1—Synthesis of Compound of XLXIII Compound of formula XLXIII can be prepared by reacting compound of formula 6 with a Lewis acid (e.g. $AlCl_3$) in an inert solvent (e.g. $CH_2Cl_2$) in the presence of an acid chloride (e.g. benzoyl chloride) as described by Katritzky, A. R. et al *J. Org. Chem.* 2003, 68, 5720. Purification is achieved with standard chromatographic techniques.

Step-2—Synthesis of Compound of Formula Ig, where $R^3$ is Aryl or Heteroaryl and $R^2$ is $C(O)R^{20}$ where $R^{20}$ is Aryl or Heteroaryl Compound of formula 1g, where $R^3$ is aryl or heteroaryl and $R^2$ is $C(O)R^{20}$ where $R^{20}$ is aryl or heteroaryl can be synthesized by reacting compound of formula XLXIII with a boronic acid (e.g. 3-mthoxyphenylboronic acid) in an inert solvent (e.g. dioxane), in the presence of a salt (e.g. KF), in the presence of a catalyst (e.g. $Pd_2(dba)_3CHCl_3$). The reaction is carried out under an inert solvent and is typically heated (100° C.) for 4-12 h as described by Allegretti, M. et. al *Synlett* 2001; 5, 609. Purification is achieved with standard chromatographic techniques.

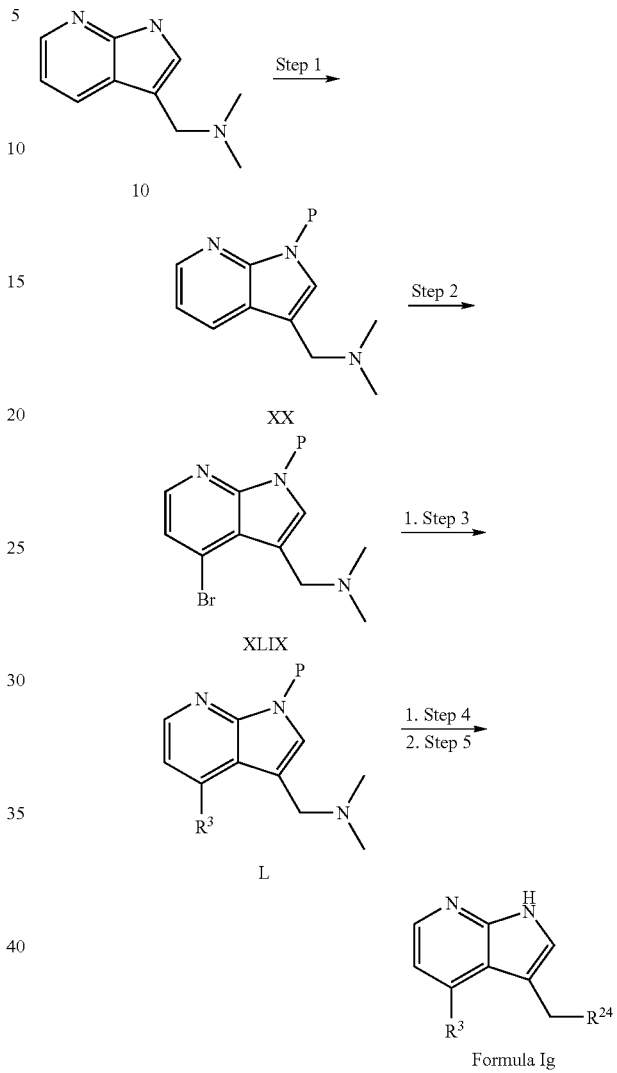

Scheme 43-Synthesis of Compounds of Formula Ig where $R^3$ is aryl or heteroaryl and $R^2$ is $CH_2R^{24}$ where $R^{24}$ is aryl or heteroaryl where $R^3$ is aryl or heteroaryl and $R^2$ is $CH_2R^{24}$ where $R^{24}$ is aryl or heteroaryl Step-1—Synthesis of Compounds of Formula XX Compounds of formula XX were prepared according to the procedure outlined in scheme 16.

Step-2—Synthesis of Compounds of Formula XLIX

Compounds of formula XLIX were prepared from compounds of the formula XX by using base (n-BuL t-BuLi, etc. . . . ) to affect the deprotonation in aprotic solvent ($Et_2O$, THF . . . ) at –78° C. The anion intermediate was then reacted with a bromide source (NBS, or dibromoethane) and allowed to warm to room temperature. The reaction was worked up in the usual manner. The compound was purified by flash silica gel chromatography.

Step-3—Synthesis of Compounds of Formula L.

Compound of formula L, where $R^3$ is aryl or heteroaryl, were synthesized from compounds of formula XLIX under Suzuki reaction conditions using aryl or heteroaryl bornonic acids (e.g. Phenyl bornonic acid, 3-thienyl bornonic acid) (M. Allegretti, Synlett, 2001, 5, p. 609.) as shown in scheme-10.

Step-4—Synthesis of Compounds of Formula Ig

Compounds of Formula Ig can be synthesized through the reaction of compounds of formula XX with isopropyl chloroformate (or ethyl chloroformate) at room temperature in toluene to give a 3-chloromethyl intermediate. This intermediate cooled to −78° C. and was immediately reacted with an organocopper reagent, which was generated from the reaction between a grignard reagent (or organolithium reagent) and a solution of copper cyanide and LiCl. The mixture was stirred at −78° C. for one hour then allowed to warm to room temperature. The reaction was quenched with a solution of 4:1 ammonium chloride: ammonium Hydroxide. The reaction was worked up in the usual manner and purified by flash silica gel chromatography to give the nitrogen protected product. The final product can be realized through the deprotection of the protecting group (Boc, TIPS) using standard conditions (TFA or $NH_4F$) at room temperature.

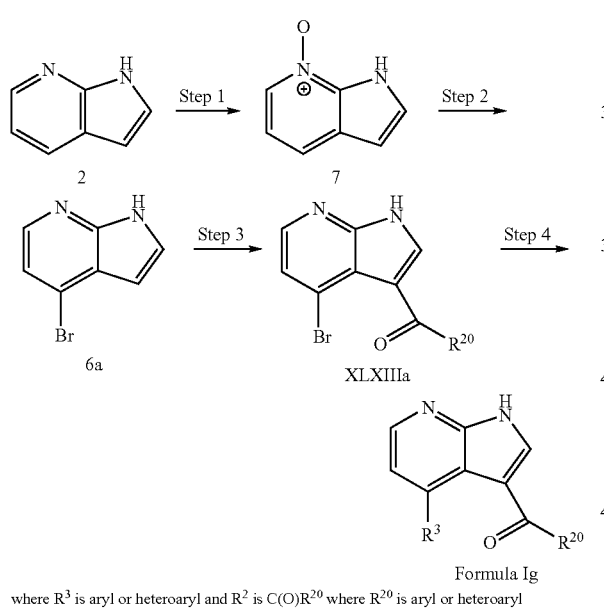

Scheme 54-Synthesis of Compounds of Formula Ig where $R^3$ is aryl or heteroaryl and $R^2$ is $CH_2R^{24}$ is aryl or heteroaryl Formula Ig
where $R^3$ is aryl or heteroaryl and $R^2$ is $C(O)R^{20}$ where $R^{20}$ is aryl or heteroaryl Step-1—Synthesis of Compound 7

Compound 7 was synthesized by reacting compound 2 with 85% meta-chloroperoxybenzoic acid in a solvent (e.g. 1,2-dimethoxyethane) typically at room temperature for 1-4 hours as described (Schneller and Luo, J. Org. Chem., 1980, 45, 4045). The resulting solid can be collected by filtration and washed with ethyl ether. The solid can be suspended in water and basified with an aqueous base (e.g. potassium carbonate). Upon cooling, the precipitate can be collected by filtration and purified by conventional means (e.g. recrystalliztion) to provide compound 7.

Step-2—Synthesis of Compound 6a

Compound 6a was synthesized by reacting compound 7 with a brominating agent (e.g. tetramethylammonium bromide) in an inert solvent (e.g. DMF). The mixture was cooled to 0° C. and methanesulfonic anhydride was added portionwise. The reaction mixture is stirred at 25° C. for typically 4-6 h as described in Thibault, C.; et al, Organic Letters, 2003, 5, 5023. The reaction mixture was immediately poured onto ice and basified with sodium hydroxide to provide a precipitate that can be collected by filtration. Purification by standard procedures (e.g. recrystallization) can provide compound 6a.

Step-3—Synthesis of Compound XLXIIIa

Compound XLXIIIa was synthesized by reacting compound 6a with an acid chloride (e.g. benzoyl chloride) in the presence of a Lewis acid (e.g. aluminum trichloride) in an inert solvent (e.g. methylene chloride) and under an inert atmosphere (e.g. argon) at room temperature or with heating up to reflux for 1-18 hours. The product was isolated by extraction and silica gel column chromatography as described by Katritzky, A. R.; et al J. Org. Chem., 2003, 68, 5720.

Step-4—Synthesis of Compound Ig

Compound Ig was synthesized from compound XLXIIIa under Suzuki reaction conditions using aryl or heteroayl boronic acids (e.g. 3-methoxyphenyl boronic acid, phenyl boronic acids), in presence of a catalyst (e.g. $Pd(PPh_3)_4$). The product was isolated by following standard procedure (quenching with ice-cold brine, work up, and purification by silica gel chromatography) as described by Allegretti, M. et. al Synlett 2001; 5, 609.

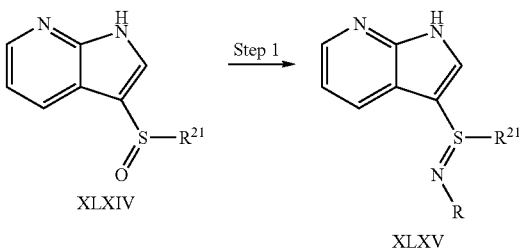

Scheme 55

Step 1:

Compound of the formula XLXV can be prepared from the compound of formula XLXIV by the addition of a primary amine and a coupling agent like DCC in AcOH at ambient temperature. The product can be isolated by following standard workup and silica gel flash chromatography purification. Ref: Hyde, Carolyn B., JCS, Perkins Trans 2, 1989, 2011-2016

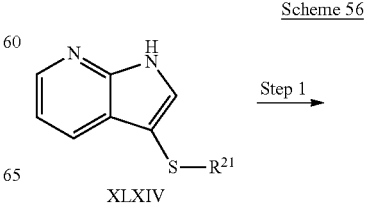

Scheme 56

-continued

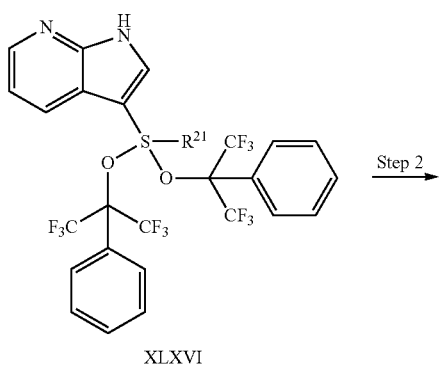

XLVI

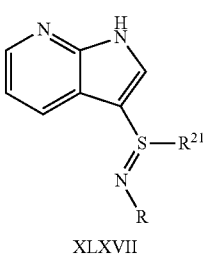

XLVII

Step 1:

The compound of formula XLVI can be prepared by reacting sulfide XLIV with the potassium salt of the ditrifluoromethylbenzyl alcohol with the sulfide in CHCl$_3$ at −78° C. The resulting product can be filtered off in quantitative yields. Ref: Martin, S C, JACS, 1971, 93, 2341.

Step 2:

Compound of the formula XLVII can be prepared by reacting the dialkoxydiarylsulfurane with a primary amine in a polar aprotic solvent (DMF, etc. . . . ) at 41° C. The product can be isolated by recrystallization or silica chromatography. Ref: Franz J A, JACS, 1973, 95, 6, 2017.

Example 1

Synthesis of 5-Cyano-7-Azaindole 14 and 7-Azaindole-5-carboxylic acid 15

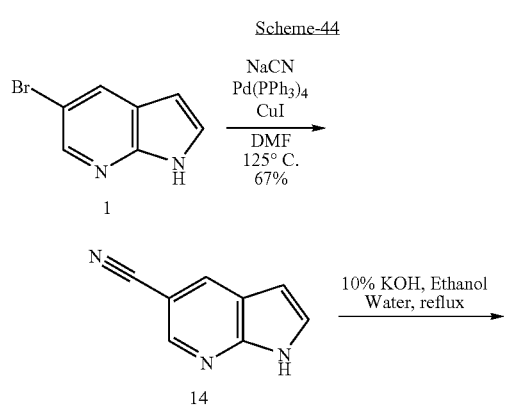

-continued

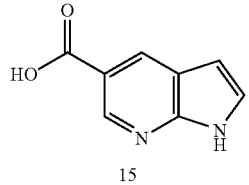

15

Step-1 Preparation of 5-Cyano-7-Azaindole 14

To a solution of 5-Bromo-7-azaindole XXX (300 mg, 1.52 mmol) in DMF (10 ml), sodium cyanide (150 mg, 3.06 mmol), cuprous iodide (45 mg, 0.24 mmol), and Tetrakis (triphenylphosphine) palladium(0) (100 mg, 0087 mmol) were added. The reaction was placed under argon heated at 125° C. for 48 hours after which the reaction was allowed to cool to ambient temperature before diluting with ethyl acetate and saturated sodium bicarbonate solution. The layers were separated and the aqueous layer was extracted with ethyl acetate (2×, 150 ml). The organic layers were then combined and washed with saturated bicarbonate solution (3×, 100 ml), before drying over sodium sulfate and evaporate under reduced pressure. The crude material was purified by preparative TLC, eluting with a solution of 70% hexane, 30% ethyl acetate with triethylamine as an additive to yield the titled compound as an off-white solid. (150 mg, M−1=142.0)

Step-2 Preparation of 7-Azaindole-5-carboxylic acid 15

To a solution of 5-cyano-7-azaindole XXX (50 mg, 0.35 mmol) in ethanol (10 ml), 10% aqueous potassium hydroxide (15 ml) was added. The reaction was heated at 90° C. for two days after which the reaction was allowed to cool to room temperature. The pH was adjusted to 6 with 10% HCl and diluted with ethyl acetate (100 ml). The layers were separated and the aqueous layer was extracted with ethyl acetate (4×, 75 ml). The organic layers were combined and washed once with brine (100 ml) before drying over sodium sulfate. The organic layer was evaporated under reduced pressure to yield the titled product as an off-white solid. (52 mg, M−1, 161.2)

Example 2

Synthesis of 3-(3-Methoxy-benzyl)-5-thiophen-3-yl-pyrrolo[2,3-b]pyridine 14 and 3-(5-Thiophen-3-yl-1H-pyrrolo[2,3-b]pyridine-3-ylmethyl)-phenol 15

Scheme 45

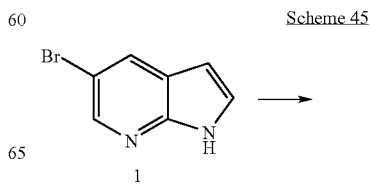

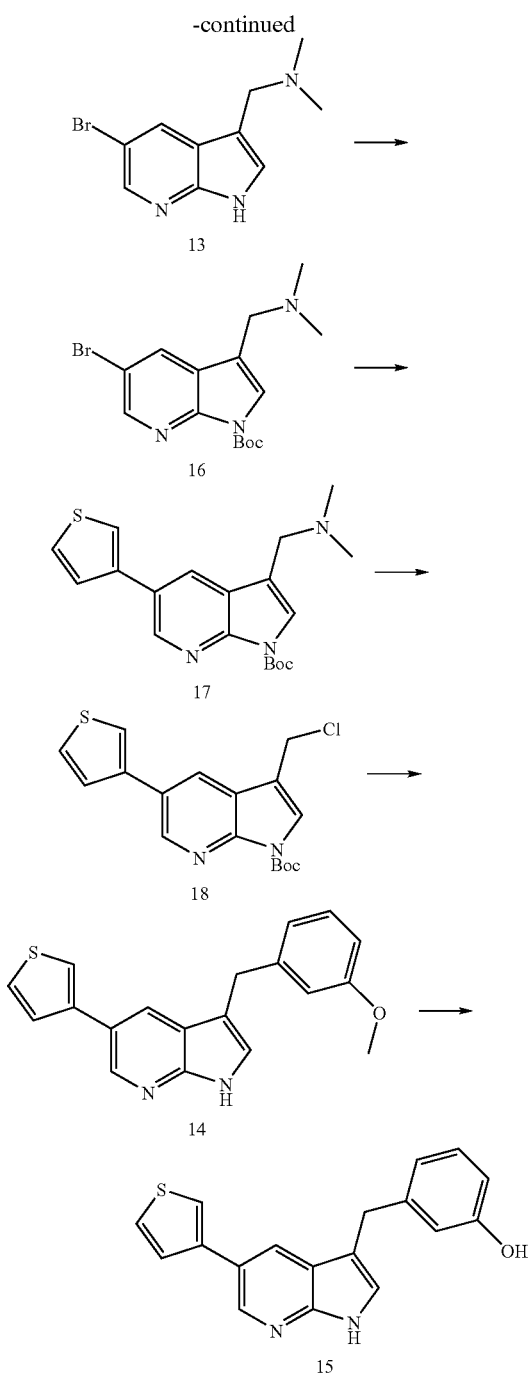

Step-1 Synthesis of 5-Bromo-1H-pyrrolo[2,3-b]pyridine-3-ylmethyl)-dimethyl-amine 13

Into a Round bottom flask was added 5-bromo-7-azaindole (540.0 mg, 0.002741 mol) and Dimethylamine hydrochloride 0.24 g, 0.0030 mol) and Paraformaldehyde (0.090 g, 0.0030 mol) and Isopropyl alcohol (40.0 mL, 0.522 mol). The reaction mixture was heated reflux for 17 hours. The reaction mixture was poured into water, followed by adding $K_2CO_3$ till PH=9. Then the aqueous layer was extracted with EtOAc. The organic layer was washed with brine, dried over sodium sulfate, concentrated and purified with biotage to give product 13 380.0 mg, together with 180.0 mg starting material recovered.

Step-2 Synthesis of 5-Bromo-3-dimethylaminomethyl-pyrrolo[2,3-b]pyridine-1-carboxylic acid tert-butyl ester 16

Into a Round bottom flask was added compound 13 (380.0 mg, 0.001495 mol) and N,N-Dimethylformamide (10.0 mL, 0.129 mol) and sodium hydride (66 mg, 0.0016 mol). 10 minutes later, was added Di-tert-Butyldicarbonate (650 mg, 0.0030 mol). The reaction mixture was stirred at room temperature for another 2 hours. TLC indicated no starting material. The reaction mixture was poured into water, extracted with EtOAc. The organic layer was washed with brine, dried over sodium sulfate, concentrated and dried with oil pump over weekend to give 540 mg product 16.

Step-3 Synthesis of 3-Dimethylaminomethyl-5-thiophen-3-yl-pyrrolo[2,3-b]pyridine-1-carboxylic acid tert-butyl ester 17

Into a Round bottom flask compound 16 (628.0 mg, 0.001773 mol) and 3-thiolphene boronic acid (390.0 mg, 0.003048 mol) and Potassium carbonate (800.0 mg, 0.005788 mol) and Tetrakis(triphenylphosphine)palladium(0) (40.0 mg, 0.0000346 mol) and Tetrahydrofuran (16.0 mL, 0.197 mol) and Water (4.0 mL, 0.22 mol) under an atmosphere of Nitrogen. The reaction was heated to reflux overnight. The reaction mixture was poured into water, extracted with EtOAc. The organic layer was washed with brine, dried over sodium sulfate, concentrated and purified with biotage to give product 17 (600.0 mg).

Step-4 3-Chloromethyl-5-thiophen-3-yl-pyrrolo[2,3-b]pyridine-1-carboxylic acid tert-butyl ester 18

Into a Round bottom flask was added compound 17 (120.0 mg, 0.000034 mol) and Toluene (4.0 mL, 0.038 mol) under an atmosphere of Nitrogen. To the reaction mixture was added Ethyl chloroformate (40.0 mg, 0.00037 mol). The reaction mixture was stirred at room temperature for 1 hour gave the desired chloride according to TLC. The reaction mixture was poured into water, extracted with EtOAc. The organic layer was washed with brine, dried over sodium sulfate, concentrated and purified with biotage to give product 18 (74.5 mg).

Step-5 Synthesis of 3-(3-Methoxy-benzyl)-5-thiophen-3-yl-pyrrolo[2,3-b]pyridine 14

Into a round bottom flask was added 1.0 M of 3-methoxyl phenyl magenesium bromide in Tetrahydrofuran (1.0 mL) and Tetrahydrofuran (5.0 mL, 0.062 mol) under an atmosphere of Nitrogen. The reaction mixture was cooled to −20 Celsius, followed by addition of 0.7 M of CuCN.2LiCl in Tetrahydrofuran (1 mL). After 10 minutes, Trimethyl Phosphite (120 mg, 0.0010 mol) was added to the reaction mixture. To the reaction mixture, was added compound 18 (60.0 mg, 0.000172 mol). The reaction mixture was stirred at room temperature overnight. The reaction mixture was poured into water, extracted with EtOAc. The organic layer was washed with brine, dried over sodium sulfate, concentrated and purified with biotage to give product 6 (M25 mg).

Step-6 Synthesis of 3-(5-Thiophen-3-yl-1H-pyrrolo[2,3-b]pyridine-3-ylmethyl)-phenol 15

Into a Round bottom flask was added compound 14 (20.0 mg, 0.0000624 mol) and Methylene chloride (4.0 mL, 0.062 mol) at room temperature. Into the reaction mixture, was added 0.1 mL BBr₃ (1.0M in). The reaction mixture was allowed to room temperature for 5 hours. TLC indicated the reaction was not complete. The reaction mixture was poured into water, extracted with EtOAc. The organic layer was washed with brine, dried over sodium sulfate, concentrated and purified with preparative TLC to give product 15 (5 mg).

Example 3

Preparation of 1H-Pyrrolo[2,3-b]pyridine-5-carboxylic acid benzylamide

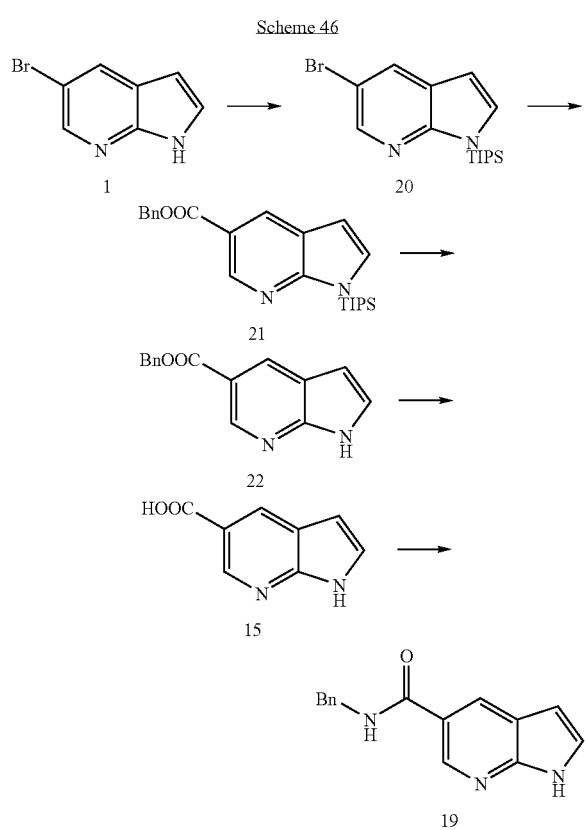

Step-1 Synthesis of 5-Bromo-1-triisopropylsilanyl-1H-pyrrolo[2,3-b]pyridine 20

Into a Round bottom flask was added 5-bromo-7-azaindole 1 (900.0 mg, 0.004568 mol) and N,N-Dimethylformamide (25.0 mL, 0.323 mol) and Sodium hydride (0.20 g, 0.0050 mol) at room temperature. After 10 minutes, Triisopropylsilyl chloride (1.1 mL, 0.0050 mol) was added to the reaction mixture. The reaction mixture was stirred at room temperature overnight. The reaction mixture was poured into water, extracted with EtOAc. The organic layer was washed with brine, dried over sodium sulfate, concentrated and purified with biotage to give product 20 (1.2 g).

Step-2 Synthesis of 1-Triisopropylsilanyl-1H-pyrrolo[2,3-b]pyridine-5-carboxylic acid benzyl ester 21

Into a Round bottom flask was added compound 20 (425.0 mg, 0.001203 mol) and Ether (8.0 mL, 0.076 mol) under an atmosphere of Nitrogen, −78 Celsius. Into the reaction mixture, was added 1.7 M of tert-Butyllithium in Heptane (1.5 mL) slowly. The reaction mixture was stirred at −78 Celsius for 90 minutes, followed by addition of benzyl chloroformate (0.20 mL, 0.0014 mol). 2 hours later at −78 Celsius, the reaction mixture was poured into water, extracted with EtOAc. The organic layer was washed with brine, dried over sodium sulfate, concentrated and purified with biotage to give product 21 (250 mg).

Step-3 Synthesis of 1H-Pyrrolo[2,3-b]pyridine-5-carboxylic acid benzyl ester 22

Into a Round bottom flask was added compound 21 (250.0 mg, 0.0006118 mol) and Tetrahydrofuran (5.0 mL, 0.062 mol) and Tetra-n-butylammonium fluoride (190 mg, 0.00073 mol). The reaction mixture was stirred at room temperature for 30 minutes. The reaction mixture was poured into water, extracted with EtOAc. The organic layer was washed with brine, dried over sodium sulfate, concentrated and purified with biotage to give product 22 (55 mg).

Step-4—Synthesis of 1H-Pyrrolo[2,3-b]pyridine-5-carboxylic acid 15

Into a round bottom flask was added compound 22 (55.0 mg, 0.000218 mol) and palladium hydroxide, 20 wt. % Pd on carbon, wet (20.0 mg, 0.000142 mol) and Methanol (5.0 mL, 0.12 mol) under an atmosphere of Hydrogen. The reaction mixture was stirred at room temperature overnight. Filtration and concentration gave product 15 (35 mg).

Step-5 Synthesis of 1H-Pyrrolo[2,3-b]pyridine-5-carboxylic acid benzylamide 19

Into a Round bottom flask was added compound 15 (35.0 mg, 0.000216 mol) and benzylamine (0.05 mL, 0.0004 mol) and PyBroP (Bromotri(pyrrolidino)phosphonium hexafluorophosphate, 200.0 mg, 0.0004318 mol) and triethylamine (0.093 mL, 0.00067 mol) and tetrahydrofuran (5.0 mL, 0.062 mol) and N,N-dimethylformamide (10.0 mL, 0.129 mol) and methylene chloride (5.0 mL, 0.078 mol) under an atmosphere of Nitrogen. The reaction mixture was stirred at room temperature overnight. The reaction mixture was poured into water, extracted with EtOAc. The organic layer was washed with brine, dried over sodium sulfate, concentrated and purified with biotage to give product 19 (15 mg).

Example 4

Synthesis of (3-Hdroxy-phenyl)-(5-thiophene-3-yl-1H-pyrrolo[2,3-b]pyridine-3-methanone 23

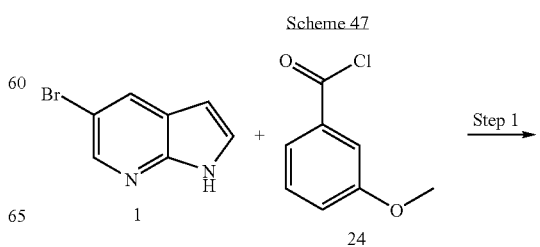

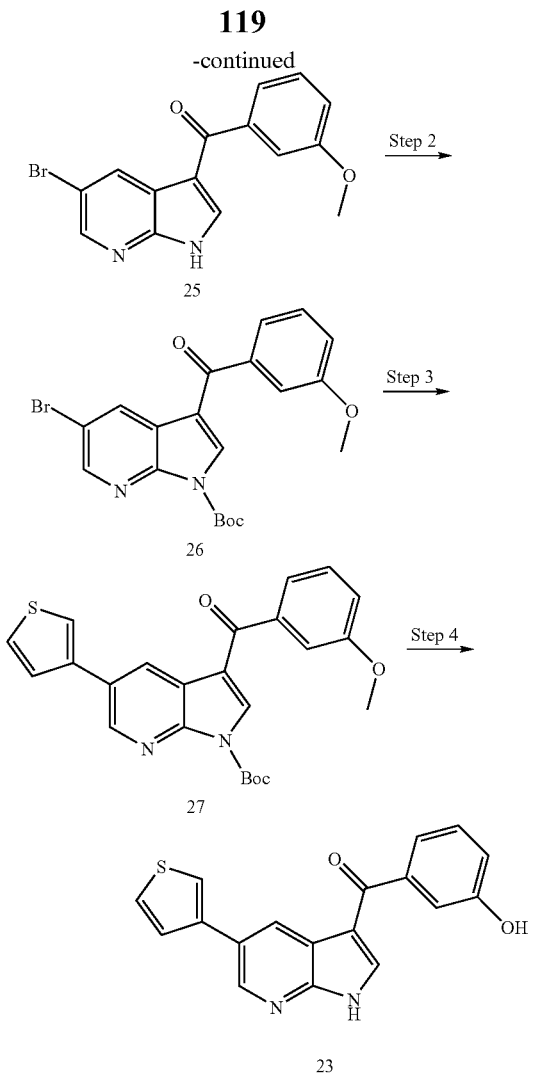

THF (15 mL) was added. After stirring for 20 min at 25° C. under a nitrogen atmosphere, di-tert-Butyldicarbonate (148 mg, 0.000678 mol, 1.5 equiv) was introduced into the flask. The reaction mixture was stirred for 18 h followed by removing the solvent at reduced pressure. The resulting residue was dissolved in EtOAc, washed with brine, dried over MgSO$_4$ to yield product 26. The desired product was carried on without further purification. The identity of product 26 was identified by H$^1$-NMR.

Step 3—Preparation of 3-(3-Methoxy-benzoyl)-5-thiophen-3-yl-pyrrolo[2,3-b]pyridine-1-carboxylic acid tert-butyl ester 27

Azaindole 26 (33 mg, 0.00076 mol), Potassium carbonate (44 mg, 0.00032 mol), 3-thiophene boronic acid (20 mg, 0.0002 mol), THF (7 mL), water (1.5 mL), and tetrakis(triphenylphosphine)palladium (0) (5 mg, 0.000004 mol) were added to a round bottom flask. The reaction mixture was stirred under nitrogen at 70° C. for overnight. The solvent was removed and the resulting residue was dissolved in EtOAc, washed with brine, dried over MgSO$_4$ and concentrated. The desired product was purified by silica gel flash chromatography using a 90:10 Hexane/ETOAc solvent system. The product 27 was identified by LC/MS and H$^1$-NMR. LRMS (ESI+): (M+H$^+$)$^+$ 436.5

Step 4—Preparation of (3-Hdroxy-phenyl)-(5-thiophene-3-yl-1H-pyrrolo[2,3-b]pyridine-3-methanone 23

Azaindole 27 (14 mg, 0.000032 mol) was added to a dry round bottom flask kept under a nitrogen atmosphere in CH$_2$Cl$_2$ (5 mL). Boron tribromide in heptane (0.06387 mL) was added dropwise. The reaction mixture was stirred for 4 h at 25° C. The solvent was removed and the resulting residue was dissolved in EtOAc, washed with brine, dried over MgSO$_4$ and concentrated. The desired product was purified by silica gel flash chromatography using a 98:2 CH$_2$Cl$_2$/MeOH solvent system. The product 23 was identified by LC/MS and H$^1$-NMR. LRMS (ESI+): (M+H$^+$)$^+$321.

Step 1—Preparation of 5-bromo-1H-pyrrolo[2,3-b]pyridine-3-yl)-3-methanone 25

5-Bromo-7-azaindole 1 (417 mg, 0.00212 mol) was added to a dry round bottom flask kept under a nitrogen atmosphere in CH$_2$Cl$_2$ (20 mL). Aluminum chloride (1400 mg, 0.010 mol, 5 equiv) was added. The reaction mixture was stirred for 1 h at 25° C. upon which 3-methoxybenzoyl chloride 24 (740 mg, 0.0053 mol, 2.5 equiv) was added. The reaction was continued to stir for an additional h. The solvent was removed at reduced pressure. The resulting residue was dissolved in EtOAc, washed with brine, dried over MgSO$_4$ and concentrated. The desired product was purified by silica gel flash chromatography using a 70:30 Hexane/ETOAc solvent system to yield compound 25. The product 25 was identified by LC/MS and H$^1$-NMR. LRMS (ESI+): (M+H$^+$) 253

Step 2—Preparation of 5-bromo-3-(3-methoxy-benzoyl)-pyrrolo[2,3-b]pyridine-1-carboxlic acid tert-butyl ester 26

Compound 25 (150 mg, 0.00045 mol) was added to a dry round bottom flask kept under a nitrogen atmosphere in THF (15 mL). Sodium hydride (35 mg, 0.0014 mol, 3.2 equiv) in Example 5

Synthesis of 1H-pyrrolo[2,3-b]pyridine-3-yl)-3-methanone 28

Scheme 48

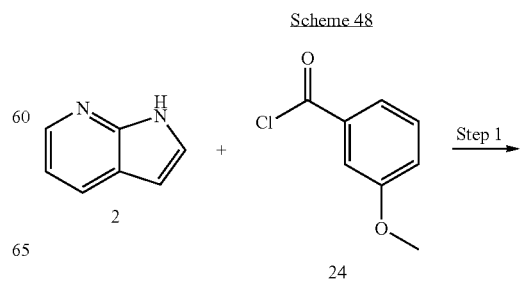

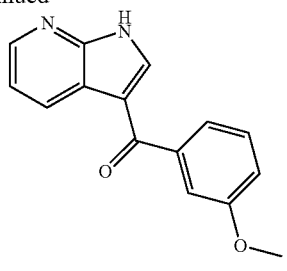

28

Into a round bottom flask, under an atmosphere of nitrogen, aluminum chloride (1.4 g, 10 mmol) was placed in solution with methylene chloride (20 mL, 0.3 mol) followed by the addition of 7-azaindole (1) (0.250 g, 2.12 mmol). After stirring for one hour at room temperature, 3-methoxy-benzoyl chloride (2) (0.74 mL, 5.3 mmol) was added dropwise. The mixture was stirred at room temperature for an additional two hours. The reaction was quenched with methanol at 0° C. and evaporated to dryness. The residue was dissolved into ethyl acetate and washed with water, 0.1 N HCl, sodium bicarbonate (s.s.), and brine. The organic portions were dried over anhydrous sodium sulfate and evaporated under reduced pressure. Purification by flash chromatography with 30% ethyl acetate/hexane provided Compound 28 as a white powder (205 mg; M+H=253.2; M−H=251.2).

Example 6

Synthesis of (3,5-dimethoxy-benzyl)-pyrrolo[2,3-b]pyridine 29

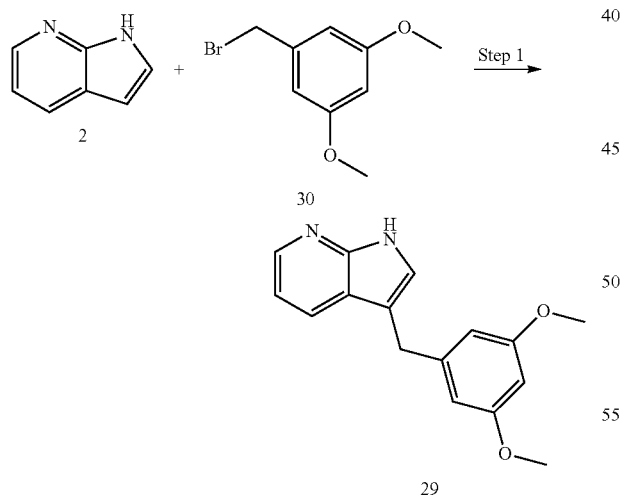

Into a round bottom flask, under an atmosphere of nitrogen, methylmagnesium bromide (0.16 mL, 1.4 mmol) was added to a solution of 7-azaindole (1) (0.150 g, 1.27 mmol) in anhydrous methylene chloride (12 mL, 0.19 mol), at room temperature. The resulting mixture was stirred at room temperature for one hour before zinc dichloride (0.21 g, 1.5 mmol) was added. After stirring for an additional hour, 3,5- dimethoxybenzyl bromide (4) (0.35 g, 1.5 mmol) was added into the reaction mixture. The reaction was stirred overnight at room temperature before it was quenched with methanol. The mixture was evaporated to dryness, dissolved into ethyl acetate and washed with water. The aqueous portion was neutralized with sodium bicarbonate (s.s.) and extracted with ethyl acetate (3×). Organic portions were combined and washed with 0.1N HCl, dried over anhydrous sodium sulfate and evaporated under reduced pressure. Purification by preparative TLC with 50% ethyl acetate/hexane gave Compound 29 as a yellow powder (15 mg; M+H=269.2, M−H=267.2).

Example 7

Synthesis of (3-Hydroxy-phenyl)-(4-(3,5-difluorophenyl)-1H-pyrrolo[2,3-b]pyridine-3-methanone 31

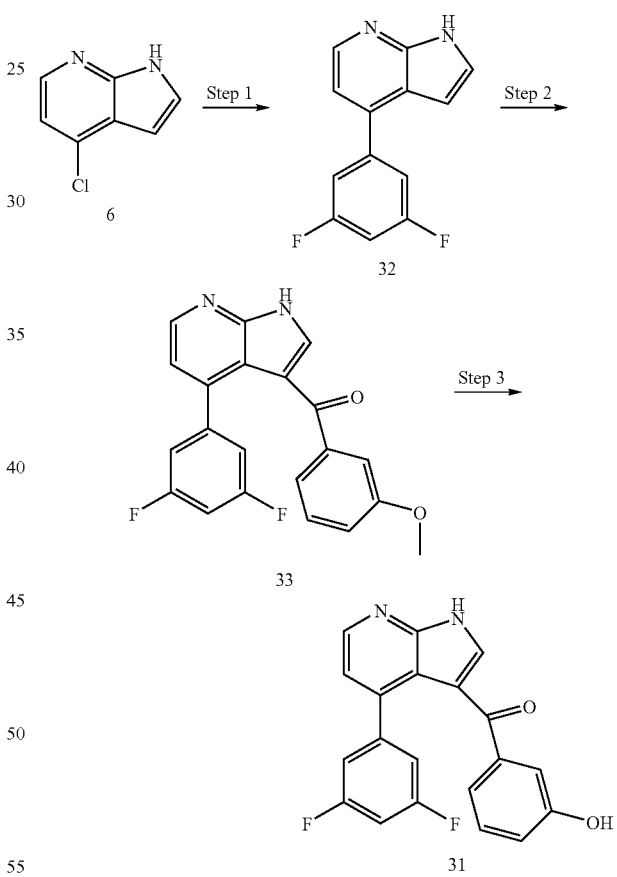

Step 1—Preparation of Compound 32

4-Chloro-azaindole 6, Potassium carbonate, 3,5-difluoro boronic acid (20 mg, 0.0002 mol), THF (7 mL), water (1.5 mL), and tetrakis(triphenylphosphine)palladium (0) were added to a round bottom flask. The reaction mixture was stirred under nitrogen at 70° C. for overnight. The solvent was removed and the resulting residue was dissolved in EtOAc, washed with brine, dried over MgSO$_4$ and concentrated. The desired product was purified by silica gel flash chromatography using a 90:10 Hexane/ETOAc solvent system to yield compound 32.

Step-2 Synthesis of (3-Methoxy-phenyl)-(4-(3,5-difluorophenyl)-1H-pyrrolo[2,3-b]pyridine-3-methanone 33

To a stirring solution of 7-azaindole 32 (100 mg, 0.43 mmol, 1 equiv) in dry methylene chloride (DCM, 2 mL), AlCl₃ (405 mg, 3.04 mmol, 7 equiv) was added. The reaction mixture was stirred at 25° C. for 1 h and 3-methoxybenzoyl chloride (185 mg, 1.08 mmol, 2.5 equiv) was added. The mixture was stirred at 25° C. for 18 h and methanol (MeOH, 2 mL) was introduced to quench the reaction. The solvents were removed at reduced pressure, and the residual solid was purified by preparative TLC using hexanes:ethyl acetate solvent system (1:1) to give compound 33 as a white solid. (M+H⁺)⁺: 365.3.

Step 2—Preparation of phenyl)-(4-(3,5-difluorophenyl)-1H-pyrrolo[2,3-b]pyridine-3-methanone 31

To a stirring solution of azaindole (3) (25 mg, 0.69 mmol) in dry tetrahydrofuran (THF, 1 mL) under a N₂ atmosphere, BBr₃ (170 μL, 1 M in Heptane, 2.4 equiv) was added dropwise and stirred at 25° C. overnight. The reaction mixture was quenched by the addition of water and the product was extracted with ethyl acetate. The organic layer was dried over magnesium sulfate, filtered and concentrated at reduced pressure. The resulting residue was purified by preparative TLC using hexanes:ethyl acetate (1:1) solvent system to give compound 31 as a white solid. (M+H⁺)⁺:351.3.

Example 8

3-(6-methoxy-pyridin-2-ylmethyl)-4-thiophen-3-yl-1H-pyrrolo[2,3-b]pyridine 35

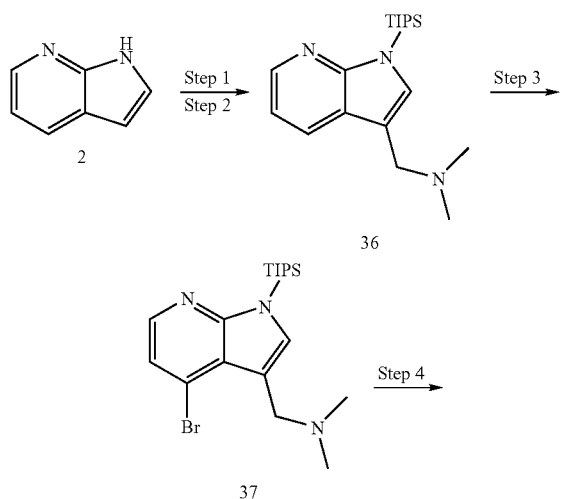

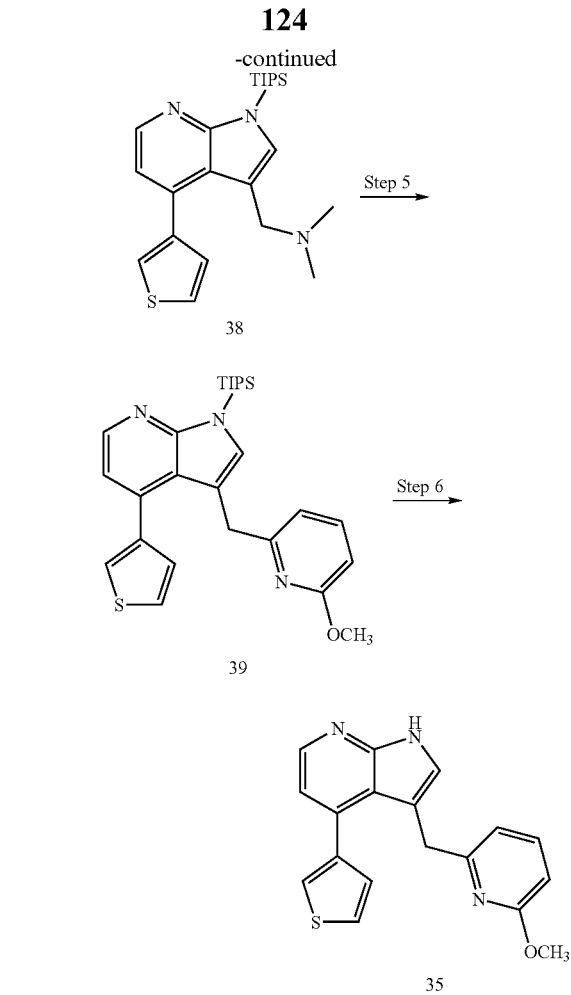

Step 1 and Step-2 Synthesis of azagramine 36

7-Azagramine (5.0 g, 28.53 mmol), synthesized from 7-azaindole by following Robinson's procedure (J. Am. Chem. Soc., 1955, 77, p. 457), was dissolved in THF (90 mL) and cooled to 0° C. with an ice bath. To this solution was added NaH (1.26 g, 31.5 mmol 60% in mineral oil) in portions. After the addition, the mixture was allowed to warm to room temperature and stirred for 1 hour. The solution was again cooled to 0° C. and triisopropylsilyl chloride (6.25 mL, 29.5 mmol) was added. The mixture was allowed to stir overnight at room temperature. The mixture was poured into ice-cold water and extracted with EtOAc. The organic layer was washed with brine, dried over MgSO₄, filtered and evaporated to give a residue. The residue was purified by silica chromatography using 5% EtOAc/Hexanes to give 9.5 g compound 36 as an oil (97% yield. MS: M+1=332.5).

Step-3 Synthesis of compound 37

Compound 36 (5.0 g, 15.08 mmol) was dissolved in Et₂O (100 mL) and cooled to −78° C. To this mixture was added t-BuLi (10.0 mL, 16.9 mmol, 1.7 M in Hexanes) drop wise over 10 minutes. The mixture was maintained at −78° C. for 1 hour, and then allowed to warm to room temperature over night. The mixture was cooled to −78° C. and 1,2-dibromoethane (1.5 mL, 17 mmol) was added drop wise. The mixture was allowed to warm to room temperature and was stirred for 2 to 3 hours. The mixture was poured into ice-cold water and extracted with EtOAc. The organic layer was washed with brine, dried over MgSO$_4$, filtered and evaporated. The residue was purified with silica chromatography using 20% EtOAc/Hexanes to give 4.64 g of compound 37, as an oil (75% yield. MS: M+1=411).

Step-4 Synthesis of compound 38

Compound 37 (1.0 g, 2.43 mmol) was dissolved in 1,4-dioxane (20 mL) followed by 3-thiophene boronic acid (625 mg, 4.88 mmol), KF (850 mg, 8.11 mmol), Pd$_2$(dba)$_3$—CHCl$_3$ (39 mg, 0.034 mmol, and tri-t-butylphosphine (58 mg, 0.29 mmol). The resulting mixture was heated at 90° C. overnight. The mixture was allowed to cool to room temperature and the solvent was evaporated. The residue was purified by silica chromatography (5% EtOAc/Hexanes) to give 452 mg of oil, compound 38 (45% yield. MS: M+1=414).

Step-5 Synthesis of Compound 39

Compound 38 was dissolved in Toluene (5.0 mL) and a solution of isopropyl chloroformate (0.36 mL, 0.364 mmol) was added. The mixture was allowed to stir at room temperature until TLC indicated the completion of the reaction (solution A). In a separate flask, 2-bromo-6-methoxypyridine (169 mg, 0.91 mmol) was dissolved in THF and cooled to −78° C. To this mixture was added n-BuLi (0.58 mL, 0.93 mmol) and the mixture was allowed to stir for 1.0 hour at −78° C. To this solution at −78° C. was added a solution of CuCN-2LiCl (0.62 mL, 0.364 mmol, 0.59 M in THF). The mixture was stirred for an additional hour at −78° C. (solution B). Keeping the cuprate mixture (solution B) at −78° C., the chloride mixture (solution A) was added. The mixture was allowed to slowly warm to room temperature and stirred overnight. The mixture was poured into a solution of ammonium chloride and ammonium hydroxide (4:1) and extracted with EtOAc. The organic layer was washed with brine, dried over MgSO$_4$, filtered and evaporated to give a residue. The residue was purified by silica gel chromatography (5% EtOAc/Hexanes) to give compound 39 as a solid (25% yield. MS: M+1=478).

Step-6 Synthesis of 3-(6-methoxy-pyridin-2-ylmethyl)-4-thiophen-3-yl-1H-pyrrolo[2,3-b]pyridine 35

Compound 39 (75 mg, 0.16 mmol) was dissolved in THF (5.0 mL) and a solution of ammonium fluoride (5.0 mL, 0.5 M in MeOH, 2.5 mmol). The mixture was stirred overnight at room temperature. The solvent was evaporated to give a residue. The residue was dissolved in EtOAc and washed with H$_2$O, brine and dried over MgSO$_4$. The organic layer was filtered off and evaporated. Toluene (10 mL) was added the mixture was evaporated to dryness. The product was dried under vacuum to give 30 mg of product 35 (59.5% yield. MS: M+1=322.3).

Example 9

Synthesis of (4-Amino-1-H-pyrrolo[2,3-b]pyridine-3-yl)-phenyl-methanone 40

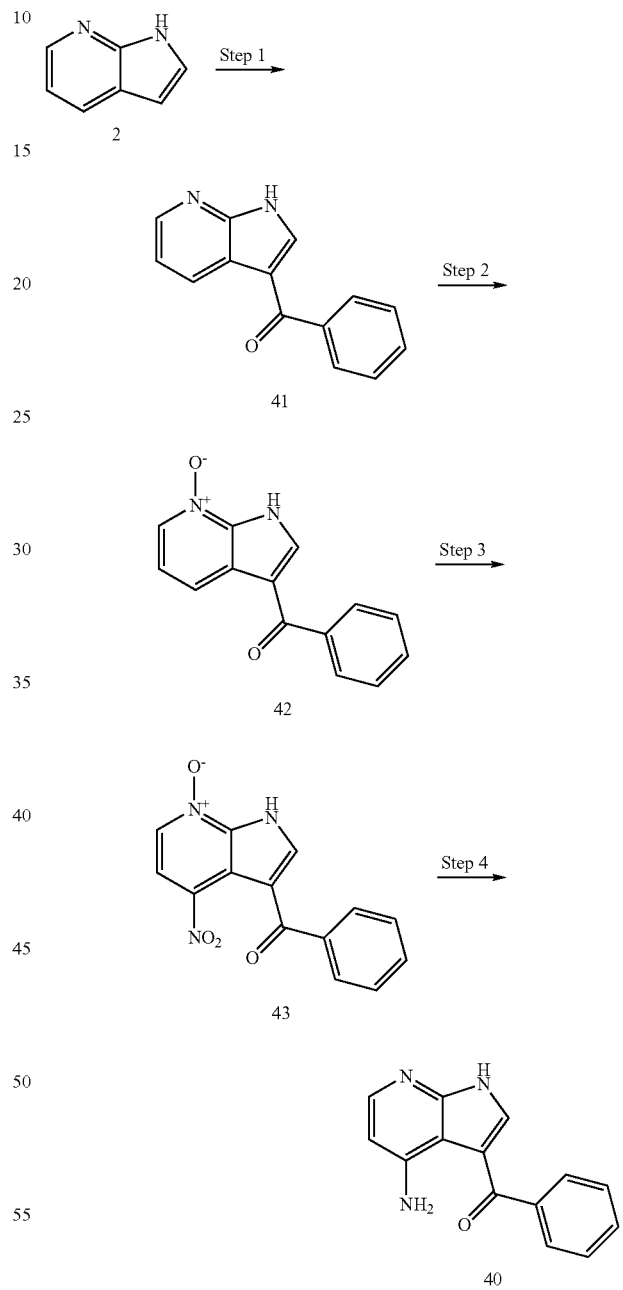

Step 1—Preparation of 3-benzoyl-7-azaindole 41

Compound 41 was prepared from 7-azaindole 2 using aluminum chloride as described previously for the synthesis of Compound 25, with benzoyl chloride substituted for m-methoxy-benzoyl chloride.

Step 2—Preparation of Compound 42 m-Chloroperbenzoic acid (1.45 g, 8.40 mmol) was dissolved in tetrahydrofuran (THF) (20.0 mL). A solution of 3-benzoyl-7-azaindole 41 (1.00 g, 4.50 mmol) THF (40.0 mL) and was added into the reaction dropwise. After several minutes a white precipitate formed. The reaction mixture was stirred for 2 hours. The reaction mixture was filtered. The precipitate was washed with THF and dried to provide Compound 42 as a white powder (870 mg; M+H=239.2).

Step 3—Preparation of Compound 43

Compound 42 (600.0 mg, 2.518 mmol) was added to nitric acid (12.00 mL) and the reaction was cooled to 0° C. Sulfuric acid (1.00 mL) was added to the reaction slowly. The reaction was heated at 70° C. for 1 hour. The reaction was cooled to room temperature. The reaction was poured into ice water and a yellow precipitate formed. The precipitate was collected by filtration and washed with water to provide Compound 43 as a yellow powder (536 mg; M−H=282.1).

Step 4—Preparation of Compound 40

Compound 43 (200 mg, 0.706 mmol) was dissolved in methanol (40.0 mL) and Raney nickel (1 g) was added. The reaction mixture was shaken on a Parr apparatus for 1.5 hours under an atmosphere of hydrogen at 20 psi. Acetic acid (0.500 mL) was added to the reaction mixture. The reaction was hydrogenated under the same conditions for another 30 minutes. The reaction mixture was filtered through Celite. The filtrate was concentrated to dryness. Water was added to the residue followed by 2 N sodium hydroxide. The reaction was extracted with ethyl acetate. The organic portions were combined and adsorbed onto silica. The mixture was purified by flash chromatography, 4% methanol:dichloromethane. The appropriate fractions were combined to provide Compound 43 as a brown solid (29 mg; M+H=238.3).

Example 10

Synthesis of phenyl-(1H-pyrrolo[2,3-b]pyridine-5-yl)amine 44

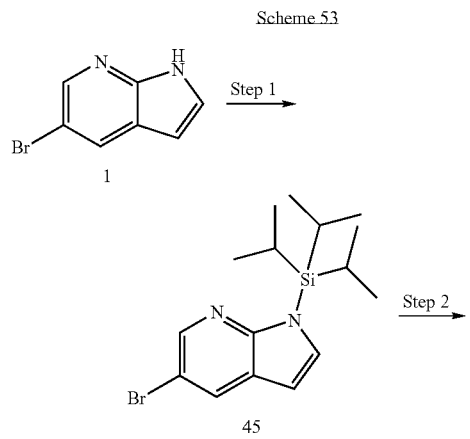

Scheme 53

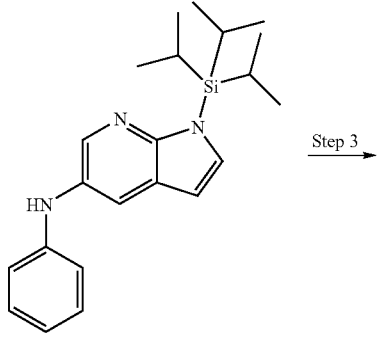

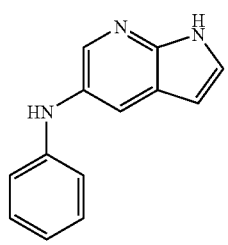

Step 1—Preparation of Compound 45

Compound 1 (500.0 mg, 2.537 mmol) was dissolved in THF (15.0 mL) in a flame-dried flask. The reaction mixture was cooled to 0° C. Sodium hydride, 60% dispersion in mineral oil, (0.102 g, 0.00254 mol) was added. The reaction was stirred at 0° C. for 20 minutes. The reaction was warmed to room temperature for 20 minutes. The reaction was cooled to 0° C. Triisopropylsilyl chloride (0.591 mL, 2.79 mmol) was added to the reaction mixture. The reaction was stirred at 0° C. for 1 hour. The reaction was warmed to room temperature and stirred overnight. The reaction mixture was poured into water and then extracted with ethyl acetate. The organic portions were combined, dried with anhydrous magnesium sulfate, and concentrated to dryness under reduced pressure to provide an oil. The oil was purified by flash chromatography, 100% hexanes, to provide Compound 45 as a white crystalline solid (486 mg).

Step 2—Preparation of Compound 46

Compound 45 (200.6 mg, 0.5676 mmol) was dissolved in toluene (11.0 mL) in a flame-dried flask under an atmosphere of argon. Aniline (0.200 mL, 2.19 mmol) was added to the reaction mixture. Tri-t-butylphosphine (5 mg, 0.02 mmol), Tris(dibenzylideneacetone)dipalladium(0) (5 mg, 0.006 mmol), and sodium t-butoxide (78.3 mg, 0.815 mmol) were added to the reaction. The reaction was heated to 85° C. for 24 hours. By TLC, the reaction was incomplete. Aniline (400.0 uL, 4.390 mmol), Tri-t-butylphosphine (10 mg, 0.05 mol), Sodium tert-butoxide (170.0 mg, 1.769 mmol), and Tris (dibenzylideneacetone)dipalladium(0) (10.0 mg, 0.011 mmol). The reaction was heated at 95° C. for 18 hours. The reaction was added to water and extracted with ethyl acetate. The organic portions were combined, dried with anhydrous magnesium sulfate, and concentrated to dryness under reduced pressure. The residue was redissolved in ethyl acetate, adsorbed onto silica, and purified by flash chromatography, 0% ethyl acetate:hexanes to 2% ethyl acetate:hexanes. The appropriate fractions were combined and concentrated to dryness to provide Compound 46 as a brown oil (45.7 mg).

Step 3—Preparation of Compound 44

Compound 46 (45.7 mg, 0.125 mol) was dissolved in TILF (5.0 mL). 0.5 M Ammonium fluoride in methanol (5.0 mL) was added to the reaction. The reaction was stirred at room temperature over the weekend. The reaction was concentrated under reduced pressure. The residue was partitioned between ethyl acetate and saturated sodium bicarbonate. The organic layer was extracted twice more with saturated sodium bicarbonate. The organic portions were combined, dried with anhydrous magnesium sulfate, and concentrated to dryness under reduced pressure to provide Compound 44 as a brown oil (16.7 mg; M+H=210.3).

Example 11

Synthesis of (3-hydroxy-phenyl)-(5-aminophenyl-1H-pyrrolo[2,3-b]pyridine-3-yl)-methanone 294

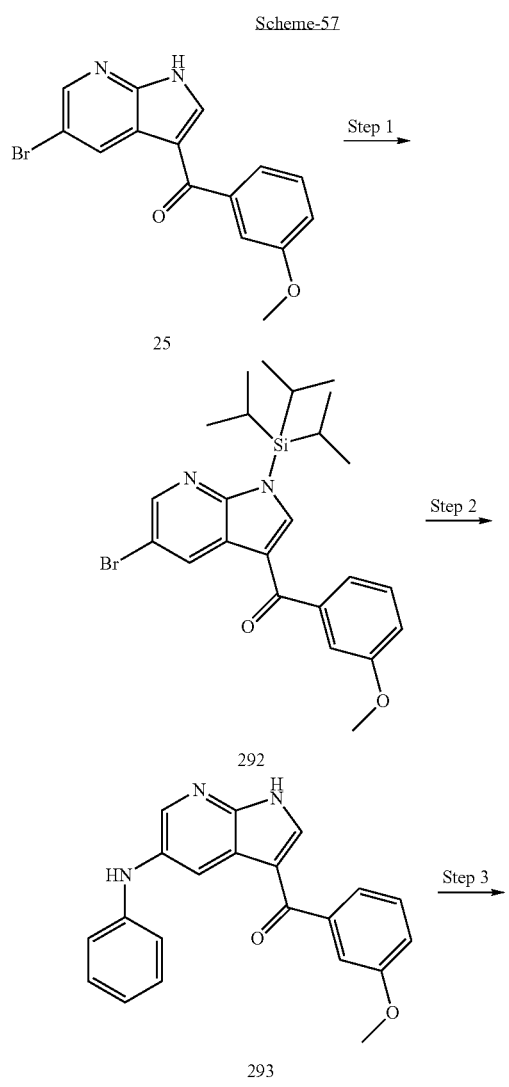

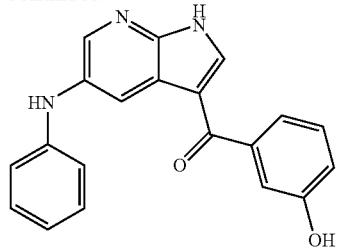

Step 1—Preparation of (3-methoxy-phenyl)-(5-bromo-1-triisopropylsilyl-pyrrolo[2,3-b]pyridine-3-yl)-methanone 292

Compound 25 (130 mg, 0.39 mmol) was dissolved in THF (10 mL). The reaction was cooled to 0° C. Into the reaction was added sodium hydride (60% dispersion in mineral oil, 157 mg, 0.39 mmol). The reaction was stirred at 0° C. for 20 minutes. The reaction was warmed to room temperature for 20 minutes. The reaction was cooled to 0° C. Into the reaction was added triisopropylsilyl chloride (0.091 mL, 0.43 mmol). The reaction was stirred at 0° C. for 1 hour and then room temperature for 1 hour. The reaction was incomplete by TLC. The reaction was cooled to 0° C. Into the reaction was added sodium hydride (60% dispersion in mineral oil, 157 mg, 0.39 mmol). The reaction was stirred at 0° C. for 20 minutes. The reaction was warmed to room temperature for 20 minutes. The reaction was cooled to 0° C. Into the reaction was added triisopropylsilyl chloride (0.091 mL, 0.43 mmol). The reaction was stirred at 0° C. for 1 hour. The reaction was concentrated to dryness. The reaction was partitioned between ethyl acetate and saturated sodium bicarbonate and washed twice more with saturated sodium bicarbonate. The organic portion was dried with anhydrous magnesium sulfate and concentrated to provide a yellow oil. The desired product 292 was identified by ¹H-NMR.

Step 2—Preparation of (3-methoxy-phenyl)-(5-phenylamino-1-H-pyrrolo[2,3-b]pyridine-3-yl)-methanone 293

Compound 292 (135 mg, 0.2769 mmol) was dissolved in toluene (4.2 mL), under and atmosphere of argon. Aniline (0.154 mL, 1.69 mmol) and sodium tert-butoxide (57.7 mg, 0.60 mmol) were added to the reaction. Into the reaction was added tri-tert-butyl-phosphine (9.0 mg, 0.040 mmol) and Tris (dibenzylideneacetone)dipalladium(0) (5.0 mg, 0.005 mmol). The reaction was heated at 95° C. for 18 hours. The solution was concentrated under reduced pressure. The remaining oil was partitioned between ethyl acetate and brine. The aqueous portion was extracted twice more with ethyl acetate. The organic portions were combined, dried with anhydrous magnesium sulfate, and concentrated to dryness. The residue was redissolved in ethyl acetate, adsorbed onto silica, and purified by silica gel flash chromatography with a step gradient of 50%-60% ethyl acetate:hexanes. The appropriate fractions were combined and concentrated to dryness to provide a light green solid. The solid was washed with hexanes and collected by filtration to provide compound 293 as a light green solid (26.6 mg, LRMS (ESI) [M+H⁺]⁺= 344.1.)

Step 2—Preparation of (3-hydroxy-phenyl)-(5-phenylamino-1-H-pyrrolo[2,3-b]pyridine-3-yl)-methanone 294

Compound 293 (26.6 mg, 0.079 mmol) was dissolved in methylene chloride (10 mL) under an atmosphere of nitrogen. Into the reaction mixture was added 1.0 M boron tribromide in methylene chloride (0.3 mL). The reaction was stirred at room temperature overnight. The solvent evaporated over time, so methylene chloride (10 mL) was added, followed by 1.0 M boron tribromide in methylene chloride (0.6 mL). The reaction was stirred overnight. The reaction was quenched with methanol (10 mL), concentrated under reduced pressure, and extracted with brine and ethyl acetate. The organic portion was dried with anhydrous magnesium sulfate and concentrated to dryness to provide a yellow solid. The material was purified by prep TLC (5% methanol:methylene chloride). The appropriate band was scraped and the compound eluted from the silica with ethyl acetate. The mixture was filtered and the filtrate concentrated to provide compound 294 as a yellow solid as identified by $^1$H-NMR and MS (1.2 mg, LRMS (ESI) [M+H$^+$]$^+$=330.1).

Example 12

Synthesis of N-[4-Fluoro-3-(1H-pyrrolo[2,3-b]pyridine-3-carbonyl)-phenyl]-methanesulfonamide 297

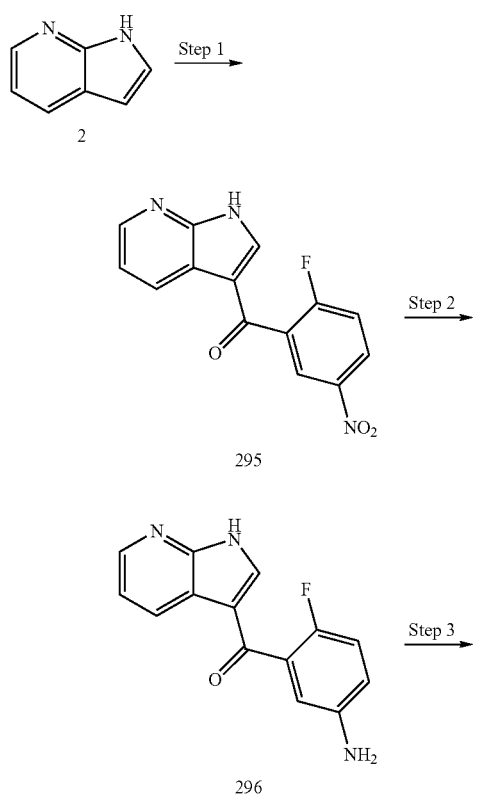

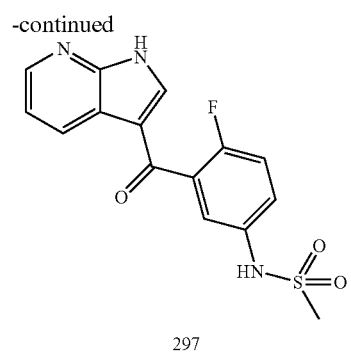

Step 1—(2-Fluoro-5-nitro-phenyl)-(1H-pyrrolo[2,3-b]pyridin-3-yl)-methanone 295

3-fluoro-5-nitrobenzoic acid (2.90 g, 10.8 mmol) was dissolved in thionyl chloride (20.0 mL) and the reaction was heated to reflux overnight. The reaction was cooled and was concentrated to provide a white solid which was dried under vacuum overnight. Compound 2 (512 mg, 4.33 mmol) was dissolved in methylene chloride (10.0 mL), under an atmosphere of argon and aluminum trichloride (2.85 g, 21.4 mmol) was added. The reaction was stirred at room temperature for 1 hour. The 3-fluoro-5-nitrobenzoyl chloride formed above was dissolved in methylene chloride (10.0 mL) and was added to the reaction. The reaction was stirred at room temperature overnight. The reaction was quenched with methanol and concentrated under reduced pressure. The resulting solid was extracted with ethyl acetate and saturated sodium bicarbonate. The organic portion was dried with anhydrous magnesium sulfate, adsorbed onto silica and purified by silica gel flash chromatography with 40%-50% ethyl acetate:hexanes. The appropriate fractions were combined and concentrated to provide compound 295 as a white solid characterized by MS and $^1$H-NMR (139 mg, LRMS (ESI) [M+H$^+$]$^+$= 286.1).

Step 2—(2-Fluoro-5-amino-phenyl)-(1H-pyrrolo[2,3-b]pyridin-3-yl)-methanone 296

Compound 295 (130 mg, 0.46 mmol) was suspended in 6 M hydrochloric acid (10.0 mL) and ethanol (5.0 mL) unser an atmosphere of nitrogen. Tetrahydrofuran (5.0 mL) was added to completely dissolve the compound. Iron (229 mg) was added to the mixture and the reaction was heated to reflux for 2.5 hours. The reaction was cooled and concentrated under reduced pressure. The solid was dissolved in ethyl acetate and washed with saturated sodium bicarbonate. The organic portions were dried with anhydrous magnesium sulfate and adsorbed onto silica and purified by silica gel flash chromatography using 3% methanol: dichloromethane. The appropriate fractions were combined and concentrated to provide compound 296 as a pure white solid characterized by MS and $^1$H-NMR (33.9 mg, LRMS (ESI) [M+H$^+$]$^+$=256.1, [M-H$^+$]$^-$=254.1).

Step 3—N-[4-Fluoro-3-(1H-pyrrolo[2,3-b]pyridine-3-carbonyl)-phenyl]-methanesulfonamide 297

Compound 296 (33.9 mg, 0.133 mmol) was dissolved in N,N-Dimethylformamide (2.00 mL) under an atmosphere of Argon. Potassium carbonate (22.9 mg, 0.166 mmol) and methanesulfonyl chloride (0.0113 mL, 0.146 mmol) were added to the reaction. The reaction was stirred at room temperature overnight. The reaction was concentrated under reduced pressure. The reaction was extracted with ethyl acetate and saturated sodium bicarbonate. The organic portions were dried with anhydrous magnesium sulfate, filtered and the filtrate was purified by prep TLC using 5% methanol: methylene chloride. The silica gel of the appropriate band was scraped and extracted with ethyl acetate. The solution was filtered and concentrated under reduced pressure to provide compound 297 characterized by MS and $^1$H-NMR. $^1$H-NMR in $d_6$-DMSO identified that product as clearly sulfonylated on the phenylamino rather than the pyrrolo nitrogen (1.0 mg, LRMS (ESI) [M+H$^+$]$^+$=334.0, [M−H$^+$]$^-$=332.1).

Example 13

Synthesis of (5-Ethyl-1H-pyrrolo[2,3-b]pyridin-3-yl)-(3-methoxy-phenyl)-methanone 298

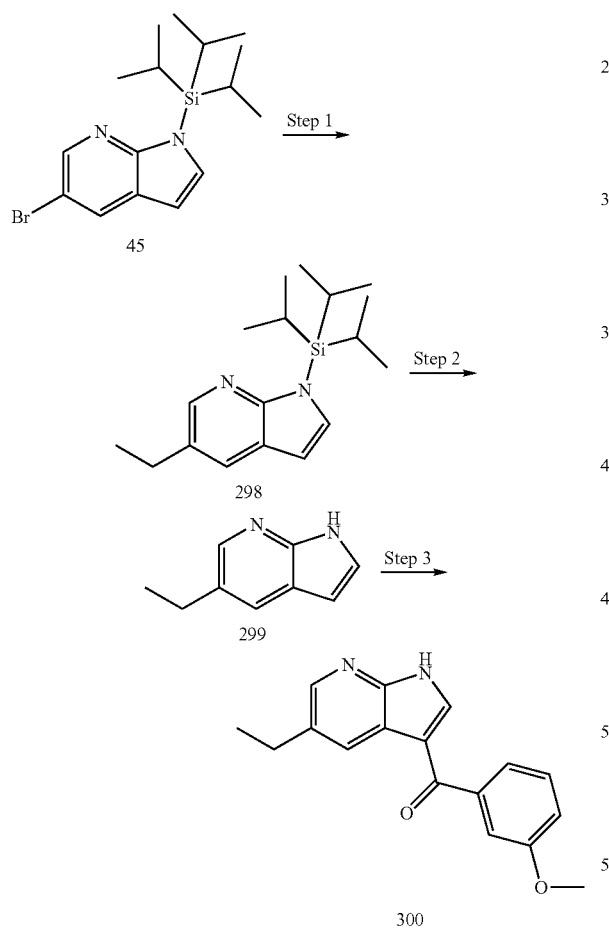

Step-1—Synthesis of Compound of Formula 298

Into a round bottom flask, under an atmosphere of nitrogen, PdCl$_2$(dppf) (0.04 g, 0.05 mmol) was added to toluene (10 mL) followed by the addition of a solution of compound 45 (0.3 g, 0.8 mmol) in toluene (1 mL). After stirring for 10 minutes at room temperature, a solution of 1 M of ethylmagnesium bromide in THF (3.4 mL, 3.0 mmol) was added dropwise. The mixture was stirred for one hour at 60° C. and 30 minutes at 90° C. After cooling to room temperature, ice-water and 0.1 N citric acid were added and the mixture was extracted with ethyl acetate. The organic portions were washed with brine, decolored with activated carbon, filtered through celite, dried over anhydrous sodium sulfate and concentrated under reduced pressure. The desired product 298 was identified by $^1$H-NMR and used without further purification (218 mg, 0.72 mmol).

Step-2—Synthesis of Compound of Formula 299

Into a round bottom flask, under an atmosphere of nitrogen, compound 298 (218 mg, 0.72 mmol) was dissolved in THF (10 mL) followed by the addition of tetrabutylammonium fluoride (226 mg, 0.86 mmol). After stirring for 30 minutes at room temperature, the mixture was poured into water and extracted with ethyl acetate. The organic portions were washed with brine, dried over anhydrous sodium sulfate and concentrated under reduced pressure. The desired product was purified by silica gel flash chromatography using 90:10 hexane:ethyl acetate. The product 299 (86 mg, 0.59 mmol) was identified by MS and $^1$H-NMR. LRMS (ESI+): (M+H$^+$)$^+$=147.2.

Step-3—Synthesis of Compound of Formula 300

Into a round bottom flask, under an atmosphere of nitrogen, compound 299 (86 mg, 0.59 mmol) was dissolved in methylene chloride (10 mL) followed by the addition of aluminum chloride (0.4 g, 3 mmol). After stirring for 10 minutes at room temperature, 3-methoxy-benzoyl chloride (0.21 mL, 1.5 mmol) was added dropwise. The mixture was stirred at room temperature for an additional hour. The reaction was quenched with methanol at 0° C. and evaporated to dryness. The residue was dissolved into ethyl acetate and washed with water, 0.1 N HCl and brine. The organic portions were dried with anhydrous sodium sulfate and concentrated. The desired product was purified by silica gel flash chromatography using a gradient 40-70% ethyl acetate:hexane. The product 300 (72.4 mg, 0.24 mmol) was identified by MS and $^1$H-NMR. (ESI+): (M+H$^+$)$^+$=281.1.

Example-14

Synthesis of N-[6-(3-methoxy-phenyl)-1H-pyrrolo[2,3-b]pyridine-3-ylmethyl]-4-methyl-benzenesulfonamide 310

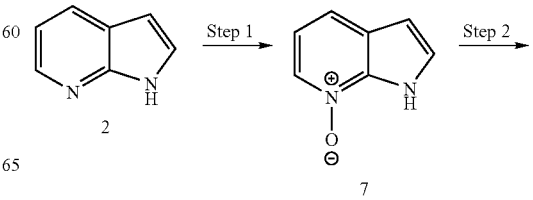

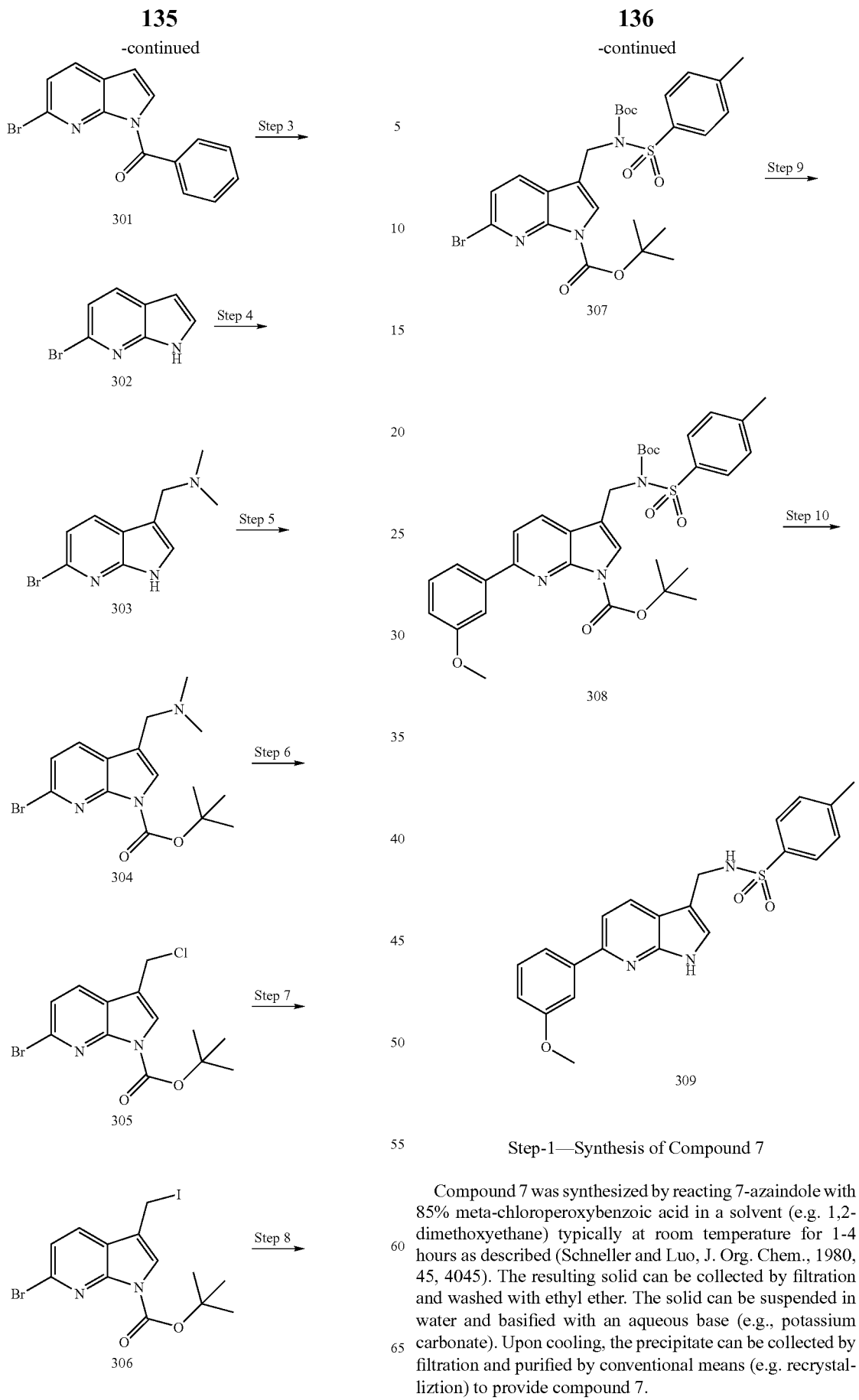

Step-1—Synthesis of Compound 7

Compound 7 was synthesized by reacting 7-azaindole with 85% meta-chloroperoxybenzoic acid in a solvent (e.g. 1,2-dimethoxyethane) typically at room temperature for 1-4 hours as described (Schneller and Luo, J. Org. Chem., 1980, 45, 4045). The resulting solid can be collected by filtration and washed with ethyl ether. The solid can be suspended in water and basified with an aqueous base (e.g., potassium carbonate). Upon cooling, the precipitate can be collected by filtration and purified by conventional means (e.g. recrystalliztion) to provide compound 7.

Step-2—Synthesis of Compound 301

Compound 301 was synthesized from compound 7 following the literature procedure (Minakata, S.; Komatsu, M.; Ohshiro, Y.; SYNTBF; Synthesis; EN; 7; 1992; 661-663).

Step-3—Synthesis of Compound 302

Compound 302 was synthesized from compound 2 following the literature procedure (Minakata, S.; Komatsu, M.; Ohshiro, Y.; SYNTBF; Synthesis; EN; 7; 1992; 661-663).

Step-4—Synthesis of Compound 303.

Compound 303 was synthesized from compound 302 following the literature procedure (Robinson, J. Am. Chem. Soc., 1955, 77, p. 457).

Step-5—Synthesis of Compound 304

Compound 304, where P is a protecting group, was synthesized by reacting compound 303 with a base (e.g. sodium hydride) in a solvent (e.g. THF), followed by an appropriate reagent (P—X, e.g. triisopropylsilylchloride) for introduction of a protecting group. The reaction was allowed to proceed, typically at room temperature, for 8-12 hours and the desired product was isolated by standard procedures (e.g. extraction and silica gel column chromatography) (Greene, T. W.; Wuts, P. G. M. *Protective Groups in Orgsnic Synthesis I*, 3*rd* ed.; *John Wiley & Sons*: New York, 1981).

Step-6—Synthesis of Compound 305

Compound 305 was synthesized from the reaction of compound 5 with isopropyl chloroformate (or ethyl chloroformate) at room temperature in toluene to give a 3-chloromethyl intermediate. The product was isolated by following standard procedure (quenching with ice-cold brine, work up, and purification by silica gel chromatography).

Step-7—Synthesis of Compound 306

Compound 306 was prepared from the compound 305 by addition of sodium iodide in acetone at 60° C. After several hours, typically 4 hours, the mixture was concentrated down to dryness. The resulting product that was obtained was carried on to the next step without further purification.

Step-8—Synthesis of Compound 307

Compound 307 was prepared from compound 306 and addition of boc protected sulfonamide deprotonation using a strong base (e.g. NaH, BuLi) in DMF and is stirred for typically 2-3 hours. The product was isolated by following standard procedure (quenching with ice-cold brine, work up, and purification by silica gel chromatography).

Step-9—Synthesis of Compound 308

Compound 308 was synthesized from compound 307 under Suzuki reaction conditions using aryl or heteroayl boronic acids (e.g. 3-methoxyphenyl boronic acid, phenyl boronic acids), in presence of a catalyst (e.g. Pd(PPh$_3$)$_4$). The product was isolated by following standard procedure (quenching with ice-cold brine, work up, and purification by silica gel chromatography) as described by Allegretti, M. et. al *Synlett* 2001; 5, 609.

Step-10—Synthesis of Compound 309

Compound 309 was prepared from compound 308 by addition of an acid (e.g., HCl, TFA) in dichloromethane at room temperature, typically for 3-4 hours. The acid is removed in vacuo.

Example-15

Synthesis of (2-fluoro-5-hydroxy-phenyl)-(5-pyridin-3-yl-1H-pyrrolo[2,3-b]pyridine-3-yl)-methone 314

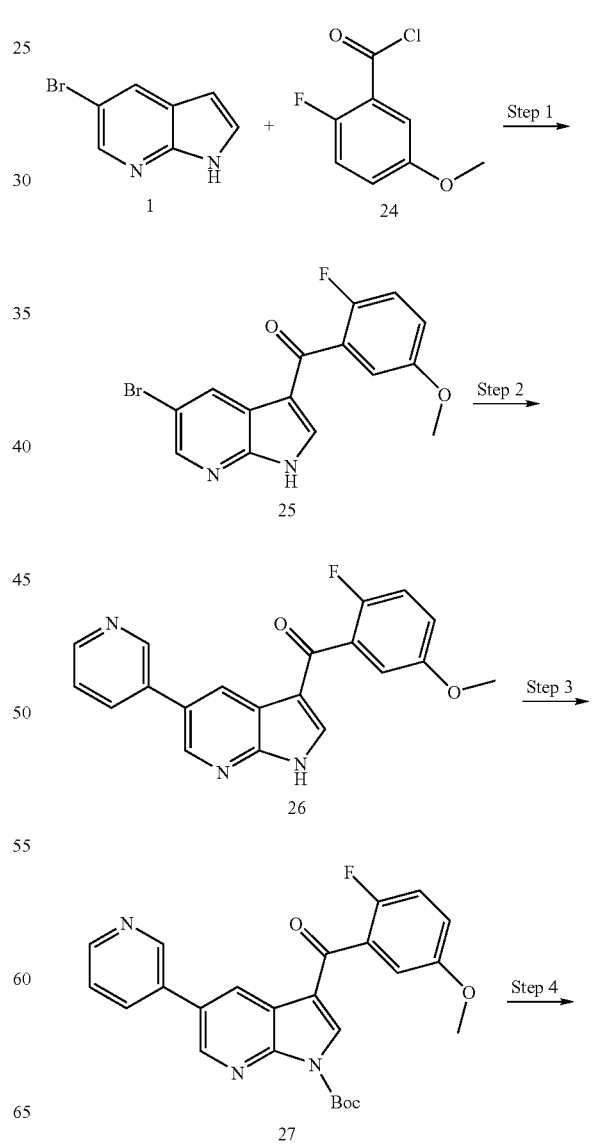

-continued

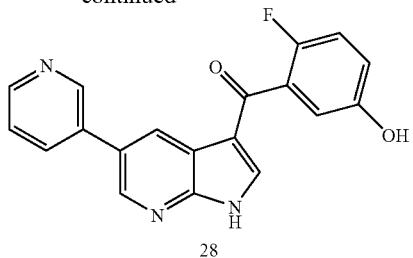

28

Step 1—Preparation of 311

Into a round bottom flask was added aluminum chloride (11.0 g, 0.0825 mol) and $CH_2Cl_2$ (100.0 mL) under an atmosphere of nitrogen. Into the reaction mixture was added 5-Bromo-7-azaindole 1 (2.4 g, 0.12 mol) in $CH_2Cl_2$ (20 mL). The reaction mixture was stirred for 1 h at 25° C. upon which 2-fluoro-5-methoxybenzoyl chloride 310 (3.6 g, 0.019 mol, 2.5 equiv) was added. The reaction was continued to stir for an additional 3 h. The reaction mixture was poured into water and extracted with EtOAc. The organic layer was washed with brine, dried over $MgSO_4$ and concentrated. The desired product was purified by silica gel flash chromatography using a 70:30 Hexane/ETOAc solvent system to yield compound 311. The product 311 was identified by LC/MS and $H^1$-NMR. LRMS (ESI+): (M+H⁺) 349.

Step 2—Preparation of 312

Into a high pressure tube was added compound 311 (300.0 mg, 0.67 mmol) and 3-pyridylboronic acid (400. mg, 3.25 mmol) and tetrakis(triphenylphosphine)palladium (0) (100.0 mg, 0.087 mmol) and potassium carbonate (1.92 g, 13.9 mmol) and acetonitrile (60.0 mL) and water (28.0 mL) under an atmosphere of nitrogen. The reaction mixture was heated to 170 Celsius overnight. The reaction mixture was diluted with water and extracted with EtOAc. The organic layer was dried, concentrated and purified with biotage to give product 312.

Step 3—Preparation of 313.

Into a round bottom flask was added compound 312 (250 mg, 0.72 mmol) and THF (10.0 mL) under nitrogen, followed by addition of sodium hydride (43.0 mg, 1.1 mmol). After stirring for 15 min at 25° C., di-tert-Butyldicarbonate (310 mg, 1.4 mol) was added to the reaction mixture. 30 min later, the reaction mixture was poured into water, extracted with EtOAc. The organic layer was dried, concentrated to yield product 313. The desired product was carried on without further purification. The identity of product 313 was identified by $H^1$-NMR.

Step 4—Preparation of 314.

Into a round bottom flask was added compound 313 (470.0 mg, 1.05 mmol) and $CH_2Cl_2$ (40.0 mL) under an atmosphere of nitrogen. Boron tribromide in heptane (1.0 M, 3.0 mL) was added. The reaction mixture was stirred at 25° C. overnight. The reaction mixture was poured into water and extracted with EtOAc. The organic layer was then washed with brine, dried over $MgSO_4$ and concentrated. The desired product 314 (210 mg) was purified by silica gel flash chromatography (M+H⁺) 334.2.

Example 16

Synthesis, of (2-chloro-5-hydroxy-phenyl)-(5-thiophene-2-yl-1H-pyrrolo[2,3-b]pyridine-3-yl)-methone 319

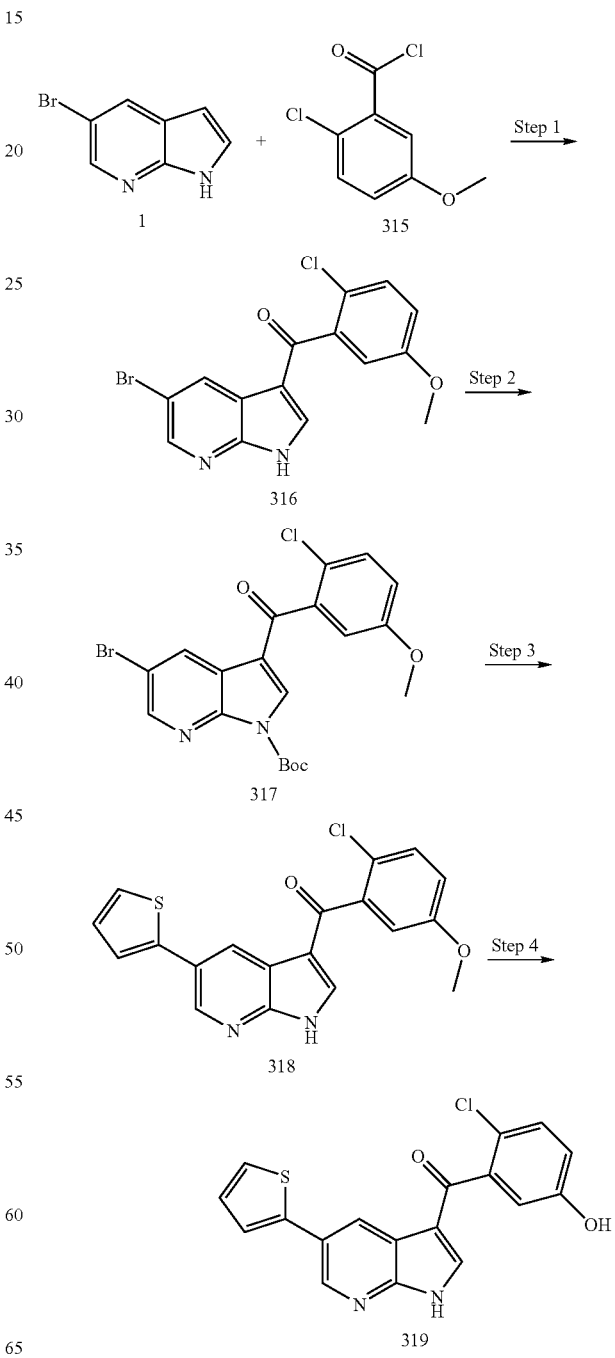

141

Step 1—Preparation of 316

Into a round bottom flask was added aluminum chloride (2.8 mg, 21 mmol) and CH$_2$Cl$_2$ (25.0 mL) under an atmosphere of nitrogen. Into the reaction mixture was added 5-Bromo-7-azaindole 1 (0.59 g, 3.0 mmol) in CH$_2$Cl$_2$ (20 mL). The reaction mixture was stirred for 1 h at 25° C. upon which 2-chloro-5-methoxybenzoyl chloride 315 (0.63 g, 3.1 mmol) in CH$_2$Cl$_2$ (10 mL) was added. The reaction was continued to stir overnight. The reaction mixture was poured into water and extracted with EtOAc. The organic layer was washed with brine, dried over MgSO$_4$ and concentrated. The desired product was purified by silica gel flash chromatography using a 70.30 Hexane/ETOAc solvent system to yield compound 316 (400.0 mg). The product 316 was identified by LC/MS and H$^1$-NMR. LRMS (ESI+): (M+H$^+$) 367.

Step 2—Preparation of 317

Into a round bottom flask was added compound 316 (300.0 mg, 0.82 mmol) and THF (10.0 mL) under nitrogen, followed by addition of sodium hydride (60.0 mg, 1.5 mmol). After stirring for 15 min at 25° C., di-tert-Butyldicarbonate (240.0 mg, 1.1 mol) was added to the reaction mixture. 30 min later, the reaction mixture was poured into water, extracted with EtOAc. The organic layer was dried, concentrated to yield product 317. The desired product was carried on without further purification. The identity of product 317 was identified by H$^1$-NMR.

Step 2—Preparation of 318

Into a round bottom flask was added compound 317 (70.0 mg, 0.15 mmol) and 2-thiophene boronic acid (24.0 mg, 0.19 mmol) and tetrakis(triphenylphosphine)palladium(0) (10.0 mg, 0.0087 mmol) and potassium carbonate (138.0 mg, 1.0 mmol) and THF (15.0 mL) and water (5.0 mL) under an atmosphere of nitrogen. The reaction mixture was heated to 80 Celsius overnight. The reaction mixture was poured into water and extracted with EtOAc. The organic layer was dried, concentrated and purified with biotage to give product 318.

Step 4—Preparation of 319

Into a round bottom flask was added compound 318 (25.0 mg, 0.068 mmol) and CH$_2$Cl$_2$ (5.0 mL) under an atmosphere of nitrogen. Boron tribromide in heptane (1.0 M, 3.5 mL) was then added. The reaction mixture was stirred at 25° C. overnight. The reaction mixture was poured into water and extracted with EtOAc. The organic layer was then washed with brine, dried over MgSO$_4$ and concentrated. The desired product 319 (5.0 mg) was purified by silica gel flash chromatography. The product 319 was identified by LC/MS and $^1$H-NMR. LRMS (ESI+): (M+H$^+$) 355.

142

Example 17

Synthesis of 3-methoxymethyl-1H-pyrrolo[2,3-b]pyridine 322

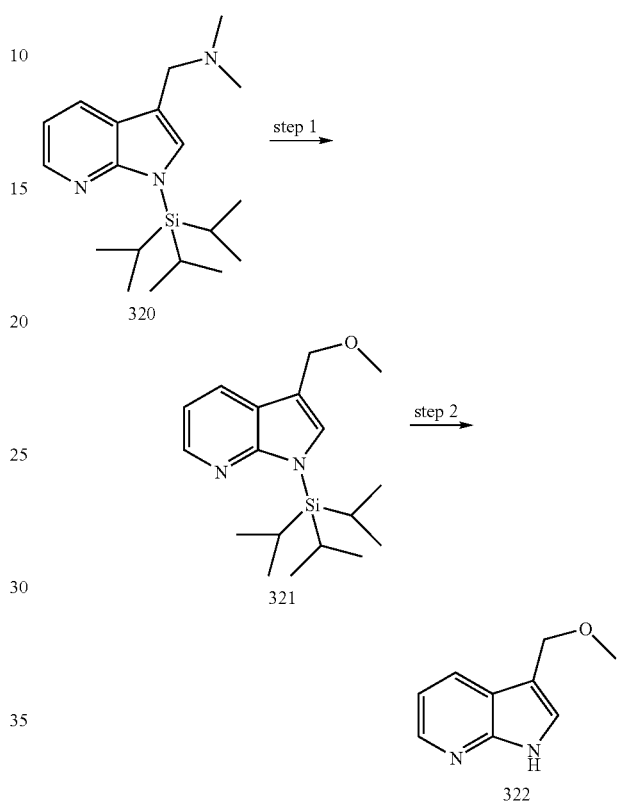

Step 1—Preparation of 321

Into a round bottom flask was added compound 320 (1.2 g, 3.5 mmol), which was prepared by the reaction of compound 10 with tri-isopropylsilyl chloride under basic conditions, and toluene (10.0 mL) and isopropyl chloroformate (1.0 M in toluene, 3.6 mL). The reaction mixture was stirred at room temperature for 2 hours. Concentration and purification using CH$_2$Cl$_2$/MeOH (100:1) yielded compound 321. The product 321 was identified by LC/MS and $^1$H-NMR. LRMS (ESI$^+$): (M+H$^+$) 319.

Step 2—Preparation of 322

Into a round bottom flask was added compound 321 (20.0 mg, 0.063 mmol) and Tetra-n-butylammonium fluoride (18.0 mg, 0.069) and THF (4.0 mL). The reaction mixture was stirred at room temperature for 30 minutes. Concentration and purification with preparative TLC plate gave product 322. The product 322 was identified by LC/MS and $^1$H-NMR. LRMS (ESI$^+$): (M+H$^+$) 163.

Example-18

Synthesis of 3-[(Z)-2-6-chloro-pyridin-3-yl)-vinyl]-1Hpyrrolo[2,3-b]pyridine 327

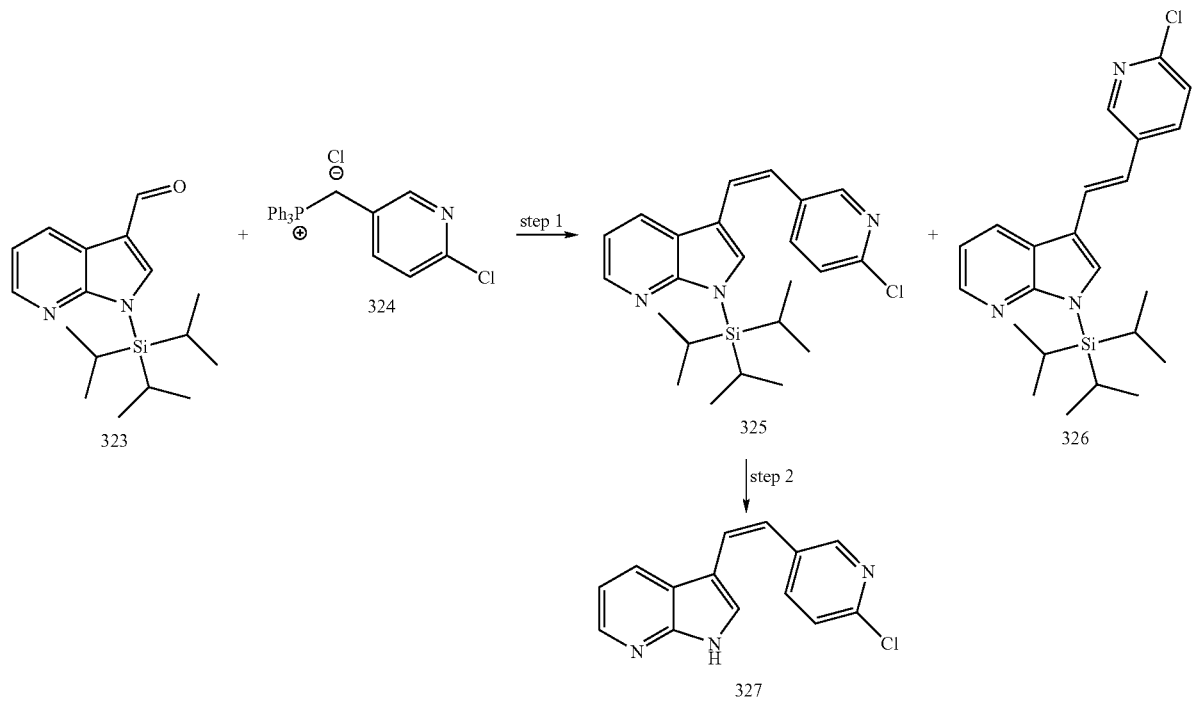

Step 1—Preparation of 325

Into a round bottom flask was added salt 324 (650.0 mg, 1.5 mmol) and THF (30.0 mL) and potassium t-butoxide (180.0 mg, 1.6 mmol) under an atmosphere of nitrogen. The reaction mixture was stirred at room temperature for 1 hour to give Yield. Into the Yield solution, was added compound 323 (256.0 mg, 0.85 mmol). After stirring at 60 Celsius for 3 hours, the reaction mixture was poured into water and extracted with EtOAc. The organic layer was washed with brine, dried over sodium sulfate, concentrated and purified with biotage to give a mixture of compound 325 and 326 (290 mg). The mixture was separated with preparative TLC plates.

Step 2—Preparation of 327

Into a round bottom flask was added compound 325 (28.0 mg, 0.0068 mmol) and THF (2.0 mL) and tetra-n-butylammonium fluoride (21.0 mg, 0.082 mmol). The reaction mixture was stirred at room temperature for 30 minutes and then concentrated and purified with biotage to give compound 327. The product 327 was identified by LC/MS and $^1$H-NMR. LRMS (ESI+): (M+H$^+$) 256.

Example 19

Synthesis of isobutyl-[5-(1H-pyrrolo[2,3-b]pyridine-3-ylmethyl)-pyridin-2-yl]-amine 333

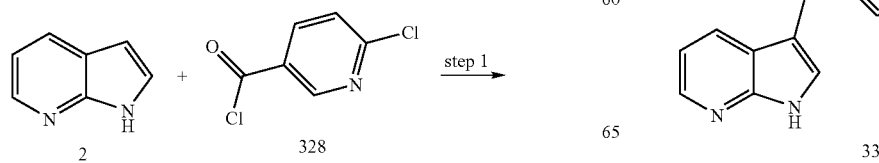

-continued

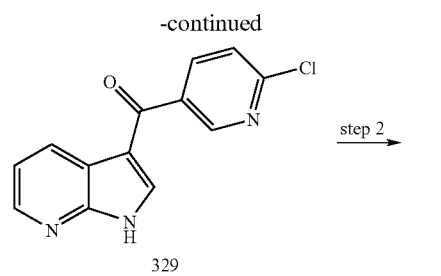

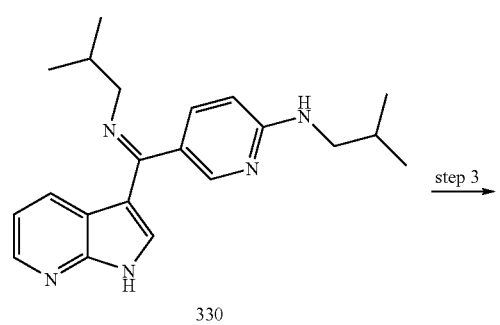

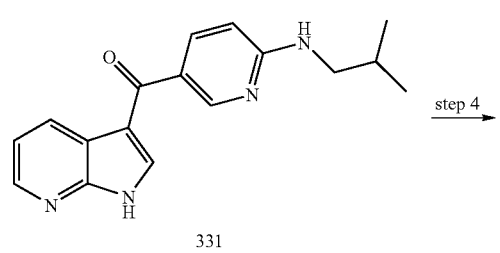

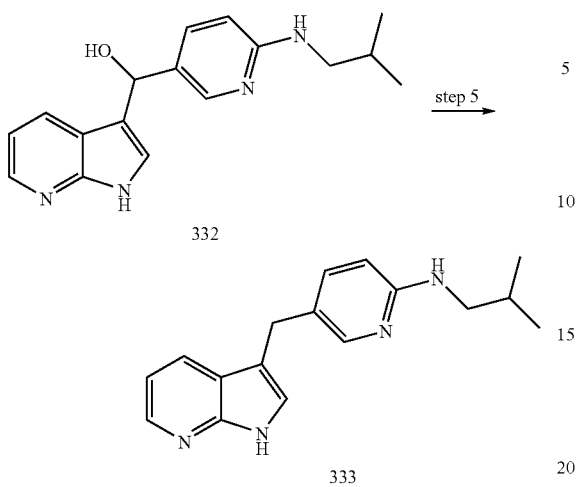

Step 1—Preparation of 329

Into a round bottom flask was added aluminium chloride (30.0 g, 0.225 mol) and methylene chloride (350.0 mL) under an atmosphere of nitrogen. Into the reaction mixture was added 7-azaindole 2 (5.0 g, 0.042 mol) in methylene chloride (20.0 mL). The reaction mixture was stirred at room temperature for 70.0 minutes, followed by addition of compound 328 (9.9 g, 0.056 mol). The reaction mixture was stirred at room temperature for additional 3 hours. The reaction mixture was poured into diluted HCl solution and extracted with EtOAc. The solid in aqueous layer was filtered and dried to give most of the product 329(8 g). The organic layer was dried and concentrated to provide another portion of product 329 (2 g). The product 329 was identified by LC/NIS and $^1$H-NMR. LRMS (ESI+): (M+H$^+$) 258.

Step 2—Preparation of 330

Into a round bottom flask was added compound 329 (128.0 mg, 0.50 mmol) and isobutylamine (3.0 g, 0.041 mol). The reaction mixture was heated to 180 Celsius overnight. Concentration and purification by biotage provided compound 330 (60 mg). The product 330 was identified by LC/MS and $^1$H-NMR. LRMS (ESI+): (M+H$^+$) 350.

Step 3—Preparation of 331

Into a round bottom flask was added compound 330 (50.0 mg, 0.14 mmol) and acetic acid (3.0 mL) and water (2.0 mL). The reaction mixture was stirred at room temperature overnight. The reaction mixture was poured into water and basified with potassium carbonate to pH=9, and then extracted with EtOAc. The organic layer was washed with brine, dried, concentrated and purified with biotage to give product 331. The product 331 was identified by LC/MS and $^1$H-NMR. LRMS (ESI+): (M+H$^+$) 295.

Step 4—Preparation of 332

Into a round bottom flask was added compound 331 (100.0 mg, 0.34 mmol) and lithium tetrahydroaluminate (39 mg, 1.0 mmol) and THF (10.0 mL). The reaction mixture was heated to 50 Celsius for 3 hours. Into the reaction mixture was added Na2SO4.10H2O. After 30 minutes, the reaction mixture was filtered, concentrated and purified with biotage to give product 332. The product 332 was identified by LC/MS and $^1$H-NMR. LRMS (ESI+): (M+H$^+$) 297.

Step 5—Preparation of 333

Into a round bottom flask was added compound 332 (13.0 mg, 0.044 mmol) and trifluoroacetic acid (1.5 mL) and triethylsilane (1.0 mL) and methylene chloride (1.0 mL). The reaction mixture was stirred at room temperature 2 hours. Concentration and purification provided product 333. The product 333 was identified by LC/MS and $^1$H-NMR. LRMS (ESI+): (M+H$^+$) 281.

Example 20

Synthesis of benzo[b]thiophene-3-carboxylicacid (1H-pyrrolo[2,3-b]pyridine-3-ylmethyl)-amide 335

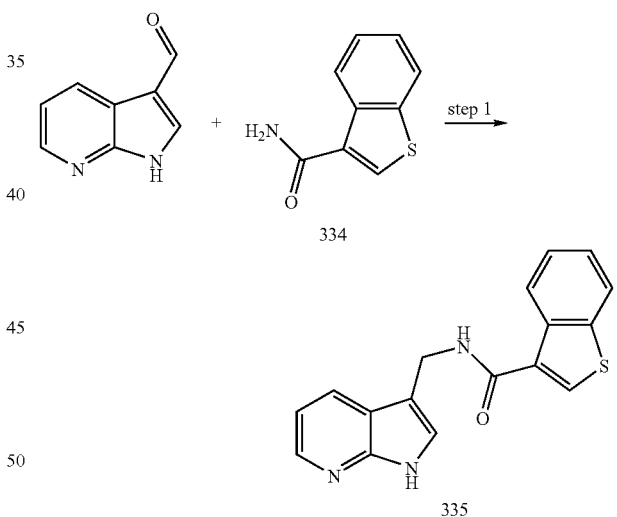

Step 1—Preparation of 335

Into a round bottom flask was added azaindole-3-carboxaldehyde (106.0 mg, 0.73 mmol) and amide 334 (300.0 mg, 1.7 mmol) and triethylsilane (0.12 mL, 0.75 mmol) and trifluoroacetic acid (0.06 mL, 0.8 mmol) and toluene (5.0 mL). The reaction mixture was refluxed overnight. The reaction mixture was then poured into water, extracted with EtOAc. The organic layer was then dried, concentrated and purified with biotage to give product 335. The product 335 was identified by LC/MS and $^1$H-NMR. LRMS (ESI+): (M+H$^+$) 281.

Example 21

[5-(3-amino-phenyl)-1H-pyrrolo[2,3-b]pyridine-3-yl]-(2-fluoro-5-hydroxy-phenyl)-methone 336

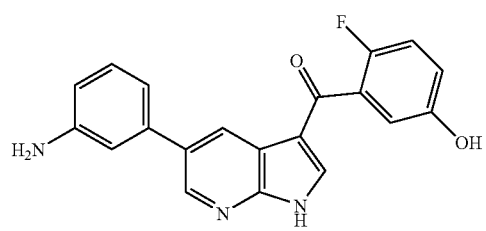

336

Compound 33.6 was prepared as described in Example 15 substituting 3-aminophenylboronic acid for 3-pyridine-boronic acid. MS (M+1)=348.3.

Example 22

[5-(3-thienyl)-1H-pyrrolo[2,3-b]pyridine-3-yl]-(2-fluoro-5-hydroxy-phenyl)-methone 337

337

Compound 337 was prepared as described in Example 15 substituting 3-thienylboronic acid for 3-pyridine-boronic acid. MS (M+1)=339.4.

Example 23

[5-(3-acetamidophenyl)-1H-pyrrolo[2,3-b]pyridine-3-yl]-(2-fluoro-5-hydroxy-phenyl)-methone 338

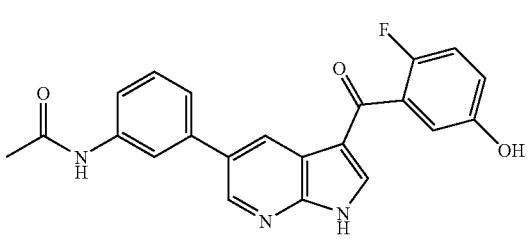

338

Compound 338 was prepared as described in Example 15 substituting 3-acetamidophenylboronic acid for 3-pyridine-boronic acid. MS (M+1)=390.4.

Example 24

[5-1H-pyrrolo[2,3-b]pyridine-3-yl]-(2-fluoro-5-hydroxy-phenyl)-methone 338

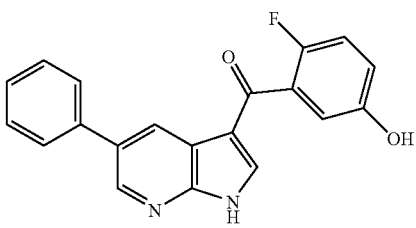

339

Compound 338 was prepared as described in Example 15 substituting phenylboronic acid for 3-pyridine-boronic acid. MS (M+1)=333.3.

TABLE 1

| Exemplary compounds active on Ret with IC50 ≦ 10 μM | |
|---|---|
| Structure | Mwt |
|  | 338.405 |

TABLE 1-continued

Exemplary compounds active on Ret with IC50 ≦ 10 μM

| Structure | Mwt |
|---|---|
| 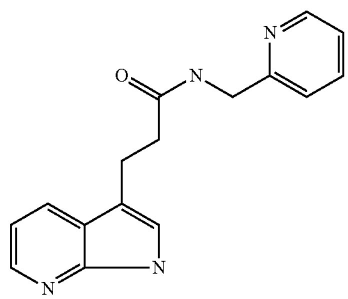 | 281.318 |
| 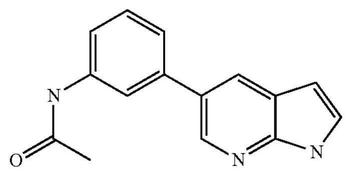 | 251.288 |
| 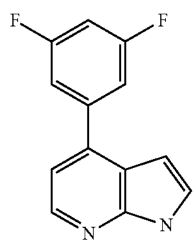 | 230.216 |
| 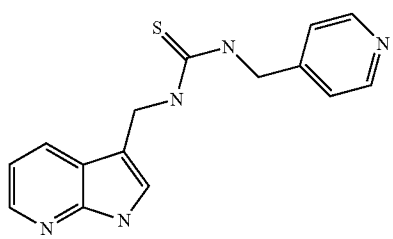 | 297.384 |
| 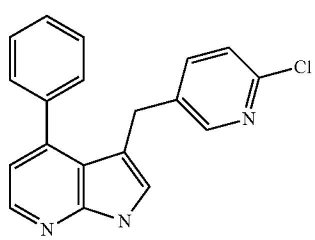 | 319.794 |
| 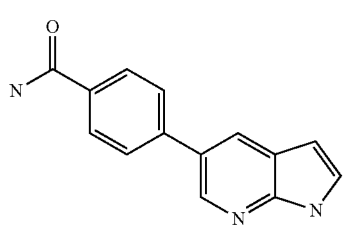 | 237.261 |

TABLE 1-continued

Exemplary compounds active on Ret with IC50 ≦ 10 µM

| Structure | Mwt |
|---|---|
| 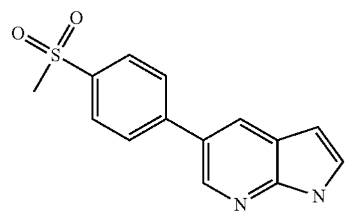 | 272.327 |
| 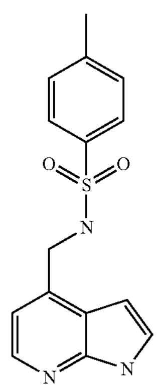 | 301.368 |
| 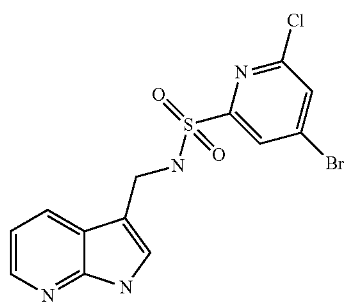 | 401.671 |
| 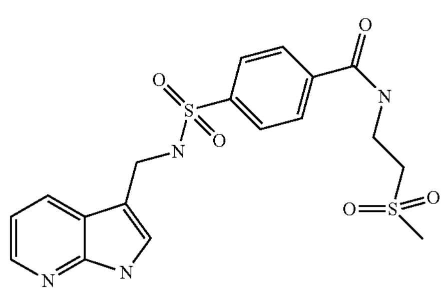 | 436.511 |
| 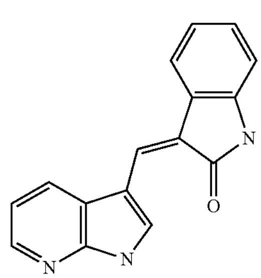 | 261.283 |

TABLE 1-continued

Exemplary compounds active on Ret with IC50 ≦ 10 μM

| Structure | Mwt |
|---|---|
| 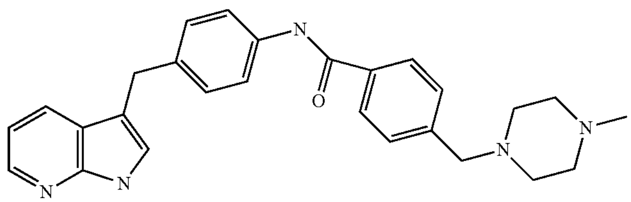 | 439.56 |
| 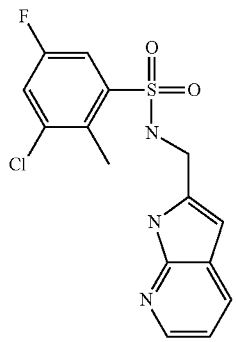 | 353.804 |
| 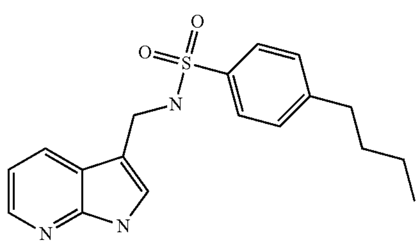 | 343.449 |
| 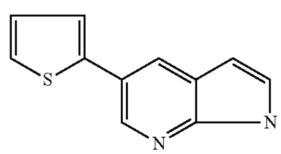 | 200.264 |
| 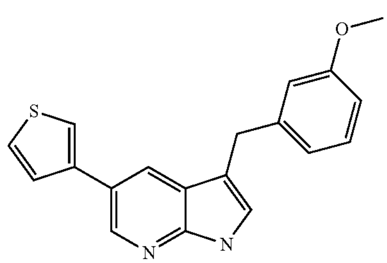 | 3-(3-Methoxy-benzyl)-5-thiophen-3-yl-1H-pyrrolo[2,3-b]pyridine 320.414 |
| 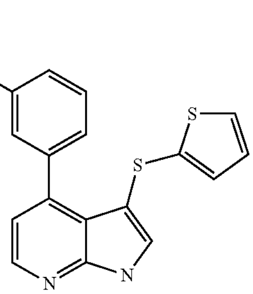 | 338.454 |

TABLE 1-continued

Exemplary compounds active on Ret with IC50 ≦ 10 µM

| Structure | Mwt |
|---|---|
| 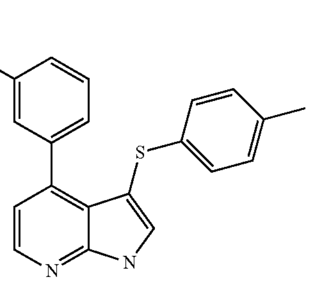 | 346.452 |
| 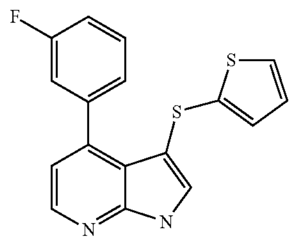 | 326.418 |
| 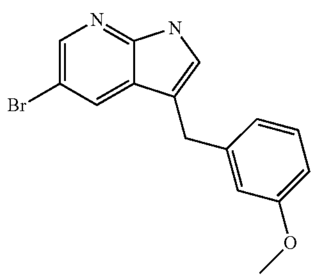 | 317.185 |
| 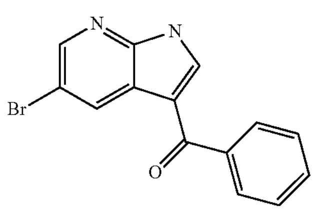 | 301.142 |
| 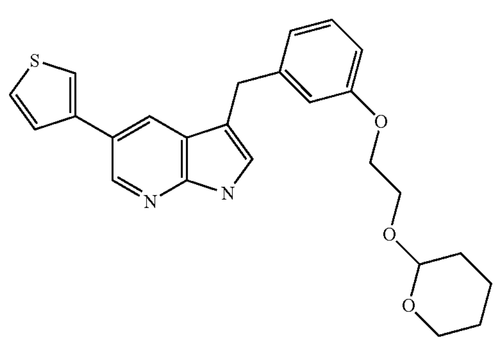 | 434.557 |

TABLE 1-continued

Exemplary compounds active on Ret with IC50 ≦ 10 μM

| Structure | Mwt |
|---|---|
| | 3-(3-Methoxy-benzyl)-5-thiophen-2-yl-1H-pyrrolo[2,3-b]pyridine<br>320.414 |
| 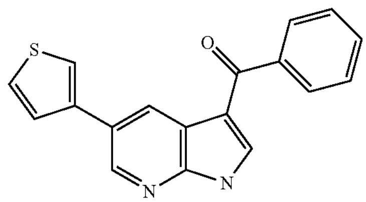 | 304.372 |
| 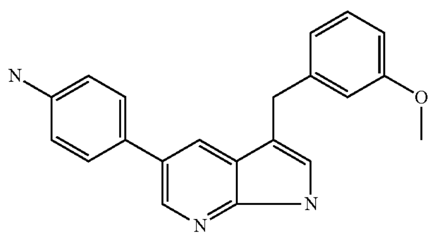 | 329.401 |
| 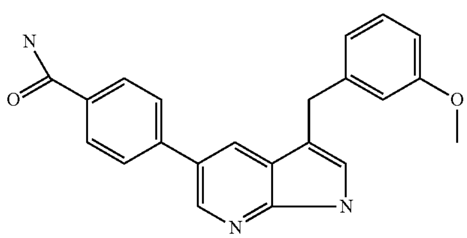 | 357.411 |
| 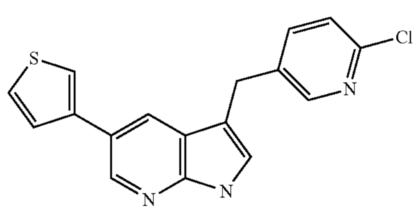 | 325.822 |
| 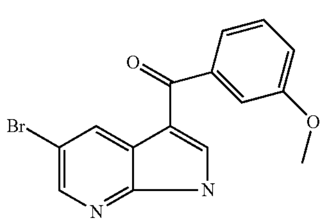 | 331.168 |

TABLE 1-continued
Exemplary compounds active on Ret with IC50 ≦ 10 μM
| Structure | Mwt |
|---|---|
| 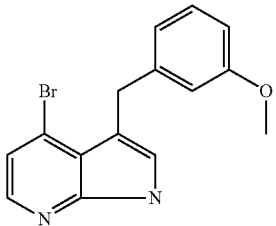 | 317.185 |
| 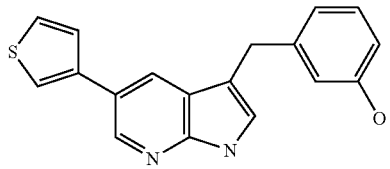 | 3-(5-Thiophen-3-yl-1H-pyrrolo[2,3-b]pyridin-3-ylmethyl)-phenol 306.388 |
| 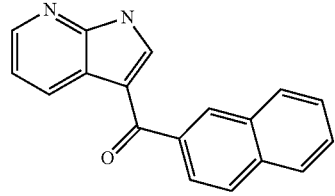 | 272.306 |
| 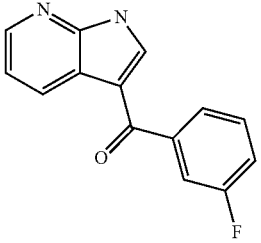 | 240.236 |
| 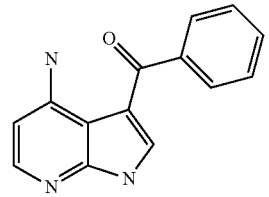 | 237.261 |
| 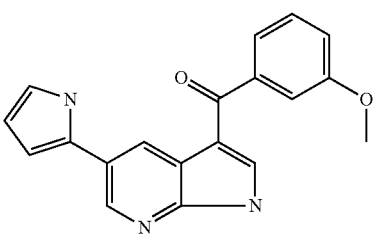 | 317.346 |
| 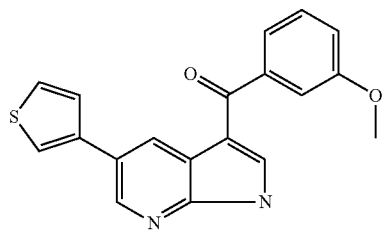 | 334.398 |

TABLE 1-continued

Exemplary compounds active on Ret with IC50 ≦ 10 μM

| Structure | Mwt |
|---|---|
| | 322.387 |
| 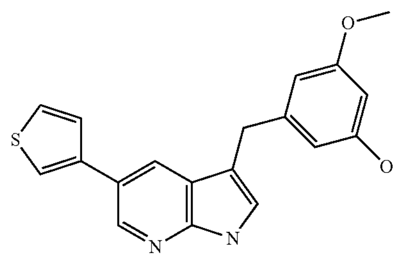 | 336.413 |
| | 322.387 |
| 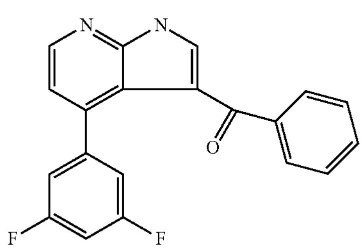 | 334.324 |
| 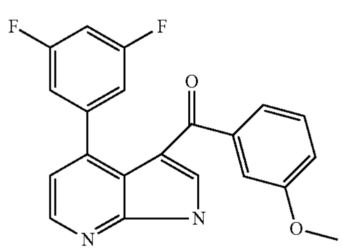 | 364.35 |
| 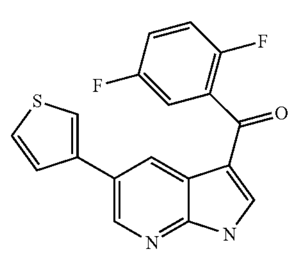 | 340.352 |

TABLE 1-continued

Exemplary compounds active on Ret with IC50 ≦ 10 μM

| Structure | Mwt |
|---|---|
| 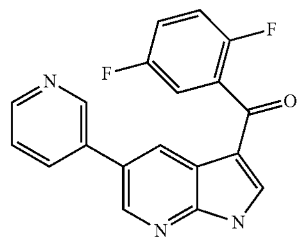 | 335.312 |
| 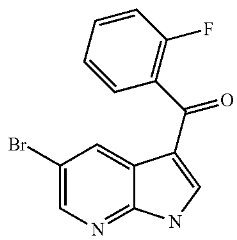 | 319.132 |
| 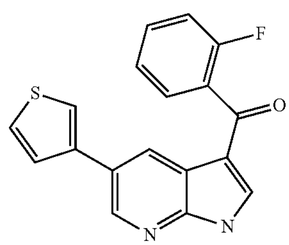 | 322.362 |
| 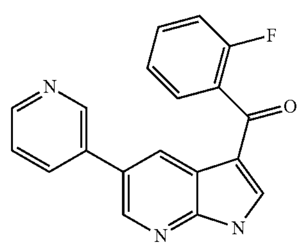 | 317.322 |
| 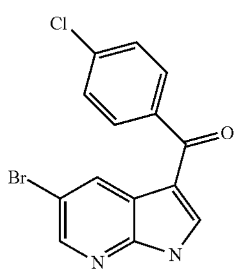 | 335.587 |
| 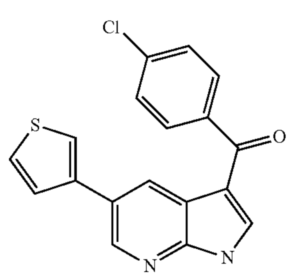 | 338.817 |

TABLE 1-continued

Exemplary compounds active on Ret with IC50 ≦ 10 μM

| Structure | Mwt |
|---|---|
| 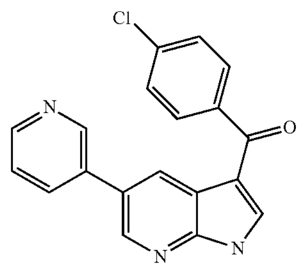 | 333.777 |
| 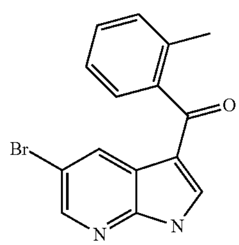 | 315.169 |
| 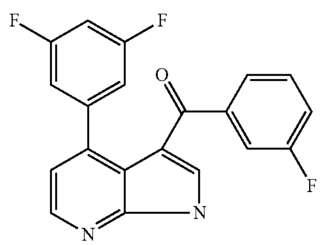 | 352.314 |
| | 321.402 |
| | 321.402 |
| 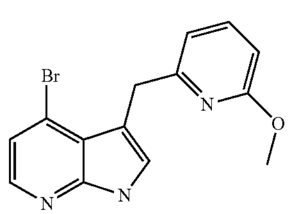 | 318.173 |

TABLE 1-continued

Exemplary compounds active on Ret with IC50 ≦ 10 μM

| Structure | Mwt |
|---|---|
| 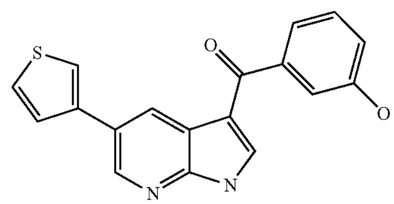 | 320.371 |
| 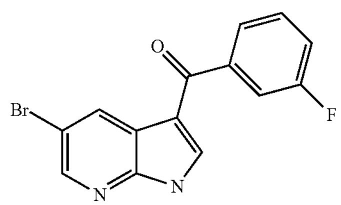 | 319.132 |
| 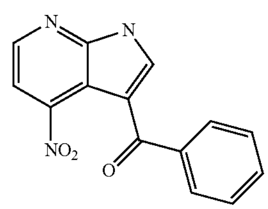 | 267.243 |
| | 370.304 |
| | 370.304 |
| | 370.304 |

TABLE 1-continued

Exemplary compounds active on Ret with IC50 ≦ 10 μM

| Structure | Mwt |
|---|---|
| 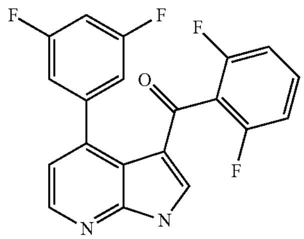 | 370.304 |
| 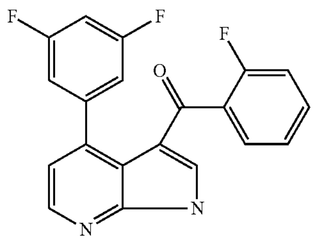 | 352.314 |
| 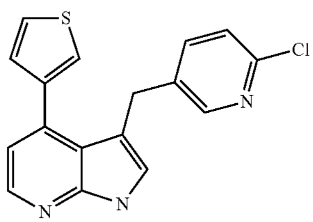 | 325.822 |
| 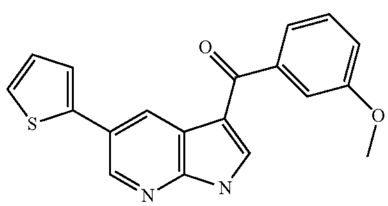 | 334.398 |
| 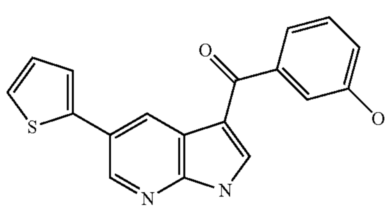 | 320.371 |
| 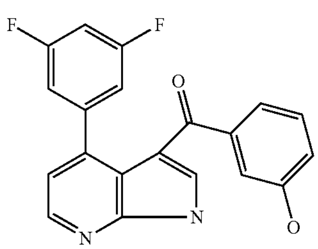 | 350.323 |

TABLE 1-continued

Exemplary compounds active on Ret with IC50 ≦ 10 μM

| Structure | Mwt |
|---|---|
| 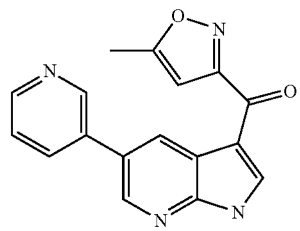 | 304.308 |
| 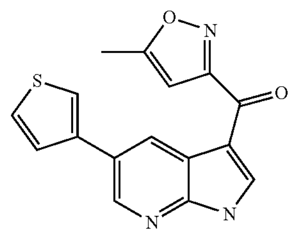 | 309.348 |
| 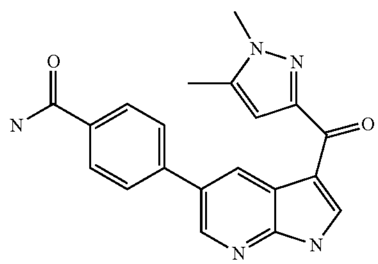 | 359.387 |
| 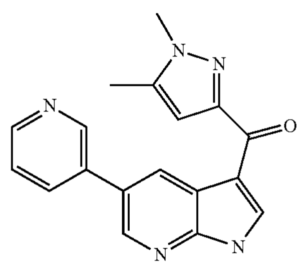 | 317.35 |
| 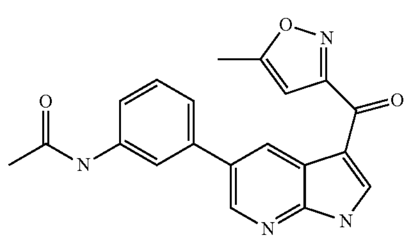 | 360.371 |
| 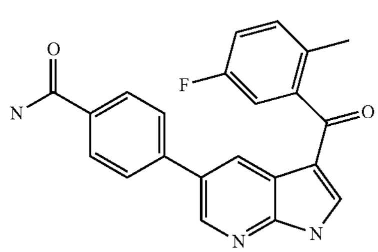 | 373.385 |

TABLE 1-continued

Exemplary compounds active on Ret with IC50 ≦ 10 μM

| Structure | Mwt |
|---|---|
| 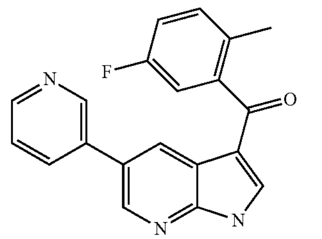 | 331.349 |
| 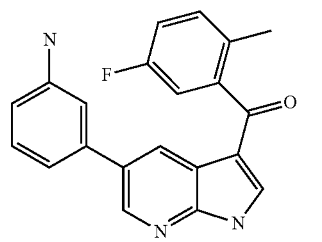 | 345.375 |
| 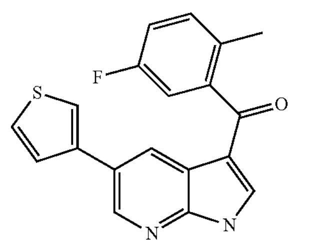 | 336.389 |
| 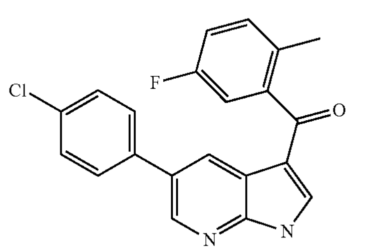 | 364.806 |
| 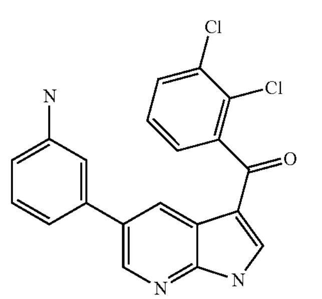 | 382.249 |
| 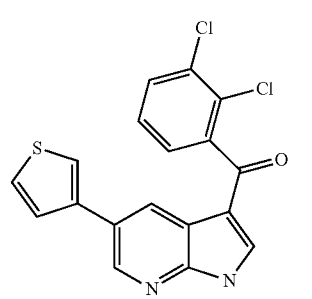 | 373.262 |

TABLE 1-continued

Exemplary compounds active on Ret with IC50 ≦ 10 μM

| Structure | Mwt |
|---|---|
| 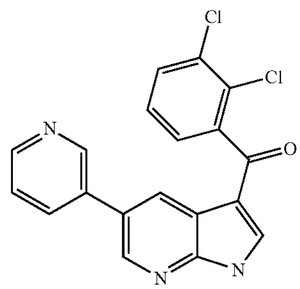 | 368.222 |
| | 359.387 |
| 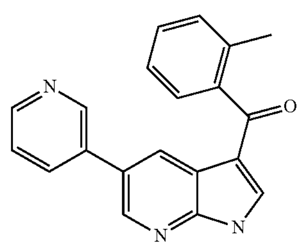 | 313.358 |
| | 359.387 |
| 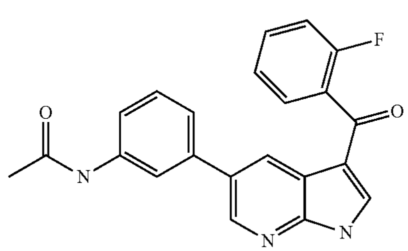 | 373.385 |

TABLE 1-continued

Exemplary compounds active on Ret with IC50 ≦ 10 μM

| Structure | Mwt |
|---|---|
| 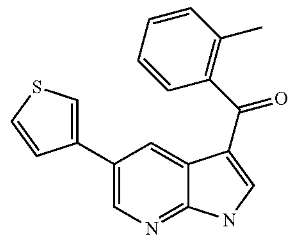 | 318.399 |
| 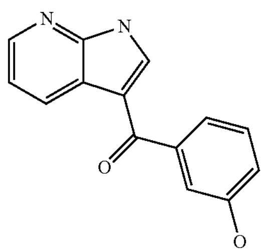 | 238.245 |
| 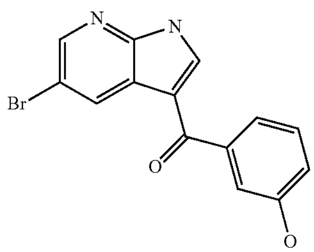 | 317.141 |
| 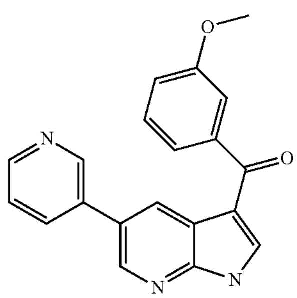 | 329.358 |
| 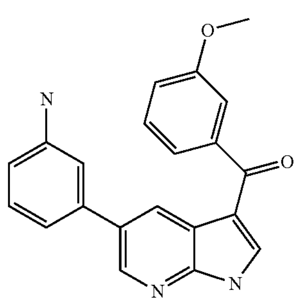 | 343.384 |

TABLE 1-continued

Exemplary compounds active on Ret with IC50 ≦ 10 μM

| Structure | Mwt |
|---|---|
| 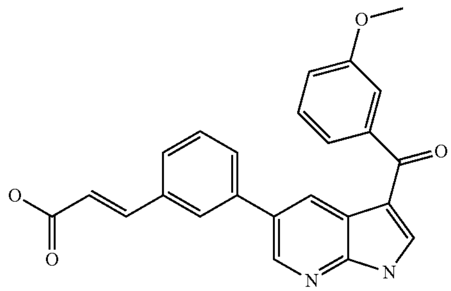 | 398.416 |
| 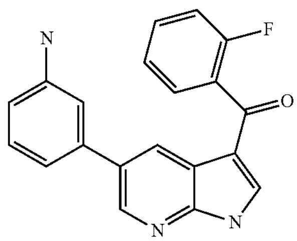 | 331.349 |
| 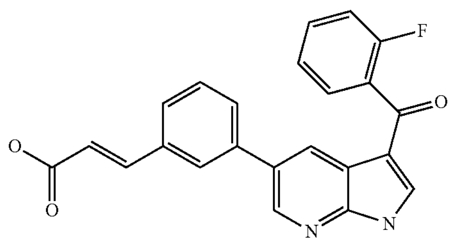 | 386.38 |
| 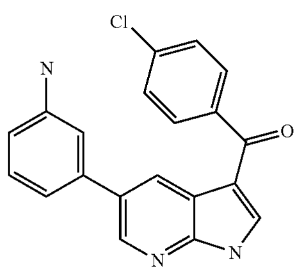 | 347.804 |
| 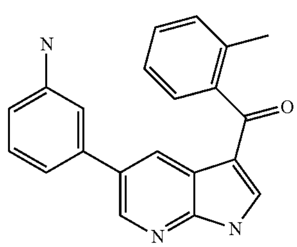 | 327.385 |
| 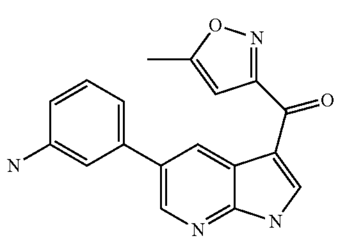 | 318.335 |

TABLE 1-continued

Exemplary compounds active on Ret with IC50 ≦ 10 μM

| Structure | Mwt |
|---|---|
| | 331.377 |
| 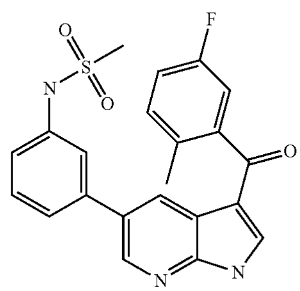 | 423.466 |
| 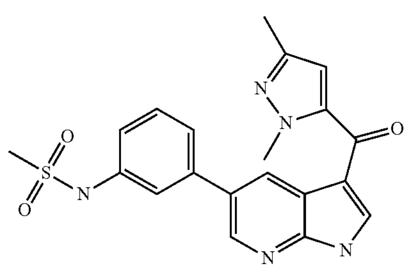 | 409.468 |
| | 331.377 |
| 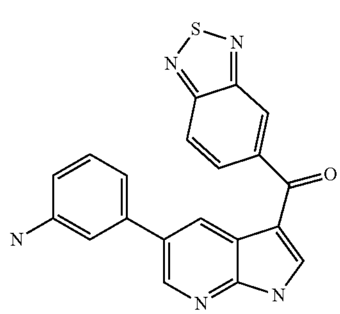 | 371.423 |

TABLE 1-continued

Exemplary compounds active on Ret with IC50 ≦ 10 μM

| Structure | Mwt |
|---|---|
| 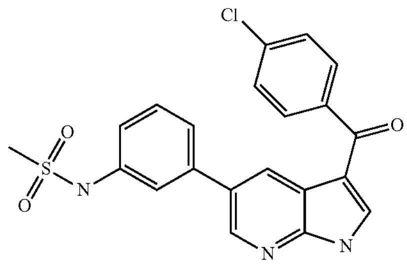 | 425.894 |
| 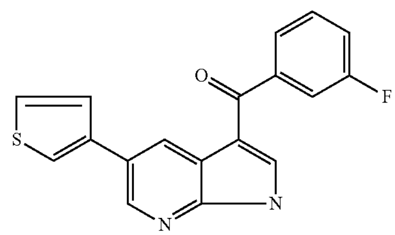 | 322.362 |
| 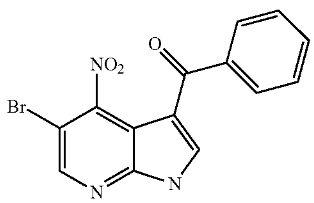 | 346.139 |
| 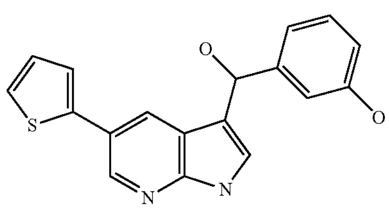 | 322.387 |
| 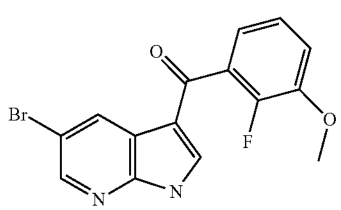 | 349.158 |
| 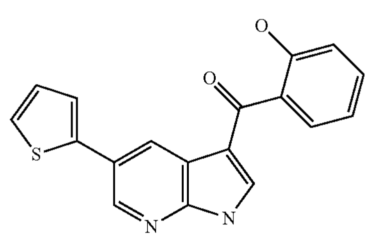 | 320.371 |
| 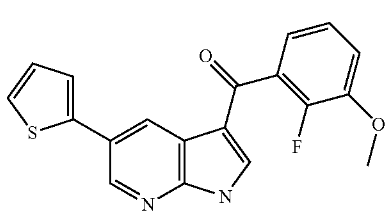 | 352.388 |

TABLE 1-continued
Exemplary compounds active on Ret with IC50 ≦ 10 μM
| Structure | Mwt |
|---|---|
| 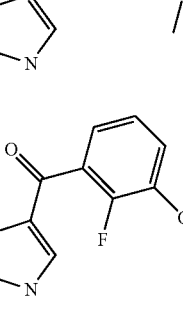 | 352.388 |
| 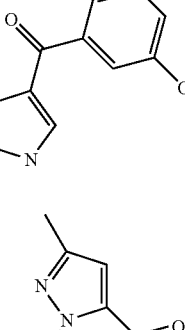 | 338.361 |
| 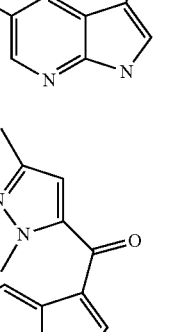 | 338.361 |
| 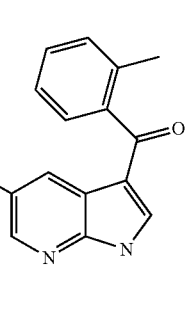 | 359.387 |
| 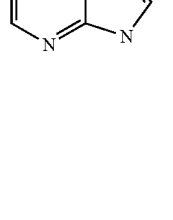 | 322.391 |
| 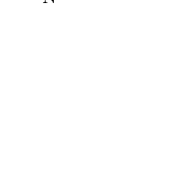 | 355.395 |

TABLE 1-continued

Exemplary compounds active on Ret with IC50 ≦ 10 μM

| Structure | Mwt |
|---|---|
| 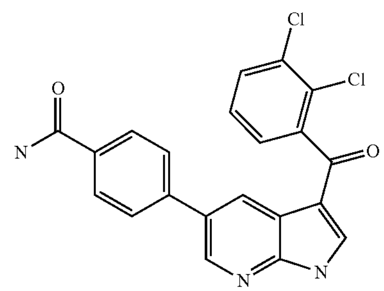 | 410.259 |
| 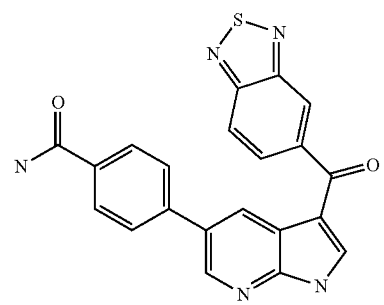 | 399.433 |
| 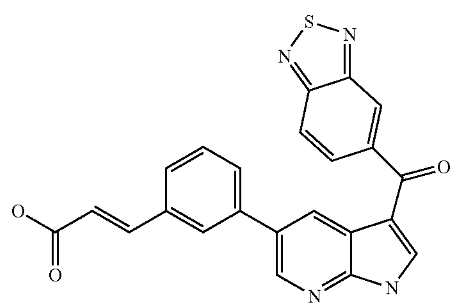 | 426.455 |
| 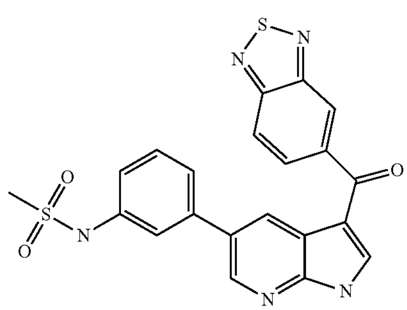 | 449.513 |
| 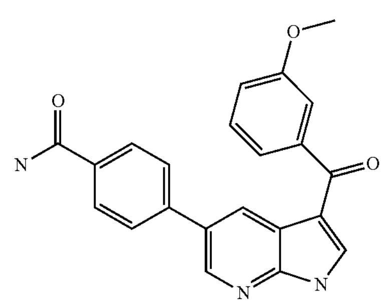 | 371.394 |

TABLE 1-continued

Exemplary compounds active on Ret with IC50 ≦ 10 μM

| Structure | Mwt |
|---|---|
| 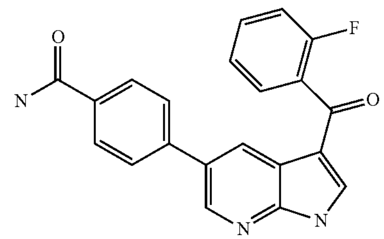 | 359.359 |
| 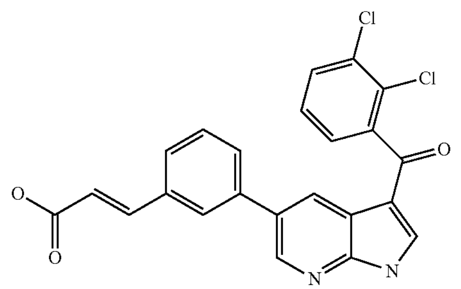 | 437.281 |
| 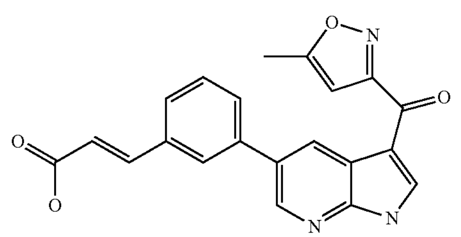 | 373.366 |
| 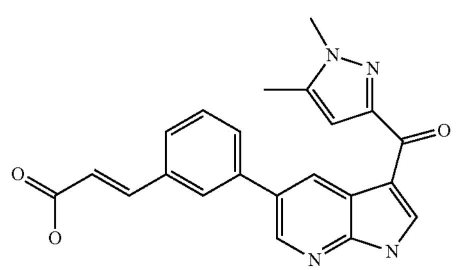 | 386.409 |
| 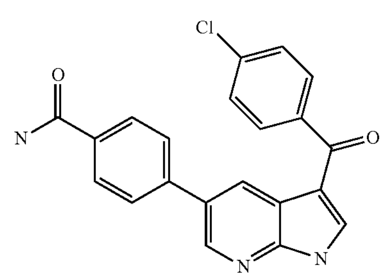 | 375.814 |
| 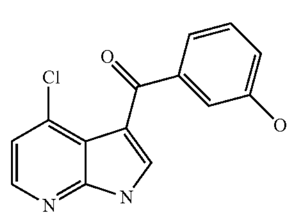 | 272.69 |

TABLE 1-continued

Exemplary compounds active on Ret with IC50 ≦ 10 μM

| Structure | Mwt |
|---|---|
| 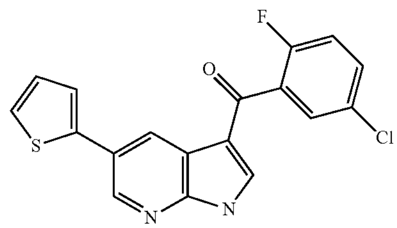 | 356.807 |
| 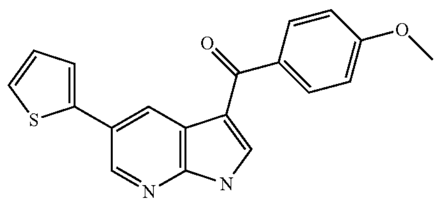 | 334.398 |
| 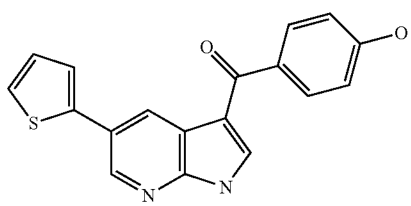 | 320.371 |
| 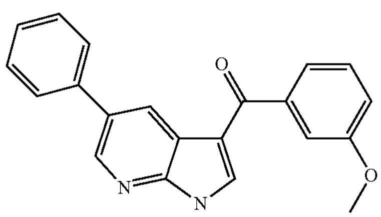 | 328.369 |
| 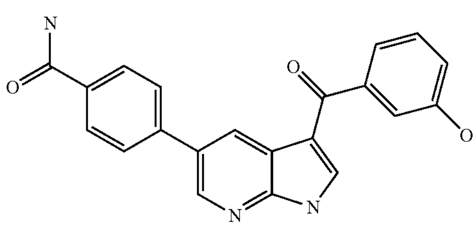 | 357.367 |
| 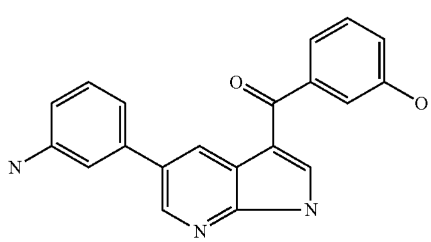 | 329.358 |

TABLE 1-continued

Exemplary compounds active on Ret with IC50 ≦ 10 μM

| Structure | Mwt |
|---|---|
| 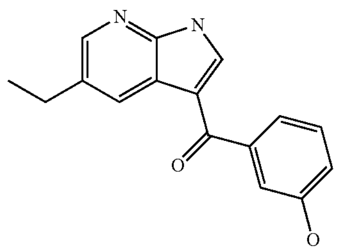 | 266.299 |
| 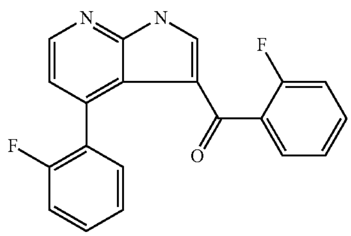 | 334.324 |
| 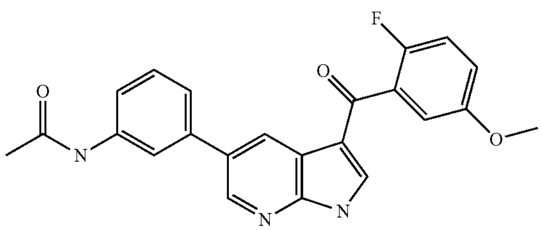 | 403.411 |
| 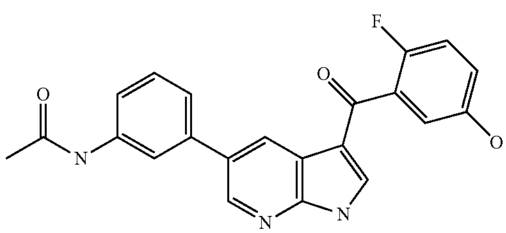 | 389.384 |
| 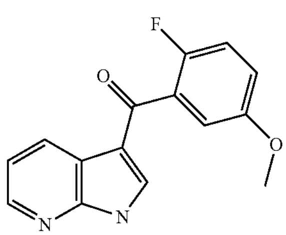 | 270.262 |
| 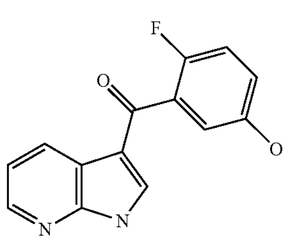 | 256.235 |

TABLE 1-continued

Exemplary compounds active on Ret with IC50 ≦ 10 μM

| Structure | Mwt |
|---|---|
| 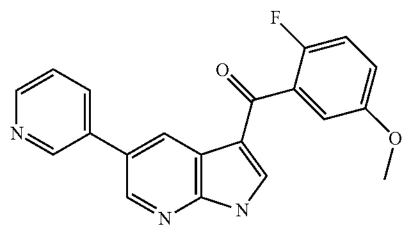 | 347.348 |
| 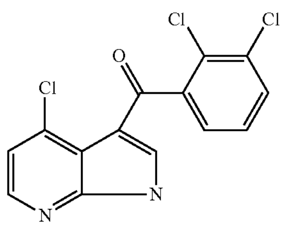 | 325.581 |
| 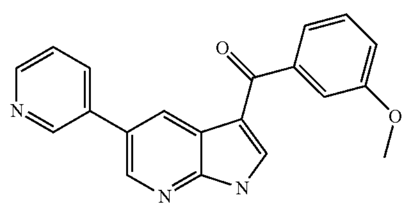 | 329.358 |
| 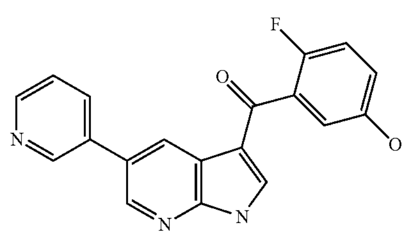 | 333.321 |
| 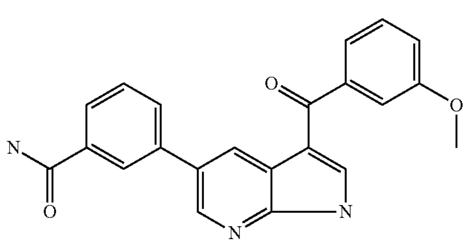 | 371.394 |
| 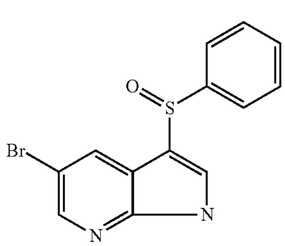 | 321.197 |

TABLE 1-continued
Exemplary compounds active on Ret with IC50 ≦ 10 μM
| Structure | Mwt |
|---|---|
| 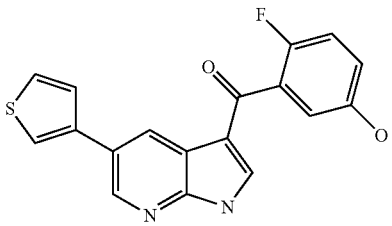 | 338.361 |
| 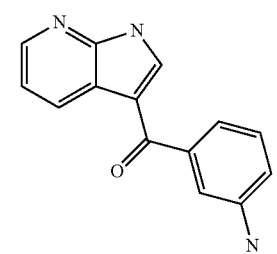 | 237.261 |
| 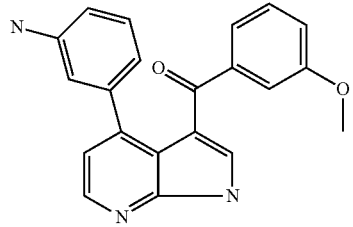 | 343.3843 |
| 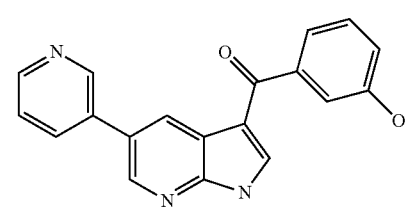 | 315.3307 |
| 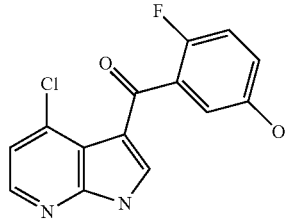 | 290.6802 |
| 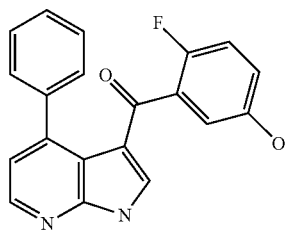 | 332.3327 |

TABLE 1-continued

Exemplary compounds active on Ret with IC50 ≤ 10 μM

| Structure | Mwt |
|---|---|
| 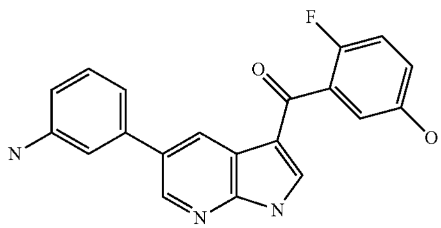 | 347.3476 |
| 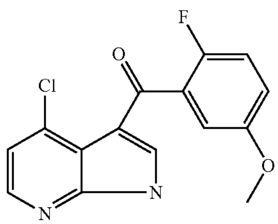 | 304.707 |
| 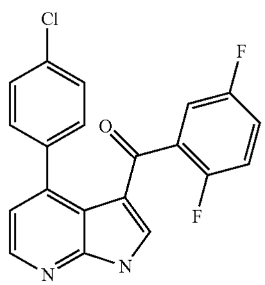 | 368.7689 |
| 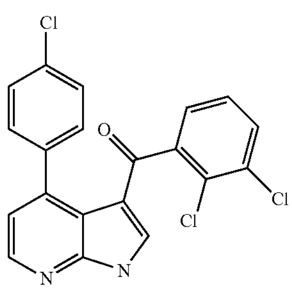 | 401.6789 |
| 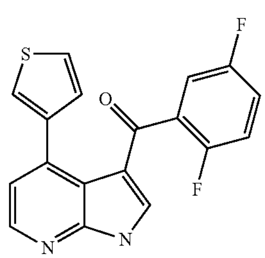 | 340.352 |
| 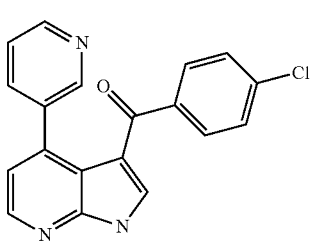 | 333.7768 |

TABLE 1-continued

Exemplary compounds active on Ret with IC50 ≦ 10 μM

| Structure | Mwt |
|---|---|
| 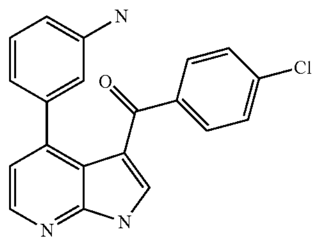 | 347.8036 |
| 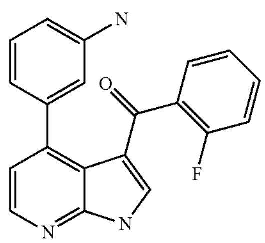 | 331.3486 |
| 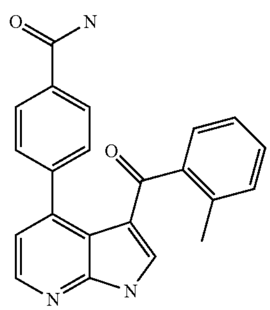 | 355.3953 |
| 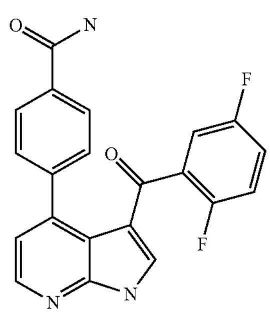 | 377.3487 |
| 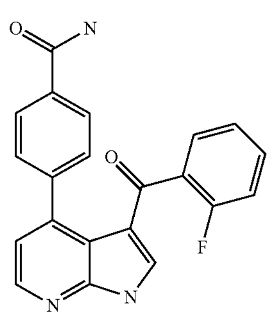 | 359.3586 |

TABLE 1-continued

Exemplary compounds active on Ret with IC50 ≦ 10 μM

| Structure | Mwt |
|---|---|
| 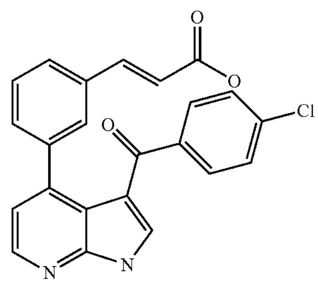 | 402.8355 |
| 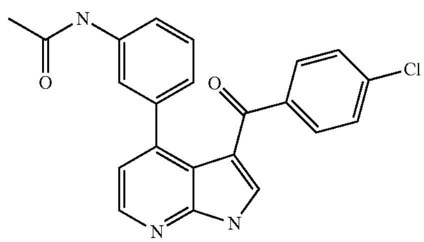 | 389.8404 |
| 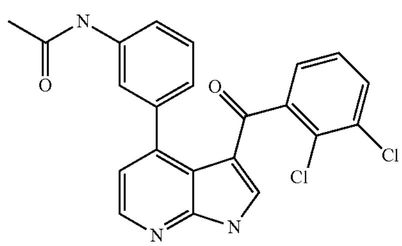 | 424.2855 |
| 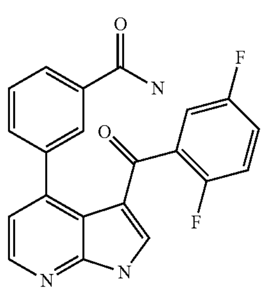 | 377.3487 |
| 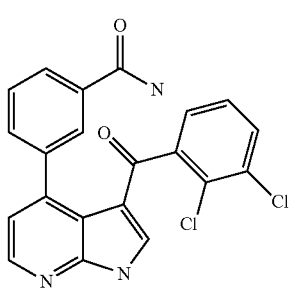 | 410.2587 |

TABLE 1-continued

Exemplary compounds active on Ret with IC50 ≤ 10 μM

| Structure | Mwt |
|---|---|
| 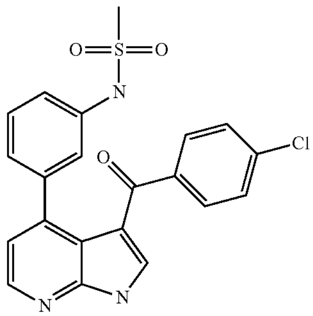 | 425.8944 |
| 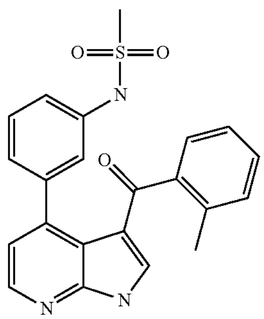 | 405.4761 |
| 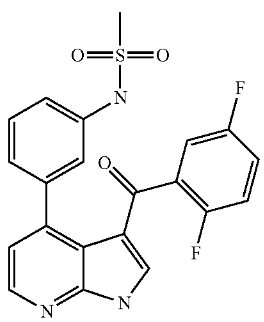 | 427.4295 |
| 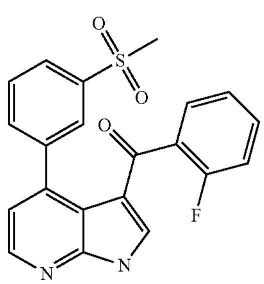 | 394.4245 |
| 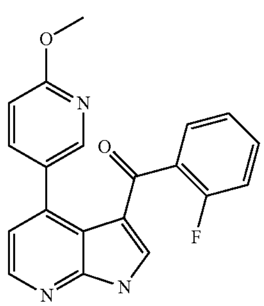 | 347.3476 |

TABLE 1-continued

Exemplary compounds active on Ret with IC50 ≦ 10 μM

| Structure | Mwt |
|---|---|
| 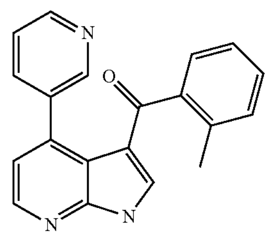 | 313.3585 |
| 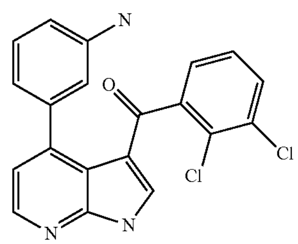 | 382.2487 |
| 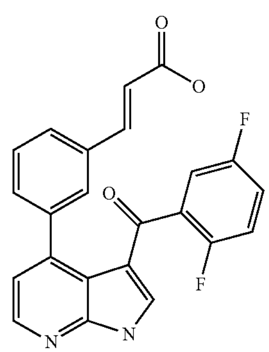 | 404.3706 |
| 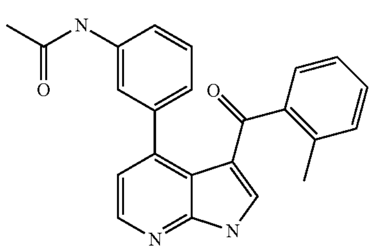 | 369.4221 |
| 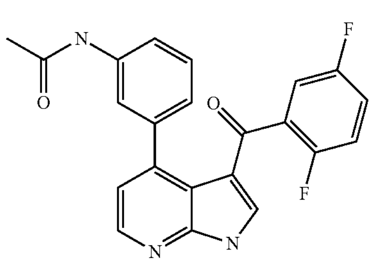 | 391.3755 |

TABLE 1-continued

Exemplary compounds active on Ret with IC50 ≦ 10 μM

| Structure | Mwt |
|---|---|
| 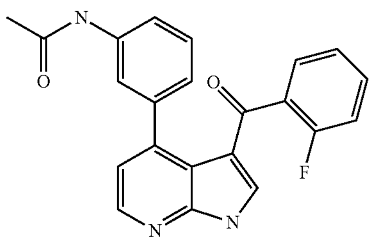 | 373.3854 |
| 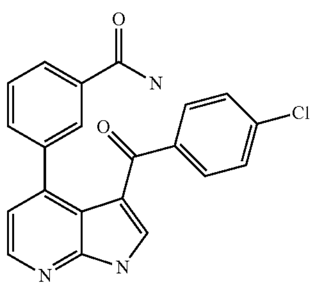 | 375.8136 |
| 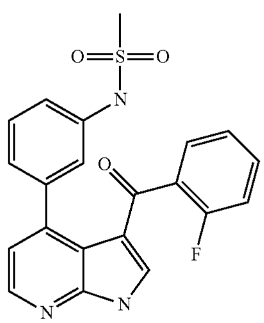 | 409.4394 |
| 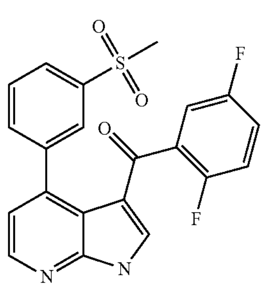 | 412.4146 |
| 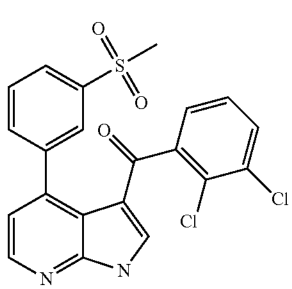 | 445.3246 |

TABLE 1-continued

Exemplary compounds active on Ret with IC50 ≦ 10 µM

| Structure | Mwt |
|---|---|
| 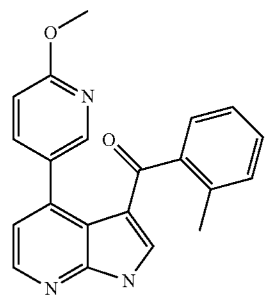 | 343.3843 |
| 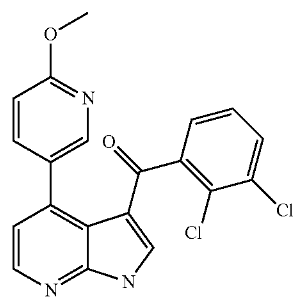 | 398.2477 |
| 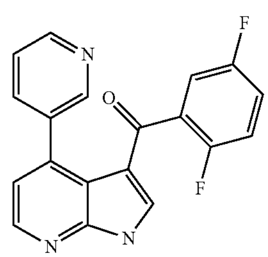 | 335.3119 |
| 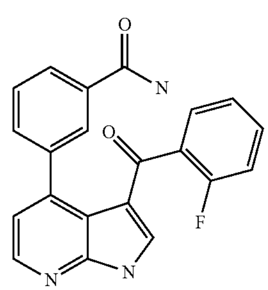 | 359.3586 |
| 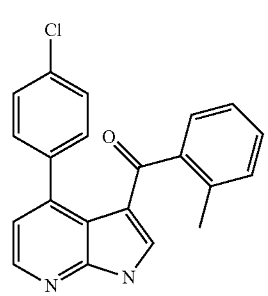 | 346.8155 |

TABLE 1-continued

Exemplary compounds active on Ret with IC50 ≦ 10 μM

| Structure | Mwt |
|---|---|
| 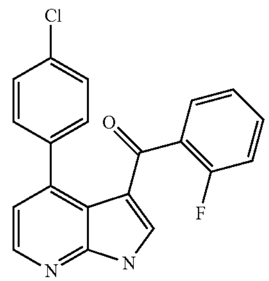 | 350.7788 |
| 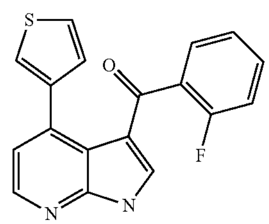 | 322.3619 |
| 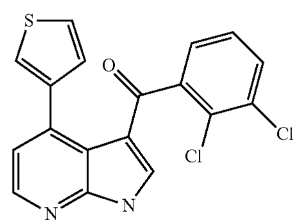 | 373.262 |
| 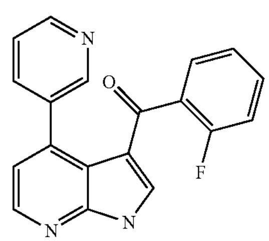 | 317.3218 |
| 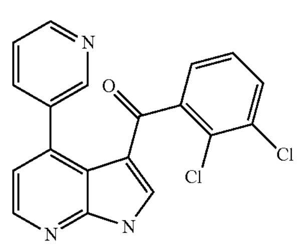 | 368.2219 |
| 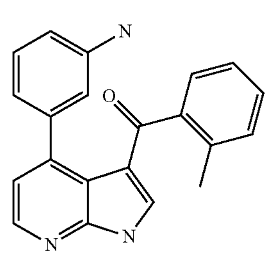 | 327.3853 |

TABLE 1-continued

Exemplary compounds active on Ret with IC50 ≦ 10 μM

| Structure | Mwt |
|---|---|
| 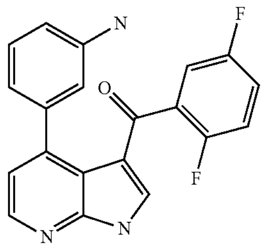 | 349.3387 |
| 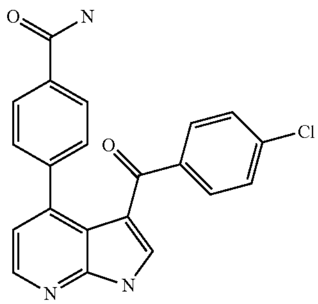 | 375.8136 |
| 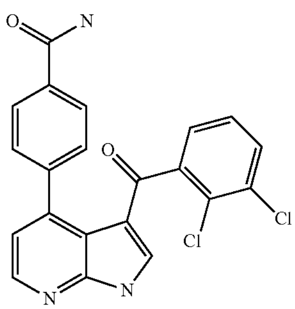 | 410.2587 |
| 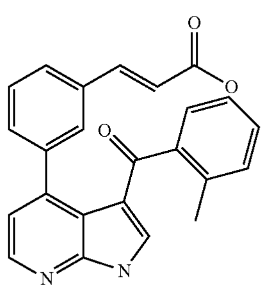 | 382.4172 |
| 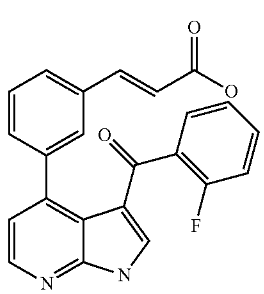 | 386.3805 |

TABLE 1-continued

Exemplary compounds active on Ret with IC50 ≦ 10 μM

| Structure | Mwt |
|---|---|
| 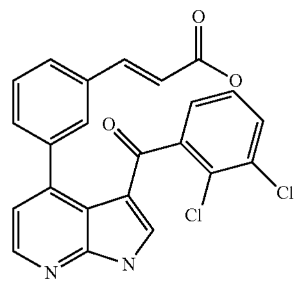 | 437.2806 |
| 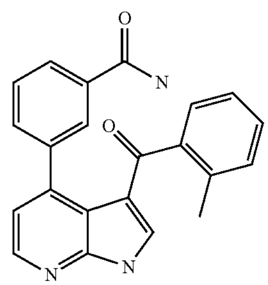 | 355.3953 |
| 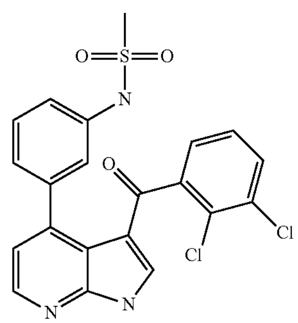 | 460.3395 |
| 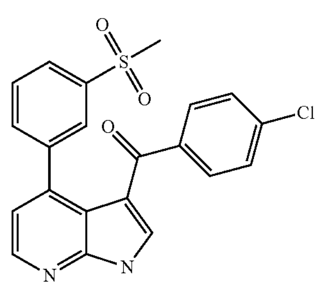 | 410.8795 |
| 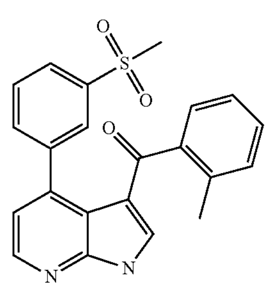 | 390.4612 |

TABLE 1-continued
Exemplary compounds active on Ret with IC50 ≦ 10 μM
| Structure | Mwt |
|---|---|
| 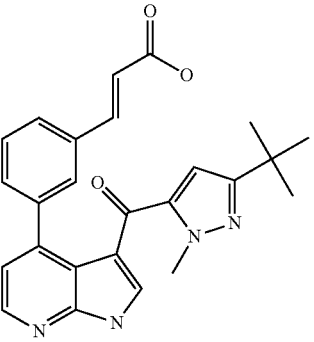 | 428.4896 |
| 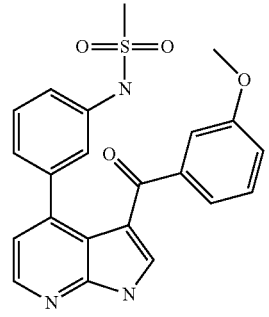 | 421.4751 |
| 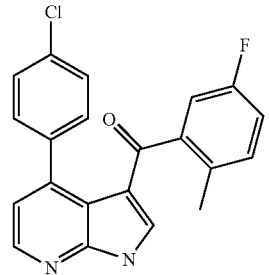 | 364.8056 |
| 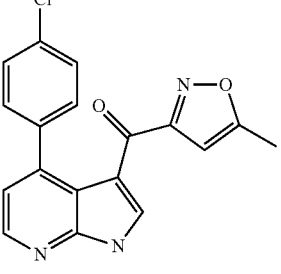 | 337.7648 |
| 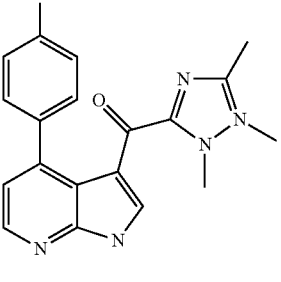 | 350.8075 |

TABLE 1-continued

Exemplary compounds active on Ret with IC50 ≦ 10 µM

| Structure | Mwt |
|---|---|
| 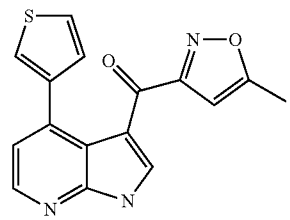 | 309.3479 |
| 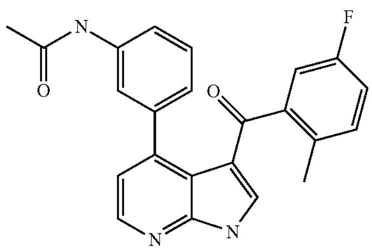 | 387.4122 |
| 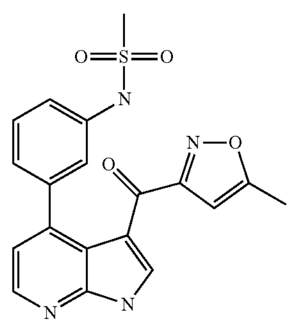 | 396.4254 |
| 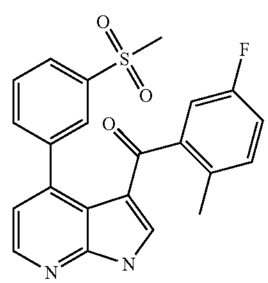 | 408.4513 |
| 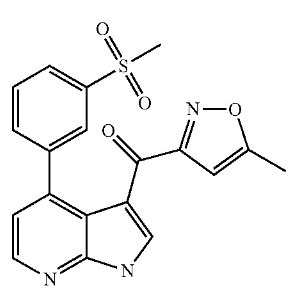 | 381.4105 |

TABLE 1-continued

Exemplary compounds active on Ret with IC50 ≦ 10 μM

| Structure | Mwt |
|---|---|
| 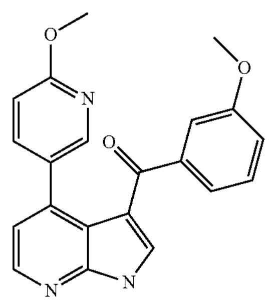 | 359.3833 |
| 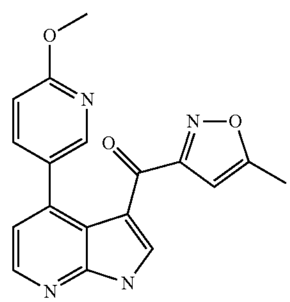 | 334.3336 |
| 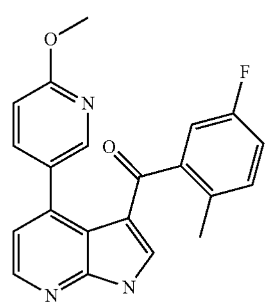 | 361.3744 |
| 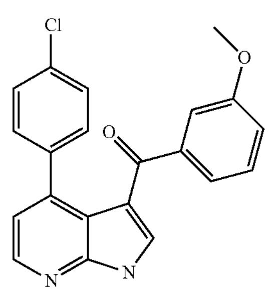 | 362.8145 |
| 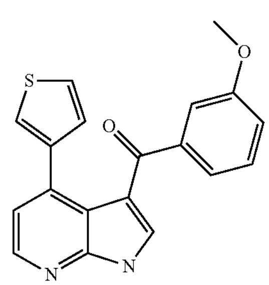 | 334.3976 |

TABLE 1-continued

Exemplary compounds active on Ret with IC50 ≦ 10 μM

| Structure | Mwt |
|---|---|
| 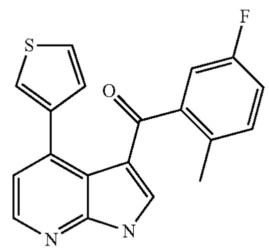 | 336.3887 |
| 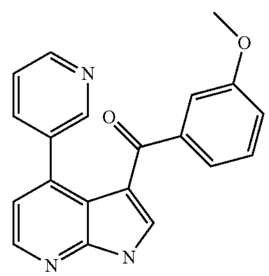 | 329.3575 |
| 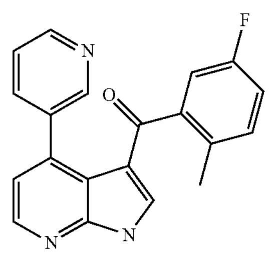 | 331.3486 |
| 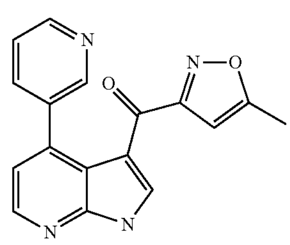 | 304.3078 |
| 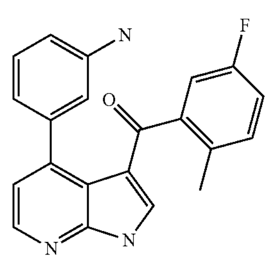 | 345.3754 |

TABLE 1-continued

Exemplary compounds active on Ret with IC50 ≦ 10 μM

| Structure | Mwt |
|---|---|
| 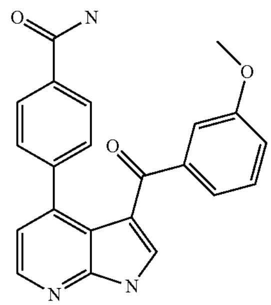 | 371.3943 |
| 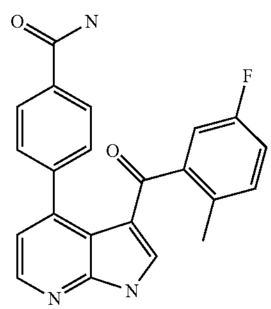 | 373.3854 |
| 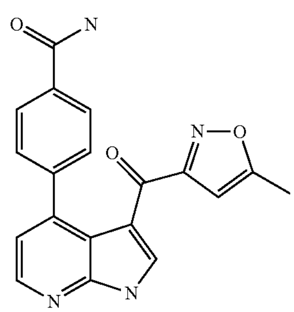 | 346.3446 |
| 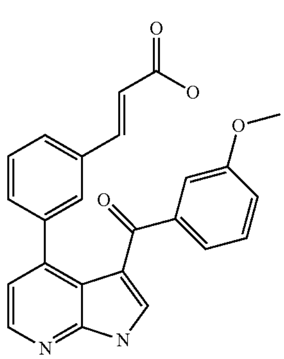 | 398.4162 |

TABLE 1-continued
Exemplary compounds active on Ret with IC50 ≦ 10 μM
| Structure | Mwt |
|---|---|
| 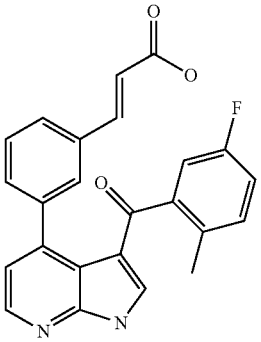 | 400.4073 |
| 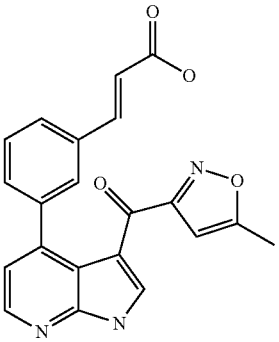 | 373.3665 |
| 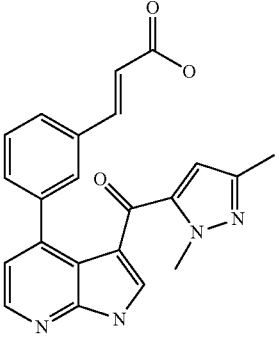 | 386.4092 |
| 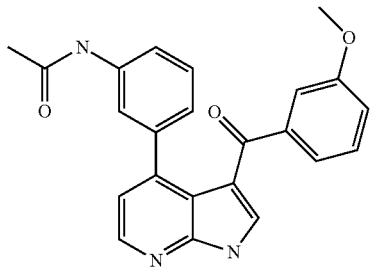 | 385.4211 |
| 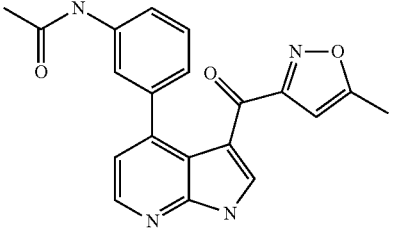 | 360.3714 |

TABLE 1-continued

Exemplary compounds active on Ret with IC50 ≤ 10 μM

| Structure | Mwt |
|---|---|
| 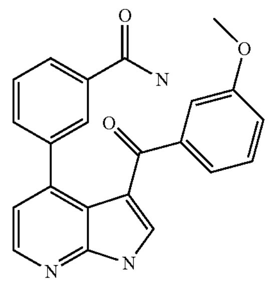 | 371.3943 |
| 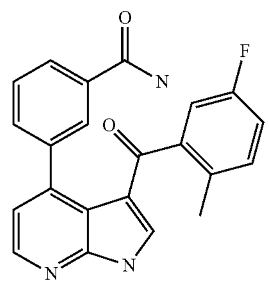 | 373.3854 |
| 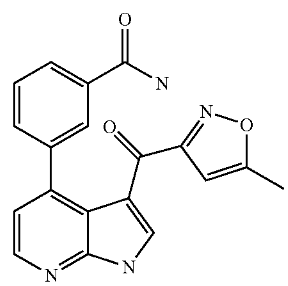 | 346.3446 |
| 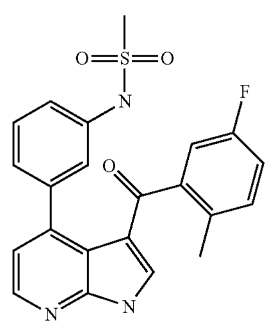 | 423.4662 |
| 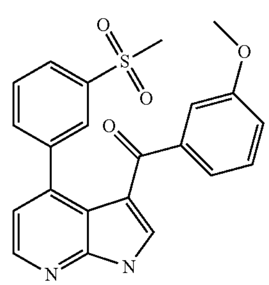 | 406.4602 |

TABLE 1-continued

Exemplary compounds active on Ret with IC50 ≤ 10 μM

| Structure | Mwt |
|---|---|
| 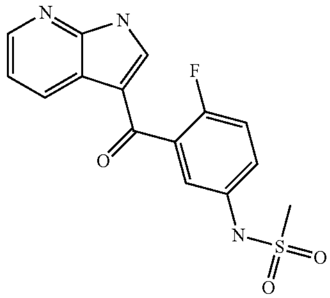 | 333.3418 |
| 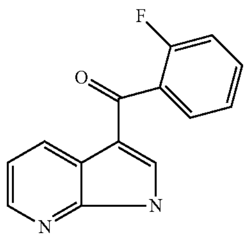 | 240.2361 |
| 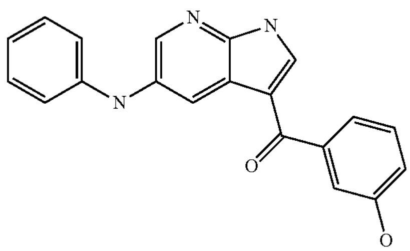 | 329.3575 |

Example 25

Cloning of Soluble Ret Kinase Domain

Construction of the vectors encoding the RETD2 and RETD3.

The RETD2 and RETD3 are two lengths of the RET kinase catalytic domain. The RETD2 spans residues S969 through R1012, and the RETD3 spans residues S705-R1012 (numbered according to NCBI file, NM_000323). The RET-encoding DNA with optimal E. coli codon usage was created as an overlapping set of oligonucleotide primers, assembled and amplified using PCR, and ligated to the plasmid pBS KS (Stratagene) through its BamHI and EcoRI restriction sites. The oligonucleotide primers used for the synthesis are (SEQ ID NOS: 1-60, respectively, in order of appearance):

```
13RE-1A
5'-CACTGTTATCACAAATTCGCACATAAACCGCCGATTTCTTCTGC

13RE-1B
5'-CCGGACGACGAAAGGTCATTTCCGCAGAAGAAATCGGCGGTTTA

13RE-2A
5'-AAATGACCTTTCGTCGTCCGGCTCAGGCATTCCCAGTGTCTTAC

13RE-2B
5'-GCGACGTGCACCAGAGGAAGAGTAAGACACTGGGAATGCCTG

13RE-3A
5'-TTCCTCTGGTGCACGTCGCCCGTCTCTGGACTCCATGGAAAACC

13RE-3B
5'-TTTGAACGCATCAACAGATACCTGGTTTTCCATGGAGTCCAGAG

13RE-4A
5'-GGTATCTGTTGATGCGTTCAAAATCCTGGAAGATCCGAAGTGGG

13RE-4B
5'-GTACCAGGTTCTTACGCGGAAATTCCCACTTCGGATCTTCCAGG

13RE-5A
5'-TTCCGCGTAAGAACCTGGTACTGGGCAAAACCCTGGGTGAAGG

13RE-5B
5'-TAGCTTTCACAACTTTACCAAACTCGCCTTCACCCAGGGTTTTGCC

13RE-6A
5'-GTTTGGTAAAGTTGTGAAAGCTACTGCATTTCACCTGAAAGGCC

13RE-6B
5'-TGCTACAGTGGTGTAACCTGCGCGGCCTTTCAGGTGAAATGCAG

13RE-7A
5'-GCAGGTTACACCACTGTAGCAGTTAAGATGCTGAAAGAAAACGCG

13RE-7B
5'-ATCACGCAGTTCGGATGGAGACGCGTTTTCTTTCAGCATCTTA

13RE-8A
5'-CTCCATCCGAACTGCGTGATCTGCTGTCCGAATTTAATGTTCTG
```

13RE-8B
5'-ACGTGCGGATGGTTTACCTGTTTCAGAACATTAAATTCGGACAGC

13RE-9A
5'-ACAGGTAAACCATCCGCACGTGATCAAACTGTACGGCGCATGTT

13RE-9B
5'-CAGCAGCGGGCCATCCTGGGAACATGCGCCGTACAGTTTGA

13RE-10A
5'-CAGGATGGCCCGCTGCTGCTGATTGTAGAATATGCGAAATACGGC

13RE-10B
5'-GCAGGAAGCCACGCAGGGAGCCGTATTTCGCATATTCTACA

13RE-11A
5'-CCCTGCGTGGCTTCCTGCGTGAGTCCCGCAAAGTTGGCCCGG

13RE-11B
5'-AGAGCCACCAGAGCCCAGGTAACCCGGGCCAACTTTGCGGGA

13RE-12A
5'-CCTGGGCTCTGGTGGCTCTCGTAACTCTTCCTCTCTGGATCACC

13RE-12B
5'-ATGGTCAGCGCACGCTCATCCGGGTGATCCAGAGAGGAAGAGT

13RE-13A
5'-GATGAGCGTGCGCTGACCATGGGCGATCTGATCTCCTTCGCGT

13RE-13B
5'-CTGCATGCCCTGGGAGATCTGCCACGCGAAGGAGATCAGATCG

13RE-14A
5'-AGATCTCCCAGGGCATGCAGTACCTGGCAGAAATGAAACTGGTG

13RE-14B
5'-CGAGCCGCCAGATCGCGGTGCACCAGTTTCATTTCTGCCAG

13RE-15A
5'-CCGCGATCTGGCGGCTCGTAACATTCTGGTAGCGGAAGGCCGT

13RE-15B
5'-GCCAAAGTCGGAGATCTTCATCTTACGGCCTTCCGCTACCAGAA

13RE-16A
5'-ATGAAGATCTCCGACTTTGGCCTGTCTCGTGATGTGTATGAAGA

13RE-16B
5'-GGGAACGTTTTACATAGGAGTCCTCTTCATACACATCACGAGACA

13RE-17A
5'-GACTCCTATGTAAAACGTTCCCAGGGCCGTATCCCGGTTAAATGG

13RE-17B
5'-ATCAAACAGAGATTCGATTGCCATCCATTTAACCGGGATACGGCC

13RE-18A
5'-GGCAATCGAATCTCTGTTTGATCATATCTACACCACTCAGTCCG

13RE-18B
5'-AGAACGCCGAAGGACCATACATCGGACTGAGTGGTGTAGATAT

13RE-19A
5'-GTATGGTCCTTCGGCGTTCTGCTGTGGGAAATCGTGACTCTGG

13RE-19B
5'-GAATACCTGGGTACGGGTTACCGCCCAGAGTCACGATTTCCCAC

13RE-20A
5'-GTAACCCGTACCCAGGTATTCCGCCAGAACGCCTGTTCAACCTG

13RE-20B
5'-TTCCATACGGTGACCAGTTTTCAGCAGGTTGAACAGGCGTTCTGG

13RE-21A
5'-GAAAACTGGTCACCGTATGGAACGCCCGGATAACTGCTCCGAA

13RE-21B
5'-CTGCAGCATCAGGCGGTACATCTCTTCGGAGCAGTTATCCGGGC

13RE-22A
5'-ATGTACCGCCTGATGCTGCAGTGCTGGAAACAGGAACCGGACAA

13RE-22B
5'-GATGTCCGCAAACACCGGACGTTTGTCCGGTTCCTGTTTCCAG

13RE-23A
5'-GTCCGGTGTTTGCGGACATCTCTAAAGACCTGGAGAAGATGATG

13RE-23B
5'-TCCAGGTAATCGCGACGTTTCACCATCATCTTCTCCAGGTCTTTA

13RE-24A
5'-GAAACGTCGCGATTACCTGGACCTGGCAGCGTCTACCCCGTC

13RE-24B
5'-GCCGTCATCGTAAATCAGAGAATCGGACGGGGTAGACGCTGCCA

13RE-25A
5'-TCTCTGATTTACGATGACGGCCTGTCTGAAGAGGAAACCCCACT

13RE-25B
5'-GCGGAGCATTGTTGCAGTCAACCAGTGGGGTTTCCTCTTCAGAC

13RE-26A
5'-TTGACTGCAACAATGCTCCGCTGCCGCGTGCTCTGCCGTCTAC

13RE-26B
5'-ACCATACAGTTTGTTTTCAATCCAGGTAGACGGCAGAGCACGCG

13RE-27A
5'-GGATTGAAAACAAACTGTATGGTATGTCTGACCCGAACTGGCCG

13RE-27B
5'-GTCAGCGGAACCGGAGATTCGCCCGGCCAGTTCGGGTCAGAC

13RE-28A
5'- GAATCTCCGGTTCCGCTGACTCGTGCAGACGGCACCAACACCG

13RE-28B
5'-AATCGTTCGGGTAACGCGGAAAACCGGTGTTGGTGCCGTCTGC

13RE-29A
5'- TTCCGCGTTACCCGAACGATTCCGTTTACGCGAACTGGATGCTG

13RE-29B
5'- TCAGTTTCGCAGCGGACGGAGACAGCATCCAGTTCGCGTAAAC

13RE-BAM
5'-GTTGGATCCCACTGTTATCACAAATTCGCAC

13RE-RI
5'-GTTGAATTCGGAGTCAAAGGTATCCATCAGTTTCGCAGCGGACGGA

For the RETD2 and RETD3, six mutations were introduced into the DNA that encodes the RET. These include five point mutations: K722D, P766Q, R770S, K989H, K994E, and one deletion mutation, del R820-M848. The PCR-based QuikChange mutagenesis protocol (Stratagene) was used to introduce the mutations. The pairs of oligonucleotide primers used for mutagenesis were synthesized (Invitrogen), and are listed below (SEQ ID NOS: 61-68, respectively, in order of appearance):

```
RECOD-KD-1
5'-GGGAATTTCCGCGTGACAACCTGGTACTGG

RECOD-KD-2
5'-CCAGTACCAGGTTGTCACGCGGAAATTCCC

RECOD-PRQS-1
5'-GAAAGAAAACGCGTCTCAGTCCGAACTGTCTGATCTGCTGTCCG

RECOD-PRQS-2
5'-CGGACAGCAGATCAGACAGTTCGGACTGAGACGCGTTTTCTTTC

RECOD-KKHE-1
5'-CTGCAGTGCTGGCACCAGGAACCGGACGAACGTCCGGTGTTTG

RECOD-KKHE-2
5'-CAAACACCGGACGTTCGTCCGGTTCCTGGTGCCAGCACTGCAG

R820-M848-1
5'-CTTCCTGCGTGAGTCCGGCGATCTGATCTCC

R820-M848-2
5'-GGAGATCAGATCGCCGGACTCACGCAGGAAG
```

After introduction of the mutations, the DNA encoding the RET kinase domain was amplified in a PCR reaction using two primers designed to add an NdeI restriction site before the sequence starting either at residue S696 (for RETD2) or residue 5705 (for RETD3) and to add a SalI restriction site after the sequence ending at residue R1012. These oligonucleotide primers were synthesized (Invitrogen) and are listed below (SEQ ID NOS: 69-71, respectively, in order of appearance):

```
RECOD-S696
5'-GTTCTTCATATGTCTCTGGACTCCATGGAAAAC

RECOD-S705-N
5'-GTTCTTCATATGTCTGTTGATGCGTTCAAAATCCT

RE-1012-COD
5'-GTTCTTGTCGACACGTTTCACCATCATCTTCTCC
```

The PCR products that encode the mutated RET sequences were digested with NdeI and Sal I restriction enzymes. A plasmid vector, pET-SF BI-PTP, was also digested with NdeI and SalI restriction enzymes. The RET-containing PCR product was ligated together with the vector DNA using T4 DNA ligase (Invitrogen). The relevant portions of the coding regions of the resultant plasmids was determined (Davis Sequencing). The pET-SF BI-PTP vector is a derivative of the pET-24 vector (Novagen) designed to utilize the T7 RNA polymerase for producing mRNA in strains of *E. coli* that are engineered to produce that polymerase. The pET-SF BI-PTP vector contains a polylinker that encodes a short amino acid tag having the sequence, VDHHHHHH (SEQ ID NO: 72), that becomes fused to the C-terminus of the RET protein at residue R1012, when the RET kinase domain is introduced using the Sal I site as described above. The pET-SF BI-PTP vector also encodes the catalytic domain of PTP1b, a protein tyrosine phosphatase.

The RETD2 protein sequence is (SEQ ID NO: 73):

```
                                       MSLDSMENQVSVDAFKILEDPKWEFP  720
721 RDNLVLGKTLGEGEFGKVVKATAFHLKGRAGYTTVAVKMLKENASQSELSDLLSEFNVLK  780
781 QVNHPHVIKLYGACSQDGPLLLIVEYAKYGSLRGFLRES
            GDLISFAWQISQGMQYLAEMKLVHRDLAARNILVAEGRKMKISDFGLSRDVY  900
901 EEDSYVKRSQGRIPVKWMAIESLFDHIYTTQSDVWSFGVLLWEIVTLGGNPYPGIPPERL  960
961 FNLLKTGHRMERPDNCSEEMYRLMLQCWHQEPDERPVFADISKDLEKMMVKRVDHHHHHH
```

The RETD3 protein sequence is (SEQ ID NO: 74):

```
                                              MSVDAFKILEDPKWEFP720
721 RDNLVLGKTLGEGEFGKVVKATAFHLKGRAGYTTVAVKMLKENASQSELSDLLSEFNVLK780
781 QVNHPHVIKLYGACSQDGPLLLIVEYAKYGSLRGFLRES
            GDLISFAWQISQGMQYLAEMKLVHRDLAARNILVAEGRKMKISDFGLSRDVY900
901 EEDSYVKRSQGRIPVKWMAIESLFDHIYTTQSDVWSFGVLLWEIVTLGGNPYPGIPPERL960
961 FNLLKTGHRMERPDNCSEEMYRLMLQCWHQEPDERPVFADISKDLEKMMVKRVDHHHHHH
```

Example 26

Expression and Purification of Soluble Ret Kinase Domains (Soluble Designer Ret (D2 and D3) from E. coli)

For protein expression Ret (S705-R1012 (D3) or S696-R1012 (D2) both with deletions Y826-P841) were transformed into E. coli strain BL21 (DE3) CodonPlus and transformants selected for on LB plates containing Kanamycin and Chloramphenicol. Single colonies were grown for 4 hrs at 37° C. in 2×200 ml LB media. 30 L of fresh TB media was sterilized in a BioFlow 5000 Fermenter and inoculated with 400 ml of seed culture. The culture continued to grow at 37° C. for ~4.5 hrs. Once cultures reached an optical density of 2.0-3.0 at 600 nm. The culture was chilled to 12° C. and 0.1 mM IPTG added, the culture was further incubated for 18 hrs at 12° C. Cells were harvested by centrifugation at 15,000×g and pellet frozen at −80° C. until ready for lysis.

The cell pellet was suspended in lysis buffer containing 0.1M Potassium phosphate buffer pH 8.00, 250 mM NaCl, 5% Glycerol, 0.1% NP-40, 25 mM Imadazole, 2 mM PMSF. Cells were lysed using a microfuidizer processor (Microfluidics Corporation) and insoluble cellular debris removed using centrifugation at 30,000×g The cleared supernatant was passed over a pre-equilibrated $Ni^{2+}$ Chelating column (Amersham) at a flow rate of 20 ml/min. The loaded column washed with 5 column volumes of lysis buffer plus 30 mM and 60 mM Imadazole to remove non-specific bound material.

The column was re-equilibrated using 20 mM Tris-HCl pH8.0, 250 mM NaCl. Ret was eluted using steps at 30, 60 and 250 mM Imadazole in 20 mM Tris-HCl pH8.0, 100 mM NaCl. Fractions were assayed by SDS-PAGE and those containing Ret were pooled, diluted into Tris buffer pH 8.0, until ~50 mM NaCl was reached.

Diluted protein was further purified using Anion Exchange Chromatography. For this step a 16/10 column was packed with. Source 30Q media and equilibrated in 20 mM Tris pH8.0 buffer. Following protein binding Ret was eluted using a linear gradient of NaCl (50-500 mM) in Tris pH8.0 buffer. Fractions were collected, pooled, and concentrated ready for a final polishing step. Ret was passed over a Pharmacia HiLoad 16/60 Superdex 200 sizing column (Pharmacia) pre-equilibrated with 20 mM Tris pH8.0, 100 mM NaCl. Fractions were collected, pooled and concentrated to 16 mg/ml.

Example 27

Crystallization and Crystal Analysis of Ret Kinase Domain

Experimental Design and Methods

Co-crystallography with RetD3: RetD3 crystals routinely grow to a usable size (200×200×700 microns) within two-three days of crystal setup. Crystallization conditions were generally as follows:
Protein at 12 mg/ml
Compound at 1 mg/ml
Crystallization buffer: 30% PEG 2000 MME, 0.15M KBr and 1 mM DTT The diffraction data from RetD3 co-crystals were collected at ALS Beamline 831. We collected datasets for only those crystals that diffracted to at least 2.8 Å or better.

RetD3: Structure Determination and Refinement

The co-crystal structures of RetD3 with various compounds have been solved by Molecular Replacement method. The data collection, processing, and refinement statistics are shown below in the table. All data were collected at ALS BeamLine 831 and processed and reduced by Mosflm and Scala in CCP4 package. The initial phases for RetD3 were obtained by Molecular Replacement using the FGFR1 model with either program EPMR or Molrep. The refinement of the model was carried out by both CNX and Refmac5. The model building/editing was performed with the program O.

TABLE

Data Collection, Processing, and Refinement Statistics

| Crystal | RetD3 + PLX101043 | RetD3 + PLX124194 |
|---|---|---|
| Crystal Parameter | | |
| Space Group | $P2_12_12_1$ | $P4_12_12$ |
| Cell (a, b, c, α, β, γ) | 57.472 70.249 70.632 90 90 90 | 94.692 94.692 176.959 90 90 90 |
| Number of molecules/ASU | 1 | 2 |
| Data Collection | | |
| Resolution (Å) | 1.85 | 2.50 |
| Unique reflections | 24710 | 27078 |
| Redundancy | 7.0 (5.9) | 8.9 (8.7) |
| Completeness (%) (outer shell) | 98.8 (97.6) | 94.8 (87.9) |
| I/σ (outer shell) | 13.4 (2.0) | 13.9 (2.3) |
| $R_{sym}$ (outer shell) | 0.081 (0.962) | 0.111 (0.857) |
| Refinemment | | |
| $R_{work}/R_{free}$ | 0.203/0.235 | 0.223/0.264 |
| Number of Atoms | 2365 (185 waters) | 4511 (128 waters) |
| Rmsd from ideal geometry | 0.011 Å/1.625° | 0.011 Å/1.387° |
| Mean Protein B-factors ($Å^2$) | 44.93 | 55.93 |
| Mean Water B-factors ($Å^2$) | 49.55 | 54.54 |
| Mean Ligand B-factors ($Å^2$) | 35.23 | 64.23 |

Figure 2:
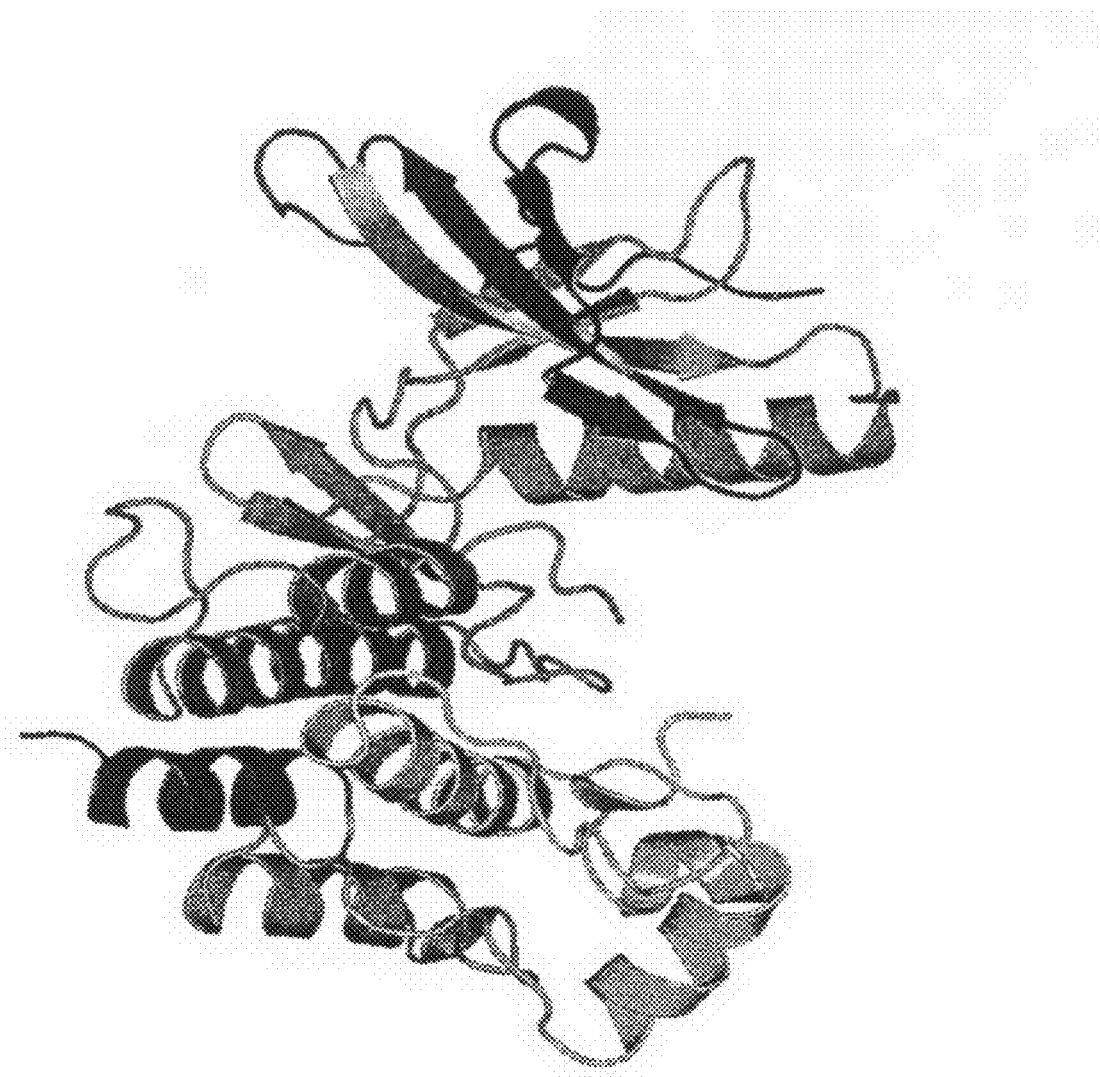
FIG. 2 shows the structure of the Ret kinase domain of RETD3.
Figure 3A:
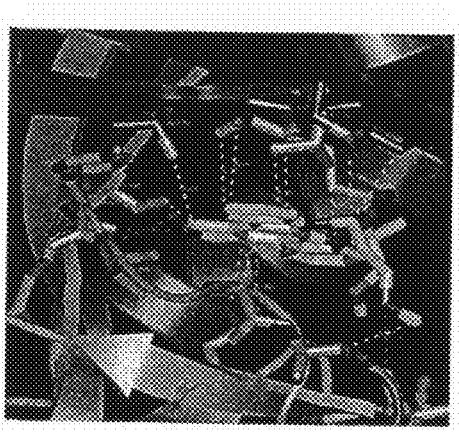
FIG. 3 collectively shows the ATP binding site of co-crystal structures of RETD3; with binding compound staurosporine (FIG. 3A) and with binding compound (2-Fluoro-5-hydroxy-phenyl)-(5-thiophen-2-yl-1H-pyrrolo[2,3-b]pyridin-3-yl)-methanone (FIG. 3B).
Figure 3B:
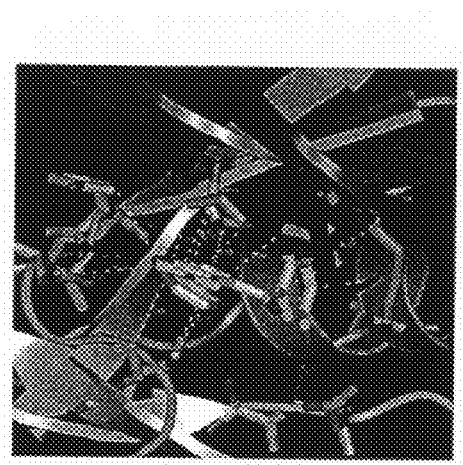

Structure Description:

The RetD3 structure has similarities to other Kinase structures. Figures of the full length kinase domain protein is shown in FIG. 2, and views of the active site in co-crystal complexes with staurosporine and an exemplary compound of Formula I (the compound shown in the description of Table 2) are shown in FIGS. 3A and 3B respectively. The ATP binding site of the protein is the cleft formed between the two domains.

FIGS. 3A and 3B show the ATP binding site in each of the co-crystal structures of RetD3 with binding compounds. In each case, the binding site is occupied by the corresponding compound that makes interactions with the protein. Water molecules, if present, are shown as spheres. The protein residues that make any interaction with the compound are shown in stick representation. The polar and hydrogen-bond interactions between the compound and the protein and hydrophobic interactions are depicted by dashed lines. In each co-crystal structure, there are numerous interactions between the compound and the protein that account for the binding affinity of the protein for that compound. In each case, the compound makes the canonical hydrogen-bond interactions with the protein residues E805 and A807, besides other polar and non-polar interactions.

Example 28

Ret Kinase Domain and Construction of Ret Surrogate Sequences

Ret cDNA sequence is available from NCBI, e.g., as NM_020630.2. Using this sequence, Ret DNA sequences can be cloned from commercially available libraries by conventional methods.

Construction of the Vectors Encoding the RET Surrogate I and RET Surrogate

For the RET surrogate I, six mutations were introduced into DNA that encodes the catalytic domain from FGFR1 Tyrosine kinase. The six mutations are: P483T, C488E, C584S, N568S, E571G, and A640S. For the RET surrogate II, a seventh mutation was introduced, M535L. The PCR-based QuikChange mutagenesis protocol (Stratagene) was used to introduce the mutations. For each of the C584S, A640S, and M535L mutations separate reactions were performed using pairs of complementary oligonucleotides containing the intended mutant sequences. The P483T and C488E mutations were introduced in a single reaction with one pair of complementary primers containing both of these intended mutant sequences. Similarly the N568S and the E571G mutations were introduced in a single reaction. All six mutations were combined in one by performing the individual mutagenic protocols sequentially. For the seventh mutation, M535L, unique to RET surrogate II, RET surrogate I was used as the starting template in the mutagenic PCR reaction. The five pairs of oligonucleotide primers used synthesized (Invitrogen), and are listed below (SEQ ID NOS: 75-84, respectively, in order of appearance):

```
P483TC488E-1
5' CTGGTCTTAGGCAAAACCCTGGGAGAGGGCGAATTTGGGCAGGTGG

P483TC488E-2
5' CCACCTGCCCAAATTCGCCCTCTCCCAGGGTTTTGCCTAAGACCAG

M535L-1
5' CTCAGAAATGGAGATGCTGAAGATGATCGGG

M535L-2
5' CCCGATCATCTTCAGCATCTCCATTTCTGAG

C584S-1
5' CAGGGCTGGAATACAGCTACAACCCCAGC

C584S-2
5' GCTGGGGTTGTAGCTGTATTCCAGCCCTG

N568SE571G-1
5' GTATGCCTCCAAGGGCTCTCTGCGGGGTTACCTGCAGGCCC

N568SE571G-2
5' GGGCCTGCAGGTAACCCCGCAGAGAGCCCTTGGAGGCATAC

A640S-1
5' CAATGTGATGAAGATATCTGACTTTGGCCTCG

A60S-2
5' CGAGGCCAAAGTCAGATATCTTCATCACATTG
```

After introduction of the mutations, the DNA encoding the FGFR1 kinase domain was amplified in a PCR reaction using two primers designed to add an Ndel restriction site before the sequence starting at residue A458 and to add a stop codon and a Sal I restriction site after the sequence ending at residue E765. These oligonucleotide primers were synthesized (Invitrogen) and are listed below (SEQ ID NOS: 85 and 86, respectively, in order of appearance):

```
FGFR1-S      5'GACTCCTCATATGGCAGGGGTCTCTGAGTATGA

FGFR-SAL     5'CAGGTCGTCGACTACTCCTGGTTGGAGGTCAAGG
```

The PCR product that encodes the mutated FGFR1 sequences, spanning residues A458 through E765, was digested with Ndel and Sal I restriction enzymes. A plasmid vector, pET-N6 BI-PTP, was also digested with Ndel and SalI restriction enzymes. The FGFR1-containing PCR product was ligated together with the vector DNA using T4 DNA ligase (Invitrogen). The relevant portions of the coding regions of the resultant plasmids was determined (Davis Sequencing). The pET-N6 BI-PTP vector is a derivative of the pET-24 vector (Novagen) designed to utilize the T7 RNA polymerase for producing mRNA in strains of *E. coli* that are engineered to produce that polymerase. The pET-N6 BI-PTP vector contains a polylinker that encodes a short amino acid tag having the sequence, MGHHHHHHM (SEQ ID NO: 87), that becomes fused to the N-terminus of the FGFR1 protein at residue A458, when the FGFR1 kinase domain is introduced using the Nde I site as described above. The pET-N6 BI-PTP vector also encodes the catalytic domain of PTP1b, a protein tyrosine phosphatase.

The RET surrogate I sequence is (SEQ ID NO: 88):

```
              MGHHHHHHM AGV SEYELPEDPR WELPRDRLVL   480
481 GKTLGEGEFG QVVLAEAIGL DKDKPNRVTK VAVKMLKSDA TEKDLSDLIS EMEMMKMIGK   540
541 HKNIINLLGA CTQDGPLYVI VEYASKGSLR GYLQARRPPG LEYSYNPSHN PEEQLSSKDL   600
601 VSCAYQVARG MEYLASKKCI HRDLAARNVL VTEDNVMKIS DFGLARDIHH IDYYKKTTNG   660
661 RLPVKWMAPE ALFDRIYTHQ SDVWSFGVLL WEIFTLGGSP YPGVPVEELF KLLKEGHRMD   720
721 KPSNCTNELY MMMRDCWHAV PSQRPTFKQL VEDLDRIVAL TSNQE                   765
```

The RET surrogate II protein sequence is (SEQ ID NO: 89):

```
                            MGHHHHHHM AGV SEYELPEDPR WELPRDRLVL    480
481 GKTLGEGEFG QVVLAEAIGL DKDKPNRVTK VAVKMLKSDA TEKDLSDLIS EMEMLKMIGK   540
541 HKNIINLLGA CTQDGPLYVI VEYASKGSLR GYLQARRPPG LEYSYNPSHN PEEQLSSKDL   600
601 VSCAYQVARG MEYLASKKCI HRDLAARNVL VTEDNVMKIS DFGLARDIHH IDYYKKTTNG   660
661 RLPVKWMAPE ALFDRIYTHQ SDVWSFGVLL WEIFTLGGSP YPGVPVEELF KLLKEGHRMD   720
721 KPSNCTNELY MMMRDCWHAV PSQRPTFKQL VEDLDRIVAL TSNQE                  765
```

Example 29

Purification of Ret and Ret Surrogate

Ret and Ret surrogate is purified as follows:

Expression and Purification of Ret Surrogate from *E. coli*

For protein expression Ret Surrogate (I and II) kinase domain (p1361 and p1362) were transformed into *E. coli* strain BL21 (DE3) CodonPlus and transformants selected for on LB plates containing Kanamycin and Chloramphenicol. Single colonies were grown for 4 hrs at 37° C. in 2×200 ml LB media. 30 L of fresh TB media were inoculated with 400 ml of seed culture and grown at 37° C. using a Bioflow 5000 45 L fermenter. Once culture reaches an optical density of 1.0-2.0 at 600 nm, 0.5 mM IPTG was added and cultures were allowed to grow for a further 18 hrs at 20° C. Cells were harvested by centrifugation at 15000×g and *E. coli* paste frozen at −80° C.

500 g of *E. coli* paste was suspended in lysis buffer containing 0.1M Potassium phosphate pH 8.00, 250 mM NaCl, 5% Glycerol, 0.1% NP-40, 25 mM Imadazole, 2 mM PMSF and EDTA free protease inhibitor cocktail tablets (Roche). Cells were lysed using a microfuidizer processor (Microfluidics Corporation) and insoluble cellular debris was removed using centrifugation at 30,000×g.

The cleared supernatant was passed over a pre-equilibrated 50 ml Ni$^{2+}$ Chelating column at a flow rate of 30 ml/min. The loaded column was washed with 20 column volumes of lysis buffer plus 30 mM Imadazole to remove non-specifically bound material.

The washed column is now connected to an AKTAfplc and re-equilibrated in 150 ml of 20 mM HEPES pH7.5, 200 mM NaCl, 5 mM mercaptoethanol, 25 mM Imadazole, and then further washed with increasing concentration of Imadazole up to 60 mM. Ret surrogate was eluted using a linear gradient of Imadazole (80-500 mM) in 20 mM HEPES pH7.5, 200 mM NaCl, 5 mM mercaptoethanol. Gradient was run over 20 column volumes and 10 ml fractions collected. Fractions were assayed by SDS-PAGE and those containing Ret surrogate were pooled, concentrated and loaded onto a Pharmacia HiLoad 50/60 Superdex 200 sizing column (Pharmacia) we-equilibrated with 20 mM Tris pH7.5, 100 mM NaCl, 14 mM mercaptoethanol. Peak fractions were collected and assayed by SDS-PAGE. Fractions containing Ret surrogate were pooled and diluted in Tris buffer pH 7.5, until 30 mM NaCl was reached. Diluted protein was further subjected to anion exchange chromatography using a an HR 16/10 column packed with Source 30Q sepharose (Pharmacia) equilibrated with 20 mM Tris pH7.5, 14 mM mercaptoethanol. Elution was performed using a linear gradient of sodium chloride (0-500 mM) over 20 column volumes with 5 ml fractions collected. Purified protein was concentrated to ~50 mg/ml and stored at −80.

Expression and Purification of Soluble Ret from *E. coli*

For protein expression Ret (D874N, aa705-1060) was transformed into *E. coli* strain BL21 CodonPlus and transformants selected for on LB plates containing Kanamycin and Chloramphenicol. Single colonies were grown for 4 hrs at 37° C. in 2×200 ml LB media. 30 L of fresh TB media was sterilized in a BioFlow 5000 Fermenter and inoculated with 400 ml of seed culture. The culture continued to grow at 37° C. for ~4.5 hrs. Once cultures reached an optical density of 1.0-2.0 at 600 nm. The culture was chilled to 12° C. and 0.5 mM IPTG added, the culture was further incubated for 18 hrs at 12° C. Cells were harvested by centrifugation at 15,000×g and pellet frozen at −80° C. until ready for lysis.

The cell pellet was suspended in lysis buffer containing 0.1M Potassium phosphate buffer pH 8.00, 250 mM NaCl, 5% Glycerol, 0.1% NP-40, 25 mM Imadazole, 2 mM PMSF and EDTA free protease inhibitor cocktail tablets (Roche). Cells were lysed using a microfuidizer processor (Microfluidics Corporation) and insoluble cellular debris removed using centrifugation at 30,000×g The cleared supernatant was passed over a pre-equilibrated Ni$^{2+}$ Chelating column (Amersham) at a flow rate of 20 ml/min. The loaded column washed with 20 column volumes of lysis buffer plus 30 mM and 60 mM Imadazole to remove non-specific bound material.

The column was re-equilibrated using 20 mM HEPES pH8.0, 250 mM NaCl. Ret was eluted using steps at 30, 60 and 250 mM Imadazole in 20 mM HEPES pH8.0, 250 mM NaCl. Fractions were assayed by SDS-PAGE and those containing Ret were pooled, diluted into Tris buffer pH 8.5, until ~50 mM NaCl was reached.

Diluted protein was further purified using Anion Exchange Chromatography. For this step a 16/10 column was packed with Source 30Q media and equilibrated in 20 mM Tris pH8.5 buffer. Following protein binding Ret was eluted using a linear gradient of NaCl (50-500 mM) in Tris pH8.5 buffer. Fractions were collected, pooled, and concentrated ready for a final polishing step. Ret was passed over a Pharmacia HiLoad 16/60 Superdex 200 sizing column (Pharmacia) pre-equilibrated with 20 mM Tris pH8.0, 100 mM NaCl. Fractions were collected, pooled and concentrated to 16 mg/ml.

Example 30

Crystallization of Ret Surrogate

Crystals of Ret surrogate 1 were grown in 18% PEG 3350, 0.1M Hepes pH 6.5, 0.2M $(NH_4)_2SO_4$, 10% ethylene glycol.

Crystals of Ret surrogate 2 were grown in 14% PEG 3350, 0.1M Hepes pH 6.5, 0.2M $(NH_4)_2SO_4$, 10% ethylene glycol.

Crystals of both Ret surrogates routinely grew to useable size (approx 200×200×700 microns) within 2-3 days of crystallization set-up.

Example 31

Structure Determination of Ret Surrogate

Co-crystallography with Ret surrogate (RetS): RetS crystals routinely grow to a usable size (200×200×700 microns) within two-three days of crystal setup. The diffraction data from RetS co-crystals were collected at ALS Beamline 831. We collected datasets for only those crystals that diffracted to at least 2.8 Å or better.

RetS: Structure Determination and Refinement

The co-crystal structures of Ret with various compounds have been solved by Molecular Replacement method. The data collection, processing, and refinement statistics are shown below. All data were collected at ALS BeamLine 831 and processed and reduced by Mosflm and Scala in CCP4 package. The initial phases for RetS were obtained by Molecular Replacement using the FGFR1 model with either program EPMR or Molrep. The refinement of the model was carried out by both CNX and Refmac5. The model building/editing was performed with the program O.

Data Collection, Processing, and Refinement Statistics

| Crystal | RetS + Cmpd 68 | RetS + Cmpd 14 | RetS + Cmpd 28 |
|---|---|---|---|
| Crystal Parameters | | | |
| Space Group | C2 | C2 | C2 |
| Cell (a, b, c, α, β, γ) | 207.40 57.83 65.49 90.0 107.63 90.0 | 207.58 58.03 65.39 90.0 107.44 90.0 | 206.98 57.99 65.30 90.0 107.35 90.0 |
| Number of molecules in ASU | 2 | 2 | 2 |
| Data Collection and Processing | | | |
| Resolution (Å) | 1.80 | 1.80 | 1.65 |
| Unique reflections | 66544 | 59209 | 86509 |
| Redundancy | 2.4 (2.4) | 2.5 (1.8) | 3.5 (2.6) |
| Completeness (%) | 97.4 (96.3) % | 87.0 (63.1) % | 96.9 (91.3) % |
| I/σ (outer shell) | 11.2 (2.19) | 10.9 (1.71) | 14.2 (1.60) |
| $R_{sym}$ (outer shell) | 0.046 (0.596) | 0.048 (0.470) | 0.042 (0.621) |
| Refinement | | | |
| $R_{work}/R_{free}$ | 0.186/0.217 | 0.187/0.210 | 0.175/0.199 |
| Number of Atoms | 5203 (429 waters) | 5255 (486 waters) | 5434 (619 waters) |
| Rmsd from ideal geometry | 0.011 Å/1.519° | 0.010 Å/1.490° | 0.013 Å/1.498° |
| Mean Protein B-factors (Å$^2$) | 18.96 | 18.07 | 20.11 |
| Mean water B-factors (Å$^2$) | 40.18 | 39.98 | 38.81 |
| Mean Ligand B-factors (Å$^2$) | 29.86 | 32.66 | 22.00 |

Figure 4:
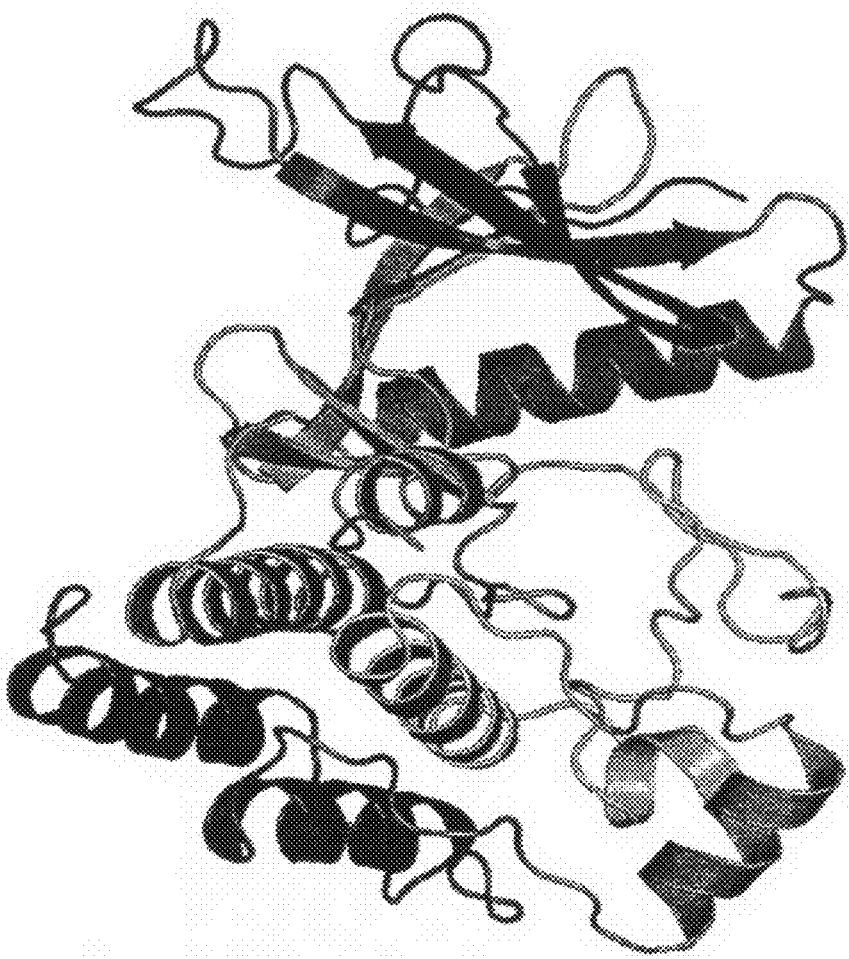
FIG. 4 shows a full length domain structure of Ret surrogate (RetS) co-crystallized with Compound 5-Thiophen-3-yl-1H-pyrrolo[2,3-b]pyridine.

Structure Description:

The RetS structure is very similar to other Kinase structures. Figures of the full length domain structure (co-crystallized with Compound 68 is shown in FIG. 4.

Figures 5A, 5B, 5C:
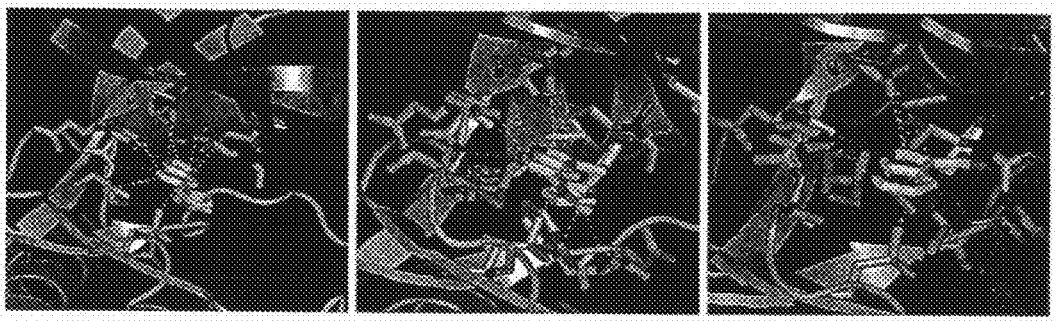
FIG. 5 collectively shows the ATP binding site of co-crystal structures of RetS; with binding compound 5-Thiophen-3-yl-1H-pyrrolo[2,3-b]pyridine (FIG. 5A), with binding compound 3-(3-Methoxy-benzyl)-5-thiophen-3-yl-1H-pyrrolo[2,3-b]pyridine (FIG. 5B), and with binding compound 3-Methoxy-phenyl)-(1H-pyrrolo[2,3-b]pyridin-3-yl)-methanone (FIG. 5C).

FIG. 5 shows schematics of the ATP binding site in each of the co-crystal structures of RetS with exemplary binding compounds, Compounds 68 (FIG. 5A), 14 (FIG. 5B), and 28 (FIG. 5C). In each case, the binding site is occupied by the corresponding binding compound that makes interactions with the protein. Water molecules, if present, are shown as spheres. Protein residues that make interaction with the compound are shown in stick representation. The polar and hydrogen-bond interactions between the compound and the protein are and the hydrophobic interactions are shown by dashed lines. In each co-crystal structure, there are numerous interactions between the compound and the protein that account for the binding affinity of the protein for that compound. In each case, the compound makes the canonical hydrogen-bond interactions with the protein residues E562 and A564, besides other polar and non-polar interactions.

Example 32

Binding Assays

Binding assays can be performed in a variety of ways, including a variety of ways known in the art. For example, as indicated above, binding assays can be performed using fluorescence resonance energy transfer (FRET) format, or using an AlphaScreen Alternatively, any method which can measure binding of a ligand to the ATP-binding site can be used. For example, a fluorescent ligand can be used. When bound to Ret, the emitted fluorescence is polarized. Once displaced by inhibitor binding, the polarization decreases.

Determination of IC50 for compounds by competitive binding assays. (Note that $K_I$ is the dissociation constant for inhibitor Binding; $K_D$ is the dissociation constant for substrate binding.) For this system, the IC50, inhibitor binding constant and substrate binding constant can be interrelated according to the following formula:

When using radiolabeled substrate $$K_I = \frac{IC50}{1 + \frac{[L^*]}{231}/K_D},$$

the IC50~$K_I$ when there is a small amount of labeled substrate.

Example 33

Ret Activity Assay

As an exemplary Ret assay, the effect of potential modulators of kinase activity of Ret and other kinases can be measured in a variety of different assays known in the art. In an exemplary assay, Ret kinase activity can be determined in the following assay format:

As an exemplary kinase assay, the kinase activity of Ret or Ret surrogate is measured in AlphaScreening (Packard BioScience). The kinase buffer (H1VLNB) contains HEPES 50 mM at pH7.2, Mg/Mn 5 mM each, NP-40 0.1%, and BSA at final 50 ug/ml. AlphaScreening is conducted as described by the manufacturer. In brief, the kinase reaction is performed in 384-well plate in 25 ul volume. The substrate is biotin-(E4Y)$_3$ at final concentration of 1 nM. The final concentration of ATP is 10 uM. For compound testing the final DMSO concentration is 1%. The reaction is incubated in 31° C. for 1 hour.

The Ret or Ret surrogate (or kinase domain thereof) is an active kinase in AlphaScreen. Inhibition of exemplary compounds by compounds of Formula I was tested with Ret and ATP at 10 uM.

Example 34

Site-Directed Mutagenesis of Ret and Other Kinases

Mutagenesis of Ret and other kinases (as well as other sequences of interest) can be carried out according to the following procedure as described in Molecular Biology: Current Innovations and Future Trends. Eds. A.M. Griffin and H. G. Griffin. (1995) ISBN 1-898486-01-8, Horizon Scientific Press, PO Box 1, Wymondham, Norfolk, U.K., among others.

In vitro site-directed mutagenesis is an invaluable technique for studying protein structure-function relationships, gene expression and vector modification. Several methods have appeared in the literature, but many of these methods require single-stranded DNA as the template. The reason for this, historically, has been the need for separating the complementary strands to prevent reannealing. Use of PCR in site-directed mutagenesis accomplishes strand separation by using a denaturing step to separate the complementing strands and allowing efficient polymerization of the PCR primers. PCR site-directed methods thus allow site-specific mutations to be incorporated in virtually any double-stranded plasmid; eliminating the need for M13-based vectors or single-stranded rescue.

It is often desirable to reduce the number of cycles during PCR when performing PCR-based site-directed mutagenesis to prevent clonal expansion of any (undesired) second-site mutations. Limited cycling which would result in reduced product yield, is offset by increasing the starting template concentration. A selection is used to reduce the number of parental molecules coming through the reaction. Also, in order to use a single PCR primer set, it is desirable to optimize the long PCR method. Further, because of the extendase activity of some thermostable polymerases it is often necessary to incorporate an end-polishing step into the procedure prior to end-to-end ligation of the PCR-generated product containing the incorporated mutations in one or both PCR primers.

The following protocol provides a facile method for site-directed mutagenesis and accomplishes the above desired features by the incorporation of the following steps: (i) increasing template concentration approximately 1000-fold over conventional PCR conditions; (ii) reducing the number of cycles from 25-30 to 5-10; (iii) adding the restriction endonuclease DpnI (recognition target sequence: 5-Gm6ATC-3, where the A residue is methylated) to select against parental DNA (note: DNA isolated from almost all common strains of E. coli is Dam-methylated at the sequence 5-GATC-3); (iv) using. Taq Extender in the PCR mix for increased reliability for PCR to 10 kb; (v) using Pfu DNA polymerase to polish the ends of the PCR product, and (vi) efficient intramolecular ligation in the presence of T4 DNA ligase.

Plasmid template DNA (approximately 0.5 pmole) is added to a PCR cocktail containing, in 25 ul of 1× mutagenesis buffer: (20 mM Tris HCl, pH 7.5; 8 mM MgCl$_2$; 40 ug/ml BSA); 12-20 pmole of each primer (one of which must contain a 5-prime phosphate), 250 uM each dNTP, 2.5 U Taq DNA polymerase, 2.5 U of Taq Extender (Stratagene).

The PCR cycling parameters are 1 cycle of: 4 min at 94 C, 2 min at 50 C and 2 min at 72° C.; followed by 5-10 cycles of 1 min at 94° C., 2 min at 54 C and 1 min at 72° C. (step 1).

The parental template DNA and the linear, mutagenesis-primer incorporating newly synthesized DNA are treated with DpnI (10 U) and Pfu DNA polymerase (2.5 U). This results in the DpnI digestion of the in vivo methylated parental template and hybrid DNA and the removal, by Pfu DNA polymerase, of the Tan DNA polymerase-extended base(s) on the linear PCR product.

The reaction is incubated at 37° C. for 30 min and then transferred to 72° C. for an additional 30 min (step 2).

Mutagenesis buffer (1×, 115 ul, containing 0.5 mM ATP) is added to the DpnI-digested, Pfu DNA polymerase-polished PCR products.

The solution is mixed and 10 ul is removed to a new microfuge tube and T4 DNA ligase (2-4 U) added.

The ligation is incubated for greater than 60 min at 37° C. (step 3).

The treated solution is transformed into competent E. coli (step 4).

In addition to the PCR-based site-directed mutagenesis described above, other methods are available. Examples include those described in Kunkel (1985) Proc. Natl. Acad. Sci. 82:488-492; Eckstein et al. (1985) Nucl. Acids Res. 13:8764-8785; and using the GeneEditor™ Site-Directed Mutageneis System from Promega.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other use will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to crystallization or co-crystallization conditions for Ret and Ret surrogate proteins and/or various kinase domain sequences can be used. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

Lengthy table referenced here

US08067434-20111129-T00001

Please refer to the end of the specification for access instructions.

Lengthy table referenced here

US08067434-20111129-T00002

Please refer to the end of the specification for access instructions.

Lengthy table referenced here

US08067434-20111129-T00003

Please refer to the end of the specification for access instructions.

Lengthy table referenced here

US08067434-20111129-T00004

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08067434B2). An electronic copy of the table will also be available from the USPTO upon request and payment of the fee set forth in 37 CFR 1.19(b)(3).

What is claimed is:

1. A method for treating a patient suffering from or at risk of a RET-mediated condition selected from the group consisting of multiple endocrine neoplasia, type IIA (MEN2A), multiple endocrine neoplasia, type IIB (MEN2B), medullary thyroid carcinoma (MTC), familial medullary thyroid carcinomas (FMTC), and papillary thyroid carcinomas (PTC) for which Ret modulation provides a therapeutic benefit, said method comprising administering to said patient a Ret modulator having a chemical structure of Formula I, Formula I

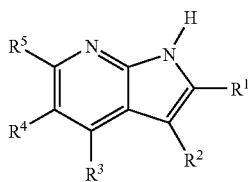

or a prodrug or pharmaceutically acceptable salt thereof, wherein:

$R^1$ and $R^5$ are hydrogen;

$R^2$ is optionally substituted aralkyl, optionally substituted heteroaralkyl, —C(X)R$^{20}$, —NR$^{22}$R$^{23}$, or —S(O)$_n$R$^{21}$;

$R^3$ and $R^4$ are independently hydrogen, halo, hydroxy, optionally substituted alkoxyl, optionally substituted thioalkoxy, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, or optionally substituted heteroaralkyl, —C(X)R$^{20}$, —C(X)NR$^{16}$R$^{17}$, —S(O)$_2$NR$^{16}$R$^{17}$, —NR$^{22}$R$^{23}$, or —S(O)$_n$R$^{21}$;

$R^{16}$ and $R^{17}$ are independently hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, or optionally substituted heteroaralkyl, or $R^{16}$ and $R^{17}$ together form a 5-7 membered carbocyclic or heterocyclic ring;

$R^{20}$ is hydroxyl, optionally substituted lower alkoxy, optionally substituted amine, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, or optionally substituted heteroaralkyl;

$R^{21}$ is optionally substituted lower alkyl, optionally substituted amine, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl;

$R^{22}$ and $R^{23}$ are independently hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, —C(X)R$^{20}$, C(X)NR$^{16}$R$^{17}$, or —S(O)$_2$R$^{21}$;

X=O or S; and n=0, 1, or 2.

2. The method of claim 1, wherein said Ret modulator is selected from the group consisting of

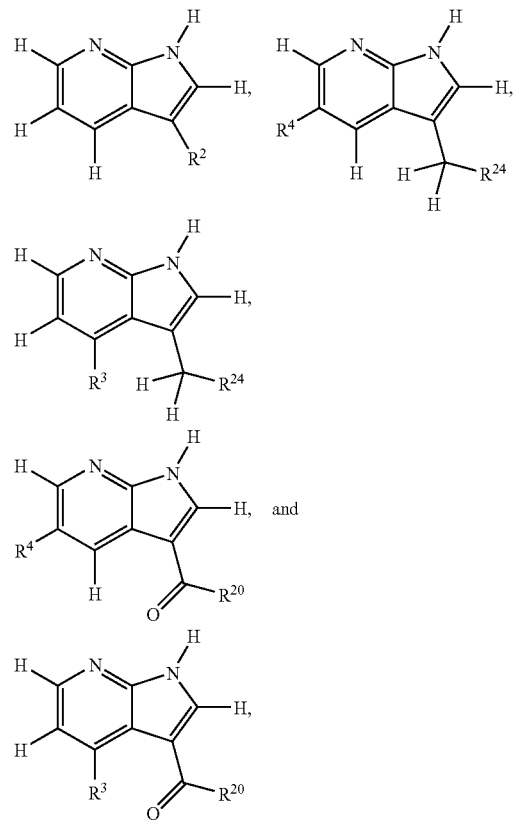

wherein:

$R^{24}$ is optionally substituted aryl or optionally substituted heteroaryl.

3. The method of claim 1, wherein said compound is selected from the group consisting of:
3-(6-Chloro-pyridin-3-ylmethyl)-4-phenyl-1H-pyrrolo[2,3-b]pyridine,
3-(3-Methoxy-benzyl)-5-thiophen-3-yl-1H-pyrrolo[2,3-b]pyridine,
{3-[3-(Thiophen-2-ylsulfanyl)-1H-pyrrolo[2,3-b]pyridin-4-yl]-phenyl}-methanol,
[3-(3-p-Tolylsulfanyl-1H-pyrrolo[2,3-b]pyridin-4-yl)-phenyl]-methanol,
4-(3-Fluoro-phenyl)-3-(thiophen-2-ylsulfanyl)-1H-pyrrolo[2,3-b]pyridine,
5-Bromo-3-(3-methoxy-benzyl)-1H-pyrrolo[2,3-b]pyridine,
(5-Bromo-1H-pyrrolo[2,3-b]pyridin-3-yl)-phenyl-methanone,
3-{3-[2-(Tetrahydro-pyran-2-yloxy)-ethoxy]-benzyl}-5-thiophen-3-yl-1H-pyrrolo[2,3-b]pyridine,
3-(3-Methoxy-benzyl)-5-thiophen-2-yl-1H-pyrrolo[2,3-b]pyridine,
Phenyl-(5-thiophen-3-yl-1H-pyrrolo[2,3-b]pyridin-3-yl)-methanone, 4-[3-(3-Methoxy-benzyl)-1H-pyrrolo[2,3-b]pyridin-5-yl]-phenylamine,
4-[3-(3-Methoxy-benzyl)-1H-pyrrolo[2,3-b]pyridin-5-yl]-benzamide,
3-(6-Chloro-pyridin-3-ylmethyl)-5-thiophen-3-yl-1H-pyrrolo[2,3-b]pyridine,
(5-Bromo-1H-pyrrolo[2,3-b]pyridin-3-yl)-(3-methoxy-phenyl)-methanone,
4-Bromo-3-(3-methoxy-benzyl)-1H-pyrrolo[2,3-b]pyridine,
3-(5-Thiophen-3-yl-1H-pyrrolo[2,3-b]pyridin-3-ylmethyl)-phenol,
(4-Amino-1H-pyrrolo[2,3-b]pyridin-3-yl)-phenyl-methanone,
(3-Methoxy-phenyl)-[5-(1H-pyrrol-2-yl)-1H-pyrrolo[2,3-b]pyridin-3-yl]-methanone,
(3-Methoxy-phenyl)-(5-thiophen-3-yl-1H-pyrrolo[2,3-b]pyridin-3-yl)-methanone,
4-(5-Thiophen-3-yl-1H-pyrrolo[2,3-b]pyridin-3-ylmethyl)-benzene-1,2-diol,
3-Methoxy-5-(5-thiophen-3-yl-1H-pyrrolo[2,3-b]pyridin-3-ylmethyl)-phenol,
5-(5-Thiophen-3-yl-1H-pyrrolo[2,3-b]pyridin-3-ylmethyl)-benzene-1,3-diol,
[4-(3,5-Difluoro-phenyl)-1H-pyrrolo[2,3-b]pyridin-3-yl]-phenyl-methanone,
[4-(3,5-Difluoro-phenyl)-1H-pyrrolo[2,3-b]pyridin-3-yl]-(3-methoxy-phenyl)-methanone,
(2,5-Difluoro-phenyl)-(5-thiophen-3-yl-1H-pyrrolo[2,3-b]pyridin-3-yl)-methanone,
(2,5-Difluoro-phenyl)-(5-pyridin-3-yl-1H-pyrrolo[2,3-b]pyridin-3-yl)-methanone,
(5-Bromo-1H-pyrrolo[2,3-b]pyridin-3-yl)-(2-fluoro-phenyl)-methanone,
(2-Fluoro-phenyl)-(5-thiophen-3-yl-1H-pyrrolo[2,3-b]pyridin-3-yl)-methanone,
(2-Fluoro-phenyl)-(5-pyridin-3-yl-1H-pyrrolo[2,3-b]pyridin-3-yl)-methanone,
(5-Bromo-1H-pyrrolo[2,3-b]pyridin-3-yl)-(4-chloro-phenyl)-methanone,
(4-Chloro-phenyl)-(5-thiophen-3-yl-1H-pyrrolo[2,3-b]pyridin-3-yl)-methanone,
(4-Chloro-phenyl)-(5-pyridin-3-yl-1H-pyrrolo[2,3-b]pyridin-3-yl)-methanone,
(5-Bromo-1H-pyrrolo[2,3-b]pyridin-3-yl)-o-tolyl-methanone,
[4-(3,5-Difluoro-phenyl)-1H-pyrrolo[2,3-b]pyridin-3-yl]-(3-fluoro-phenyl)-methanone,
3-(6-Methoxy-pyridin-2-ylmethyl)-4-thiophen-3-yl-1H-pyrrolo[2,3-b]pyridine,
3-(6-Methoxy-pyridin-3-ylmethyl)-4-thiophen-3-yl-1H-pyrrolo[2,3-b]pyridine,
4-Bromo-3-(6-methoxy-pyridin-2-ylmethyl)-1H-pyrrolo[2,3-b]pyridine,
(3-Hydroxy-phenyl)-(5-thiophen-3-yl-1H-pyrrolo[2,3-b]pyridin-3-yl)-methanone,
(5-Bromo-1H-pyrrolo[2,3-b]pyridin-3-yl)-(3-fluoro-phenyl)-methanone,
(2,5-Difluoro-phenyl)-[4-(3,5-difluoro-phenyl)-1H-pyrrolo[2,3-b]pyridin-3-yl]-methanone,
(2,3-Difluoro-phenyl)-[4-(3,5-difluoro-phenyl)-1H-pyrrolo[2,3-b]pyridin-3-yl]-methanone,
(2,4-Difluoro-phenyl)-[4-(3,5-difluoro-phenyl)-1H-pyrrolo[2,3-b]pyridin-3-yl]-methanone,
(2,6-Difluoro-phenyl)-[4-(3,5-difluoro-phenyl)-1H-pyrrolo[2,3-b]pyridin-3-yl]-methanone,
[4-(3,5-Difluoro-phenyl)-1H-pyrrolo[2,3-b]pyridin-3-yl]-(2-fluoro-phenyl)-methanone,
3-(6-Chloro-pyridin-3-ylmethyl)-4-thiophen-3-yl-1H-pyrrolo[2,3-b]pyridine,
(3-Methoxy-phenyl)-(5-thiophen-2-yl-1H-pyrrolo[2,3-b]pyridin-3-yl)-methanone,
(3-Hydroxy-phenyl)-(5-thiophen-2-yl-1H-pyrrolo[2,3-b]pyridin-3-yl)-methanone,
[4-(3,5-Difluoro-phenyl)-1H-pyrrolo[2,3-b]pyridin-3-yl]-(3-hydroxy-phenyl)-methanone,
(5-Methyl-isoxazol-3-yl)-(5-pyridin-3-yl-1H-pyrrolo[2,3-b]pyridin-3-yl)-methanone,
(5-Methyl-isoxazol-3-yl)-(5-thiophen-3-yl-1H-pyrrolo[2,3-b]pyridin-3-yl)-methanone,
4-[3-(1,5-Dimethyl-1H-pyrazole-3-carbonyl)-1H-pyrrolo[2,3-b]pyridin-5-yl]-benzamide,
(1,5-Dimethyl-1H-pyrazol-3-yl)-(5-pyridin-3-yl-1H-pyrrolo[2,3-b]pyridin-3-yl)-methanone,
N-{3-[3-(5-Methyl-isoxazole-3-carbonyl)-1H-pyrrolo[2,3-b]pyridin-5-yl]-phenyl}-acetamide,
4-[3-(5-Fluoro-2-methyl-benzoyl)-1H-pyrrolo[2,3-b]pyridin-5-yl]-benzamide,
(5-Fluoro-2-methyl-phenyl)-(5-pyridin-3-yl-1H-pyrrolo[2,3-b]pyridin-3-yl)-methanone,
[5-(3-Amino-phenyl)-1H-pyrrolo[2,3-b]pyridin-3-yl]-(5-fluoro-2-methyl-phenyl)-methanone,
(5-Fluoro-2-methyl-phenyl)-(5-thiophen-3-yl-1H-pyrrolo[2,3-b]pyridin-3-yl)-methanone,
[5-(4-Chloro-phenyl)-1H-pyrrolo[2,3-b]pyridin-3-yl]-(5-fluoro-2-methyl-phenyl)-methanone,
[5-(3-Amino-phenyl)-1H-pyrrolo[2,3-b]pyridin-3-yl]-(2,3-dichloro-phenyl)-methanone,
(2,3-Dichloro-phenyl)-(5-thiophen-3-yl-1H-pyrrolo[2,3-b]pyridin-3-yl)-methanone,
(2,3-Dichloro-phenyl)-(5-pyridin-3-yl-1H-pyrrolo[2,3-b]pyridin-3-yl)-methanone,
3-[3-(1,5-Dimethyl-1H-pyrazole-3-carbonyl)-1H-pyrrolo[2,3-b]pyridin-5-yl]-benzamide,
(5-Pyridin-3-yl-1H-pyrrolo[2,3-b]pyridin-3-yl)-o-tolyl-methanone,
3-[3-(2,5-Dimethyl-2H-pyrazole-3-carbonyl)-1H-pyrrolo[2,3-b]pyridin-5-yl]-benzamide,
N-{3-[3-(2-Fluoro-benzoyl)-1H-pyrrolo[2,3-b]pyridin-5-yl]-phenyl}-acetamide,
(5-Thiophen-3-yl-1H-pyrrolo[2,3-b]pyridin-3-yl)-o-tolyl-methanone,
(5-Bromo-1H-pyrrolo[2,3-b]pyridin-3-yl)-(3-hydroxy-phenyl)-methanone,
(3-Methoxy-phenyl)-(5-pyridin-3-yl-1H-pyrrolo[2,3-b]pyridin-3-yl)-methanone,
[5-(3-Amino-phenyl)-1H-pyrrolo[2,3-b]pyridin-3-yl]-(3-methoxy-phenyl)-methanone,
(E)-3-{3-[3-(3-Methoxy-benzoyl)-1H-pyrrolo[2,3-b]pyridin-5-yl]-phenyl}-acrylic acid,
[5-(3-Amino-phenyl)-1H-pyrrolo[2,3-b]pyridin-3-yl]-(2-fluoro-phenyl)-methanone,
(E)-3-{3-[3-(2-Fluoro-benzoyl)-1H-pyrrolo[2,3-b]pyridin-5-yl]-phenyl}-acrylic acid,
[5-(3-Amino-phenyl)-1H-pyrrolo[2,3-b]pyridin-3-yl]-(4-chloro-phenyl)-methanone,
[5-(3-Amino-phenyl)-1H-pyrrolo[2,3-b]pyridin-3-yl]-o-tolyl-methanone,
[5-(3-Amino-phenyl)-1H-pyrrolo[2,3-b]pyridin-3-yl]-(5-methyl-isoxazol-3-yl)-methanone,
[5-(3-Amino-phenyl)-1H-pyrrolo[2,3-b]pyridin-3-yl]-(1,5-dimethyl-1H-pyrazol-3-yl)-methanone, N-{3-[3-(5-Fluoro-2-methyl-benzoyl)-1H-pyrrolo[2,3-b]pyridin-5-yl]-phenyl}-methanesulfonamide,
N-{3-[3-(2,5-Dimethyl-2H-pyrazole-3-carbonyl)-1H-pyrrolo[2,3-b]pyridin-5-yl]-phenyl}-methanesulfonamide,
[5-(3-Amino-phenyl)-1H-pyrrolo[2,3-b]pyridin-3-yl]-(2,5-dimethyl-2H-pyrazol-3-yl)-methanone,
[5-(3-Amino-phenyl)-1H-pyrrolo[2,3-b]pyridin-3-yl]-benzo[1,2,5]thiadiazol-5-yl-methanone,
N-{3-[3-(4-Chloro-benzoyl)-1H-pyrrolo[2,3-b]pyridin-5-yl]-phenyl}-methanesulfonamide,
(3-Fluoro-phenyl)-(5-thiophen-3-yl-1H-pyrrolo[2,3-b]pyridin-3-yl)-methanone,
(5-Bromo-1H-pyrrolo[2,3-b]pyridin-3-yl)-(2-fluoro-3-methoxy-phenyl)-methanone,
(2-Hydroxy-phenyl)-(5-thiophen-2-yl-1H-pyrrolo[2,3-b]pyridin-3-yl)-methanone,
(2-Fluoro-3-methoxy-phenyl)-(5-thiophen-2-yl-1H-pyrrolo[2,3-b]pyridin-3-yl)-methanone,
(2-Fluoro-5-methoxy-phenyl)-(5-thiophen-2-yl-1H-pyrrolo[2,3-b]pyridin-3-yl)-methanone,
(2-Fluoro-3-hydroxy-phenyl)-(5-thiophen-2-yl-1H-pyrrolo[2,3-b]pyridin-3-ye-methanone,
(2-Fluoro-5-hydroxy-phenyl)-(5-thiophen-2-yl -1H-pyrrolo[2,3-b]pyridin-3-yl)-methanone,
4-[3-(2,5-Dimethyl-2H-pyrazole-3-carbonyl)-1H-pyrrolo[2,3-b]pyridin-5-yl]-benzamide,
(2,5-Dimethyl-2H-pyrazol-3-yl)-(5-thiophen-3-yl-1H-pyrrolo[2,3-b]pyridin-3-yl)-methanone,
4-[3-(2-Methyl-benzoyl)-1H-pyrrolo[2,3-b]pyridin-5-yl]-benzamide,
4-[3-(2,3-Dichloro-benzoyl)-1H-pyrrolo[2,3-b]pyridin-5-yl]-benzamide,
4-[3-(Benzo[1,2,5]thiadiazole-5-carbonyl)-1H-pyrrolo[2,3-b]pyridin-5-yl]-benzamide,
(E)-3-{3-[3-(Benzo[1,2,5]thiadiazole-5-carbonyl)-1H-pyrrolo[2,3-b]pyridin-5-yl]-phenyl}-acrylic acid,
N-{3-[3-(Benzo[1,2,5]thiadiazole-5-carbonyl)-1H-pyrrolo[2,3-b]pyridin-5-yl]-phenyl}-methanesulfonamide,
4-[3-(3-Methoxy-benzoyl)-1H-pyrrolo[2,3-b]pyridin-5-yl]-benzamide,
4-[3-(2-Fluoro-benzoyl)-1H-pyrrolo[2,3-b]pyridin-5-yl]-benzamide,
(E)-3-{3-[3-(2,3-Dichloro-benzoyl)-1H-pyrrolo[2,3-b]pyridin-5-yl]-phenyl}-acrylic acid,
(E)-3-{3-[3-(5-Methyl-isoxazole-3-carbonyl)-1H-pyrrolo[2,3-b]pyridin-5-yl]-phenyl}-acrylic acid,
(E)-3-{3-[3-(1,5-Dimethyl-1H-pyrazole-3-carbonyl)-1H-pyrrolo[2,3-b]pyridin-5-yl]-phenyl}-acrylic acid,
4-[3-(4-Chloro-benzoyl)-1H-pyrrolo[2,3-b]pyridin-5-yl]-benzamide,
(4-Chloro-1H-pyrrolo[2,3-b]pyridin-3-yl)-(3-hydroxy-phenyl)-methanone,
(5-Chloro-2-fluoro-phenyl)-(5-thiophen-2-yl-1H-pyrrolo[2,3-b]pyridin-3-yl)-methanone,
(4-Methoxy-phenyl)-(5-thiophen-2-yl-1H-pyrrolo[2,3-b]pyridin-3-yl)-methanone,
(4-Hydroxy-phenyl)-(5-thiophen-2-yl-1H-pyrrolo[2,3-b]pyridin-3-yl)-methanone,
(3-Methoxy-phenyl)-(5-phenyl-1H-pyrrolo[2,3-b]pyridin-3-yl)-methanone,
4-[3-(3-Hydroxy-benzoyl)-1H-pyrrolo[2,3-b]pyridin-5-yl]-benzamide,
[5-(3-Amino-phenyl)-1H-pyrrolo[2,3-b]pyridin-3-yl]-(3-hydroxy-phenyl)-methanone,
(5-Ethyl-1H-pyrrolo[2,3-b]pyridin-3-yl)-(3-hydroxy-phenyl)-methanone,
(2-Fluoro-phenyl)-[4-(2-fluoro-phenyl)-1H-pyrrolo[2,3-b]pyridin-3-yl]-methanone,
N-{3-[3-(2-Fluoro-5-methoxy-benzoyl)-1H-pyrrolo[2,3-b]pyridin-5-yl]-phenyl}-acetamide,
N-{3-[3-(2-Fluoro-5-hydroxy-benzoyl)-1H-pyrrolo[2,3-b]pyridin-5-yl]-phenyl}-acetamide,
(2-Fluoro-5-methoxy-phenyl)-(5-pyridin-3-yl-1H-pyrrolo[2,3-b]pyridin-3-yl)-methanone,
(4-Chloro-1H-pyrrolo[2,3-b]pyridin-3-yl)-(2,3-dichloro-phenyl)-methanone,
(3-Methoxy-phenyl)-(5-pyridin-3-yl-1H-pyrrolo[2,3-b]pyridin-3-yl)-methanone,
(2-Fluoro-5-hydroxy-phenyl)-(5-pyridin-3-yl-1H-pyrrolo[2,3-b]pyridin-3-yl)-methanone,
3-[3-(3-Methoxy-benzoyl)-1H-pyrrolo[2,3-b]pyridin-5-yl]-benzamide,
3-Benzenesulfinyl-5-bromo-1H-pyrrolo[2,3-b]pyridine,
(2-Fluoro-5-hydroxy-phenyl)-(5-thiophen-3-yl-1H-pyrrolo[2,3-b]pyridin-3-yl)-methanone,
[4-(3-Amino-phenyl)-1H-pyrrolo[2,3-b]pyridin-3-yl]-(3-methoxy-phenyl)-methanone,
(3-Hydroxy-phenyl)-(5-pyridin-3-yl-1H-pyrrolo[2,3-b]pyridin-3-yl)-methanone,
(4-Chloro-1H-pyrrolo[2,3-b]pyridin-3-yl)-(2-fluoro-5-hydroxy-phenyl)-methanone,
(2-Fluoro-5-hydroxy-phenyl)-(4-phenyl-1H-pyrrolo[2,3-b]pyridin-3-yl)-methanone,
[5-(3-Amino-phenyl)-1H-pyrrolo[2,3-b]pyridin-3-yl]-(2-fluoro-5-hydroxy-phenyl)-methanone,
(4-Chloro-1H-pyrrolo[2,3-b]pyridin-3-yl)-(2-fluoro-5-methoxy-phenyl)-methanone,
[4-(4-Chloro-phenyl)-1H-pyrrolo[2,3-b]pyridin-3-yl]-(2,5-difluoro-phenyl)-methanone,
[4-(4-Chloro-phenyl)-1H-pyrrolo[2,3-b]pyridin-3-yl]-(2,3-dichloro-phenyl)-methanone,
(2,5-Difluoro-phenyl)-(4-thiophen-3-yl-1H-pyrrolo[2,3-b]pyridin-3-yl)-methanone,
(4-Chloro-phenyl)-(4-pyridin-3-yl-1H-pyrrolo[2,3-b]pyridin-3-yl)-methanone,
[4-(3-Amino-phenyl)-1H-pyrrolo[2,3-b]pyridin-3-yl]-(4-chloro-phenyl)-methanone,
[4-(3-Amino-phenyl)-1H-pyrrolo[2,3-b]pyridin-3-yl]-(2-fluoro-phenyl)-methanone,
4-[3-(2-Methyl-benzoyl)-1H-pyrrolo[2,3-b]pyridin-4-yl]-benzamide,
4-[3-(2,5-Difluoro-benzoyl)-1H-pyrrolo[2,3-b]pyridin-4-yl]-benzamide,
4-[3-(2-Fluoro-benzoyl)-1H-pyrrolo[2,3-b]pyridin-4-yl]-benzamide,
(E)-3-{3-[3-(4-Chloro-benzoyl)-1H-pyrrolo[2,3-b]pyridin-4-yl]-phenyl}-acrylic acid,
N-{3-[3-(4-Chloro-benzoyl)-1H-pyrrolo[2,3-b]pyridin-4-yl]-phenyl}-acetamide,
N-{3-[3-(2,3-Dichloro-benzoyl)-1H-pyrrolo[2,3-b]pyridin-4-yl]-phenyl}-acetamide,
3-[3-(2,5-Difluoro-benzoyl)-1H-pyrrolo[2,3-b]pyridin-4-yl]-benzamide,
3-[3-(2,3-Dichloro-benzoyl)-1H-pyrrolo[2,3-b]pyridin-4-yl]-benzamide,
N-{3-[3-(4-Chloro-benzoyl)-1H-pyrrolo[2,3-b]pyridin-4-yl]-phenyl}-methanesulfonamide,
N-{3-[3-(2-Methyl-benzoyl)-1H-pyrrolo[2,3-b]pyridin-4-yl]-phenyl}-methanesulfonamide,
N-{3-[3-(2,5-Difluoro-benzoyl)-1H-pyrrolo[2,3-b]pyridin-4-yl]-phenyl}-methanesulfonamide,
(2-Fluoro-phenyl)-[4-(3-methanesulfonyl-phenyl)-1H-pyrrolo[2,3-b]pyridin-3-yl]-methanone, (2-Fluoro-phenyl)-[4-(6-methoxy-pyridin-3-yl)-1H-pyrrolo[2,3-b]pyridin-3-yl]-methanone,
(4-Pyridin-3-yl-1H-pyrrolo[2,3-b]pyridin-3-yl)-o-tolyl-methanone,
[4-(3-Amino-phenyl)-1H-pyrrolo[2,3-b]pyridin-3-yl]-(2,3-dichloro-phenyl)-methanone,
(E)-3-{3-[3-(2,5-Difluoro-benzoyl)-1H-pyrrolo[2,3-b]pyridin-4-yl]-phenyl}-acrylic acid,
N-{3-[3-(2-Methyl-benzoyl)-1H-pyrrolo[2,3-b]pyridin-4-yl]-phenyl}-acetamide,
N-{3-[3-(2,5-Difluoro-benzoyl)-1H-pyrrolo[2,3-b]pyridin-4-yl]-phenyl}-acetamide,
N-{3-[3-(2-Fluoro-benzoyl)-1H-pyrrolo[2,3-b]pyridin-4-yl]-phenyl}-acetamide,
3-[3-(4-Chloro-benzoyl)-1H-pyrrolo[2,3-b]pyridin-4-yl]-benzamide,
N-{3-[3-(2-Fluoro-benzoyl)-1H-pyrrolo[2,3-b]pyridin-4-yl]-phenyl}-methanesulfonamide,
(2,5-Difluoro-phenyl)-[4-(3-methanesulfonyl-phenyl)-1H-pyrrolo[2,3-b]pyridin-3-yl]-methanone,
(2,3-Dichloro-phenyl)-[4-(3-methanesulfonyl-phenyl)-1H-pyrrolo[2,3-b]pyridin-3-yl]-methanone,
[4-(6-Methoxy-pyridin-3-yl)-1H-pyrrolo[2,3-b]pyridin-3-yl]-o-tolyl-methanone,
(2,3-Dichloro-phenyl)-[4-(6-methoxy-pyridin-3-yl)-1H-pyrrolo[2,3-b]pyridin-3-yl]-methanone,
(2,5-Difluoro-phenyl)-(4-pyridin-3-yl-1H-pyrrolo[2,3-b]pyridin-3-yl)-methanone,
3-[3-(2-Fluoro-benzoyl)-1H-pyrrolo[2,3-b]pyridin-4-yl]-benzamide,
[4-(4-Chloro-phenyl)-1H-pyrrolo[2,3-b]pyridin-3-yl]-o-tolyl-methanone,
[4-(4-Chloro-phenyl)-1H-pyrrolo[2,3-b]pyridin-3-yl]-(2-fluoro-phenyl)-methanone,
(2-Fluoro-phenyl)-(4-thiophen-3-yl-1H-pyrrolo[2,3-b]pyridin-3-yl)-methanone,
(2,3-Dichloro-phenyl)-(4-thiophen-3-yl-1H-pyrrolo[2,3-b]pyridin-3-yl)-methanone,
(2-Fluoro-phenyl)-(4-pyridin-3-yl-1H-pyrrolo[2,3-b]pyridin-3-yl)-methanone,
(2,3-Dichloro-phenyl)-(4-pyridin-3-yl-1H-pyrrolo[2,3-b]pyridin-3-yl)-methanone,
[4-(3-Amino-phenyl)-1H-pyrrolo[2,3-b]pyridin-3-yl]-o-tolyl-methanone,
[4-(3-Amino-phenyl)-1H-pyrrolo[2,3-b]pyridin-3-yl]-(2,5-difluoro-phenyl)-methanone,
4-[3-(4-Chloro-benzoyl)-1H-pyrrolo[2,3-b]pyridin-4-yl]-benzamide,
4-[3-(2,3-Dichloro-benzoyl)-1H-pyrrolo[2,3-b]pyridin-4-yl]-benzamide,
(E)-3-{3-[3-(2-Methyl-benzoyl)-1H-pyrrolo[2,3-b]pyridin-4-yl]-phenyl}-acrylic acid,
(E)-3-{3-[3-(2-Fluoro-benzoyl)-1H-pyrrolo[2,3-b]pyridin-4-yl]-phenyl}-acrylic acid,
(E)-3-{3-[3-(2,3-Dichloro-benzoyl)-1H-pyrrolo[2,3-b]pyridin-4-yl]-phenyl}-acrylic acid,
3-[3-(2-Methyl-benzoyl)-1H-pyrrolo[2,3-b]pyridin-4-yl]-benzamide,
N-{3-[3-(2,3-Dichloro-benzoyl)-1H-pyrrolo[2,3-b]pyridin-4-yl]-phenyl}-methanesulfonamide,
(4-Chloro-phenyl)-[4-(3-methanesulfonyl-phenyl)-1H-pyrrolo[2,3-b]pyridin-3-yl]-methanone,
[4-(3-Methanesulfonyl-phenyl)-1H-pyrrolo[2,3-b]pyridin-3-yl]-o-tolyl-methanone,
(E)-3-{3-[3-(5-tert-Butyl-2-methyl-2H-pyrazole-3-carbonyl)-1H-pyrrolo[2,3-b]pyridin-4-yl]-phenyl}-acrylic acid,
N-{3-[3-(3-Methoxy-benzoyl)-1H-pyrrolo[2,3-b]pyridin-4-yl]-phenyl}-methanesulfonamide,
[4-(4-Chloro-phenyl)-1H-pyrrolo[2,3-b]pyridin-3-yl]-(5-fluoro-2-methyl-phenyl)-methanone,
[4-(4-Chloro-phenyl)-1H-pyrrolo[2,3-b]pyridin-3-yl]-(5-methyl-isoxazol-3-yl)-methanone,
[4-(4-Chloro-phenyl)-1H-pyrrolo[2,3-b]pyridin-3-yl]-(2,5-dimethyl-2H-pyrazol-3-yl)-methanone,
(5-Methyl-isoxazol-3-yl)-(4-thiophen-3-yl-1H-pyrrolo[2,3-b]pyridin-3-yl)-methanone,
N-{3-[3-(5-Fluoro-2-methyl-benzoyl)-1H-pyrrolo[2,3-b]pyridin-4-yl]-phenyl}-acetamide,
N-{3-[3-(5-Methyl-isoxazole-3-carbonyl)-1H-pyrrolo[2,3-b]pyridin-4-yl]-phenyl}-methanesulfonamide,
(5-Fluoro-2-methyl-phenyl)-[4-(3-methanesulfonyl-phenyl)-1H-pyrrolo[2,3-b]pyridin-3-yl]-methanone,
[4-(3-Methanesulfonyl-phenyl)-1H-pyrrolo[2,3-b]pyridin-3-yl]-(5-methyl-isoxazol-3-yl)-methanone,
(3-Methoxy-phenyl)-[4-(6-methoxy-pyridin-3-yl)-1H-pyrrolo[2,3-b]pyridin-3-yl]-methanone,
[4-(6-Methoxy-pyridin-3-yl)-1H-pyrrolo[2,3-b]pyridin-3-yl]-(5-methyl-isoxazol-3-yl)-methanone,
(5-Fluoro-2-methyl-phenyl)-[4-(6-methoxy-pyridin-3-yl)-1H-pyrrolo[2,3-b]pyridin-3-yl]-methanone,
[4-(4-Chloro-phenyl)-1H-pyrrolo[2,3-b]pyridin-3-yl]-(3-methoxy-phenyl)-methanone,
(3-Methoxy-phenyl)-(4-thiophen-3-yl-1H-pyrrolo[2,3-b]pyridin-3-yl)-methanone,
(5-Fluoro-2-methyl-phenyl)-(4-thiophen-3-yl-1H-pyrrolo[2,3-b]pyridin-3-yl)-methanone,
(3-Methoxy-phenyl)-(4-pyridin-3-yl-1H-pyrrolo[2,3-b]pyridin-3-yl)-methanone,
(5-Fluoro-2-methyl-phenyl)-(4-pyridin-3-yl-1H-pyrrolo[2,3-b]pyridin-3-yl)-methanone,
(5-Methyl-isoxazol-3-yl)-(4-pyridin-3-yl-1H-pyrrolo[2,3-b]pyridin-3-yl)-methanone,
[4-(3-Amino-phenyl)-1H-pyrrolo[2,3-b]pyridin-3-yl]-(5-fluoro-2-methyl-phenyl)-methanone,
4-[3-(3-Methoxy-benzoyl)-1H-pyrrolo[2,3-b]pyridin-4-yl]-benzamide,
4-[3-(5-Fluoro-2-methyl-benzoyl)-1H-pyrrolo[2,3-b]pyridin-4-yl]-benzamide,
4-[3-(5-Methyl-isoxazole-3-carbonyl)-1H-pyrrolo[2,3-b]pyridin-4-yl]-benzamide,
(E)-3-{3-[3-(3-Methoxy-benzoyl)-1H-pyrrolo[2,3-b]pyridin-4-yl]-phenyl}-acrylic acid,
(E)-3-{3-[3-(5-Fluoro-2-methyl-benzoyl)-1H-pyrrolo[2,3-b]pyridin-4-yl]-phenyl}-acrylic acid,
(E)-3-{3-[3-(5-Methyl-isoxazole-3-carbonyl)-1H-pyrrolo[2,3-b]pyridin-4-yl]-phenyl}-acrylic acid,
(E)-3-{3-[3-(2,5-Dimethyl-2H-pyrazole-3-carbonyl)-1H-pyrrolo[2,3-b]pyridin-4-yl]-phenyl}-acrylic acid,
N-{3-[3-(3-Methoxy-benzoyl)-1H-pyrrolo[2,3-b]pyridin-4-yl]-phenyl}-acetamide,
N-{3-[(5-Methyl-isoxazole-3-carbonyl)-1H-pyrrolo[2,3-b]pyridin-4-yl]-phenyl}-acetamide,
3-[3-(3-Methoxy-benzoyl)-1H-pyrrolo[2,3-b]pyridin-4-yl]-benzamide,
3-[3-(5-Fluoro-2-methyl-benzoyl)-1H-pyrrolo[2,3-b]pyridin-4-yl]-benzamide,
3-[3-(5-Methyl-isoxazole-3-carbonyl)-1H-pyrrolo[2,3-b]pyridin-4-yl]-benzamide,
N-{3-[3-(5-Fluoro-2-methyl-benzoyl)-1H-pyrrolo[2,3-b]pyridin-4-yl]-phenyl}-methanesulfonamide,
[4-(3-Methanesulfonyl-phenyl)-1H-pyrrolo[2,3-b]pyridin-3-yl]-(3-methoxy-phenyl)-methanone, (3-Hydroxy-phenyl)-(5-phenylamino-1H-pyrrolo[2,3-b]pyridin-3-yl)-methanone, and pharmaceutically acceptable salts thereof.

4. The method of claim 1, wherein said Ret modulator is approved for administration to a human.

5. The method of claim 1, wherein $R^2$ is selected from the group consisting of —$CH_2$-(optionally substituted aryl), —$CH_2$-(optionally substituted heteroaryl), —C(O)-(optionally substituted aryl), —C(O)-(optionally substituted heteroaryl), —S-(optionally substituted aryl), —S-(optionally substituted heteroaryl), —S(O)-(optionally substituted aryl), —S(O)-(optionally substituted heteroaryl), —$S(O)_2$-(optionally substituted aryl), and —$S(O)_2$-(optionally substituted heteroaryl).

6. The method of claim 5, wherein $R^2$ is selected from the group consisting of —$CH_2$-(optionally substituted aryl), —$CH_2$-(optionally substituted heteroaryl), —C(O)-(optionally substituted aryl), and —C(O)-(optionally substituted heteroaryl).

7. The method of claim 5, wherein $R^3$ is hydrogen and $R^4$ is selected from the group consisting of optionally substituted lower alkyl, optionally substituted aryl, optionally substituted heteroaryl, —O-(optionally substituted lower alkyl), —O-(optionally substituted aryl), —O-(optionally substituted heteroaryl), —NH-(optionally substituted lower alkyl), —NH-(optionally substituted aryl), and —NH-(optionally substituted heteroaryl).

8. The method of claim 6, wherein $R^3$ is hydrogen and $R^4$ is selected from the group consisting of optionally substituted lower alkyl, optionally substituted aryl, optionally substituted heteroaryl, —O-(optionally substituted lower alkyl), —O-(optionally substituted aryl), —O-(optionally substituted heteroaryl), —NH-(optionally substituted lower alkyl), —NH-(optionally substituted aryl), and —NH-(optionally substituted heteroaryl).

9. The method of claim 5, wherein $R^4$ is hydrogen and $R^3$ is selected from the group consisting of optionally substituted lower alkyl, optionally substituted aryl, optionally substituted heteroaryl, —NH-(optionally substituted lower alkyl), —NH-(optionally substituted aryl), and —NH-(optionally substituted heteroaryl).

10. The method of claim 6, wherein $R^4$ is hydrogen and $R^3$ is selected from the group consisting of optionally substituted lower alkyl, optionally substituted aryl, optionally substituted heteroaryl, —NH-(optionally substituted lower alkyl), —NH-(optionally substituted aryl), and —NH-(optionally substituted heteroaryl).

* * * * *

UNITED STATES PATENT AND TRADEMARK OFFICE
CERTIFICATE OF CORRECTION

PATENT NO. : 8,067,434 B2  
APPLICATION NO. : 12/082665  
DATED : November 29, 2011  
INVENTOR(S) : Ibrahim et al.

Page 1 of 1

It is certified that error appears in the above-identified patent and that said Letters Patent is hereby corrected as shown below:

IN THE CLAIMS

Claim 1, Column 285, Line 5, replace "type JIB" with --type IIB--.

Claim 1, Column 285, Line 13, replace "Formula 1" with --Formula I--.

Claim 3, Column 288, Lines 34-35, replace "(2,3-Diehloro-phenyl)-(5-thiophen-3-yl-1H-pyrrolo[2,3-b]pyridin-3-yl)-methanone," with --(2,3-Dichloro-phenyl)-(5-thiophen-3-yl-1H-pyrrolo[2,3-b]pyridin-3-yl)-methanone,--.

Signed and Sealed this
Thirteenth Day of October, 2015

Michelle K. Lee
*Director of the United States Patent and Trademark Office*